(12) United States Patent
Van Der Oost et al.

(10) Patent No.: US 9,902,973 B2
(45) Date of Patent: Feb. 27, 2018

(54) METHODS OF MODIFYING A TARGET NUCLEIC ACID WITH AN ARGONAUTE

(71) Applicant: Caribou Biosciences, Inc., Berkeley, CA (US)

(72) Inventors: John Van Der Oost, Renkum (NL); Daniël Christianus Swarts, Wageningen (NL); Andrew Paul May, San Francisco, CA (US); Rachel E. Haurwitz, Kensington, CA (US)

(73) Assignee: Caribou Biosciences, Inc., Berkeley, CA (US)

( * ) Notice: Subject to any disclaimer, the term of this patent is extended or adjusted under 35 U.S.C. 154(b) by 488 days.

(21) Appl. No.: 14/250,224

(22) Filed: Apr. 10, 2014

(65) Prior Publication Data
US 2015/0089681 A1   Mar. 26, 2015

Related U.S. Application Data

(60) Provisional application No. 61/939,680, filed on Feb. 13, 2014.

(30) Foreign Application Priority Data

Apr. 11, 2013   (GB) .................................. 1306574.3

(51) Int. Cl.
| | | |
|---|---|---|
| C12N 15/52 | (2006.01) | |
| C12N 15/11 | (2006.01) | |
| C12N 15/113 | (2010.01) | |
| C12Q 1/00 | (2006.01) | |
| G01N 33/573 | (2006.01) | |
| C12N 15/90 | (2006.01) | |
| G01N 33/542 | (2006.01) | |
| C12N 15/10 | (2006.01) | |

(52) U.S. Cl.
CPC ........... *C12N 15/902* (2013.01); *C12N 15/10* (2013.01); *C12N 15/102* (2013.01); *G01N 33/542* (2013.01)

(58) Field of Classification Search
None
See application file for complete search history.

(56) References Cited

U.S. PATENT DOCUMENTS

| | | |
|---|---|---|
| 7,919,277 B2 | 4/2011 | Russell et al. |
| 8,361,725 B2 | 1/2013 | Russell et al. |
| 2008/0124725 A1 | 5/2008 | Barrangou et al. |
| 2009/0170069 A1 | 7/2009 | Ghosh et al. |
| 2010/0034924 A1 | 2/2010 | Fremaux et al. |
| 2010/0093617 A1 | 4/2010 | Barrangou et al. |
| 2010/0104690 A1 | 4/2010 | Barrangou et al. |
| 2011/0002889 A1 | 1/2011 | Barrangou et al. |
| 2011/0217739 A1 | 9/2011 | Terns et al. |
| 2011/0236530 A1 | 9/2011 | Manoury et al. |
| 2011/0300538 A1 | 12/2011 | Barrangou et al. |
| 2013/0011828 A1 | 1/2013 | Barrangou et al. |
| 2013/0158245 A1 | 6/2013 | Russell et al. |
| 2013/0288251 A1 | 10/2013 | Horvath et al. |
| 2014/0315985 A1 | 10/2014 | May et al. |

FOREIGN PATENT DOCUMENTS

| | | |
|---|---|---|
| EP | 2292731 A1 | 3/2011 |
| WO | WO 2006/073445 A2 | 7/2006 |
| WO | WO 2007/025097 A2 | 3/2007 |
| WO | WO 2007/136815 A2 | 11/2007 |
| WO | WO 2007/144770 A2 | 12/2007 |
| WO | WO 2008/108989 A2 | 9/2008 |
| WO | WO 2010/011961 A2 | 1/2010 |
| WO | WO 2010/054154 A2 | 5/2010 |
| WO | WO 2010/066907 A1 | 6/2010 |
| WO | WO 2011/143124 A2 | 11/2011 |
| WO | WO 2012/054726 A1 | 4/2012 |
| WO | WO 2013/088446 A1 | 6/2013 |
| WO | WO 2013/098244 A1 | 7/2013 |
| WO | WO 2013/141680 A1 | 9/2013 |
| WO | WO 2013/142578 A1 | 9/2013 |

OTHER PUBLICATIONS

Gao et al, DNA-guided genome editing using the Natronobacterium gregoryi Argonaute, Nature Biotechnology, 2016, pp. 1-7.*
Wang et al, Delivery of siRNA Therapeutics: Barriers and Carriers, The AAPS Journal, vol. 12, No. 4, Dec. 2010, p. 492-503.*
Horlbeck et al, Nucleosomes impede Cas9 access to DNA in vivo and in vitro, eLife 2016, pp. 1-21.*
Wang et al, Distinct passenger strand and mRNA cleavage activities of human Argonaute proteins, nature structural & molecular biology, 2009, pp. 1259-1267.*
Swarts et al, DNA-guided DNA interference by a prokaryotic Argonaute, Nature, 2009, pp. 1-17.*
Flores-Jasso, Rapid and specific purification of Argonaute-small RNA complexes from crude cell lysates, RNA (2013), 19:271-279.*
Chylinski, et al. The tracrRNA and Cas9 families of type II CRISPR-Cas immunity systems. RNA Biol. May 2013;10(5):726-737. doi: 10.4161/rna.24321. Epub Apr. 5, 2013.
Carbonell, A., et al., "Functional Analysis of Three *Arabidopsis* Argonautes Using Slicer-Defective Mutants," The Plant Cell (2012) 24:3613-3629.
Kitamura, S., et al., "Characterization of RNase HII substrate recognition using RNase HII-argonaute chimaeric enzymes from Pyrococcus furiosus," Biochem (2010) 426, 337-344.
Makarova, K., et al., "Prokaryotic homologs of Argonaute proteins are predicted to function as key components of a novel system of defense against mobile genetic elements," Biology Direct 2009, 4(29), 1-15.
Rapozzi, V., and Xodo, L.E., "Efficient Silencing of bcr/abl Oncogene by Single- and Double-Stranded siRNAs Targeted against b2a2 Transcripts," Biochemistry 2004, 43, 16134-16141.
Wang, Y., et al., "Nucleation, propagation and cleavage of target RNAs in argonaute silencing complexes," Nature. Oct. 8, 2009; 461(7265): 754-761.
Swarts D., et al., "DNA-guided DNA interference by a prokaryotic Argonaute." Nature. Mar. 13, 2014; 507(7491): 258-261. doi: 10.1038/nature12971.

(Continued)

*Primary Examiner* — Maria Marvich

(74) *Attorney, Agent, or Firm* — Gary R. Fabian; Barbara G. McClung

(57) ABSTRACT

This disclosure provides for compositions and methods for the use of designed nucleic acid-targeting nucleic acids, Argonautes, and complexes thereof.

12 Claims, 58 Drawing Sheets

(56) References Cited

OTHER PUBLICATIONS

Carbonell, et al. Functional analysis of three *Arabidopsis* Argonautes using slicer-defective mutants. Plant Cell. Sep. 2012;24(9):3613-29. doi: 10.1105/tpc.112.099945. Epub Sep. 28, 2012.
Kitamura, et al. Characterization of RNase HII substrate recognition using RNase HII-argonaute chimaeric enzymes from Pyrococcus furiosus. Biochem J. Feb. 24, 2010;426(3):337-44. doi: 10.1042/BJ20091553.
Rapozzi, et al. Efficient silencing of bcr/abl oncogene by single- and double-stranded siRNAs targeted against b2a2 transcripts. Biochemistry. Dec. 28, 2004;43(51):16134-41.
Wang, et al. Nucleation, propagation and cleavage of target RNAs in argonature silencing complexes. Nature. Oct. 8, 2009;461(7265):754-61. doi: 10.1038/nature08434.
Beloglazova, et al. A novel family of sequence-specific endoribonucleases associated with the clustered regularly interspaced short palindromic repeats. J Biol Chem. Jul. 18, 2008;283(29):20361-71. doi: 10.1074/jbc.M803225200. Epub May 15, 2008.
Burroughs, et al. Two novel PIWI families: roles in inter-genomic conflicts in bacteria and Mediator-dependent modulation of transcription in eukaryotes. Biol Direct. Jun. 8, 2013;8:13. doi: 10.1186/1745-6150-8-13.
Carte, et al. Binding and cleavage of CRISPR RNA by Cas6. RNA 2010, 16(11): 2181-2188.
Carte, et al. Cas6 is an endoribonuclease that generates guide RNAs for invader defense in prokaryotes. Genes Dev. Dec. 15, 2008;22(24):3489-96. doi: 10.1101/gad.1742908.
Cenik, et al. Argonaute proteins. Curr Biol. Jun. 21, 2011;21(12):R446-9. doi: 10.1016/j.cub.2011.05.020.
GenBank Direct Submission M33159.1. T. thermophilus insertion sequences 1s1000A and 1s1000B. May 5, 1993. [Retrieved from the Internet Oct. 24, 2013:<http://www.ncbi.nlm.nih.gov/nuccore/M33159>] (nucleotides 6325-6290).
Hale, et al. RNA-guided RNA cleavage by a CRISPR RNA-Cas protein complex. Cell. Nov. 25, 2009;139(5):945-56. doi: 10.1016/j.cell.2009.07.040.
Haurwitz, et al. Csy4 relies on an unusual catalytic dyad to position and cleave CRISPR RNA. EMBO J Epub Apr. 20, 2012, 31(12):2824-32.
Haurwitz, et al. Sequence- and structure-specific RNA processing by a CRISPR endonuclease. Science. Sep. 10, 2010;329(5997):1355-8. doi: 10.1126/science.1192272.
Jinek, et al. A three-dimensional view of the molecular machinery of RNA interference. Nature. Jan. 22, 2009;457(7228):405-12. doi: 10.1038/nature07755.
Ketting. The many faces of RNAi. Dev Cell. Feb. 15, 2011;20(2):148-61. doi: 10.1016/j.devcel.2011.01.012.
Lee, et al. RNA-protein analysis using a conditional CRISPR nuclease. Proc Natl Acad Sci USA. Apr. 2, 2013, 110(14):5416-21.
Makarova, et al. Prokaryotic homologs of Argonaute proteins are predicted to function as key components of a novel system of defense against mobile genetic elements. Biol Direct. Aug. 25, 2009;4:29. doi: 10.1186/1745-6150-4-29.
Nakanishi, et al. Structure of yeast Argonaute with guide RNA. Nature. Jun. 20, 2012;486(7403):368-74. doi: 10.1038/nature11211.
Olovnikov, et al. Bacterial argonaute samples the transcriptome to identify foreign DNA. Mol Cell. Sep. 12, 2013;51(5):594-605. doi: 10.1016/j.molcel.2013.08.014.
Parker, et al. Molecular mechanisms of target RNA transcript recognition by argonaute-guide complexes. Cold Spring Harb Symp Quant Biol. 2006;71:45-50.
Rashid, et al. Structure of Aquifex aeolicus argonaute highlights conformational flexibility of the PAZ domain as a potential regulator of RNA-induced silencing complex function. J Biol Chem. May 4, 2007;282(18):13824-32. Epub Nov. 27, 2006.
Sheng, et al. Structure-based cleavage mechanism of Thermus thermophilus Argonaute DNA guide strand-mediated DNA target cleavage. Proc Natl Acad Sci U S A. Jan. 14, 2014;111(2):652-7. doi: 10.1073/pnas.1321032111. Epub Dec. 27, 2013.
Swarts, et al. DNA-guided DNA interference by a prokaryotic Argonaute. Nature. Mar. 13, 2014;507(7491):258-61. doi: 10.1038/nature12971. Epub Feb. 16, 2014.
Todorova. Comparative analysis of the methods of drug and protein delivery for the treatment of cancer, genetic diseases and diagnostics. Drug Deliv. Nov. 2011;18(8):586-98. doi: 10.3109/10717544.2011.600783. Epub Aug. 24, 2011.
UniProt Direct Submission D7BB61_MEISD. CRISPR-associated protein Cas6. May 16, 2012. [Retrieved from the Internet Oct. 24, 2013:<http://www.uniprot.org/uniproUD7BB61.txt?version=9>]; in entirety.
Wang, et al. Nucleation, propagation and cleavage of target RNAs in Ago silencing complexes. Nature. Oct. 8, 2009;461(7265):754-61. doi: 10.1038/nature08434.
Wang, et al. Structure of an argonaute silencing complex with a seed-containing guide DNA and target RNA duplex. Nature. Dec. 18, 2008;456(7224):921-6. doi: 10.1038/nature07666.
Yuan, et al. Crystal structure of A. aeolicus argonaute, a site-specific DNA-guided endoribonuclease, provides insights into RISC-mediated mRNA cleavage. Mol Cell. Aug. 5, 2005;19(3):405-19.
Sheng, G., et al., "Structure-based cleavage mechanism of Thermus thermophilus Argonaute DNA guide strand-mediated DNA target cleavage," Proceedings of the National Academy of Sciences. Dec. 27, 2013; vol. 111, No. 2; pp. 652-657. Doi: 10.1073/pnas.1321032111.
Swarts, D., et al., "DNA-guided DNA interference by a prokaryotic Argonaute," Nature. Feb. 16, 2014; vol. 507, No. 7491; pp. 258-261. Doi: 10.1038jnature12971.
Swarts, D., et al., "The evolutionary journey of Argonaute proteins," Nature Structural and Molecular Biology. Sep. 5, 2014; vol. 21, No. 9; pp. 743-753. Doi: 10.1038jnsnnb.2879.
Swarts, D., et al., "Argonaute of the archaean Pyrococcus furiosus is a DNA-guided nuclease that targets cognate DNA," Nucleic Acids Research. Apr. 29, 2015; vol. 43, No. 10; pp. 5120-5129. Doi: 10.1093jnarjgkv415.
Wang, B., et al., "Distinct passenger strand and mRNA cleavage activities of human Argonaute proteins," Nature Structural and Molecular Biology. Dec. 29, 2009; vol. 16, No. 12; pp. 1259-1266. Doi: 10.1038jnsnnb.1712.

\* cited by examiner

Figure 18

Fig. 20A
Fig. 20B
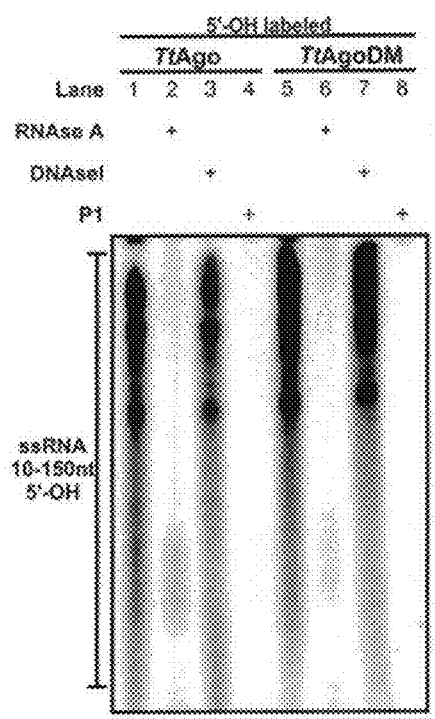
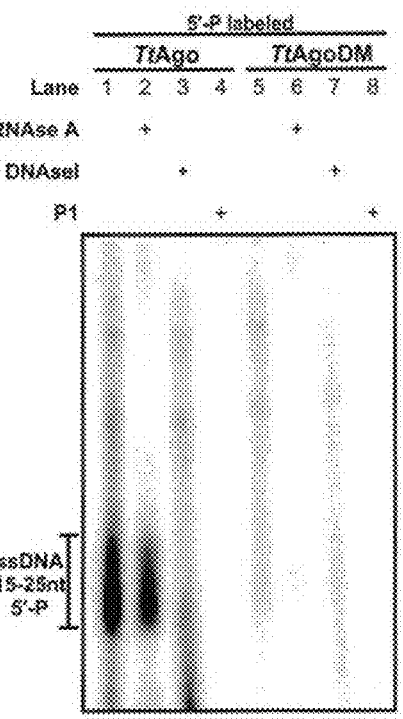

Fig. 30C 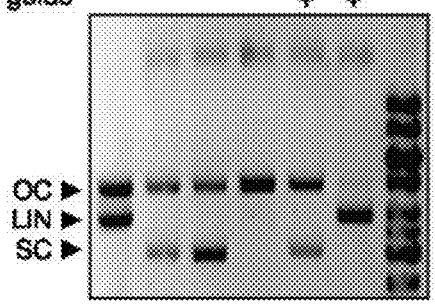 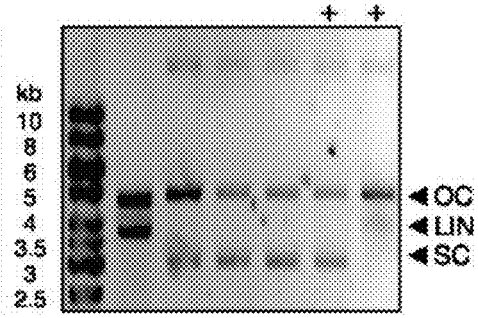

Figure 37

| Genes involved in competence | | | Genes involved in host-defence | | |
|---|---|---|---|---|---|
| Gene | Encoded protein | Log₂ fold change (P-value) | Gene | Encoded protein | Log₂ fold change (P-value) |
| TTC1603 | ComEC | 0.09 (0.49) | TT_P0026 | TtAgo TtAgo | <-10 (<0.01) |
| TTC1602 | ComEA | 0.05 (0.74) | TTC1025 | Cse2 | 0.18 (0.03) |
| TTC1873 | DprA | 0.22 (0.18) | TTC1927 | Cas6 | 0.02 (0.88) |
| TTC0664 | PilA1 | 1.15 (0.02) | TT_P0101 | Cas2 | 0.18 (0.61) |
| TTC0855 | PilA2 | 0.97 (<0.01) | TT_P0102 | Csm1 | 0.39 (0.04) |
| TTC0856 | PilA3 | 0.82 (<0.01) | TT_P0103 | Csm2 | 0.46 (<0.01) |
| TTC0858 | PilA4 | 0.45 (0.17) | TT_P0104 | Csm3 | 0.54 (<0.01) |
| TTC1715 | PilD | 0.40 (0.11) | TT_P0105 | Csm4 | 0.64 (0.01) |
| TTC1522 | PilF | 0.10 (0.11) | TT_P0106 | Csm5 | 0.52 (<0.01) |
| TTC0440 | PilC | 0.43 (<0.01) | TT_P0107 | Csx1 | 0.23 (0.07) |
| TTC1017 | PilQ | 0.15 (0.36) | TT_P0115 | Cmr2 | 0.32 (0.06) |
| TTC0857 | ComZ | 0.61 (0.05) | TT_P0116 | Cmr3 | 0.30 (0.16) |
| TTC1013 | PilM | 0.25 (0.06) | TT_P0117 | Cmr1 | 0.43 (0.01) |
| TTC1014 | PilN | 0.21 (0.05) | TT_P0118 | Cmr4 | 0.41 (<0.01) |
| TTC1015 | PilO | 0.20 (0.43) | TT_P0119 | Cmr5 | 0.46 (<0.01) |
| TTC1016 | PilW | -0.17 (0.12) | TT_P0120 | RAMP | 0.38 (0.33) |
| TT_P0190 | PilA | -0.01 (0.93) | TT_P0132 | Cas3 | 0.22 (0.20) |
| | | | TT_P0133 | Cas4 | 1.14 (<0.01) |
| | | | TT_P0134 | Cas8C | 0.61 (<0.01) |
| | | | TT_P0135 | Cas7 | 0.59 (<0.01) |
| | | | TT_P0136 | Cas4 | 0.48 (0.01) |
| | | | TT_P0195 | Cas2 | 1.42 (0.15) |
| | | | TT_P0196 | Cas1 | 0.52 (0.28) |
| | | | TT_P0197 | Cas4 | 0.34 (0.44) |
| | | | TT_P0204 | Cas6 | 0.73 (0.01) |
| | | | TT_P0215 | Cas1 | 0.16 (0.42) |

Figure 38

Proteins with most abundant peptides

| Protein ID | Name | Peptides | Sequence coverage (%) | Mol. Weight (kDa) | PEP | iBAQ |
|---|---|---|---|---|---|---|
| Q72G73 | TT_C1975 | 31 | 42.8 | 76.8 | 1.84E-109 | 327562000 |
| P61889 | groL | 16 | 28.4 | 57.9 | 1.09E-36 | 7043390 |
| Q746M7 | TtAgo | 14 | 19 | 76.7 | 1.95E-37 | 2942600 |
| Q72JL4 | TT_C0758 | 11 | 26.3 | 49.3 | 1.72E-41 | 2230800 |
| Q72JL5 | TT_C0966 | 9 | 25.3 | 41.8 | 3.37E-29 | 11686200 |
| Q72H63 | TT_C1627 | 7 | 15.1 | 48.1 | 1.06E-19 | 3409090 |
| Q72HK7 | TT_C1365 | 7 | 8.7 | 82.5 | 1.05E-19 | 2727240 |
| Q72GH6 | TT_C1872 | 5 | 15.9 | 53.3 | 4.09E-17 | 812660 |
| Q72K98 | TT_C0548 | 5 | 19.3 | 35.9 | 3.04E-13 | 595940 |
| Q72GW4 | tuf1 | 5 | 12.3 | 44.8 | 1.97E-14 | 437870 |

Peptides matched against TtAgo

| Sequence | Mass (Da) | Protein | PEP |
|---|---|---|---|
| AFGASGASLR | 935.48249 | TtAgo | 0.000543219 |
| AGETALALALR | 1054.6241 | TtAgo | 5.37E-06 |
| AVSKPADALR | 1025.5822 | TtAgo | 0.00820086 |
| EGHAVELVGVR | 1220.6401 | TtAgo | 0.0012876 |
| EHASWHGR | 936.49252 | TtAgo | 0.00265671 |
| LADGLYVPLEDK | 1331.69473 | TtAgo | 0.000097536 |
| LGEEDPK | 786.37893 | TtAgo | 0.013635 |
| LGLGTPEAVR | 1011.57 13 | TtAgo | 0.000683792 |
| LYPASGHAPHR | 1226.6291 | TtAgo | 0.1021229 |
| MGGNYAYR | 1001.4369 | TtAgo | 0.00260966 |
| SWLSALAR | 815.4865 | TtAgo | 0.0613518 |
| TEVFLNR | 877.46577 | TtAgo | 0.0013227 |
| VANVVADPKDPR | 1352.6564 | TtAgo | 0.0933599 |
| YYPVDGR | 817.44464 | TtAgo | 0.028618 |

Only proteins of which five or more peptides were identified are shown. The Peptides column shows how many sections are matched against a certain protein. iBAQ, intensity-based absolute quantification; PEP, posterior error probability; 1t, Peptides identified that match TtAgo sequences.

Figure 39

| DNA locus | Size | Copies per cell | Total DNA per cell | Reads aligned to DNA locus | Normalized reads* | Normalized reads* corrected for DNA per cell |
|---|---|---|---|---|---|---|
| E. coli K12 chromosome | 4.64 Mb | 1 | 4.64 Mb | 23*10$^6$ | 1 | 1 |
| pWUR702 | 5.6 kb | 20-40 | 0.17 Mb | 45*10$^6$ | 2 | 54 |
| pRARE | 4.7 kb | 10-12 | 52 kb | 2*10$^6$ | 0.1 | 8.8 |

Estimated relative quantities of guides complementary to plasmid and chromosome DNA per cell.
*Reads are normalized against the number of reads mapped against the E. coli K12 chromosome.

>tr|Q746M7|Q746M7_THET2 Uncharacterized protein OS=Thermus thermophilus (strain HB27 / ATCC BAA-163 / DSM 7039) GN=TT_P0026 PE=1 SV=1

MNHLGKTEVFLNRFALRPLNPEELRPWRLEVVLDPPPGREEVYPLLAQVARRA
GGVTVRMGDGLASWSPPEVLVLEGTLARMGQTYAYRLYPKGRRPLDPKDPGE
RSVLSALARRLLQERLRRLEGVVVEGLAVYRREHARGPGWRVLGGAVLDLWV
SDSGAFLLEVDPAYRILCEMSLEAWLAQGHPLPKRVRNAYDRRTWELLRLGEE
DPKELPLPGGLSLLDYHASKGRLQGREGGRVAVVADPKDPRKPIPHLTGLLVP
VLTLEDLHEEEGSLALSLPWEERRRRTREIASWIGRRLGLGTPEAVRAQAYRLSI
PKLMGRRAVSKPADALRVGFYRAQETALALLRLDGAQGWPEFLRRALLRAFGA
SGASLRLHTLHAHPSQGLAFREALRKAKEEGVQAVLVLTPPMAWEDRNRLKAL
LLREGLPSQILNVPLREEERHRWENALLGLLAKAGLQVVALSGAYPAELAVGFD
AGGRESFRFGGAACAVGGDGGHLLWTLPEAQAGERIPQEVVWDLLEETLWAF
RRKAGRLPSRVLLLRDGRVPQDEFALALEALAREGIAYDLVSVRKSGGGRVYPV
QGRLADGLYVPLEDKTFLLLTVHRDFRGTPRPLKLVHEAGDTPLEALAHQIFHLT
RLYPASGFAFPRLPAPLHLAD RLVKEVGRLGIRHLKEVDREKLFFV

Figure 42B

>tr|H9ZUR4|H9ZUR4_THETH Uncharacterized protein containing
piwi/argonaute domain OS=Thermus thermophilus JL-18 GN=TtJL18_2241
PE=4 SV=1
MNHLGKTEVFLNRFALRPLNPEELRPWRLEVVLDPPPGREEVYPLLAQVA
RRAGGVTVRMGDGLASWSPPEVLVLEGTLARMGQTYAYRLYPKGRRPLD
PKDPGERSALSSLARRLLQERLRRLEGVVVEGLAVYRREHARGPGWRVL
GGAVLDLWVSDSGAFLLEVDPAYRILCEMSLE
AWLAQGHPLPKRVRNAYDRRTWELLRLGEEDPKELPLPGGLSLLDYHASK
GRLQGREGGRVAWVADPKDPRKPIPHLTGLLVPVLTLEDLHEEEGGLALS
LPWEERRRTREIASWIGRRLGLGTPEAVRAQAYRLSIPKLMGRRAVSKP
ADALRVGLYRAQETALALLRLDGAQGWPEFLRRALLQAFGAGGASLRLHT
LHAHPSQGLAFREALRKAKEKGVQAVLVLTPPMAWEDRNR
LKALLLREGLPSQILNVPLREEERHRWENALLGLLAKAGLQVVALSGAYPA
ELAVGFDAGGRESFRFGGAACAVGGDGGHLLWTLPEAQAGERIPQEVVW
DLLEETLWAFRRKAGRLPSRVLLRDGRVPQDEFALALEALAREGIAYDLV
SVRKSGGGRVYPVQGRLADGLYVPLEDRTFLLLTVHRDFFRGTPRPLKLVH
EAGDTPLEALAHQIFHLTRLYPASGFAFPRLPAPLHLAD

Figure 42C

>tr|O67434|O67434_AQUAE Uncharacterized protein OS=Aquifex aeolicus (strain VF5) GN=aq_1447 PE=1 SV=1
MGKEALLNLYRIEYRPKDTTFTVFKPTHEIQKEKLNKVRWRVFLQTGLPTFR
REDEFWCAGKVEKDTLYLTLSNGEIVELKRVGEEEFRGFQNERECQELFRD
FLTKTKVKDKFISDFYKKFRDKITVQGKNRKIALIPEVNEKVLKSEEGYFLLHL
DLKFRIQPFETLQTLLERNDFNP
KRIRVKPIGIDFVGRVQDVFKAKEKGEEFFRLCMERSTHKSSKKAWEELLKN
RELREKAFLVVLEKGYTYPATILKPVLTYENLEDEERNEVADIVRMEPGKRL
NLIRYILRRYVKALRDYGWYISPEEERAKGKLNFKDTVLDAKGKNTKVITNLR
KFLELCRPFVKKDVLSVEIISVSVYKKLEWRKEEFLKELINFLKNKGIKLKIKG
KSLILAQTREEAKEKLIPVINKIKDVDLVIVFLEEYPKVDPYKSFLLYDFVKREL
LKKMIPSQVILNRTLKNENLKFVLLNVAEQVLAKTGNIPYKLKEIEGKVDAFV
GIDISRITRDGKTVNAVAFTKIFNSKGELVRYYLTSYPAFGEKLTEKAIGDVFS
LLEKLGFKKGSKIVVHRDGRLYRDEVAAFKKYGELYGYSLELLEIIKRNNPRF
FSNEKFIKGYFYKLSEDSVILATYNQVYEGTHQPIKVRKVYGELPVEVLCSQI
L SLTLMNYSSFQPIKLPATVHYSDKITKLMLRGIEPIKKEGDIMYWL

Figure 42D

>tr|Q8U3D2|Q8U3D2_PYRFU Uncharacterized protein OS=Pyrococcus furiosus (strain ATCC 43587 / DSM 3638 / JCM 8422 / Vc1) GN=PF0537 PE=1 SV=1

MKAKVVINLVKINKKIIPDKIYVYRLFNDPEEELQKEGYSIYRLAYENVGIVIDPE
NLII
ATTKELEYEGEFIPEGEISFSELRNDYQSKLVLRLLKENGIGEYELSKLLRKFRK
PKTFGDYKVIPSVEMSVIKHDEDFYLVIHIIHQIQSMKTLWELVNKDPKELEEFL
MTHKENLMLKDIASPLKTVYKPCFEEYTKKPKLDHNQEIVKYWYNYHIERYWN
TPEAKLEFYRKFGQVDLKQPAILAKFASKIKKNKNYKIYLLPQLVVPTYNAEQL
ESDVAKEILEYTKLMPEERKELLENILAEVDSDIIDKSLSEIEVEKIAQELENKIRV
RDDKGNSVPISQLNVQKSQLLLWTNYSRKYPVILPYEVPEKFRKIREIPMFIILD
SGLLADIQNFATNEFRELVKSMYYSLAKKYNSLAKKARSTNEIGLPFLDFRGK
EKVITEDLNSDKGIIEVVEQVSSFMKGKELGLAFIAARNKLSSEKFEEIKRRLFN
LNVISQVVNEDTLKNKRDKYDRNRLDLFVRHNLLFQVLSKLGVKYYVLDYRFN
YDYIIGIDVAPMKRSEGYIGGSAVMFDSQGYIRKIVPIKIGEQRGESVDMNEFF
KEMVDKFKEFNIKLDNKKILLLRDGRITNNEEEGLKYISEMFDIEVVTMDVIKNH
PVRAFANMKMYFNLGGAIYLIPHKLKQAKGTPIPIKLAKKRIIKNGKVEKQSITR
QDVLDIFILTRLNYGSISADMRLPAPVHYAHKFANAIRNEWKIKEEFLAEGFLYF
V

Figure 42E

>tr|I6U616|I6U616_9EURY Uncharacterized protein OS=Pyrococcus furiosus COM1 GN=PFC_01805 PE=4 SV=1
MKAKVVINLVKINKKIIPDKIYVYRLFNDPEEELQKEGYSIYRLAYENV
GIVIDPENLIIATTKELEYEGEFIPEGEISFSELRNDYQSKLVLRLLKEN
GIGEYELSKLLRKFRKPKTFG
DYKVIPSVEMSVIKHDEDFYLVIHIIHQIQSMKTLWELVNKDPKELEEF
LMTHKENLMLKDIASPLKTVYKPCFEEYTKKPKLDHNQEIVKYWYNY
HIERYWNTPEAKLEFYRKFGQVDLKQPAILAKFASKIKKNKNYKIYLLP
QLVVPTYNAEQLESDVAKEILEYTKLMPEERKELLENILAEVDSDIIDK
SLSEIEVEKIAQELENKIRVRDDKGNSVPISQLNVQKSQLLLWTNY
SRKYPVILPYEVPEKFRKIREIPMFIILDSGLLADIQNFATNEFRELVKS
MYYSLAKKYNSLAKKARSTNEIGLPFLDFRGKEKVITEDLNSDKGIIEV
VEQVSSFMGKELGLAFIAARNKLSSEKFEEIKRRLFNLNVISQVVNE
DTLKNKRDKYDRNRLDLFVRHNLLFQVLSKLGVKYYVLDYRFNYDYII
GIDVAPMKRSEGYIGGSAVMFDSQGYIRKIVPIKIGEQRGESVDM
NEFFKEMVDKFKEFNIKLDNKKILLLRDGRITNNEEEGLKYISEMFDIE
VVTMDVIKNHPVRAFANMKMYFNLGGAIYLIPHKLKQAKGTPIPIKLAK
KRIIKNGKVEKQSITRQDVLDIFILTRLNYGSISADMRLPAPVHYAHKF
ANAIRNEWKIKEEFLAEGFLYFV

Figure 42F

>sp|O28951|PIWI_ARCFU Piwi protein AF_1318 OS=Archaeoglobus fulgidus (strain ATCC 49558 / VC-16 / DSM 4304 / JCM 9628 / NBRC 100126) GN=AF_1318 PE=1 SV=1
MMEYKIVENGLTYRIGNGASVPISNTGELIKGLRNYGPYEVPSLKYNQIALIHN
NQFSSLINQLKSQISSKIDEVWHIHNINISEFIYDSPHFDSIKSQVDNAIDTGVDG
IMLVLPEYNTPLYYKLKSYLINSIPSQFMRYDILSNRNLTFYVDNLLVQFVSKLG
GKPWILNVDPEKGSDIIIGTGATRIDNVNLFCFAMVFKKDGTMLWNEISPIVTS
SEYLTYLKSTIKKVVYGFKKSNPDWDVEKLTLHVSGKRPKMKDGETKILKETV
EELKKQEMVSRDVKYAILHLNETHPFWVMGDPNNRFHPYEGTKVKLSSKRYL
LTLLQPYLKRNGLEMVTPIKPLSVEIVSDNWTSEEYYHNVHEILDEIYYLSKMN
WRGFRSRNLPVTVNYPKLVAGIIANVNRYGGYPINPEGNRSL QTNPWFL

Figure 42G

>tr|B7GJX9|B7GJX9_ANOFW Argonaute, predicted to be implicated in RNA metabolism OS=Anoxybacillus flavithermus (strain DSM 21510 / WK1) GN=Aflv_1627 PE=4 SV=1
MNQYYITECMANENANNIPLHIYTVSLLNPNQKYSFAHHIVYELRKRNPNVTIAVHGQYI
ASFQEIAHWGDHEYIKHEYRAIECFNATERTVLERLLKQELIERCKSDYKIYKDLFCLKT
EQSIEMNEIIVYPAIYLSFTVEENGNILIGFEYQHRFEYKKTLEDLLRDRSPLIKEGVEV
VDSYNKKSYYYTFVEVAPYTAGEKSPYLQQSVIDYYITKNEKVWKLKGVHNKTPIVHVRS
QTGDIFPYLPHLLRLTCSYEQLMPSTAKQVNRIIKLPPNKKMPKLYQEIFRLLQYQDMLT
FRKENVRAANLNYNIFKLSPPLMKFGRNYTTTKVSDGLGQAGVYEPKSVTVSYFVDPE
LNYDQRKKDEILDFTKKLQDLSGKLGVKLNVSKKPRQLFGVLPVDFFKSERLSFELKSI
TNAFEGTIVVIGTEENIERAYMAIKKEFGAKADIMTQFVIFDSSIVNNSFYYYNVLLGIYAK
SGVQPWILLDHMNSDCFIGLDVSHEQGKHASGIIQVIGKDGRIIKQKSVMATEAGETIAR
CTMEEIINESIFSYEKMYGMKPSHITFHRDGVCREDLAHLTQYMQSFQIPFDFVEIIKKP
RRRMAVYKNKSWFTEQGLCYAKERMAYLCATDPRESVGMAQVVKIVQKTNCLSIRDI
VSDAY KLSFMHIHSMLKTRLPITIHYADLSSTFHNRGLIHPRSVHERALPFV

Figure 42H

>tr|E4NRV1|E4NRV1_HALBP Uncharacterized protein OS=Halogeometricum borinquense (strain ATCC 700274 / DSM 11551 / JCM 10706 / PR3) GN=Hbor_13050 PE=4 SV=1
MAVKADIEDGEEIDIALHVTGIDEWEHDAIARKIQLEDVDGAAIDLTVFHNND
VSDFEWEIGEWYLLENVVGNEFRGEMQLNPGYDLTVTLLNDPPAAAGNDK
SPGSVPPEEPVDQSGESGSSGAAASTSGEPGDAEFVRGSEVDDGSRPTA
DGGGKLLHQQPLSDGNYLLQFELGSLPELPVHEYELRATGSGGIDPDDFTN
GIEGFTAKAANYYQSRIGSPVTTADASRRRIYATEKLHGTISMHGYTVKPVH
QGETTLEARSYTNDGPLQEFVKQDVKRAVAGRFEVSGIDSIIEPT
PQRTANSGLFEAYRKYKCRIRVDADGTVICGVNVAYHLESTFSAAEWVQRG
HDIADVTVEHDTDLYDSARTATVKEIIDMDYDDMLDGPGVPMSEYHEKHVE
QDVIDSMRAGNPVIADLQYGSGEDSIFPQLLEYCKVIPTFDQLGRVDETFLN
VIHNESRMKPEERFNVVTSFVDLLGPTPYFDFGPVPQPTNAGYREQKTPNI
PNLRFGDGRTGYYGAGGLERKGYYGVYKAPESFDIIALYPDSEQAAARPYVL
SVLGKLAEYDGKPTKFDQETYELGSEFHYSQHAQKTSDYDAALIVVPDKDK
AAAADYDDPYPEFKRRLGQLGVPSQMITIDNLGNDSYLGNISSSLIGKAGGV
PWRIDDVPGDVDAFVGLDVTYDHATKQHLGAAANVIMADGTILASEAVTKQ
AGETFDEDDVANVIKHVLEIFAEEEGRPPRHVVIHRDGKFYLDIESLIKRLDK
ARDLIQRFDLVEIRKSGNPRIAEYDESKSRFDIADKGVAFHVHNGDHSYLTT
TGGKEGSPGTPRPLQIVKRHGSTDLDTLAEQTYWLSEAHVGSLSRSTRLPI
TTYYADKCADFAMKGYLTKGSVIRGVPYI

Figure 46

Sequence of *S. elongatus* Ago

MDLLSNLRRSSIVLNRFYVKSLSQSDLTAYEYRCIFKKTPELGDEKRLLASICYKLGAIA
VRIGSNIITKEAVRPEKLQGHDWQLVQMGTKQLDCRNDAHRCALETFERKFLERD
LSASSQTEVRKAAEGGLIWWVVGAKGIEKSGNGWEVHRGRRIDVSLDAEGNLYLE
IDIHRFYTPWTVHQWLEQYPEIPLSYVRNNYLDERHGFINWQYGRFTQERPQDI
LLDCLGMSLAEYHLNKGATEEVQQSYVVVKPISWRKGKLTAHLSRRLSPSLTME
MLAKVAEDSTVCDREKREIRAVFKSIKQSINQRLQEAQKTASWILTKTYGISSPAIALS
CDGYLLPAAKLLAANKQPVSKTADIRNKGCAKIGETSFGYLNLYNNQLQYPLEVHKC
LLEIANKNNLQLSLDQRRVLSDYPQDDLDQQMFWQTWSSQGIKTVLVVMPWDS
HHDKQKIRIQAIQAGIATQFMVPLPKADKYKALNVTLGLLCKAGWQPIQLESVDH
PEVADLIIGFDTGTNRELYYGTSAFAVLADGQSLGWELPAVQRGETFSGQAIWQTV
SKLIIKFYQICQRYPQKLLLMRDGLVQEGEFQQTIELLKERKIAVDVISVRKSGAGRM
GQEIYENGQLVYRDAAIGSVILQPAERSFIMVTSQPVSKTIGSIRPLRIVHEYGSTDLE
LLALQTYHLTQLHPASGFRSCRLPWVLHLADRSSKEFQRIGQJSVLQNISRDKLIAV

METHODS OF MODIFYING A TARGET NUCLEIC ACID WITH AN ARGONAUTE

CROSS-REFERENCE

This application claims the benefit of U.S. Provisional Application No. 61/939,680, filed Feb. 13, 2014 and GB Application No. 1306574.3, filed Apr. 11, 2013 the entire contents of which are incorporated herein by reference. A certified copy of GB Application No. 1306574.3 is of record in the present application.

The instant application contains a Sequence Listing which has been submitted electronically in ASCII format and is hereby incorporated by reference in its entirety. Said ASCII copy, created on May 27, 2014, is named 44287-724.201_SL.txt and is 78,292 bytes in size.

BACKGROUND

Genome engineering can refer to altering the genome by deleting, inserting, mutating, or substituting specific nucleic acid sequences. The altering can be gene or location specific. Genome engineering can use Argonaute proteins to cut a nucleic acid thereby generating a site for the alteration. Prokaryotic Argonautes are prokaryotic homologs of eukaryotic Argonaute proteins, which are key enzymes in RNA interference pathways. An Argonaute can bind and cleave a target nucleic acid by forming a complex with a designed nucleic acid-targeting nucleic acid. Cleavage can introduce double stranded breaks in the target nucleic acid. A nucleic acid can be repaired e.g. by endogenous non-homologous end joining (NHEJ) machinery. A piece of nucleic acid can be inserted. Engineering of non-genomic nucleic acid is also contemplated. Modifications of designed nucleic acid-targeting nucleic acids and Argonautes can introduce new functions to be used for genome engineering.

SUMMARY

In one aspect, the disclosure provides for a composition comprising: a complex comprising: an Argonaute and a designed nucleic acid-targeting nucleic acid; and a target nucleic acid, wherein the designed nucleic acid-targeting nucleic acid is hybridized to the target nucleic acid. In some embodiments, the target nucleic acid is double-stranded. In some embodiments, the Argonaute comprises at least 30% amino acid identity to a prokaryotic Argonaute. In some embodiments, the Argonaute comprises at least 30% amino acid identity to a bacterial Argonaute. In some embodiments, the Argonaute comprises at least 30% amino acid identity to an archaeal Argonaute. In some embodiments, the Argonaute comprises at least 30% amino acid identity to an Argonaute from a mesophile. In some embodiments, the Argonaute comprises at least 30% amino acid identity to an Argonaute from a thermophile. In some embodiments, the Argonaute comprises at least 30% amino acid identity to an Argonaute from a species selected from the group consisting of: *Thermus thermophilus*, *Thermus thermophilus* JL-18, *Thermus thermophilus* strain HB27, *Aquifex aeolicus* strain VF5, *Pyrococcus furiosus*, *Archaeoglobus fulgidus*, *Anoxybacillus flavithermus*, *Halogeometricum borinquense*, *Microsystis aeruginosa*, *Clostridium bartlettii*, *Halorubrum lacusprofundi*, *Thermosynechococcus elongatus*, and *Synechococcus elongatus*, or any combination thereof. In some embodiments, the Argonaute comprises at least 30% amino acid identity to an Argonaute from *T. thermophilus*. In some embodiments, a nuclease domain of the Argonaute comprises at least 30% amino acid identity to a nuclease domain of Argonaute from *T. thermophilus*. In some embodiments, the Argonaute comprises at least 30% amino acid identity to an Argonaute from *S. elongatus*. In some embodiments, a nuclease domain of the Argonaute comprises at least 30% amino acid identity to a nuclease domain of Argonaute from *S. elongatus*. In some embodiments, a nuclease domain of the Argonaute comprises at least 30% amino acid identity to a nuclease domain of Argonaute from *T. thermophilus*, wherein the nuclease domain is a PIWI domain. In some embodiments, a nuclease domain of the Argonaute comprises at least 30% amino acid identity to a nuclease domain of Argonaute from *S. elongatus*, wherein the nuclease domain is a PIWI domain. In some embodiments, a MID domain of the Argonaute comprises at least 30% amino acid to a MID domain of an Argonaute from *T. thermophilus*. In some embodiments, a PAZ domain of the Argonaute comprises at least 30% amino acid to a PAZ domain of an Argonaute from *T. thermophilus*. In some embodiments, a MID domain of the Argonaute comprises at least 30% amino acid to a MID domain of an Argonaute from *S. elongatus*. In some embodiments, a PAZ domain of the Argonaute comprises at least 30% amino acid to a PAZ domain of an Argonaute from *S. elongatus*. In some embodiments, the Argonaute comprises one or more manganese ions. In some embodiments, the Argonaute comprises one or more magnesium ions. In some embodiments, the designed nucleic acid-targeting nucleic acid is single-stranded DNA. In some embodiments, the designed nucleic acid-targeting nucleic acid is single-stranded RNA. In some embodiments, the designed nucleic acid-targeting nucleic acid is from 9-25 nucleotides in length. In some embodiments, the designed nucleic acid-targeting nucleic acid is 21 nucleotides in length. In some embodiments, the designed nucleic acid-targeting nucleic acid comprises a 5' phosphorylated end. In some embodiments, the designed nucleic acid-targeting nucleic acid comprises a deoxycytosine at its 5' end. In some embodiments, the designed nucleic acid-targeting nucleic acid comprises a deoxycytosine-deoxyadenosine dinucleotide at its 5' end. In some embodiments, from 2-16 nucleotides of the designed nucleic acid-targeting nucleic acid hybridize to the double-stranded target nucleic acid. In some embodiments, from 2-9 nucleotides of the designed nucleic acid-targeting nucleic acid hybridize to the double-stranded target nucleic acid. In some embodiments, a portion of the designed nucleic acid-targeting nucleic acid hybridizes to the double-stranded target nucleic acid. In some embodiments, a portion of the designed nucleic acid-targeting nucleic acid hybridizes to the double-stranded target nucleic acid, wherein the portion completely hybridizes to the double-stranded target nucleic acid. In some embodiments, a portion of the designed nucleic acid-targeting nucleic acid hybridizes to the double-stranded target nucleic acid, wherein the portion partially hybridizes to the double-stranded target nucleic acid. In some embodiments, the designed nucleic acid-targeting nucleic acid hybridizes to one strand of the double-stranded target nucleic acid. In some embodiments, the double-stranded target nucleic acid is DNA.

In one aspect, the disclosure provides for methods for cleaving a double-stranded target nucleic acid comprising: contacting at least one strand of the double-stranded target nucleic acid with a complex comprising: an Argonaute and a designed nucleic acid-targeting nucleic acid; and cleaving at least one strand of the double-stranded target nucleic acid. In some embodiments, the contacting occurs at a temperature from 20-60 degrees celsius. In some embodiments, the contacting occurs at a temperature from 40-60 degrees celsius. In some embodiments, the contacting occurs at a temperature from 20-40 degrees celsius. In some embodiments, the contacting occurs at 37 degrees celsius. In some embodiments, the cleaving comprises cleaving both strands of the double-stranded target nucleic acid. In some embodiments, the method is performed in vivo. In some embodiments, the method is performed in vitro. In some embodiments, the method is performed in situ. In some embodiments, the cleaving generates a cleaved double-stranded target nucleic acid. In some embodiments, wherein the cleaving generates a cleaved double-stranded target nucleic acid, the methods further comprise inserting a donor polynucleotide into the cleaved double-stranded target nucleic acid. In some embodiments, the cleaving generates sticky ends. In some embodiments, the cleaving generates blunt ends.

In one aspect, the disclosure provides for a composition comprising: a first complex comprising: a first Argonaute and a first designed nucleic acid-targeting nucleic acid; a second complex comprising: a second Argonaute and a second designed nucleic acid-targeting nucleic acid; and a double-stranded target nucleic acid, wherein the first and second designed nucleic acid-targeting nucleic acid are hybridized to the double-stranded target nucleic acid. In some embodiments, the first designed nucleic acid-targeting nucleic acid hybridizes to a region of a first strand of the double-stranded target nucleic acid. In some embodiments, the second designed nucleic acid-targeting nucleic acid hybridizes to a region of a second strand of the double-stranded target nucleic acid. In some embodiments, the first designed nucleic acid-targeting nucleic acid hybridizes to a region of a first strand of the double-stranded target nucleic acid and wherein the second designed nucleic acid-targeting nucleic acid hybridizes to a region of a second strand of the double-stranded target nucleic acid. In some embodiments, the first designed nucleic acid-targeting nucleic acid hybridizes to a region of a first strand of the double-stranded target nucleic acid and wherein the second designed nucleic acid-targeting nucleic acid hybridizes to a region of a second strand of the double-stranded target nucleic acid, wherein the region of the first strand and the region of the second strand are complementary. In some embodiments, the first designed nucleic acid-targeting nucleic acid hybridizes to a region of a first strand of the double-stranded target nucleic acid and wherein the second designed nucleic acid-targeting nucleic acid hybridizes to a region of a second strand of the double-stranded target nucleic acid, wherein a portion the region of the first strand and the region of the second strand are complementary. In some embodiments, the first designed nucleic acid-targeting nucleic acid hybridizes to a region of a first strand of the double-stranded target nucleic acid and wherein the second designed nucleic acid-targeting nucleic acid hybridizes to a region of a second strand of the double-stranded target nucleic acid, wherein the region of the first strand and the region of the second strand overlap. In some embodiments, the first designed nucleic acid-targeting nucleic acid hybridizes to a region of a first strand of the double-stranded target nucleic acid and wherein the second designed nucleic acid-targeting nucleic acid hybridizes to a region of a second strand of the double-stranded target nucleic acid, wherein a portion of the region of the first strand and the region of the second strand overlap. In some embodiments, the composition comprises: a first complex comprising: a first Argonaute and a first designed nucleic acid-targeting nucleic acid; a second complex comprising: a second Argonaute and a second designed nucleic acid-targeting nucleic acid; and a double-stranded target nucleic acid, wherein the first and second designed nucleic acid-targeting nucleic acid are hybridized to the double-stranded target nucleic acid, wherein the first and second designed nucleic acid-targeting nucleic acids are complementary. In some embodiments, a portion of the first and second designed nucleic acid-targeting nucleic acids are complementary. In some embodiments, the first and second Argonaute are the same Argonaute. In some embodiments, at least one of the first or second Argonaute comprises at least 30% amino acid identity to a prokaryotic Argonaute. In some embodiments, at least one of the first or second Argonaute comprises at least 30% amino acid identity to a bacterial Argonaute. In some embodiments, at least one of the first or second Argonaute comprises at least 30% amino acid identity to an archeal Argonaute. In some embodiments, at least one of the first or second Argonaute comprises at least 30% amino acid identity to an Argonaute from a species selected from the group consisting of: *Thermus thermophilus*, *Thermus thermophilus* JL-18, *Thermus thermophilus* strain HB27, *Aquifex aeolicus* strain VF5, *Pyrococcus furiosus*, *Archaeoglobus fulgidus*, *Anoxybacillus flavithermus*, *Halogeometricum borinquense*, *Microsystis aeruginosa*, *Clostridium bartlettii*, *Halorubrum lacusprofundi*, *Thermosynechococcus elongatus*, and *Synechococcus elongatus*, or any combination thereof. In some embodiments, at least one of the first or second Argonaute comprises at least 30% amino acid identity to an Argonaute from *T. thermophilus*. In some embodiments, a nuclease domain of at least one of the first or second Argonaute comprises at least 30% amino acid identity to a nuclease domain of Argonaute from *T. thermophilus*. In some embodiments, at least one of the first or second Argonaute comprises at least 30% amino acid identity to an Argonaute from *S. elongatus*. In some embodiments, a nuclease domain of at least one of the first or second Argonaute comprises at least 30% amino acid identity to a nuclease domain of Argonaute from *T. thermophilus*. In some embodiments, a nuclease domain of at least one of the first or second Argonaute comprises at least 30% amino acid identity to a nuclease domain of Argonaute from *S. elongatus*, wherein the nuclease domain is a PIWI domain. In some embodiments, a nuclease domain of at least one of the first or second Argonaute comprises at least 30% amino acid identity to a nuclease domain of Argonaute from *S. elongatus*, wherein the nuclease domain is a PIWI domain. In some embodiments, a MID domain of at least one of the first and second Argonaute comprises at least 30% amino acid to a MID domain of an Argonaute from *T. thermophilus*. In some embodiments, a PAZ domain of at least one of the first and second Argonaute comprises at least 30% amino acid to a PAZ domain of an Argonaute from *T. thermophilus*. In some embodiments, a MID domain of at least one of the first and second Argonaute comprises at least 30% amino acid to a MID domain of an Argonaute from *S. elongatus*. In some embodiments, a PAZ domain of at least one of the first and second Argonaute comprises at least 30% amino acid to a PAZ domain of an Argonaute from *S. elongatus*. In some embodiments, at least one of the first and second designed nucleic acid-targeting nucleic acids are single-stranded DNA. In some embodiments, at least one of the first and second designed nucleic acid-targeting nucleic acids are from 9-25 nucleotides in length. In some embodiments, the first and second designed nucleic acid-targeting nucleic acids differ by at least one nucleotide. In some embodiments, at least one of the first or second designed nucleic acid-targeting nucleic acids are 21 nucleotides in length. In some embodiments, at least one of the first or second designed nucleic acid-targeting nucleic acid comprise a 5' phosphorylated end. In some embodiments, at least one of the first or second designed nucleic acid-targeting nucleic acid comprises a deoxycytosine at its 5' end. In some embodiments, at least one of the first or second designed nucleic acid-targeting nucleic acid comprises a deoxycytosine-deoxyadenosine dinucleotide at its 5' end. In some embodiments, from 2-16 nucleotides of at least one of the first or second designed nucleic acid-targeting nucleic acid hybridize to the double-stranded target nucleic acid. In some embodiments, from 2-9 nucleotides of at least one of the first or second designed nucleic acid-targeting nucleic acid hybridize to the double-stranded target nucleic acid. In some embodiments, a portion of at least one of the first or second designed nucleic acid-targeting nucleic acid hybridizes to the double-stranded target nucleic acid. In some embodiments, a portion of at least one of the first or second designed nucleic acid-targeting nucleic acid hybridizes to the double-stranded target nucleic acid, wherein the portion completely hybridizes to the double-stranded target nucleic acid. In some embodiments, a portion of at least one of the first or second designed nucleic acid-targeting nucleic acid hybridizes to the double-stranded target nucleic acid, wherein the portion partially hybridizes to the double-stranded target nucleic acid. In some embodiments, the double-stranded target nucleic acid is DNA.

In one aspect, the disclosure provides for methods for cleaving a double-stranded target nucleic acid using comprising: contacting the double-stranded target nucleic acid with a first complex comprising: a first Argonaute and a first designed nucleic acid-targeting nucleic acid; and a second complex comprising: a second Argonaute and a second designed nucleic acid-targeting nucleic acid; and cleaving the double-stranded target nucleic acid. In some embodiments, the contacting comprises contacting the first designed nucleic acid-targeting nucleic acid to a region of a first strand of the double-stranded target nucleic acid. In some embodiments, the contacting comprises contacting the second designed nucleic acid-targeting nucleic acid to a region of a second strand of the double-stranded target nucleic acid. In some embodiments, the contacting comprises contacting the first designed nucleic acid-targeting nucleic acid to a region of a first strand of the double-stranded target nucleic acid and wherein the second designed nucleic acid-targeting nucleic acid to a region of a second strand of the double-stranded target nucleic acid. In some embodiments, the contacting comprises contacting the first designed nucleic acid-targeting nucleic acid to a region of a first strand of the double-stranded target nucleic acid and wherein the second designed nucleic acid-targeting nucleic acid to a region of a second strand of the double-stranded target nucleic acid, wherein the region of the first strand and the region of the second strand are complementary. In some embodiments, the contacting comprises contacting the first designed nucleic acid-targeting nucleic acid to a region of a first strand of the double-stranded target nucleic acid and wherein the second designed nucleic acid-targeting nucleic acid to a region of a second strand of the double-stranded target nucleic acid, wherein a portion the region of the first strand and the region of the second strand are complementary. In some embodiments, the contacting comprises contacting the first designed nucleic acid-targeting nucleic acid to a region of a first strand of the double-stranded target nucleic acid and wherein the second designed nucleic acid-targeting nucleic acid to a region of a second strand of the double-stranded target nucleic acid, wherein the region of the first strand and the region of the second strand overlap, wherein a portion the region of the first strand and the region of the second strand overlap. In some embodiments, the contacting comprises contacting the first complex with a first strand of the double-stranded target nucleic acid and contacting the second complexes with a second strand of the double-stranded target nucleic acid. In some embodiments, the cleaving generates a sticky end cut. In some embodiments, the the cleaving generates a blunt end cut. In some embodiments, the cleaving generates a cleaved double-stranded target nucleic acid. In some embodiments, wherein the cleaving generates a cleaved double-stranded target nucleic acid, the methods further comprise inserting a donor polynucleotide into the cleaved double-stranded target nucleic acid.

In one aspect, the disclosure provides for methods for producing a donor polynucleotide-tagged cell comprising: cleaving a target nucleic acid in a cell using a complex comprising an Argonaute and a designed nucleic acid-targeting nucleic acid; inserting a donor polynucleotide into a cleaved target nucleic acid; propagating the cell carrying the donor polynucleotide; and determining an origin of the donor-polynucleotide tagged cell. In some embodiments, the method is performed in vivo. In some embodiments, the method is performed in vitro. In some embodiments, the method is performed in situ. In some embodiments, the propagating produces a population of cells. In some embodiments, the propagating produces a cell line. In some embodiments, the methods further comprise determining a nucleic acid sequence of a nucleic acid in the cell. In some embodiments, the methods further comprise determining a nucleic acid sequence of a nucleic acid in the cell, wherein the nucleic acid sequence determines an origin of the cell. In some embodiments, the methods further comprise determining a nucleic acid sequence of a nucleic acid in the cell, wherein the determining comprises determining a genotype of the cell. In some embodiments, the propagating comprises differentiating the cell. In some embodiments, the propagating comprises de-differentiating the cell. In some embodiments, the propagating comprises differentiating the cell and then dedifferentiating the cell. In some embodiments, the propagating comprises passaging the cell. In some embodiments, the propagating comprises inducing the cell to divide. In some embodiments, the propagating comprises inducing the cell to enter the cell cycle. In some embodiments, the propagating comprises the cell forming a metastasis. In some embodiments, the propagating comprises differentiating a pluripotent cell into a differentiated cell. In some embodiments, the cell is a differentiated cell. In some embodiments, the cell is a de-differentiated cell. In some embodiments, the cell is a stem cell. In some embodiments, the cell is a pluripotent stem cell. In some embodiments, the cell is a eukaryotic cell line. In some embodiments, the cell is a primary cell line. In some embodiments, the cell is a patient-derived cell line. In some embodiments, the methods further comprise transplanting the cell into an organism. In some embodiments, the methods further comprise transplanting the cell into an organism, wherein the organism is a human. In some embodiments, the methods further comprise transplanting the cell into an organism, wherein the organism is a mammal. In some embodiments, the methods further comprise transplanting the cell into an organism, wherein the organism is selected from the group consisting of: a human, a dog, a rat, a mouse, a chicken, a fish, a cat, a plant, and a primate. In some embodiments, the methosd further comprise selecting the cell. In some embodiments, the donor polynucleotide is inserted into a target nucleic acid that is expressed in one cell state. In some embodiments, the donor polynucleotide is inserted into a target nucleic acid that is expressed in a plurality of cell types. In some embodiments, the donor polynucleotide is inserted into a target nucleic acid that is expressed in a pluripotent state. In some embodiments, the donor polynucleotide is inserted into a target nucleic acid that is expressed in a differentiated state.

In one aspect the disclosure provides for methods for making a clonally expanded cell line comprising: introducing into a cell a complex comprising: an Argonaute and a designed nucleic acid-targeting nucleic acid; contacting the complex to a target nucleic acid; cleaving the target nucleic acid, wherein the cleaving is performed by the complex, thereby producing a cleaved target nucleic acid; inserting a donor polynucleotide into the cleaved target nucleic acid; propagating the cell, wherein the propagating produces the clonally expanded cell line. In some embodiments, the cell is selected from the group consisting of: HeLa cell, Chinese Hamster Ovary cell, 293-T cell, a pheochromocytoma, a neuroblastomas fibroblast, a rhabdomyosarcoma, a dorsal root ganglion cell, a NSO cell, CV-I (ATCC CCL 70), COS-I (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C 1271 (ATCC CRL 1616), BS-C-I (ATCC CCL 26), MRC-5 (ATCC CCL 171), L-cells, HEK-293 (ATCC CRL1 573) and PC 12 (ATCC CRL-1721), HEK293T (ATCC CRL-11268), RBL (ATCC CRL-1378), SH-SY5Y (ATCC CRL-2266), MDCK (ATCC CCL-34), SJ-RH30 (ATCC CRL-2061), HepG2 (ATCC HB-8065), ND7/23 (ECACC 92090903), CHO (ECACC 85050302), Vera (ATCC CCL 81), Caco-2 (ATCC HTB 37), K562 (ATCCL CCL 243), Jurkat (ATCC TIB-152), Per.Có, Huvec (ATCC Human Primary PCS 100-010, Mouse CRL 2514, CRL 2515, CRL 2516), HuH-7D12 (ECACC 01042712), 293 (ATCC CRL 10852), A549 (ATCC CCL 185), IMR-90 (ATCC CCL 186), MCF-7 (ATC HTB-22), U-2 OS (ATCC HTB-96), and T84 (ATCC CCL 248), or any combination thereof. In some embodiments, the cell is stem cell. In some embodiments, the cell is a differentiated cell. In some embodiments, the cell is a pluripotent cell.

In one aspect the disclosure provides for methods for multiplex cell type analysis comprising: cleaving at least one target nucleic acid in two or more cells using a complex comprising an Argonaute and a designed nucleic acid-targeting nucleic acid, to create two cleaved target nucleic acids; inserting a different a donor polynucleotide into each of the cleaved target nucleic acids; and analyzing the two or more cells. In some embodiments, the analyzing comprises simultaneously analyzing the two or more cells. In some embodiments, the analyzing comprises determining a sequence of the target nucleic acid. In some embodiments, the analyzing comprises comparing the two or more cells. In some embodiments, the analyzing comprises determining a genotype of the two or more cells. In some embodiments, the cell is a differentiated cell. In some embodiments, the cell is a de-differentiated cell. In some embodiments, the cell is a stem cell. In some embodiments, the cell is a pluripotent stem cell. In some embodiments, the cell is a eukaryotic cell line. In some embodiments, the cell is a primary cell line. In some embodiments, the cell is a patient-derived cell line. In some embodiments, a plurality of donor polynucleotides are inserted into a plurality of cleaved target nucleic acids in the cell.

In one aspect the disclosure provides for compositions comprising: a designed nucleic acid-targeting nucleic acid comprising a 3' hybridizing extension; and a donor polynucleotide, wherein the donor polynucleotide is hybridized to the 3' hybridizing extension. In some embodiments, the 3' hybridizing extension is adapted to hybridize to at least 5 nucleotides from the 3' of the donor polynucleotide. In some embodiments, the 3' hybridizing extension is adapted to hybridize to at least 5 nucleotides from the 5' of the donor polynucleotide. In some embodiments, the 3' hybridizing extension is adapted to hybridize to at least 5 adjacent nucleotides in the donor polynucleotide. In some embodiments, the 3' hybridizing extension is adapted to hybridize to all of the donor polynucleotide. In some embodiments, the 3' hybridizing extension is configured to hybridize to an RNA. In some embodiments, the donor polynucleotide is DNA. In some embodiments, the 3' hybridizing extension is RNA. In some embodiments, the engineered designed nucleic acid-targeting nucleic acid is an isolated engineered designed nucleic acid-targeting nucleic acid. In some embodiments, the engineered designed nucleic acid-targeting nucleic acid is a recombinant engineered designed nucleic acid-targeting nucleic acid.

In one aspect the disclosure provides for methods for introducing a donor polynucleotide into a target nucleic acid comprising: contacting the target nucleic acid with the composition comprising: a designed nucleic acid-targeting nucleic acid comprising a 3' hybridizing extension; and a donor polynucleotide, wherein the donor polynucleotide is hybridized to the 3' hybridizing extension. In some embodiments, the method further comprises cleaving the target nucleic acid to produce a cleaved target nucleic acid. In some embodiments, the cleaving is performed by an Argonaute. In some embodiments, the method further comprises inserting the donor polynucleotide into the cleaved target nucleic acid.

Disclosed herein, in some embodiments, are compositions comprising: an effector protein; and a designed nucleic acid-targeting nucleic acid, comprising a non-native sequence, wherein the designed nucleic acid-targeting nucleic acid is adapted to bind to the effector protein. In some embodiments, the composition further comprises a polypeptide comprising at least 10% amino acid sequence identity to a nuclease domain of Argonaute from an organism selected from the group consisting of: *T. thermophilus* and *S. elongatus*, wherein the nucleic acid binds to the polypeptide. In some embodiments, the polypeptide comprises at least 60% amino acid sequence identity in a nuclease domain to a nuclease domain of Argonaute from an organism selected from the group consisting of: *T. thermophilus* and *S. elongatus*. In some embodiments, the polypeptide is Argonaute from an organism selected from the group consisting of: *T. thermophilus* and *S. elongatus*. In some embodiments, the non-native sequence is located at a position of the designed nucleic acid-targeting nucleic acid selected from the group consisting of: a 5' end and a 3' end, or any combination thereof In some embodiments, the non-native sequence comprises a DNA-binding protein binding sequence. In some embodiments, the non-native sequence comprises a DNA-binding protein binding sequence, wherein the DNA-binding protein binding sequence comprises a sequence selected from the group consisting of: a zinc finger binding sequence, a TALEN binding sequence, and a transcription factor binding sequence, or any combination thereof In some embodiments, the effector protein comprises a DNA-binding protein. In some embodiments, the effector protein comprises at least 15% amino acid sequence identity to a protein selected from the group consisting of: a zinc finger, a TALEN, and a transcription factor, or any combination thereof. In some embodiments, the effector protein further comprises one or more non-native sequences. In some embodiments, the effector protein further comprises one or more non-native sequences, wherein the non-native sequence confers an enzymatic activity to the effector protein. In some embodiments, the effector protein further comprises one or more non-native sequences, wherein the non-native sequence confers an enzymatic activity to the effector protein, wherein the enzymatic activity is selected from the group consisting of: methyltransferase activity, demethylase activity, acetylation activity, deacetylation activity, ubiquitination activity, deubiquitination activity, deamination activity, dismutase activity, alkylation activity, depurination activity, oxidation activity, pyrimidine dimer forming activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, and demyristoylation activity, or any combination thereof. In some embodiments, the designed nucleic acid-targeting nucleic acid is DNA. In some embodiments, the designed nucleic acid-targeting nucleic acid is an isolated nucleic acid. In some embodiments, the designed nucleic acid-targeting nucleic acid is a recombinant nucleic acid.

Disclosed herein, in some embodiments, are methods for introducing a donor polynucleotide into a target nucleic acid comprising: contacting a target nucleic acid with a complex comprising an Argonaute and the composition comprising an effector protein; and a designed nucleic acid-targeting nucleic acid, comprising a non-native sequence, wherein the designed nucleic acid-targeting nucleic acid is adapted to bind to the effector protein. In some embodiments, the method further comprises cleaving the target nucleic acid. In some embodiments, the method further comprises cleaving the target nucleic acid, wherein the cleaving is performed by the Argonaute. In some embodiments, the method further comprises inserting the donor polynucleotide into the target nucleic acid.

Disclosed herein, in some embodiments, are methods for modulating a target nucleic acid comprising: contacting a target nucleic acid with one or more complexes, each complex comprising an Argonaute and the composition comprising an effector protein; and a designed nucleic acid-targeting nucleic acid, comprising a non-native sequence, wherein the designed nucleic acid-targeting nucleic acid is adapted to bind to the effector protein; and modulating the target nucleic acid. In some embodiments, the Argonaute comprises at least 30% amino acid sequence identity to a nuclease domain of Argonaute from *T. thermophilus*. In some embodiments, the Argonaute comprises at least 30% amino acid sequence identity to a nuclease domain of Argonaute from *S. elongatus*. In some embodiments, the modulating is performed by the effector protein. In some embodiments, the modulating comprises an activity selected from the group consisting of: methyltransferase activity, demethylase activity, acetylation activity, deacetylation activity, ubiquitination activity, deubiquitination activity, deamination activity, dismutase activity, alkylation activity, depurination activity, oxidation activity, pyrimidine dimer forming activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, and demyristoylation activity, or any combination thereof. In some embodiments, the effector protein comprises one or more effector proteins. In some embodiments, the Argonaute comprises at least 50% reduced enzymatic activity compared to a wild-type Argonaute from *T. thermophilus*. In some embodiments, the Argonaute comprises at least 50% reduced enzymatic activity compared to a wild-type Argonaute from *S. elongatus*. In some embodiments, the Argonaute is enzymatically inactive.

Disclosed herein, in some embodiments, are methods for detecting if two complexes are in proximity to one another comprising: contacting a first target nucleic acid with a first complex, wherein the first complex comprises a first Argonaute, a first designed nucleic acid-targeting nucleic acid, and a first effector protein, wherein the effector protein is adapted to bind to the designed nucleic acid-targeting nucleic acid, and wherein the first effector protein comprises a non-native sequence that comprises a first portion of a split system; and contacting a second target nucleic acid with a second complex, wherein the second complex comprises a second Argonaute, a second designed nucleic acid-targeting nucleic acid, and a second effector protein, wherein the effector protein is adapted to bind to the designed nucleic acid-targeting nucleic acid, and wherein the second effector protein comprises a non-native sequence that comprises a second portion of a split system. In some embodiments, the first target nucleic acid and the second target nucleic acid are on the same polynucleotide polymer. In some embodiments, the split system comprises two or more protein fragments that individually are not active, but, when formed into a complex, result in an active protein complex. In some embodiments, the methods further comprise detecting an interaction between the first portion and the second portion. In some embodiments, the methods further comprise detecting an interaction between the first portion and the second portion, wherein the detecting indicates the first and second complex are in proximity to one another. In some embodiments, at least one of the first and second Argonaute is adapted to be unable to cleave the target nucleic acid. In some embodiments, the methods further comprise detecting an interaction between the first portion and the second portion, wherein the detecting comprises determining the occurrence of a genetic mobility event. In some embodiments, the methods further comprise detecting an interaction between the first portion and the second portion, wherein the detecting comprises determining the occurrence of a genetic mobility event, wherein the genetic mobility event comprises a translocation. In some embodiments, the methods further comprise detecting an interaction between the first portion and the second portion, wherein the detecting comprises determining the occurrence of a genetic mobility event, wherein prior to the genetic mobility event the two portions of the split system do not interact. In some embodiments, the methods further comprise detecting an interaction between the first portion and the second portion, wherein the detecting comprises determining the occurrence of a genetic mobility event, wherein after the genetic mobility event the two portions of the split system do interact. In some embodiments, the methods further comprise detecting an interaction between the first portion and the second portion, wherein the detecting comprises determining the occurrence of a genetic mobility event, wherein the genetic mobility event is a translocation between a BCR and an Abl gene. In some embodiments, the methods further comprise detecting an interaction between the first portion and the second portion, wherein the detecting comprises determining the occurrence of a genetic mobility event, wherein the interaction activates the split system. In some embodiments, the methods further comprise detecting an interaction between the first portion and the second portion, wherein the detecting comprises determining the occurrence of a genetic mobility event, wherein the interaction indicates the target nucleic acids bound by the complexes are close together. In some embodiments, the split system is selected from the group consisting of: split GFP system, a split ubiquitin system, a split transcription factor system, and a split affinity tag system, or any combination thereof. In some embodiments, the split system comprises a split GFP system. In some embodiments, the methods further comprise detecting an interaction between the first portion and the second portion, wherein the detecting comprises determining the occurrence of a genetic mobility event, wherein the detecting indicates a genotype. In some embodiments, the methods further comprise detecting an interaction between the first portion and the second portion, wherein the detecting comprises determining the occurrence of a genetic mobility event, wherein the detecting indicates a genotype, further comprising: determining a course of treatment for a disease based on the genotype. In some embodiments, the methods further comprise detecting an interaction between the first portion and the second portion, wherein the detecting comprises determining the occurrence of a genetic mobility event, wherein the detecting indicates a genotype, further comprising: determining a course of treatment for a disease based on the genotype, further comprising treating the disease. In some embodiments, treating the disease comprises administering a drug. In some embodiments, treating comprises administering a complex comprising a designed nucleic acid-targeting nucleic acid and an Argonaute and modifying a genetic element involved in the disease, wherein the modifying is performed by the complex. In some embodiments, modifying is selected from the group consisting of: adding a nucleic acid sequence to the genetic element, substituting a nucleic acid sequence in the genetic element, and deleting a nucleic acid sequence from the genetic element, or any combination thereof. In some embodiments, the methods further comprise communicating the genotype from a caregiver to a patient. In some embodiments, the communicating comprises communicating from a storage memory system to a remote computer. In some embodiments, the detecting diagnoses a disease. In some embodiments, the method further comprises communicating the diagnosis from a caregiver to a patient. In some embodiments, the detecting indicates the presence of a single nucleotide polymorphism (SNP). In some embodiments, the method further comprises: communicating the occurrence of a genetic mobility event from a caregiver to a patient. In some embodiments, communicating comprises communicating from a storage memory system to a remote computer. In some embodiments, at least one of the first or second Argonaute comprises at least 20% amino acid sequence identity to Argonaute from *T. thermophilus*. In some embodiments, at least one of the first or second Argonaute comprises at least 60% amino acid sequence identity to Argonaute from *T. thermophilus*. In some embodiments, at least one of the first or second Argonaute comprises at least 20% amino acid sequence identity to Argonaute from *S. elongatus*. In some embodiments, at least one of the first or second Argonaute comprises at least 60% amino acid sequence identity to Argonaute from *S. elongatus*. In some embodiments, at least one of the first or second Argonaute comprises at least 60% amino acid sequence identity in a nuclease domain to a nuclease domain of Argonaute from *T. thermophilus*. In some embodiments, at least one of the first or second Argonaute is Argonaute from *T. thermophilus*. In some embodiments, at least one of the first or second Argonaute comprises at least 50% reduced enzymatic activity compared to a wild-type Argonaute from *T. thermophilus*. In some embodiments, at least one of the first or second Argonaute comprises at least 50% reduced enzymatic activity compared to a wild-type Argonaute from *S. elongatus*. In some embodiments, at least one of the first or second Argonaute is enzymatically inactive. In some embodiments, the designed nucleic acid-targeting nucleic acid comprises a non-native sequence. In some embodiments, the non-native sequence is located at a position of the designed nucleic acid-targeting nucleic acid selected from the group consisting of: a 5' end, and a 3' end, or any combination thereof In some embodiments, the non-native sequence comprises a binding sequence selected from the group consisting of: a zinc finger-binding sequence, a TALEN-binding sequence, and a transcription factor-binding sequence, or any combination thereof. In some embodiments, the designed nucleic acid-targeting nucleic acid is adapted to bind to an effector protein. In some embodiments, the effector protein is a DNA-binding protein. In some embodiments, the effector protein comprises at least 15% amino acid sequence identity to a protein selected from the group consisting of: zinc finger protein, TALEN protein, and transcription factor, or any combination thereof. In some embodiments, the designed nucleic acid-targeting nucleic acid is DNA. In some embodiments, the target nucleic acid is DNA. In some embodiments, the interaction comprises forming an affinity tag. In some embodiments, the detecting comprises capturing the affinity tag. In some embodiments, the methods further comprise sequencing a nucleic acid bound to the first and second complexes. In some embodiments, the methods further comprise fragmenting the nucleic acid prior to the capturing. In some embodiments, wherein the methods comprise detecting an interaction between the first portion and the second portion, the interaction forms an activated system. In some embodiments, the methods further comprise altering transcription of a first target nucleic acid or a second target nucleic acid, wherein the altering is performed by the activated system. In some embodiments, the second target nucleic acid is unattached to the first target nucleic acid. In some embodiments, the altering transcription of the second target nucleic acid is performed in trans. In some embodiments, the altering transcription of the first target nucleic acid is performed in cis. In some embodiments, the first or second target nucleic acid is selected from the group consisting of: an endogenous nucleic acid, and an exogenous nucleic acid, or any combination thereof In some embodiments, the altering comprises increasing transcription of the first or second target nucleic acids. In some embodiments, the first or second target nucleic acid comprises a polynucleotide encoding one or more genes that cause cell death. In some embodiments, the first or second target nucleic acid comprises a polynucleotide encoding a cell-lysis inducing peptide. In some embodiments, the first or second target nucleic acid comprises a polynucleotide encoding an immune-cell recruiting antigen. In some embodiments, the first or second target nucleic acid comprises a polynucleotide encoding one or more genes involved in apoptosis. In some embodiments, the one or more genes involved in apoptosis comprises caspases. In some embodiments, the one or more genes involved in apoptosis comprises cytokines. In some embodiments, the one or more genes involved in apoptosis are selected from the group consisting of: tumor necrosis factor (TNF), TNF receptor 1 (TNFR1), TNF receptor 2 (TNFR2), Fas receptor, FasL, caspase-8, caspase-10, caspase-3, caspase-9, caspase-3, caspase-6, caspase-7, Bcl-2, and apoptosis inducing factor (AIF), or any combination thereof. In some embodiments, the first or second target nucleic acid comprises a polynucleotide encoding one or more designed nucleic acid-targeting nucleic acids. In some embodiments, the one or more designed nucleic acid-targeting nucleic acids target a plurality of target nucleic acids. In some embodiments, the detecting comprises generating genetic data. In some embodiments, the methods further comprise communicating the genetic data from a storage memory system to a remote computer. In some embodiments, the genetic data indicates a genotype. In some embodiments, the genetic data indicates the occurrence of a genetic mobility event. In some embodiments, the genetic data indicates a spatial location of genes.

Disclosed herein, in some embodiments, are kits comprising: an Argonaute; a designed nucleic acid-targeting nucleic acid, wherein the designed nucleic acid-targeting nucleic acid comprises a non-native sequence; an effector protein that is adapted to bind to the non-native sequence; and a buffer. In some embodiments, the kits further comprise instructions for use.

Disclosed herein, in some embodiments, are vectors comprising a polynucleotide sequence encoding a designed nucleic acid-targeting nucleic acid, wherein the designed nucleic acid-targeting nucleic acid comprises a non-native sequence. In some embodiments, the polynucleotide sequence is operably linked to a promoter. In some embodiments, the promoter is an inducible promoter.

Disclosed herein, in some embodiments, are vectors comprising: a polynucleotide sequence encoding: a designed nucleic acid-targeting nucleic acid, wherein the designed nucleic acid-targeting nucleic acid comprises a sequence configured to bind to an effector protein; and an Argonaute. In some embodiments, the polynucleotide sequence is operably linked to a promoter. In some embodiments, the promoter is an inducible promoter.

Disclosed herein, in some embodiments, are vectors comprising: a polynucleotide sequence encoding: a designed nucleic acid-targeting nucleic acid, wherein the designed nucleic acid-targeting nucleic acid comprises a non-native sequence; an Argonaute; and an effector protein. In some embodiments, the polynucleotide sequence is operably linked to a promoter. In some embodiments, the promoter is an inducible promoter.

Disclosed herein, in some embodiments, are genetically modified cells comprising the composition comprising an effector protein; and a designed nucleic acid-targeting nucleic acid, comprising a non-native sequence, wherein the designed nucleic acid-targeting nucleic acid is adapted to bind to the effector protein.

Disclosed herein, in some embodiments, are genetically modified cells comprising the vector comprising a polynucleotide sequence encoding a designed nucleic acid-targeting nucleic acid, wherein the designed nucleic acid-targeting nucleic acid comprises a non-native sequence.

Disclosed herein, in some embodiments, are genetically modified cells comprising the vector comprising: a polynucleotide sequence encoding: a designed nucleic acid-targeting nucleic acid, wherein the designed nucleic acid-targeting nucleic acid comprises a sequence configured to bind to an effector protein; and an Argonaute.

Disclosed herein, in some embodiments, are genetically modified cells comprising the vector comprising: a polynucleotide sequence encoding: a designed nucleic acid-targeting nucleic acid, wherein the designed nucleic acid-targeting nucleic acid comprises a non-native sequence; an Argonaute; and an effector protein.

Disclosed herein, in some embodiments, are kits comprising: the vector comprising a polynucleotide sequence encoding a designed nucleic acid-targeting nucleic acid, wherein the designed nucleic acid-targeting nucleic acid comprises a non-native sequence; and a buffer. In some embodiments, the kits further comprise instructions for use.

Disclosed herein, in some embodiments, are kits comprising; the vector comprising: a polynucleotide sequence encoding: a designed nucleic acid-targeting nucleic acid, wherein the designed nucleic acid-targeting nucleic acid comprises a sequence configured to bind to an effector protein; and an Argonaute; and a buffer. In some embodiments, the kits further comprise instructions for use.

Disclosed herein, in some embodiments, are kits comprising: the vector comprising: a polynucleotide sequence encoding: a designed nucleic acid-targeting nucleic acid, wherein the designed nucleic acid-targeting nucleic acid comprises a non-native sequence; an Argonaute; and an effector protein; and a buffer. In some embodiments, the kits further comprise instructions for use.

Disclosed herein, in some embodiments, are compositions comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid. In some embodiments, the one or more nucleic acid modules hybridize to one or more target nucleic acids. In some embodiments, the one or more nucleic acid modules differ by at least one nucleotide in a spacer region of the one or more nucleic acid modules. In some embodiments, the one or more nucleic acid modules is DNA. In some embodiments, the multiplexed genetic targeting agent is DNA. In some embodiments, the non-native sequence comprises a nuclease binding sequence. In some embodiments, the the nuclease binding sequence is located at a 5' end of the nucleic acid module. In some embodiments, the the nuclease binding sequence is located at a 3' end of the nucleic acid module. In some embodiments, the nuclease binding sequence is adapted to be bound by a restriction endonuclease. In some embodiments, the the one or more nucleic acid modules are adapted to he bound by different nucleases. In some embodiments, the multiplexed genetic target agent is an isolated multiplexed genetic targeting agent. In some embodiments, the multiplexed genetic target agent is a recombinant multiplexed genetic target agent.

Disclosed herein, in some embodiments, are vectors comprising a polynucleotide sequence encoding the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid. In some embodiments, the polynucleotide sequence is operably linked to a promoter. In some embodiments, the promoter is an inducible promoter.

Disclosed herein, in some embodiments, are genetically modified cell comprising the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid.

Disclosed herein, in some embodiments, are genetically modified cells comprising the vector comprising a polynucleotide sequence encoding the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid.

Disclosed herein, in some embodiments, are kits comprising: the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid; and a buffer. In some embodiments, the kits further comprise instructions for use.

Disclosed herein, in some embodiments, are kits comprising: the vector comprising a polynucleotide sequence encoding the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acids, and a buffer. In some embodiments, the kits further comprise instructions for use.

Disclosed herein, in some embodiments, are methods for generating a nucleic acid, wherein the nucleic acid binds to a polypeptide comprising at least 30% amino acid sequence identity to a nuclease domain of Argonaute and hybridizes to a target nucleic acid comprising: introducing the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid, into a host cell; processing the multiplexed genetic targeting agent into the one or more nucleic acid modules; and contacting the processed one or more nucleic acid modules to one or more target nucleic acids in the cell. In some embodiments, the methods further comprise cleaving the target nucleic acid. In some embodiments, the methods further comprise modifying the target nucleic acid. In some embodiments, the modifying comprises altering transcription of the target nucleic acid. In some embodiments, the modifying comprises inserting a donor polynucleotide into the target nucleic acid.

Disclosed herein, in some embodiments, are modified Argonautes comprising: a modified MID domain.

Disclosed herein, in some embodiments, are kits comprising the modified Argonaute comprising: the modified MID domain.

Disclosed herein, in some embodiments, are vectors comprising: a polynucleotide encoding for the modified Argonaute comprising: the modified MID domain.

Disclosed herein, in some embodiments, are genetically modified organisms comprising the modified Argonaute comprising: the modified MID domain.

Disclosed herein, in some embodiments, are modified Argonautes comprising: a modified PAZ domain.

Disclosed herein, in some embodiments, are kit comprising the modified Argonautes comprising: the modified PAZ domain.

Disclosed herein, in some embodiments, are vectors comprising: a polynucleotide encoding for the modified Argonaute comprising: the modified PAZ domain.

Disclosed herein, in some embodiments, are genetically modified organisms comprising the modified Argonaute comprising: the modified PAZ domain.

Disclosed herein, in some embodiments, are modified Argonautes comprising: a modification configured to enable the Argonaute to retain activity at 37 degrees celsius.

Disclosed herein, in some embodiments, are kits comprising the modified Argonaute comprising: the modification configured to enable the Argonaute to retain activity at 37 degrees celsius.

Disclosed herein, in some embodiments, are vector comprising: a polynucleotide encoding for the modified Argonaute comprising: the modification configured to enable the Argonaute to retain activity at 37 degrees celsius.

Disclosed herein, in some embodiments, are genetically modified organism comprising the modified Argonaute comprising: the modification configured to enable the Argonaute to retain activity at 37 degrees celsius.

Disclosed herein, in some embodiments, are modified Argonautes comprising: a first nuclease domain, and an inserted nuclease domain. In some embodiments, the Argonaute comprises at least 30% identity to a nuclease domain of Argonaute from *T. thermophilus*. In some embodiments, the Argonaute comprises at least 30% identity to a nuclease domain of Argonaute from *S. elongatus*. In some embodiments, the first nuclease domain comprises PIWI domain. In some embodiments, the second nuclease domain comprises a nuclease domain selected from the group consisting of: a HNH domain, and a RuvC domain, or any combination thereof. In some embodiments, the inserted nuclease domain comprises a HNH domain. In some embodiments, the inserted nuclease domain comprises a RuvC domain. In some embodiments, the inserted nuclease domain is N-terminal to the first nuclease domain. In some embodiments, the inserted nuclease domain is C-terminal to the first nuclease domain. In some embodiments, the inserted nuclease domain is in tandem to the first nuclease domain. In some embodiments, the inserted nuclease domain is adapted to cleave a target nucleic acid at a site different than the first nuclease domain. In some embodiments, the inserted nuclease domain is adapted to cleave an RNA in a DNA-RNA hybrid. In some embodiments, the inserted nuclease domain is adapted to cleave a DNA in a DNA-RNA hybrid. In some embodiments, the inserted nuclease domain is adapted to increase specificity of binding of the modified Argonaute to a target nucleic acid. In some embodiments, the inserted nuclease domain is adapted to increase strength of binding of the modified Argonaute to a target nucleic acid.

Disclosed herein, in some embodiments, are vectors comprising a polynucleotide sequence encoding the modified Argonaute comprising: the first nuclease domain, and the inserted nuclease domain.

Disclosed herein, in some embodiments, are kits comprising: the modified Argonaute comprising: the first nuclease domain, and the inserted nuclease domain; and a buffer. In some embodiments, the kits further comprise instructions for use.

Disclosed herein, in some embodiments, are compositions comprising: a modified Argonaute, wherein the polypeptide is modified such that it is adapted to bind a second designed nucleic acid-targeting nucleic acid compared to a wild-type Argonaute. In some embodiments, the Argonaute is modified by a modification selected from the group consisting of: an amino acid addition, an amino acid substitution, an amino acid replacement, and an amino acid deletion, or any combination thereof. In some embodiments, the modified Argonaute comprises a non-native sequence. In some embodiments, the modified Argonaute is adapted to bind the second designed nucleic acid-targeting nucleic acid with greater specificity than the wild-type Argonaute. In some embodiments, the modified Argonaute is adapted to bind the second designed nucleic acid-targeting nucleic acid with a lower dissociation constant compared to the wild-type Argonaute. In some embodiments, the modified Argonaute is adapted to bind the second designed nucleic acid-targeting nucleic acid with a higher dissociation constant compared to the wild-type Argonaute.

Disclosed herein, in some embodiments, are vectors comprising: a polynucleotide sequence encoding the composition comprising: a modified Argonaute, wherein the polypeptide is modified such that it is adapted to bind a second designed nucleic acid-targeting nucleic acid compared to a wild-type Argonaute.

Disclosed herein, in some embodiments, are kits comprising: the composition comprising: a modified Argonaute, wherein the polypeptide is modified such that it is adapted to bind a second designed nucleic acid-targeting nucleic acid compared to a wild-type Argonaute; and a buffer. In some embodiments, the kits further comprise instructions for use.

Disclosed herein, in some embodiments, are compositions comprising: a modified Argonaute comprising a modified nuclease domain as compared to Argonaute from an organism selected from the group consisting of: *T. thermophilus* and *S. elongatus*. In some embodiments, the composition is configured to cleave a target nucleic acid. In some embodiments, the modified nuclease domain comprises a PIWI domain nuclease domain. In some embodiments, the modified nuclease domain is adapted to increase specificity of the amino acid sequence for a target nucleic acid compared to an unmodified Argonaute. In some embodiments, the modified nuclease domain is adapted to increase specificity of the amino acid sequence for a designed nucleic acid-targeting nucleic acid compared to an unmodified Argonaute. In some embodiments, the modified nuclease domain comprises a modification selected from the group consisting of: an amino acid addition, an amino acid substitution, an amino acid replacement, and an amino acid deletion, or any combination thereof. In some embodiments, the modified nuclease domain comprises an inserted non-native sequence. In some embodiments, the non-native sequence confers an enzymatic activity to the modified Argonaute. In some embodiments, the enzymatic activity is selected from the group consisting of: nuclease activity, methylase activity, acetylase activity, demethylase activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, and demyristoylation activity, or any combination thereof In some embodiments, the enzymatic activity is adapted to modulate transcription of a target nucleic acid. In some embodiments, the modified nuclease domain is adapted to allow binding of the Argonaute to a designed nucleic acid-targeting nucleic acid that is different from a designed nucleic acid-targeting nucleic acid to which an unmodified Argonaute is adapted to bind. In some embodiments, the modified Argonaute is adapted to bind to a longer target nucleic acid sequence than an unmodified Argonaute. In some embodiments, the modified Argonaute is adapted to cleave double-stranded DNA. In some embodiments, the modified Argonaute is adapted to cleave the RNA strand of a hybridized RNA and DNA. In some embodiments, the modified Argonaute is adapted to cleave cleave the DNA strand of a hybridized RNA and DNA. In some embodiments, the composition further comprises a designed nucleic acid-targeting nucleic acid, wherein the modification of the Argonaute is adapted to enable the Argonaute to bind to the modified designed nucleic acid-targeting nucleic acid. In some embodiments, the designed nucleic acid-targeting nucleic acid and the modified Argonaute comprise compensatory mutations.

Disclosed herein, in some embodiments, are vectors comprising a polynucleotide encoding the composition comprising: a modified Argonaute comprising a modified nuclease domain as compared to Argonaute from an organism selected from the group consisting of: *T. thermophilus* and *S. elongatus*.

Disclosed herein, in some embodiments, are methods for enriching a target nucleic acid for sequencing comprising: contacting a target nucleic acid with a complex comprising a designed nucleic acid-targeting nucleic acid and an Argonaute; enriching the target nucleic acid using the complex; and determining a sequence of the target nucleic acid. In some embodiments, the method does not comprise an amplification step. In some embodiments, the methods further comprise analyzing the sequence of the target nucleic acid. In some embodiments, the methods further comprise fragmenting the target nucleic acid prior to the enriching. In some embodiments, the designed nucleic acid-targeting nucleic acid comprises DNA. In some embodiments, the contacting comprises hybridizing a portion of the designed nucleic acid-targeting nucleic acid with a portion of the target nucleic acid. In some embodiments, the designed nucleic acid-targeting nucleic acid hybridizes with the target nucleic acid over a region comprising 6-20 nucleotides. In some embodiments, wherein the Argonaute comprises Argonaute from *T. thermophilus*. In some embodiments, the Argonaute comprises at least 20% homology to a nuclease domain of Argonaute from *T. thermophilus*. In some embodiments, the Argonaute comprises at least 60% homology to Argonaute from *T. thermophilus*. In some embodiments, the Argonaute comprises Argonaute from *S. elongatus*. In some embodiments, the Argonaute comprises at least 20% homology to a nuclease domain of Argonaute from *S. elongatus*. In some embodiments, the Argonaute comprises at least 60% homology to Argonaute from *S. elongatus*. In some embodiments, the Argonaute comprises an engineered nuclease domain wherein the nuclease domain comprises reduced nuclease activity compared to an Argonaute that comprises an unengineered nuclease domain. In some embodiments, the Argonaute introduces a single-strand break in the target nucleic acid. In some-embodiments, the Argonaute comprises an affinity tag. In some embodiments, the affinity tag is located at the N-terminus of the Argonaute. the C-terminus of the Argonaute, a surface-accessible region, or any combination thereof. In some embodiments, the affinity tag is selected from a group comprising: biotin, FLAG, His6x,(SEQ ID NO: 23), His9x (SEQ ID NO: 24), and a fluorescent protein, or any combination there of In some embodiments, the designed nucleic acid-targeting nucleic acid comprises a nucleic acid affinity tag. In some embodiments, nucleic acid affinity tag is located at the 5' end of the designed nucleic acid-targeting nucleic acid, the 3' end of the designed nucleic acid-targeting nucleic acid, a surface-accessible region, or any combination thereof. In some embodiments, the nucleic acid affinity tag is selected from the group comprising a small molecule, fluorescent label, a radioactive label, or any combination thereof. In some embodiments, the methods further comprise diagnosing a disease and making a patient-specific treatment decision, or any combination thereof. In some embodiments, the determining comprises determining a genotype. In some embodiments, the methods further comprise communicating the sequence from a storage memory system to a remote computer. In some embodiments, the enriching comprises contacting an affinity tag of the complex with a capture agent. In some embodiments, the capture agent comprises an antibody, in some embodiments, the capture agent comprises a solid support. In some embodiments, the capture agent comprises an affinity tag. In some embodiments, the target nucleic acid is bound to the complex. In some embodiments, the target nucleic acid is an excised nucleic acid that is not bound to the complex. In some embodiments, a plurality of complexes are contacted to a plurality of target nucleic acids. In some embodiments, the plurality of target nucleic acids differ by at least one nucleotide. In some embodiments, the plurality of complexes comprise a plurality of designed nucleic acid-targeting nucleic acids that differ by at least one nucleotide.

Disclosed herein, in some embodiments, are methods for excising a nucleic acid comprising: contacting a target nucleic acid with two or more complexes, wherein each complex comprises an Argonaute and a designed nucleic acid-targeting nucleic acid; and cleaving the target nucleic acid, wherein the cleaving produces an excised target nucleic acid. In some embodiments, the cleaving is performed by a nuclease domain of the Argonaute. In some embodiments, the methods do not comprise amplification. In some embodiments, the methods further comprise enriching the excised target nucleic acid. In some embodiments, the methods further comprise sequencing the excised target nucleic acid. In some embodiments, the designed nucleic acid-targeting nucleic acid is DNA. In some embodiments, the designed nucleic acid-targeting nucleic acid hybridizes with a target nucleic acid. In some embodiments, the designed nucleic acid-targeting nucleic acid hybridizes with a target nucleic acid over a region, wherein the region comprises at least 6 nucleotides and at most 20 nucleotides. In some embodiments, the Argonaute is Argonaute from *T. thermophilus*. In some embodiments, the Argonaute comprises a polypeptide comprising at least 20% homology to a nuclease domain of Argonaute from *T. thermophilus*. In some embodiments, the Argonaute comprises a polypeptide comprising at least 60% homology to Argonaute from *T. thermophilus*. In some embodiments, the Argonaute is Argonaute from *S. elongatus*. In some embodiments, the Argonaute comprises a polypeptide comprising at least 20% homology to a nuclease domain of Argonaute from *S. elongatus*. In some embodiments, the Argonaute comprises a polypeptide comprising at least 60% homology to Argonaute from *S. elongatus*. In some embodiments, the Argonaute comprises an affinity tag. In some embodiments, the affinity tag is located at the N-terminus of the Argonaute, the C-terminus of the Argonaute, a surface-accessible region, or any combination thereof. In some embodiments, the affinity tag is selected from a group comprising: biotin, FLAG, His6x (SEQ ID NO: 23), His9x (SEQ ID NO: 24), and a fluorescent protein. or any combination thereof. In some embodiments, the designed nucleic acid-targeting nucleic acid comprises a nucleic acid affinity tag. In some embodiments, the nucleic acid affinity tag is located at the 5' end of the designed nucleic acid-targeting nucleic acid, the 3' end of the designed nucleic acid-targeting nucleic acid, a surface-accessible region, or any combination thereof. In some embodiments, the nucleic acid affinity tag is selected from the group comprising a small molecule, fluorescent label, a radioactive label, or any combination thereof. In some embodiments, the target nucleic acid is an excised nucleic acid that is not bound to the two or more complexes. In some embodiments, the two or more complexes are contacted to a plurality of target nucleic acids. In some embodiments, the plurality of target nucleic acids differ by at least one nucleotide. In some embodiments, two or more complexes comprise designed nucleic acid-targeting nucleic acids that differ by at least one nucleotide.

Disclosed herein, in some embodiments, are methods for generating a library of target nucleic acids comprising: contacting a plurality of target nucleic acids with a complex comprising an Argonaute and a designed nucleic acid-targeting nucleic acid; cleaving the plurality of target nucleic acids; and purifying the plurality of target nucleic acids to create the library of target nucleic acids. In some embodiments, the methods further comprise screening the library of target nucleic acids.

Disclosed herein, in some embodiments, are vectors comprising a polynucleotide sequence encoding: two or more designed nucleic acid-targeting nucleic acids that differ by at least one nucleotide; and an Argonaute.

Disclosed herein, in some embodiments, are genetically modified host cell comprising: the vector comprising a polynucleotide sequence encoding: two or more designed nucleic acid-targeting nucleic acids that differ by at least one nucleotide; and an Argonaute.

Disclosed herein, in some embodiments, are kits comprising: the vector comprising a polynucleotide sequence encoding: two or more designed nucleic acid-targeting nucleic acids that differ by at least one nucleotide; and an Argonaute; and a suitable buffer. In some embodiments, the kits further comprise: a capture agent, a solid support, sequencing adaptors, and a positive control, or any combination thereof. In some embodiments, the kits further comprise instructions for use.

Disclosed herein, in some embodiments, are kits comprising: an Argonaute comprising reduced enzymatic activity compared to a wild-type Argonaute; a designed nucleic acid-targeting nucleic acid; and a capture agent. In some embodiments, the kits further comprise instructions for use. In some embodiments, the kits further comprise a buffer selected from the group comprising: a wash buffer, a stabilization buffer, a reconstituting buffer, or a diluting buffer.

Disclosed herein, in some embodiments, are compositions comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site. In some embodiments, the one or more of the plurality of nucleic acid-binding proteins comprise a non-native sequence. In some embodiments, the non-native sequence is located at a position selected from the group consisting of: the N-terminus, the C-terminus, a surface accessible region, or any combination thereof. In some embodiments, the non-native sequence encodes for a nuclear localization signal. In some embodiments, the plurality of nucleic acid-binding proteins are separated by a linker. In some embodiments, some of the plurality of nucleic acid-binding proteins are the same nucleic acid-binding protein. In some embodiments, all of the plurality of nucleic acid-binding proteins are the same nucleic acid-binding protein. In some embodiments, the plurality of nucleic acid-binding proteins are different nucleic acid-binding proteins. In some embodiments, the plurality of nucleic acid-binding proteins comprise DNA-binding proteins. In some embodiments, the DNA-binding proteins are selected from the group consisting of: a zinc finger, a TALEN, and a transcription factor, or any combination thereof. In some embodiments, some of the plurality of nucleic acid molecules comprise the same nucleic acid-binding protein binding site. In some embodiments, all of the plurality of nucleic acid molecules comprise the same nucleic acid-binding protein binding site. In some embodiments, none of the plurality of nucleic acid molecules comprise the same nucleic acid-binding protein binding site. In some embodiments, the Argonaute comprises at least 30% sequence identity to a nuclease domain of Argonaute from *T. thermophilus*. In some embodiments, the Argonaute is Argonaute from *T. thermophilus*. In some embodiments, the Argonaute comprises at least 30% sequence identity to a nuclease domain of Argonaute from *S. elongatus*. In some embodiments, the Argonaute is Argonaute from *S. elongatus*. In some embodiments, at least one of the nucleic acid molecules encodes for a nuclease. In some embodiments, the the nuclease is a restriction endonuclease. In some embodiments, the plurality of nucleic acid-binding proteins comprise reduced enzymatic activity. In some embodiments, the plurality of nucleic acid-binding proteins are adapted to bind to the nucleic acid-binding protein binding site but cannot cleave the nucleic acid-binding protein binding site. In some embodiments, the designed nucleic acid-targeting nucleic acid comprises from 9-25 nucleotides in length. In some embodiments, the designed nucleic acid-targeting nucleic acid comprises 21 nucleotides in length. In some embodiments, the designed nucleic acid-targeting nucleic acid comprises a deoxycytosine at its 5' end. In some embodiments, the designed nucleic acid-targeting nucleic acid comprises a deoxycytosine-deoxyadenosine dinucleotide at its 5' end. In some embodiments, the composition is configured to be delivered to a cell. In some embodiments, the composition is configured to deliver equal amounts of the plurality of nucleic acid molecules to a cell. In some embodiments, the compositions further comprise a donor polynucleotide molecule, wherein the donor polynucleotide molecule comprises a nucleic acid-binding protein binding site, wherein the binding site is bound by a nucleic acid-binding protein of the fusion polypeptide.

Disclosed herein, in some embodiments, are methods for delivery of nucleic acids to a subcellular location in a cell comprising: introducing into a cell the composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site; stoichiometrically delivering the composition to the subcellular location; forming a unit comprising an Argonaute translated from the nucleic acid molecule encoding for an Argonaute and the designed nucleic acid-targeting nucleic acid; and cleaving a target nucleic acid, wherein the Argonaute of the unit cleaves the target nucleic acid. In some embodiments, the plurality of nucleic acid-binding proteins bind to their cognate nucleic acid-binding protein binding site. In some embodiments, a nuclease cleaves one of the one or more nucleic acid-binding protein binding sites. In some embodiments, a nuclease cleaves the nucleic acid-binding protein binding sites of the nucleic acid encoding the designed nucleic acid-targeting nucleic acid, thereby liberating the designed nucleic acid-targeting nucleic acid. In some embodiments, the subcellular location is selected from the group consisting of: the nuclease, the ER, the golgi, the mitochondria, the cell wall, the lysosome, and the nucleus. In some embodiments, the subcellular location is the nucleus.

Disclosed herein, in some embodiments, are vectors comprising: a polynucleotide sequence encoding the composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site. In some embodiments, the methods further comprise a polynucleotide encoding a promoter. In some embodiments, the promoter is operably linked to the polynucleotide. In some embodiments, the promoter is an inducible promoter.

Disclosed herein, in some embodiments, are genetically modified organisms comprising: the vector comprising: a polynucleotide sequence encoding the composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site.

Disclosed herein, in some embodiments, are genetically modified organisms comprising: the composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site.

Disclosed herein, in some embodiments, are kits comprising: the composition comprising a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site; and a buffer.

Disclosed herein, in some embodiments, are kits comprising: the vector comprising: a polynucleotide sequence encoding the composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site; and a buffer. In some embodiments, the methods further comprise instructions for use. In some embodiments, the buffer is selected from the group comprising: a dilution buffer, a reconstitution buffer, and a stabilization buffer, or any combination thereof.

Disclosed herein, in some embodiments, are donor polynucleotides comprising: a genetic element of interest; and a reporter element, wherein the reporter element comprises a polynucleotide sequence encoding an Argonaute, and one or more nucleic acids, wherein the one or more nucleic acids comprises a designed nucleic acid-targeting nucleic acid. In some embodiments, the genetic element of interest comprises a gene. In some embodiments, the genetic element of interest comprises a non-coding gene. In some embodiments, the reporter element comprises a gene selected from the group consisting of: a gene encoding a fluorescent protein, a gene encoding a chemiluminescent protein, and an antibiotic resistance gene, or any combination thereof. In some embodiments, the reporter element comprises a gene encoding a fluorescent protein. In some embodiments, the fluorescent protein comprises green fluorescent protein. In some embodiments, the reporter element is operably linked to a promoter. In some embodiments, the promoter comprises an inducible promoter. In some embodiments, the promoter comprises a tissue-specific promoter. In some embodiments, the Argonaute comprises at least 15% amino acid sequence identity to a nuclease domain of Argonaute from *T. thermophilus*. In some embodiments, the Argonaute comprises at least 95% amino acid sequence identity over 10 amino acids to Argonaute from *T. thermophilus*. In some embodiments, the Argonaute comprises at least 15% amino acid sequence identity to a nuclease domain of Argonaute from *S. elongatus*. In some embodiments, the Argonaute comprises at least 95% amino acid sequence identity over 10 amino acids to Argonaute from *S. elongatus*.

Disclosed herein, in some embodiments, are expression vectors comprising a polynucleotide sequence encoding for the donor polynucleotide comprising: a genetic element of interest; and a reporter element, wherein the reporter element comprises a polynucleotide sequence encoding an Argonaute, and one or more nucleic acids, wherein the one or more nucleic acids comprises a designed nucleic acid-targeting nucleic acid.

Disclosed herein, in some embodiments, are genetically modified cell comprising the donor polynucleotide comprising: a genetic element of interest; and a reporter element, wherein the reporter element comprises a polynucleotide sequence encoding an Argonaute, and one or more nucleic acids, wherein the one or more nucleic acids comprises a designed nucleic acid-targeting nucleic acid.

Disclosed herein, in some embodiments, are kits comprising: the donor polynucleotide comprising; a genetic element of interest; and a reporter element, wherein the reporter element comprises a polynucleotide sequence encoding an Argonaute, and one or more nucleic acids, wherein the one or more nucleic acids comprises a designed nucleic acid-targeting nucleic acid; and a buffer. In some embodiments, the kits further comprise: a polypeptide comprising at least 10% amino acid sequence identity to Argonaute from an organism selected from the group consisting of: *T. thermophilus* and *S. elongatus*; and a nucleic acid, wherein the nucleic acid binds to the polypeptide and hybridizes to a target nucleic acid. In some embodiments, the kits further comprise instructions for use. In some embodiments, the kits further comprise a polynucleotide encoding a polypeptide, wherein the polypeptide comprises at last 15% amino acid sequence identity to Argonaute from *T. thermophilus*. In some embodiments, the kits further comprise a polynucleotide encoding a polypeptide, wherein the polypeptide comprises at last 15% amino acid sequence identity to Argonaute from *S. elongatus*. In some embodiments, the kits further comprise a polynucleotide encoding a designed nucleic acid-targeting nucleic acid.

Disclosed herein, in some embodiments, are methods for selecting a cell using a reporter clement and excising the reporter element from the cell comprising: contacting a target nucleic acid with a complex comprising an Argonaute and a designed nucleic acid-targeting nucleic acid; cleaving the target nucleic acid with the Argonaute to generate a cleaved target nucleic acid; inserting the donor polynucleotide into the cleaved target nucleic acid; and selecting the cell based on the donor polynucleotide to generate a selected ceil. In some embodiments, selecting comprises selecting the cell from a subject being treated for a disease. In some embodiments, selecting comprises selecting the cell from a subject being diagnosed for a disease. In some embodiments, after the selecting, the cell comprises the donor polynucleotide. In some embodiments, the methods further comprise excising all, some or none of the reporter element, thereby generating a second selected cell. In some embodiments, the excising comprises contacting the 5' end of the reporter element with a complex comprising an Argonaute and a designed nucleic acid-targeting nucleic acid, wherein the complex cleaves the 5' end. In some embodiments, the excising comprises contacting the 3' end of the reporter element with a complex comprising an Argonaute and a designed nucleic acid-targeting nucleic acid, wherein the complex cleaves the 3' end. In some embodiments, the excising comprises contacting the 5' and 3' end of the reporter element with one or more complexes comprising an Argonaute and a designed nucleic acid-targeting nucleic acid, wherein the complex cleaves the 5' and 3' end. In some embodiments, the methods further comprise screening the second selected cell. In some embodiments, the screening comprises observing an absence of all or some of the reporter element.

Disclosed herein, in some embodiments, are methods of creating a synthetically designed nucleic acid-targeting nucleic acid comprising: designing the nucleic acid-targeting nucleic that hybridizes to the target nucleic acid.

Disclosed herein, in some embodiments, are pharmaceutical compositions comprising a composition comprising a designed nucleic acid-targeting nucleic acid comprising a 3' hybridizing extension; and a donor polynucleotide, wherein the donor polynucleotide is hybridized to the 3' hybridizing extension.

Disclosed herein, in some embodiments, are pharmaceutical compositions comprising a composition comprising an effector protein; and a designed nucleic acid-targeting nucleic acid, comprising a non-native sequence, wherein the designed nucleic acid-targeting nucleic acid is adapted to bind to the effector protein.

Disclosed herein, in some embodiments, are pharmaceutical compositions comprising a composition comprising a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid.

Disclosed herein, in some embodiments, are pharmaceutical compositions comprising a composition comprising a modified Argonaute, wherein the polypeptide is modified such that it is adapted to bind a second designed nucleic acid-targeting nucleic acid compared to a wild-type Argonaute.

Disclosed herein, in some embodiments, are pharmaceutical compositions comprising a composition comprising a modified Argonaute comprising a modified nuclease domain as compared to Argonaute from an organism selected from the group consisting of: *T. thermophilus* and *S. elongatus*.

Disclosed herein, in some embodiments, are pharmaceutical compositions comprising a composition comprising a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site.

Disclosed herein, in some embodiments, are pharmaceutical compositions comprising the modified Argonaute comprising: a modified MID domain.

Disclosed herein, in some embodiments, are pharmaceutical compositions comprising the modified Argonaute comprising: a modified PAZ domain Disclosed herein, in some embodiments, are pharmaceutical compositions comprising the modified Argonaute comprising a modification configured to enable the Argonaute to retain activity at 37 degrees celsius.

Disclosed herein, in some embodiments, are pharmaceutical compositions comprising the modified Argonaute comprising a first nuclease domain, and an inserted nuclease domain.

Disclosed herein, in some embodiments, are pharmaceutical compositions comprising a vector selected from the group consisting of: a vector comprising a polynucleotide sequence encoding a designed nucleic acid-targeting nucleic acid, wherein the designed nucleic acid-targeting nucleic acid comprises a non-native sequence; a vector comprising: a polynucleotide sequence encoding: a designed nucleic acid-targeting nucleic acid, wherein the designed nucleic acid-targeting nucleic acid comprises a sequence configured to bind to an effector protein; and an Argonaute; a vector comprising: a polynucleotide sequence encoding: a designed nucleic acid-targeting nucleic acid, wherein the designed nucleic acid-targeting nucleic acid comprises a non-native sequence; an Argonaute; and an effector protein; a vector comprising a polynucleotide sequence encoding the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid; a vector comprising: a polynucleotide encoding for the modified Argonaute comprising: a modified MID domain; a vector comprising: a polynucleotide encoding for the modified Argonaute comprising a modified PAZ domain; a vector comprising: a polynucleotide encoding for the modified Argonaute comprising: a modification configured to enable the Argonaute to retain activity at 37 degrees celsius; a vector comprising a polynucleotide sequence encoding the modified Argonaute comprising: a first nuclease domain, and an inserted nuclease domain; a vector comprising: a polynucleotide sequence encoding the composition comprising: a modified Argonaute, wherein the polypeptide is modified such that it is adapted to bind a second designed nucleic acid-targeting nucleic acid compared to a wild-type Argonaute; a vector comprising a polynucleotide encoding the composition comprising: a modified Argonaute comprising a modified nuclease domain as compared to Argonaute from an organism selected from the group consisting of: *T. thermophilus* and *S. elongatus*; a vector comprising a polynucleotide sequence encoding: two or more designed nucleic acid-targeting nucleic acids that differ by at least one nucleotide; and an Argonaute; a vector comprising: a polynucleotide sequence encoding the composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site; and a vector comprising a polynucleotide sequence encoding for the donor polynucleotide comprising: a genetic element of interest; and a reporter element, wherein the reporter element comprises a polynucleotide sequence encoding an Argonaute, and one or more nucleic acids, wherein the one or more nucleic acids comprises a designed nucleic acid-targeting nucleic acid; or any combination thereof.

Disclosed herein, in some embodiments, are pharmaceutical compositions comprising a composition selected from the group consisting of: the composition comprising: a designed nucleic acid-targeting nucleic acid comprising a 3' hybridizing extension; and a donor polynucleotide, wherein the donor polynucleotide is hybridized to the 3' hybridizing extension; the composition comprising: an effector protein; and a designed nucleic acid-targeting nucleic acid, comprising a non-native sequence, wherein the designed nucleic acid-targeting nucleic acid is adapted to bind to the effector protein; the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid; the composition comprising: a modified Argonaute, wherein the polypeptide is modified such that it is adapted to bind a second designed nucleic acid-targeting nucleic acid compared to a wild-type Argonaute; the composition comprising: a modified Argonaute comprising a modified nuclease domain as compared to Argonaute from an organism selected from the group consisting of: *T. thermophilus* and *S. elongatus*; and the composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site.

Disclosed herein, in some embodiments, are pharmaceutical compositions comprising a modified Argonaute selected from the modified Argonaute comprising: a modified MID domain; the modified Argonaute comprising: a modified PAZ domain; the modified Argonaute comprising: a modification configured to enable the Argonaute to retain activity at 37 degrees celsius; and the modified Argonaute comprising: a first nuclease domain, and an inserted nuclease domain.

Disclosed herein, in some embodiments, are pharmaceutical compositions comprising the donor polynucleotide comprising: a genetic element of interest; and a reporter element, wherein the reporter element comprises a polynucleotide sequence encoding an Argonaute, and one or more nucleic acids, wherein the one or more nucleic acids comprises a designed nucleic acid-targeting nucleic acid.

Disclosed herein, in some embodiments, are pharmaceutical compositions comprising a vector selected from the group consisting of: the vector comprising a polynucleotide sequence encoding a designed nucleic acid-targeting nucleic acid, wherein the designed nucleic acid-targeting nucleic acid comprises a non-native sequence; the vector comprising: a polynucleotide sequence encoding: a designed nucleic acid-targeting nucleic acid, wherein the designed nucleic acid-targeting nucleic acid comprises a sequence configured to bind to an effector protein; and an Argonaute; the vector comprising: a polynucleotide sequence encoding: a designed nucleic acid-targeting nucleic acid, wherein the designed nucleic acid-targeting nucleic acid comprises a non-native sequence; an Argonaute; and an effector protein; the vector comprising a polynucleotide sequence encoding the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid; the vector comprising: a polynucleotide encoding for the modified Argonaute comprising: a modified MID domain; the vector comprising: a polynucleotide encoding for the modified Argonaute a modified PAZ domain; the vector comprising: a polynucleotide encoding for the modified Argonaute comprising: a modification configured to enable the Argonaute to retain activity at 37 degrees celsius; the vector comprising a polynucleotide sequence encoding the modified Argonaute comprising a first nuclease domain, and an inserted nuclease domain; the vector comprising: a polynucleotide sequence encoding the composition comprising: a modified Argonaute, wherein the polypeptide is modified such that it is adapted to bind a second designed nucleic acid-targeting nucleic acid compared to a wild-type Argonaute; the vector comprising a polynucleotide encoding the composition of composition comprising: a modified Argonaute comprising a modified nuclease domain as compared to Argonaute from an organism selected from the group consisting of: *T. thermophilus* and *S. elongatus*; the vector comprising a polynucleotide sequence encoding: two or more designed nucleic acid-targeting nucleic acids that differ by at least one nucleotide; and an Argonaute; the vector comprising: a polynucleotide sequence encoding the A composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site; and an expression vector comprising a polynucleotide sequence encoding for the donor polynucleotide comprising: a genetic element of interest; and a reporter element, wherein the reporter element comprises a polynucleotide sequence encoding an Argonaute, and one or more nucleic acids, wherein the one or more nucleic acids comprises a designed nucleic acid-targeting nucleic acid; or any combination thereof. In some embodiments, the pharmaceutical composition further comprises an adjuvant. In some embodiments, the pharmaceutical composition further comprises an excipient. In some embodiments, the pharmaceutical composition further comprises a carrier selected from the group consisting of: tablets, powders, pills, dragees, capsules, liquids, gels, syrups, elixirs, slurries, and suspensions, or any combination thereof.

Disclosed herein, are methods of treating a disease comprising: administering to a subject a composition selected from the group consisting of the composition comprising: a designed nucleic acid-targeting nucleic acid comprising a 3' hybridizing extension; and a donor polynucleotide, wherein the donor polynucleotide is hybridized to the 3' hybridizing extension; the composition comprising: an effector protein; and a designed nucleic acid-targeting nucleic acid, comprising a non-native sequence, wherein the designed nucleic acid-targeting nucleic acid is adapted to bind to the effector protein; the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid; the composition comprising: a modified Argonaute, wherein the polypeptide is modified such that it is adapted to bind a second designed nucleic acid-targeting nucleic acid compared to a wild-type Argonaute; the composition comprising: a modified Argonaute comprising a modified nuclease domain as compared to Argonaute from an organism selected from the group consisting of: *T. thermophilus* and *S. elongatus*; the composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site; a modified Argonaute selected from the group consisting of: the modified Argonaute comprising: a modified MID domain; the modified Argonaute comprising: a modified PAZ domain; the modified Argonaute comprising: a modification configured to enable the Argonaute to retain activity at 37 degrees celsius; the modified Argonaute comprising: a first nuclease domain, and an inserted nuclease domain; a donor polynucleotide comprising: a genetic element of interest; and a reporter element, wherein the reporter element comprises a polynucleotide sequence encoding an Argonaute, and one or more nucleic acids, wherein the one or more nucleic acids comprises a designed nucleic acid-targeting nucleic acid; and a vector selected from the group consisting of: the vector comprising a polynucleotide sequence encoding a designed nucleic acid-targeting nucleic acid, wherein the designed nucleic acid-targeting nucleic acid comprises a non-native sequence; the vector comprising: a polynucleotide sequence encoding: a designed nucleic acid-targeting nucleic acid, wherein the designed nucleic acid-targeting nucleic acid comprises a sequence configured to bind to an effector protein; and an Argonaute; the vector comprising: a polynucleotide sequence encoding: a designed nucleic acid-targeting nucleic acid, wherein the designed nucleic acid-targeting nucleic acid comprises a non-native sequence; an Argonaute; and an effector protein; the vector comprising a polynucleotide sequence encoding the composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 30% amino acid sequence identity to a nuclease domain of Argonaute and wherein the nucleic acid module is configured to hybridize to a target nucleic acid; the vector comprising: a polynucleotide encoding for the modified Argonaute comprising: a modified MID domain; the vector comprising: a polynucleotide encoding for the modified Argonaute comprising a modified PAZ domain; the vector comprising: a polynucleotide encoding for the modified Argonaute comprising: a modification configured to enable the Argonaute to retain activity at 37 degrees celsius; the vector comprising a polynucleotide sequence encoding the A modified Argonaute comprising: a first nuclease domain, and an inserted nuclease domain; the vector comprising: a polynucleotide sequence encoding the composition comprising: a modified Argonaute, wherein the polypeptide is modified such that it is adapted to bind a second designed nucleic acid-targeting nucleic acid compared to a wild-type Argonaute; the vector comprising a polynucleotide encoding the composition comprising: a modified Argonaute comprising a modified nuclease domain as compared to Argonaute from an organism selected from the group consisting of: *T. thermophilus* and *S. elongatus*; the vector comprising a polynucleotide sequence encoding: two or more designed nucleic acid-targeting nucleic acids that differ by at least one nucleotide; and an Argonaute; the vector comprising: a polynucleotide sequence encoding the composition comprising: a plurality of nucleic acid molecules, wherein each nucleic acid molecule comprises a nucleic acid-binding protein binding site, wherein at least one of the plurality of nucleic acid molecules encodes for a designed nucleic acid-targeting nucleic acid and one of the plurality of nucleic acid molecules encodes for an Argonaute; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site; and an expression vector comprising a polynucleotide sequence encoding for the donor polynucleotide comprising: a genetic element of interest; and a reporter element, wherein the reporter element comprises a polynucleotide sequence encoding an Argonaute, and one or more nucleic acids, wherein the one or more nucleic acids comprises a designed nucleic acid-targeting nucleic acid; or any combination thereof In some embodiments, administering comprises administering comprises administering by viral delivery. In some embodiments, the viral delivery comprises a viral delivery method selected from the group consisting of: lentiviral delivery, adenoviral delivery, adeno-associated viral delivery, and retroviral delivery, or any combination thereof In some embodiments, the administering comprises administering comprises administering by electroporation. In some embodiments, the administering comprises administering comprises administering by nanoparticle delivery. In some embodiments, the administering comprises administering comprises administering by liposome delivery. In some embodiments, the administering comprises administering by a method selected from the group consisting of: intravenously, subcutaneously, intramuscularly, orally, rectally, by aerosol, parenterally, ophthalmicly, pulmonarily, transdermally, vaginally, otically, nasally, and by topical administration, or any combination thereof. In some embodiments, the methods are performed in a cell selected from the group consisting of: plant cell, microbe cell, and fungi cell, or any combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

Figure 18:
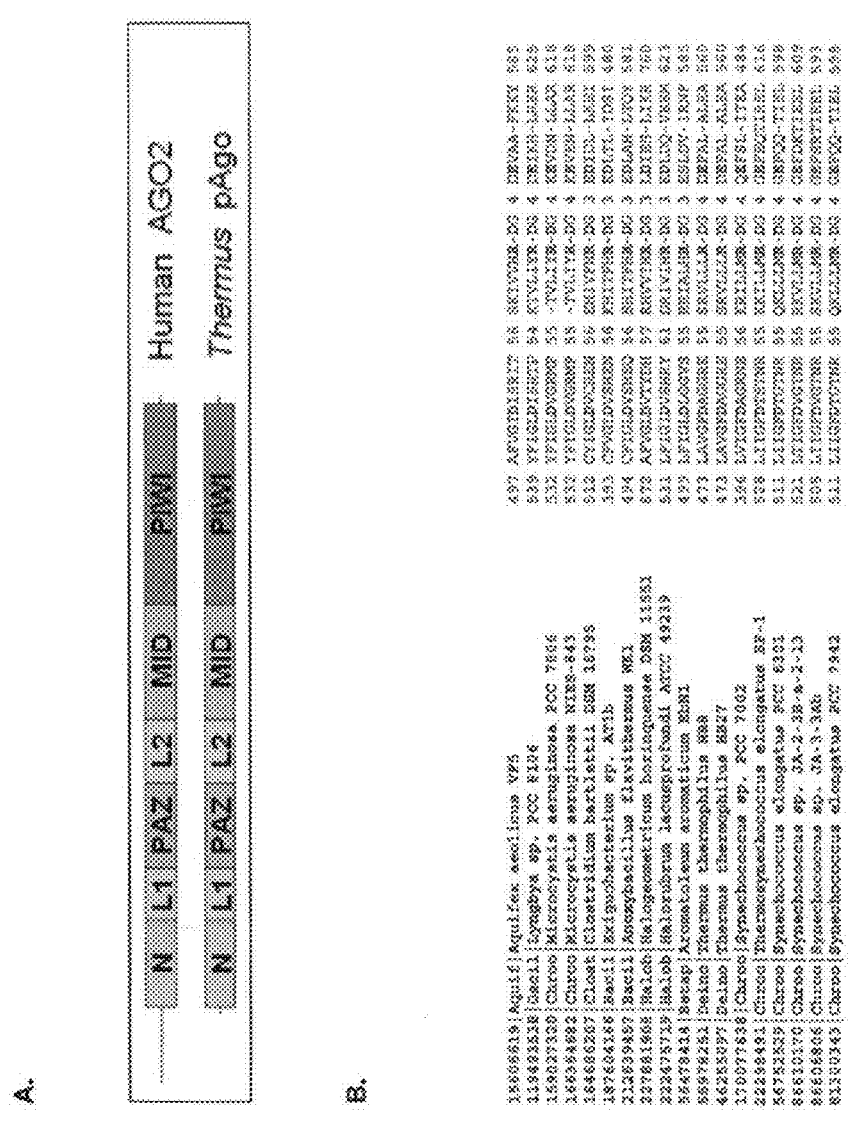

FIG. 18A: Comparison of the domain structure of *Thermus* pAgo with the human AGO2, which can have the domain architecture (N-L1-PAZ-L2-MID-PIWI) of eukaryotic Argonaute proteins, in which N and PAZ domains form the N-terminal lobe, the MID and PIWI domains form the C-terminal lobe, and L1 and L2 form linker regions. Eukaryotic Ago can comprise both the PAZ domain (oligonucleotide binding) and the PIWI domain (sheer nuclease activity). FIG. 18B shows a listing of predicted active pAgos with alignment of conserved PIWI domain sequences (SEQ ID NOS 32-85, in order). The multiple sequence alignment includes the core motifs of PIWI domains encompassing the amino acid residues that comprise the (D/E)-(D/E)XK active site. The sequences are denoted by their GI numbers and species names. The positions of the first and the last residues of the aligned region in the corresponding protein are indicated for each sequence. The numbers within the alignment represent poorly conserved inserts that are not shown. The catalytic residues of the D-RD-EXK active site are shown in bold

FIGS. 20A and B depict nucleic acids that co-purified with TtAgo. Nucleic acids were either forward labelled ((left-hand gel, FIG. 20A), 5'-OH groups are labelled) or exchange labelled ((right-hand gel, FIG. 20B), 5'-P groups are mainly labelled) with T4 PNK and resolved on 15% denaturing polyacrylamide gels. Nucleic acids were untreated (lanes 1, 5), RNAse A treated (lanes 2, 6), DNAseI treated (lanes 3, 7) or nuclease P1 treated (lanes 4, 8). The co-purified DNA exhibits a length between 15-25 nucleotides.

Cleavage positions as determined after cloning and sequencing of cleavage products are shown by crosses.

Figure 24:
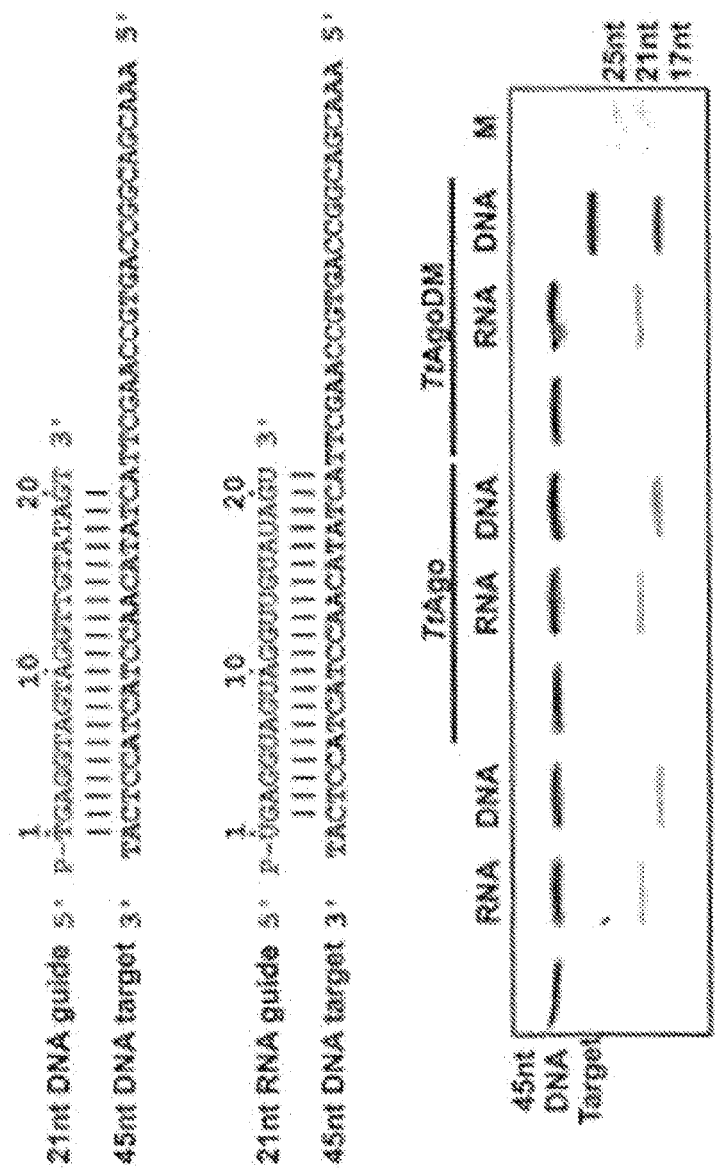

FIG. 24 shows 45-nt ssDNA cleavage by TtAgo. M: microRNA Marker (NEB). Cleavage is observed when TtAgo is provided with a 21nt DNA guide that is complementary to the target, but not when two active site residues are mutated (TtAgoDM) or when a complementary RNA guide is provided. FIG. 24 discloses SEQ ID NOS 21, 86-87 and 86, in order.

Figure 25:
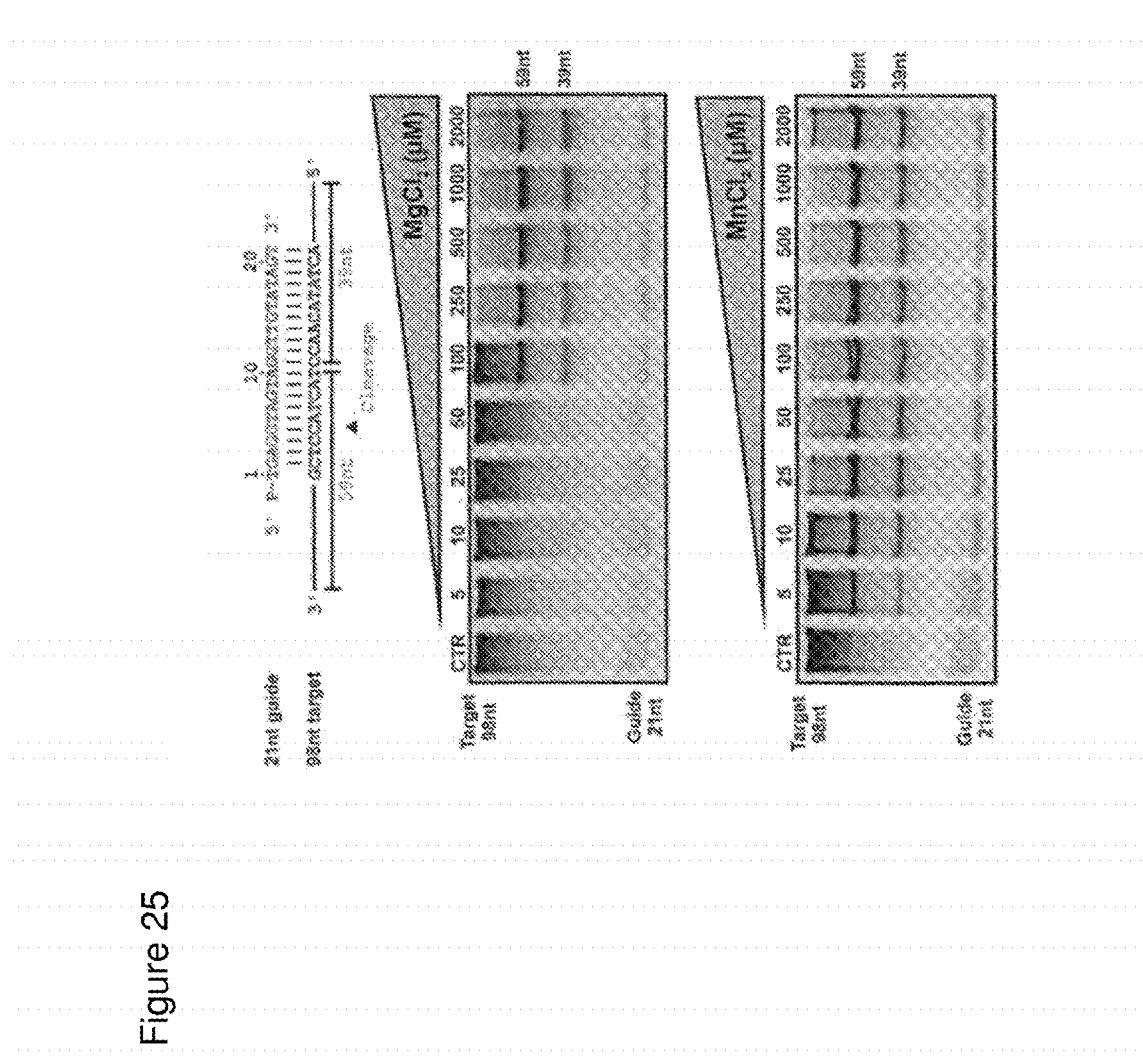

FIG. 25 shows the effect of divalent cation concentration on 96nt ssDNA cleavage by TtAgo supplied with a 21nt DNA guide. The ssDNA target is cleaved at a minimum $MnCl_2$ concentration of 5-10 μM (25 μM is sufficient to facilitate full target cleavage), while a $MgCl_2$ concentration of 100 μM is required to facilitate target cleavage. FIG. 25 discloses SEQ ID NOS 21 and 88, in order.

Figure 26:
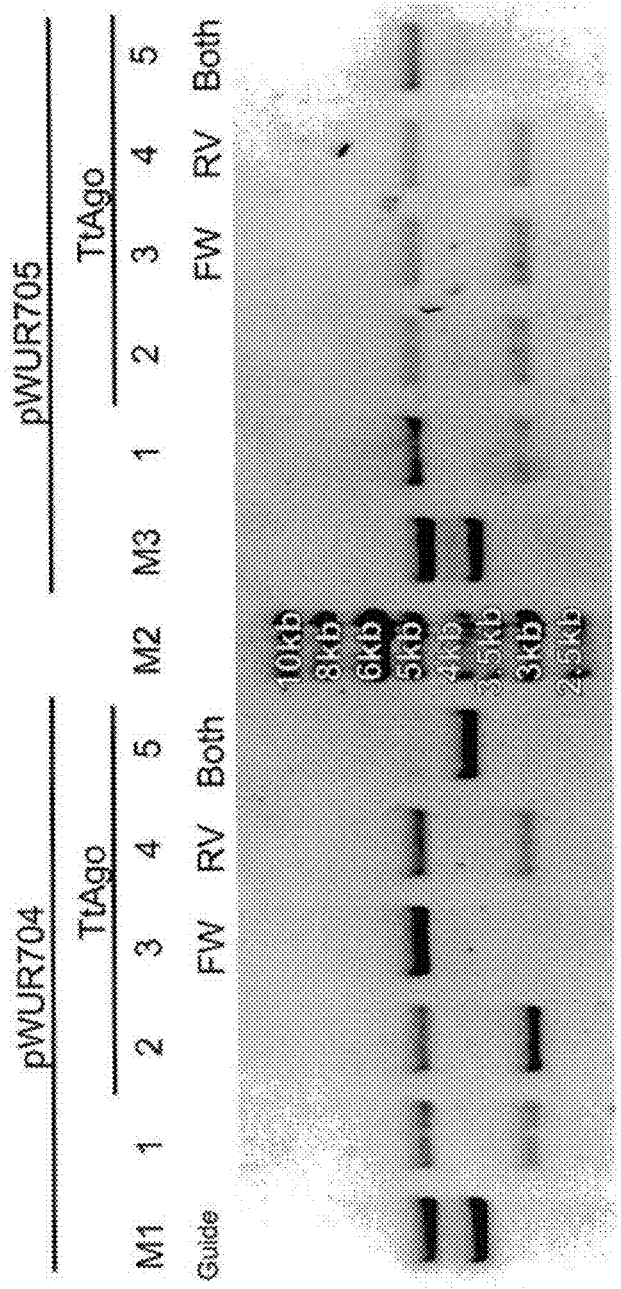

FIG. 26 shows plasmid cleavage by TtAgo and provided guides. M1: nicked and linearized pWUR704. M2: 1 kb ladder (Fermentas). M3: nicked and linearized pVVUR705. Addition of TtAgo without the addition of a guide does not lead to increased nicking or cleavage of the target plasmid (lane 2). Plasmid pWUR704 has a GC content of 15% in the targeted region. Addition of TtAgo and a single guide leads to nicking (lane 3-4), while addition of TtAgo and both guides leads to complete linearization of the plasmid (lane 5). Plasmid pWUR705 has a GC content of 58% in the targeted region. Addition of TtAgo and a single guide does result in plasmid nicking (lane 3-4), while addition of TtAgo and both guides leads to either nicking or linearization of the plasmid (lane 5).

Figure 27:
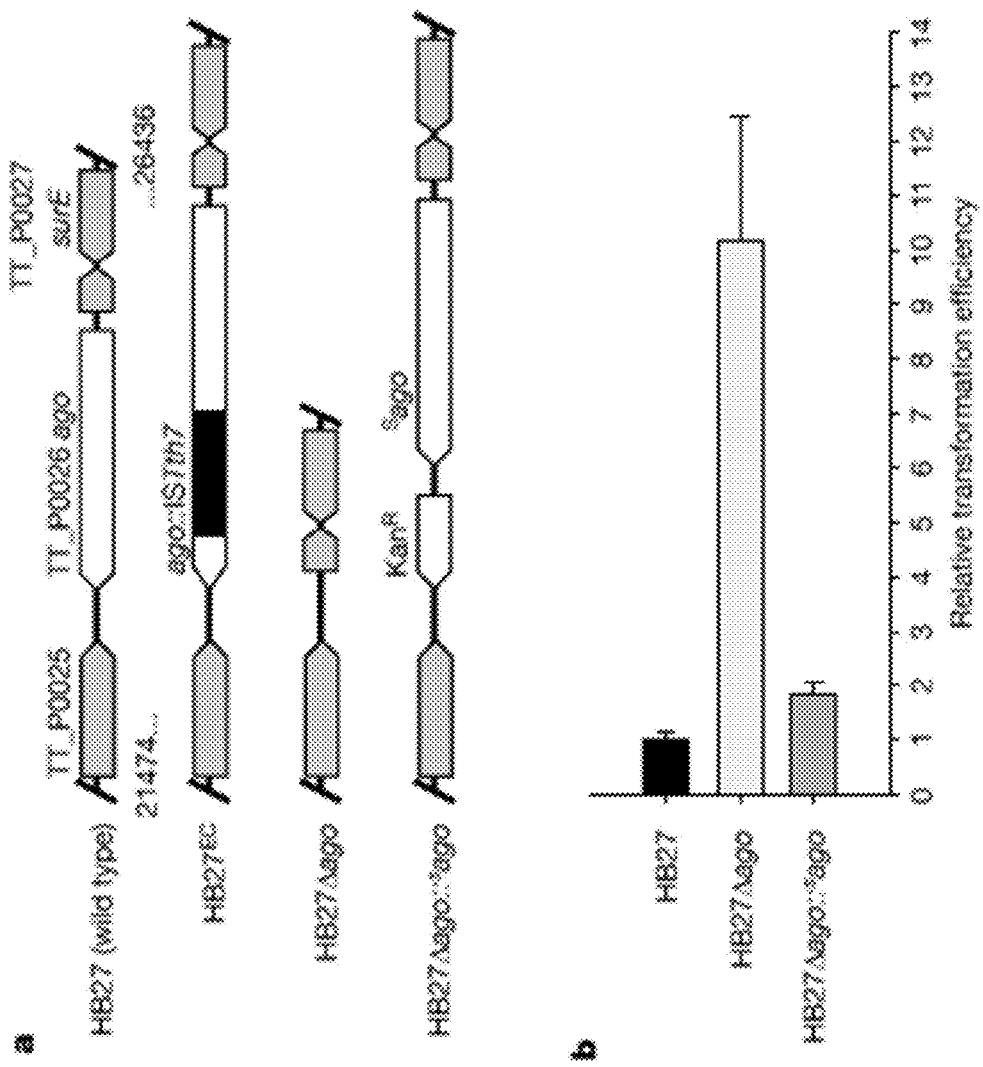
Figure 27:
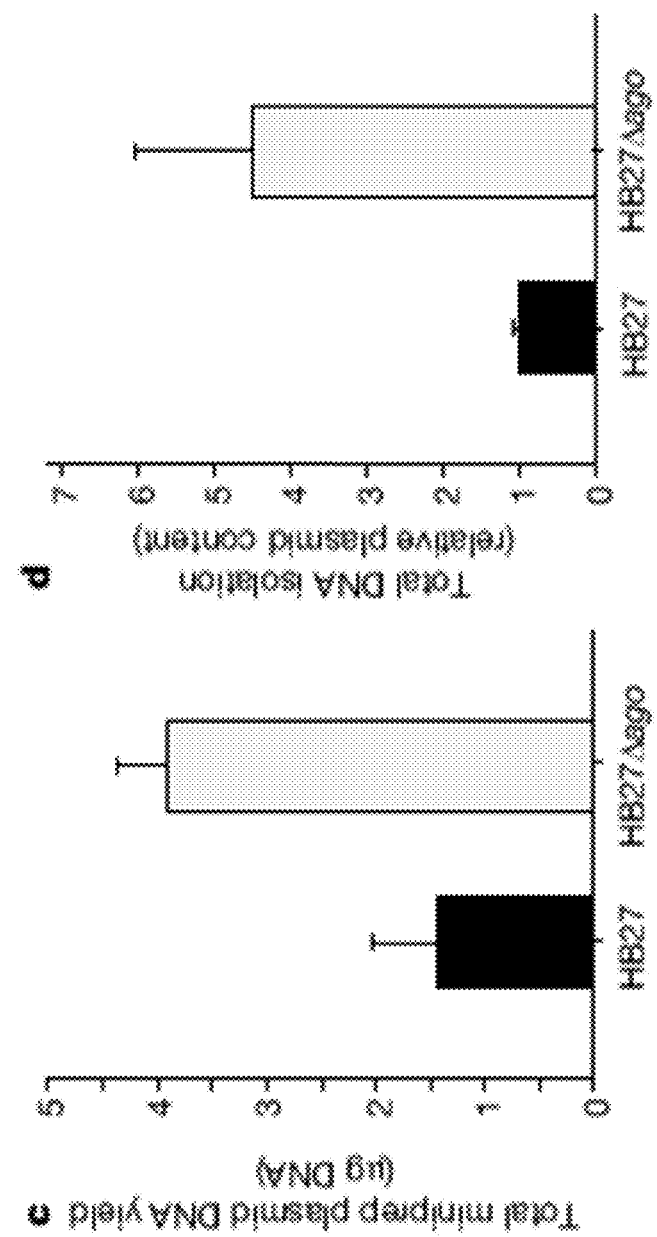
Figure 41:
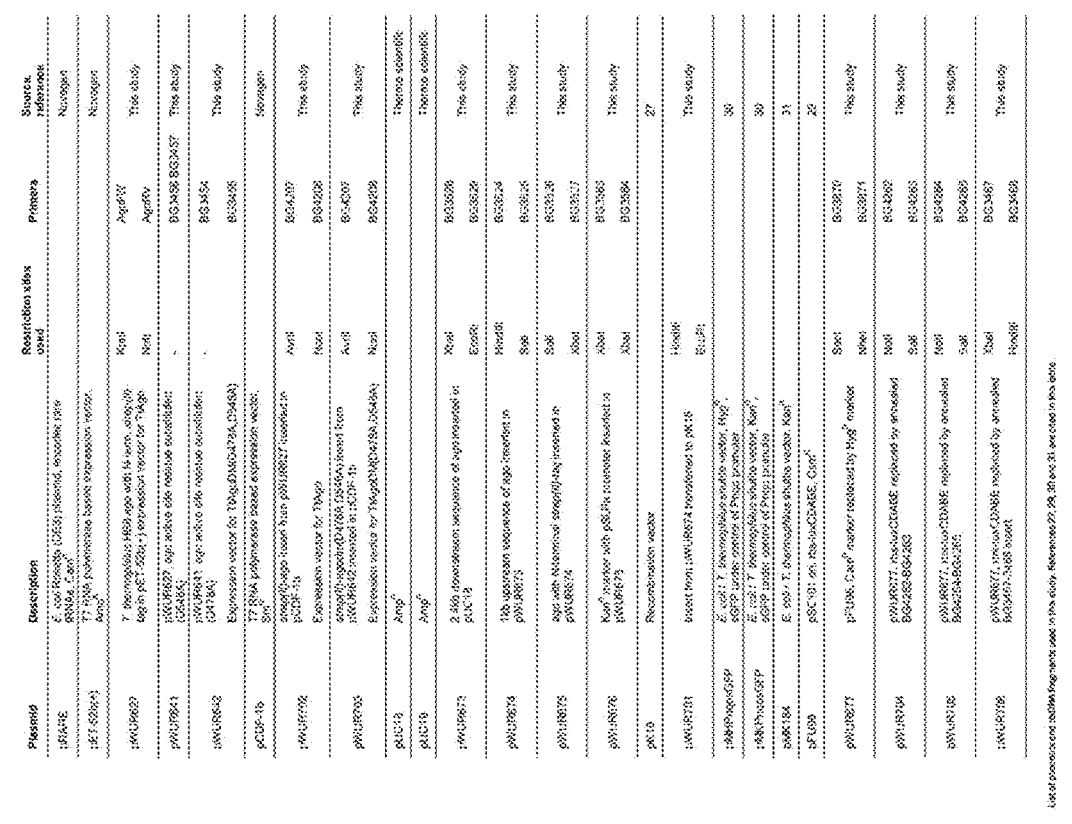

FIG. 27 depicts TtArgonaute interface with plasmid DNA. FIG. 27A shows an exemplary overview of ago gene loci of *T. thermophilus* strains: HB27 (wild type), HB27$^{EC}$ (spontaneous derivative with enhanced competence), HB27Δago (knockout), and HB27Δago::$^s$ ago (HB27Δago complemented with a strep(II)-tag-ago gene fusion insert). Kan$^R$, kanamycin resistance marker. FIG. 27B shows exemplary transformation efficiencies of *T. thermophilus* strains on transformation with the plasmid pMHPnqosGFP (FIG. 41). Error bars indicate standard deviations of biological duplicates. FIG. 27C shows exemplary yields of pMHPnqosGFP plasmid mini preparation (miniprep) of HB27 and HB27Δago. Error bars indicate standard deviations of biological triplicates. FIG. 27D exemplifies plasmid content of total DNA purified from HB27Δago relative to that from HB27, as quantified by Genetools (Syngene) after resolving the DNA on a 0.8% agarose gel. Error bars indicate standard deviations of biological triplicates.

Figure 28:
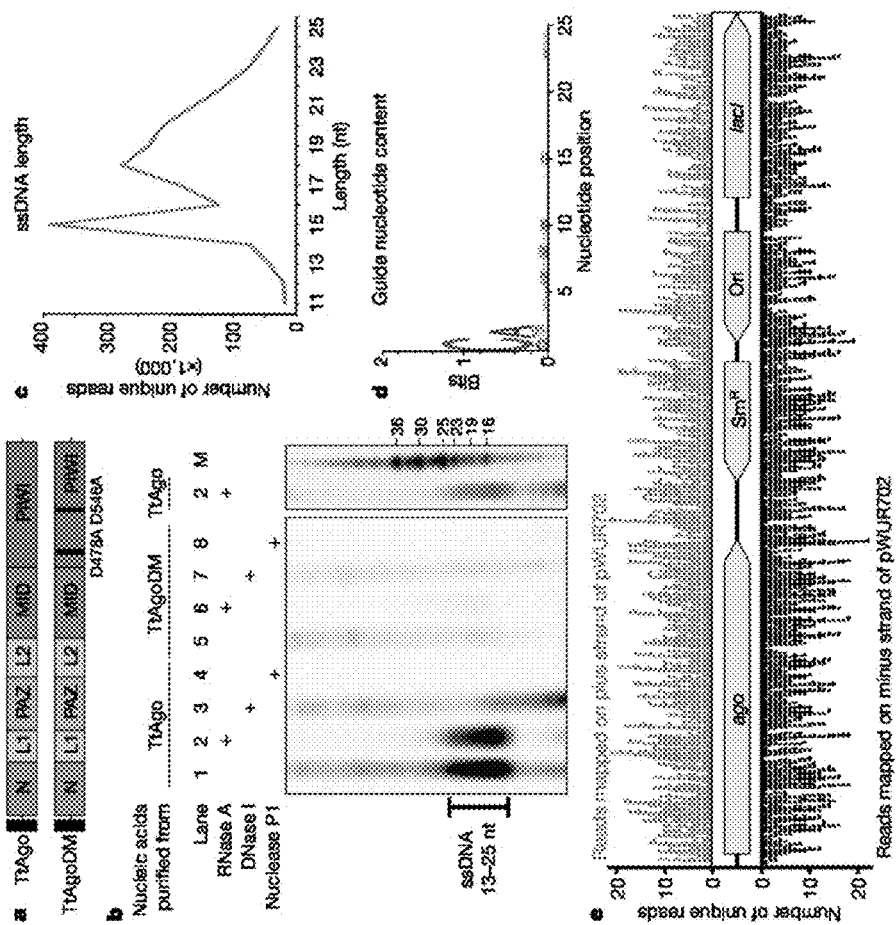

FIG. 28 depicts an-exemplary embodiment of TtArgonaute guides as 5'-phosphorylated DNA molecules. FIG. 28A exemplifies a schematic representation of TtArgonaute and TtArgonauteDM proteins used for all experiments (N, PAZ, MID, and PIWI are structural domains, L1 and L2 are linkers). The amino-terminal Strep(II)-tag is indicated as a black square. FIG. 28B shows co-purified nucleic acids from TtArgonaute and TtArgonauteDM are labelled with [γ-$^{32}$P] ATP after phosphate exchange by PNK from bacteriophage T4, and treated with enzymes as indicated. M, custom ssDNA marker; nt, nucleotides. FIG. 28C exemplifies length distribution of unique ssDNA sequencer co-purified with TtArgonaute. FIG. 28D exemplifies nucleotide composition of unique ssDNA sequences co-purified with TtArgonaute. FIG. 28E exemplifies unique reads of TtArgonaute co-purified ssDNA molecules mapped on the TtArgonaute expression vector pWUR702.

Figure 29:
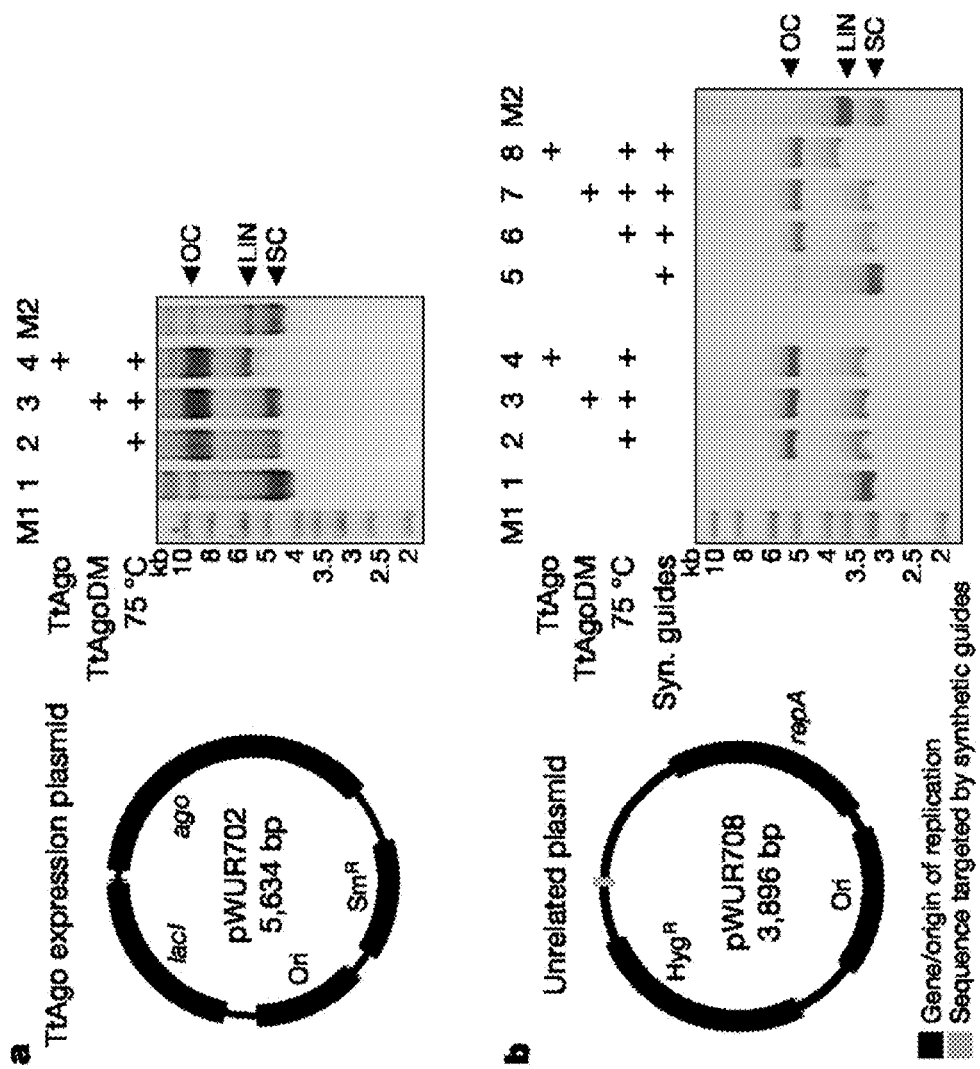

FIG. 29 depicts TtArgonaute cleavage of plasmids complementary to its guides. FIG. 29A depicts a TtArgonaute expression vector pWUR702. FIG. 29B depicts a target plasmid pWUR708, which shares no sequence identity with expression vector pWUR702 or pRARE. FIG. 29A shows TtArgonaute expression plasmid untreated (lane 1, 5), incubated at 75° C. in the absence of proteins (lane 2), in the presence of TtArgonauteDM (lane 3) or in the presence of TtArgonaute (lane 4) purified from *E. coli*, resolved on 0.8% agarose gels. FIG. 29B show unrelated target plasmid untreated (lane 1, 5), incubated at 75° C. in the absence of proteins (lane 2, 6), or in the presence of TtArgonauteDM (lane 3, 7) or TtArgonaute (lane 4, 8) purified from *E. coli*, resolved on 0.8% agarose gels. LIN, linear; M1, 1 kb Generuler marker (Fermentas); M2, linearized and untreated target plasmid; OC, open circular; SC, supercoiled plasmid. Additionally, synthetic (Syn.) ssDNA guides were added to the reactions with pWUR708 (lane 5-8).

Figure 30A:
Figure 30B:
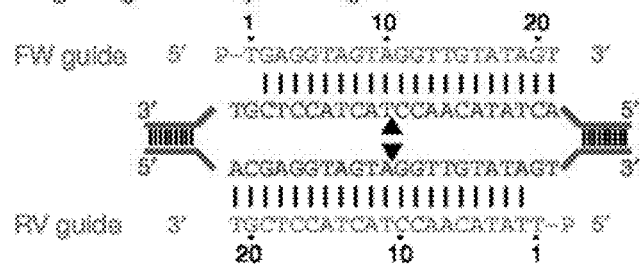

FIG. 30 depicts TtArgonaute cleavage of plasmids by nicking two strands. FIG. 30A exemplifies plasmids pWUR704 and pWUR705 containing a 98 bp target region with a GC content of 17% or 59%, respectively, as indicated in blue (for details, see Extended Data FIG. 5a, b). FIG. 30B exemplifies part of the pWUR704 and pWUR705 target site (indicated in blue) and complementary ssDNA guides used in this experiment (indicated in red). Black triangles indicate predicted cleavage sites. FIG. 30B discloses SEQ ID NOS 21, 89-90 and 22, in order FIG. 30C shows 0.8% agarose gels loaded with pWUR704 and pWUR705plasmids that were incubated without proteins (lane 1), or with TtArgonaute (lane 2), TtArgonaute—forward (FW) guide complex (lane 3), TtArgonaute—reverse (RV) guide complex (lane 4), or TtArgonaute—FW and TtArgonaute—RV guide complexes. LIN, linear; M1, open circular and linear pWUR704 or pWUR705; M2, 1 kb Generuler marker (Fermentas); OC, open circular; SC, supercoiled plasmid.

Figure 31:
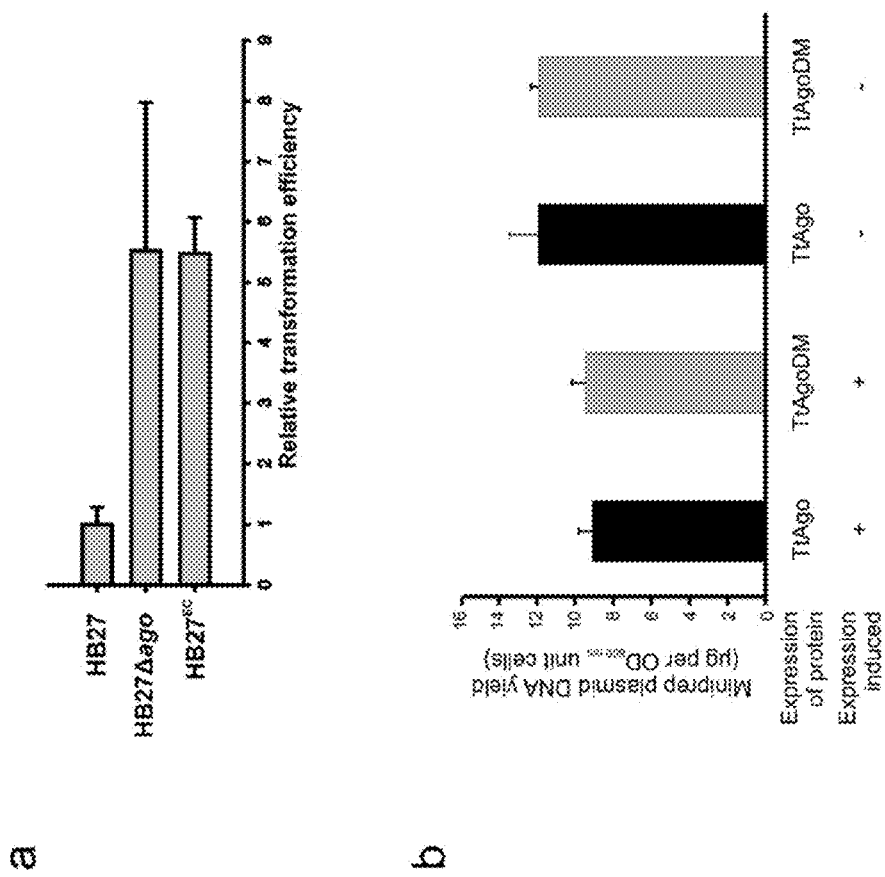

FIG. 31 shows analyses of TtArgonaute in *T. thermophilus* and *E.coli*. FIG. 31A exemplifies TtArgonaute decrease of plasmid transformation efficiency of *T. thermophilus*. Transformation efficiency of different ago mutant strains relative to the transformation efficiency of wild-type strain HB27, HB27$^{EC}$ is an HB27 mutant selected for high competence, and HB27Δago is an ago gene knockout strain (FIG. 1a). Strains were transformed with plasmid pMK184. Transformations were performed in biological duplicates for each strain. Error bars indicate standard deviations. FIG. 31B exemplifies the effect on TtArgonaute expression on plasmid content in *E. coli* KRX. TtArgonaute and TtArgonauteDM were expressed in *E. coli* KRX from plasmid pWUR702 and pWUR703. Plasmids were purified from biological triplicate cultures in which expression was induced (+) or not induced (−). compared with TtArgonauteDM expression, TtArgonaute expression in *E. coli* KRX does not lead to reduced plasmid content. Changes in plasmid yield between induced and not induced cultures may originate from protein expression energy costs. Error bars indicate standard deviations.

Figure 32:
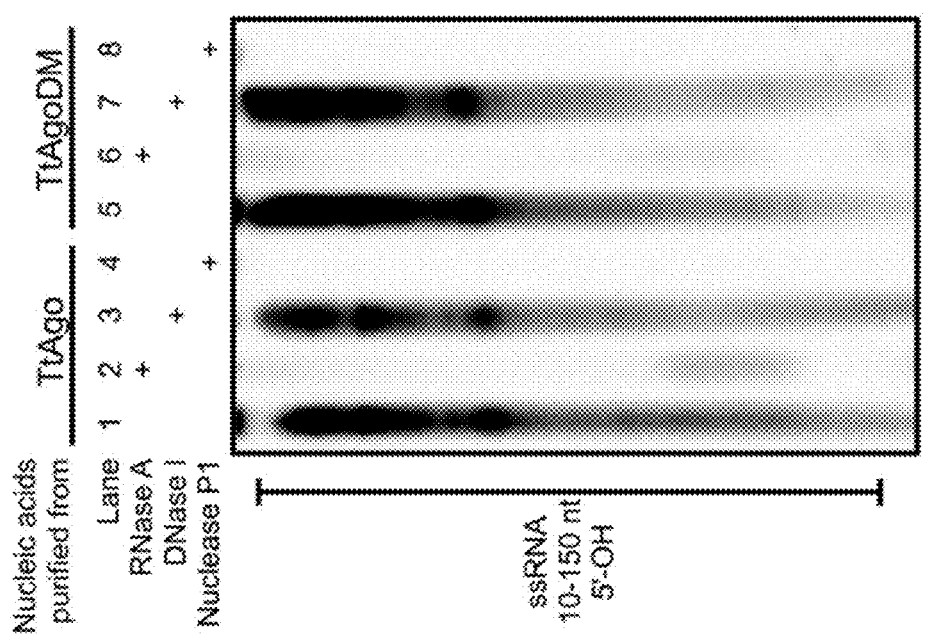

FIG. 32 shows 10-150-nucleotide (nt) RNA with 5'-OH group co-purification with TtArgonaute. 15% denaturing polyacrylamide gels with nucleic acids co-purified with TtArgonaute and TtArgonauteDM. Nucleic acids are phosphorylated in a T4 PNK forward reaction (5'-OH groups, and to a lesser extend 5'-P groups, are labelled) using [γ-$^{32}$P] ATP, and resolved on 15% denaturing polyacrylamide gels. Nucleic acids were not treated (lane 1, 5), RNaseA treated (lanes 2, 6), DNascI treated (lane 3, 7) or Nuclease P1 treated (lane 4, 8).

Figure 33:
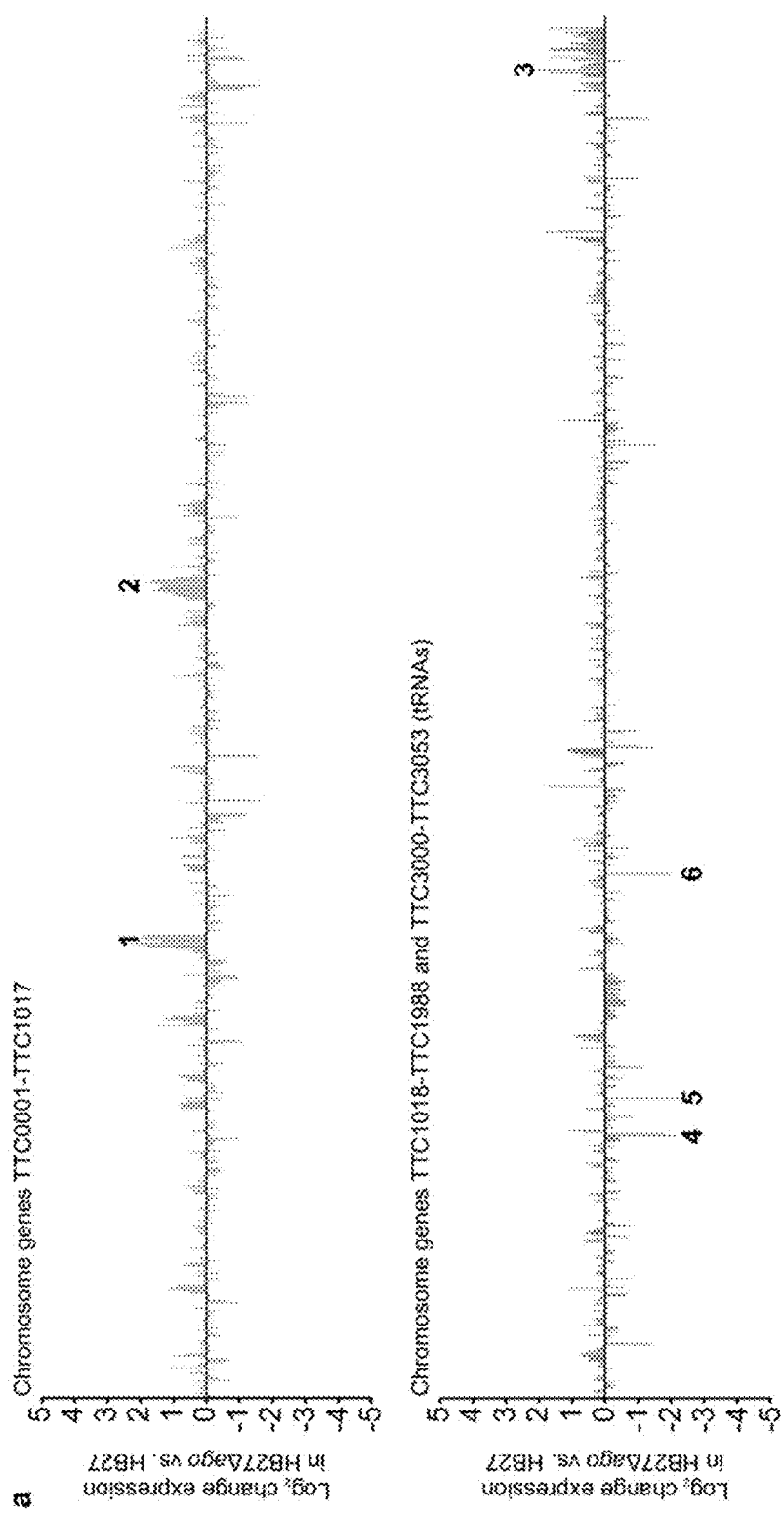
Figure 33:
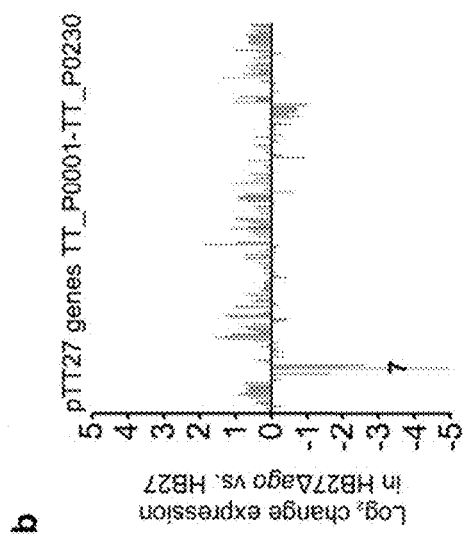

FIG. 33 shows changes in transcription of *T. thermophilus* genes after ago gene knockout. RNA-seq analysis was performed on biological triplicates for each strain. Change in gene expression of genes encoded on the chromosome (FIG. 33A) or on the megaplasmid (FIG. 33B) is shown as the $\log_2$ of the fold difference in. expression of the average of normalized mapped reads on that gene in HB27Δago compared with the average of normalized mapped reads on that gene in HB27. FIG. 33C exemplifies genes operons containing genes with a $\log_2$ expression change greater than 2 or −2.

Figure 34:
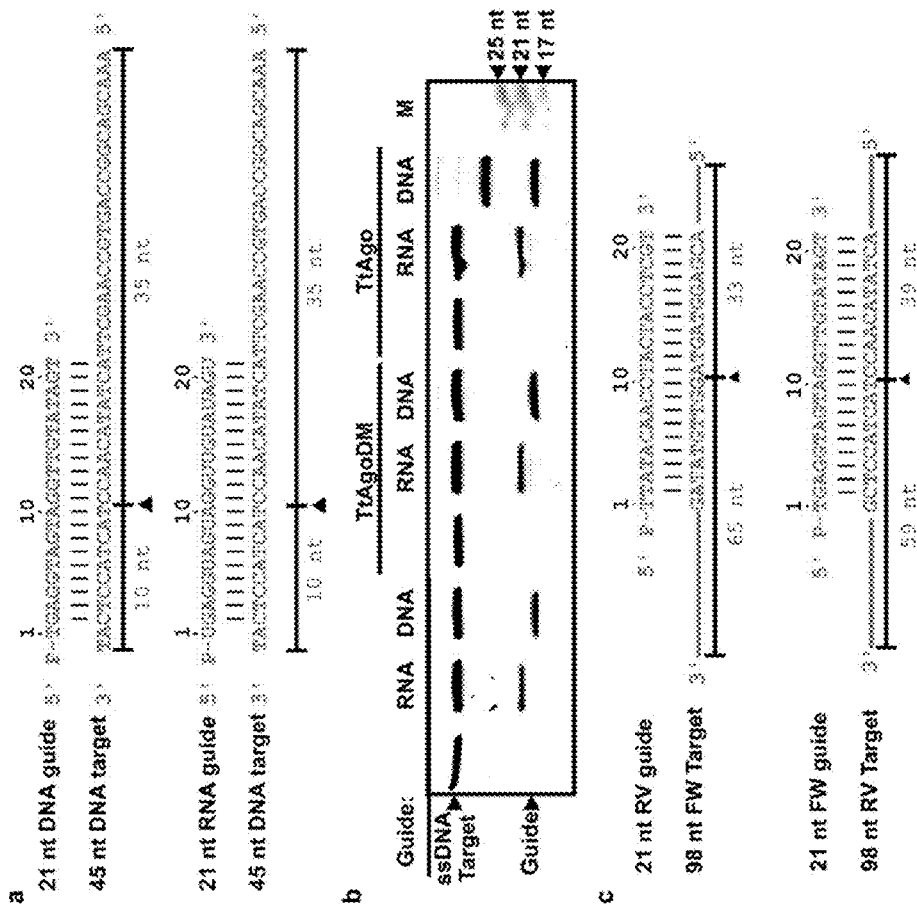
Figure 34:
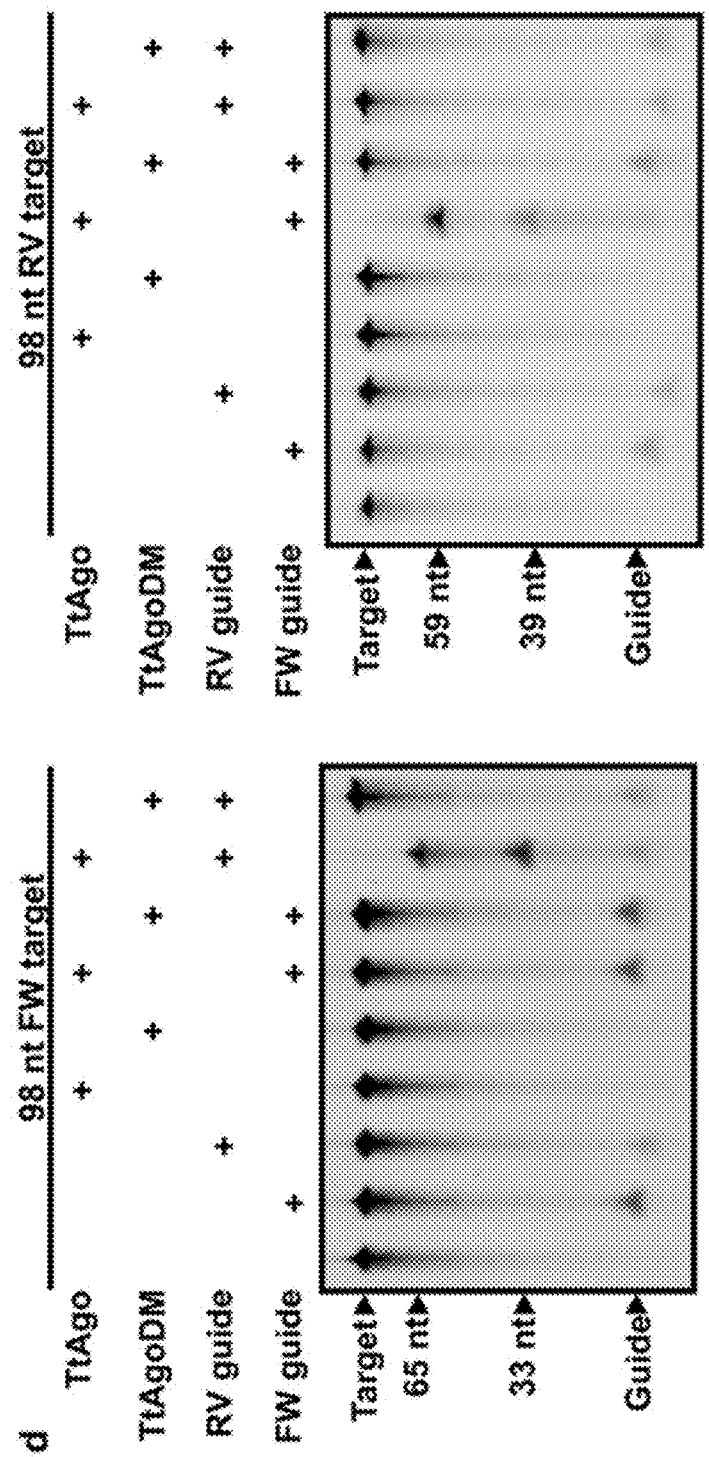

FIG. 34 depicts TtArgonaute cleavage of ssDNA Using ssDNA guides. FIG. 34A shows 21-nucleotide (nt) DNA and RNA guides can be complementary to the 45-nucleotide DNA targets. Predicted cleavage positions are indicated with a black triangle. FIG. 34A discloses SEQ ID NOS 21, 86-87 and 86, in order. FIG. 34B shows a 20% denaturing polyacrylamide gel loaded with samples in which TtArgonaute and TtArgonauteDM were provided with an RNA or an DNA guide to cleave a 45-nucleotide ssDNA target. FIG. 34C shows that 21-nucleotide RV and FW DNA guides are complementary to the 98-nucleotide ssDNA targets. Predicted cleavage positions are indicated with a black triangle. FIG. 34C discloses SEQ ID NOS 22, 91,21 and 88, in order. FIG. 34D shows 98-nucleotide ssDNA targets incubated with TtArgonaute and TtArgonauteDM, provided with complementary and non-complementary DNA guides, and resolved on 15% denaturing polyacrylamide gels.

Figure 35:
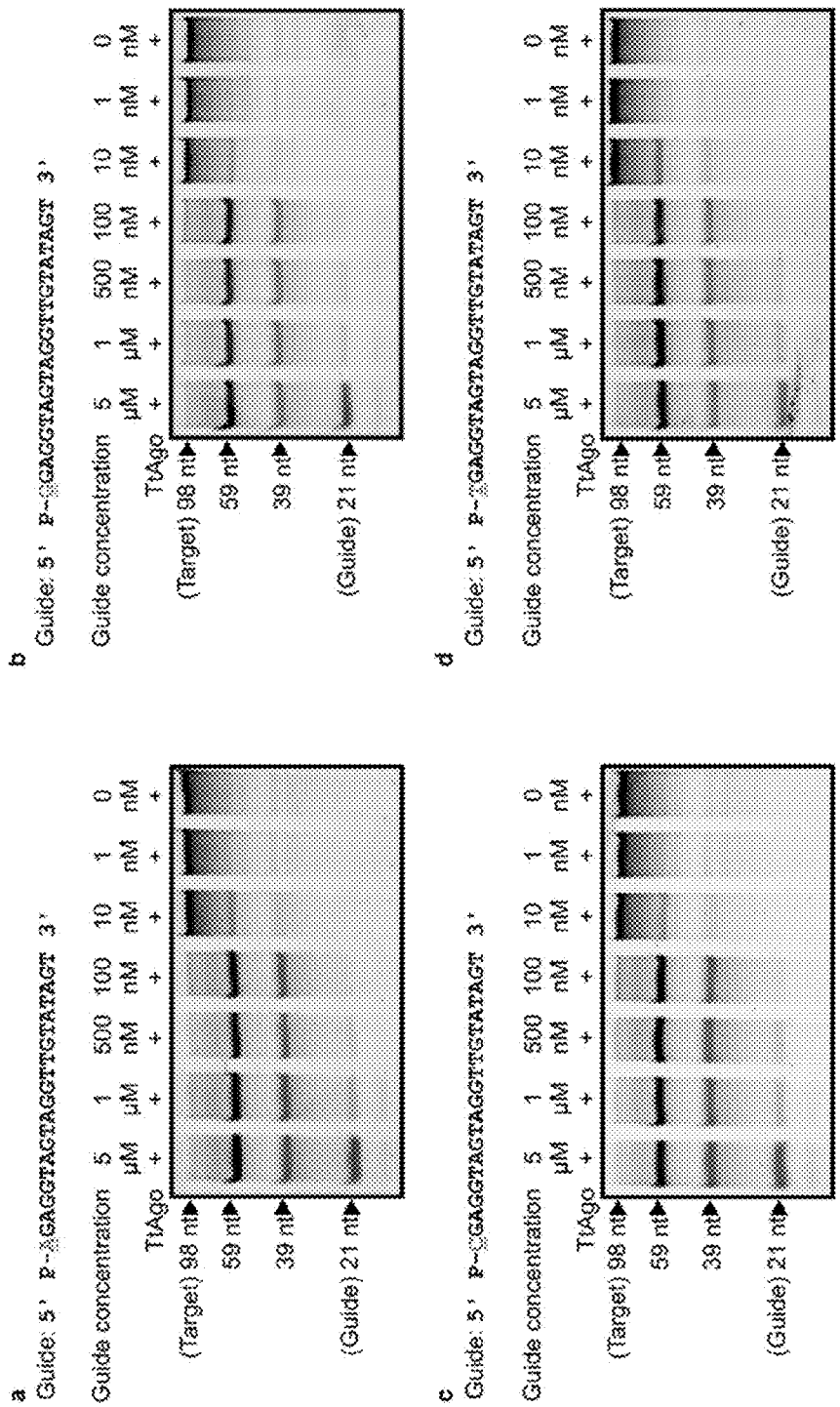
Figure 35:
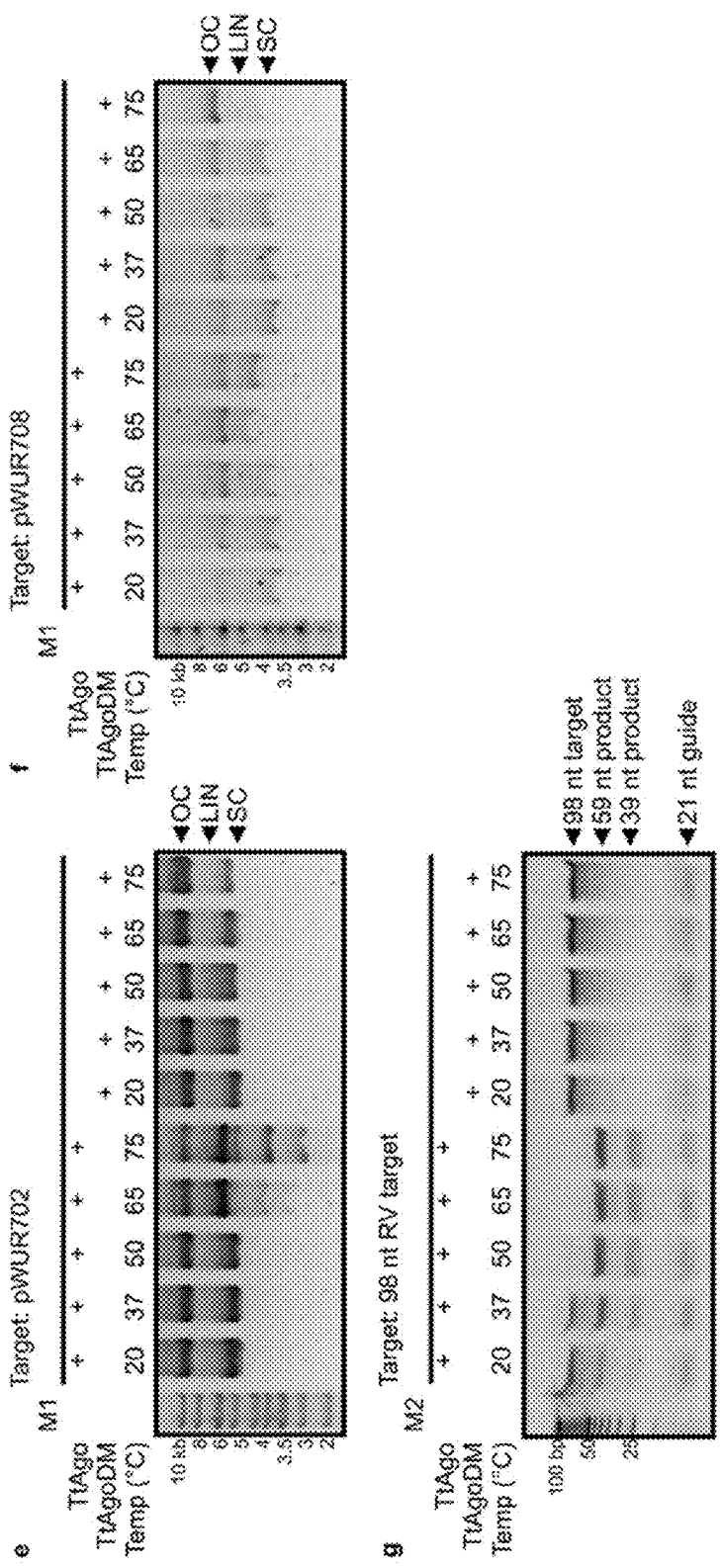

FIG. 35 exemplifies the effect of variation of the 5'-end deoxynucleoside of the siDNA and effect of the temperature on TtArgonaute cleavage efficiency. FIG. 35A-D show cleavage of 98-nucleotide ssDNA target (FIG. X3Nc) by TtArgonaute loaded with complementary siDNAs containing a different 5' deoxynucleoside, as shown in red. The concentrations of each siDNA were varied (indicated on top of the gels). Products of the reaction were resolved on 15% denaturing polyacrylamide gels. FIG. 35A-D discloses SEQ ID NOS 31, 92-93 and 21, in order. FIG. 35E shows a TtArgonaute expression plasmid pWUR702 (no guides added) incubated with TtArgonaute and TtArgonauteDM at different temperatures. FIG. 35F, pWUR708 plasmid (FW and RV guides added; FIG. X4Nb) incubated with TtArgonaute and TtArgonauteDM at different temperatures, resolved on 0.8% agarose gels. LIN, linear; M1, 1 kb Generuler marker (Fermentas): OC, open circular; SC, supercoiled. FIG. 35G, 98-nucleotide RV target cleavage (FW guide added) incubated with TtArgonaute and TtArgonauteDM at different temperatures, resolved on a 15% denaturing acrylamide gel, M2, O'RangeRuler 5 bp DNA Ladder (Thermo Scientific).

Figure 36:
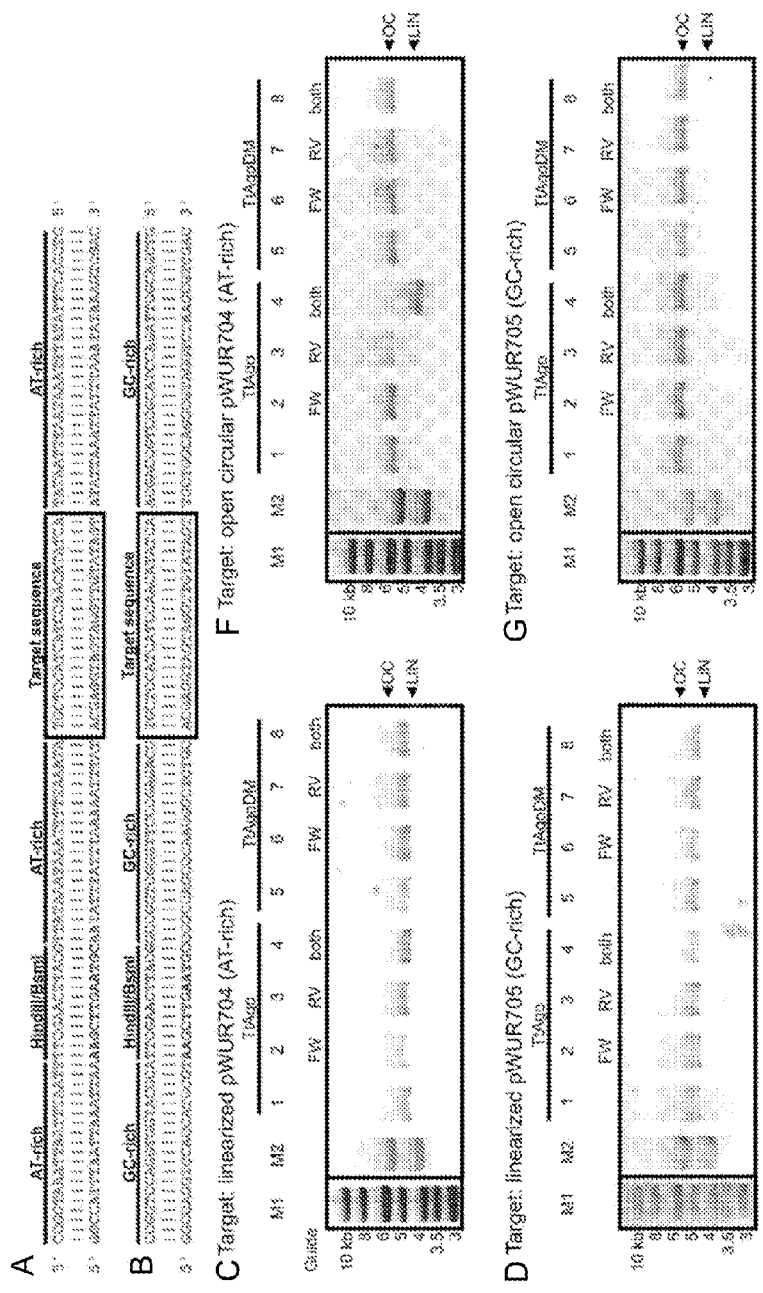
Figure 36:
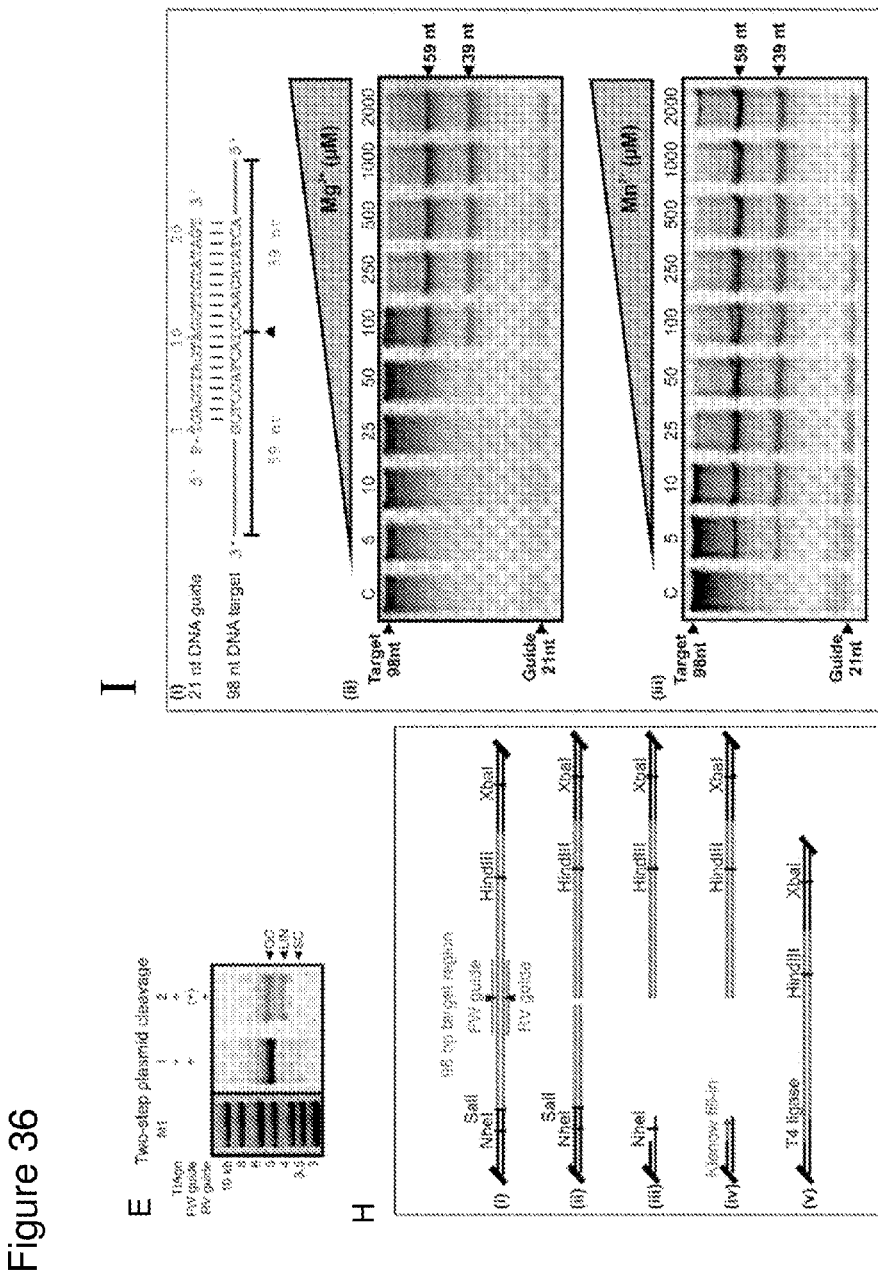

FIG. 36 shows activity analyses of TtArgonaute. FIGS. 36A and B shows an AT-rich (17% GC) insert of pWUR704 (FIG. 36A) and GC-rich insert (59% GC) of pWUR705 (FIG. 36B), The target sequence is boxed. Restriction sites HindIII BsmI are indicated in grey. Sequences are displayed in the 3'-5' direction to allow comparison with FIG. 36B which shows guide base pairing to this sequence. FIGS. 36A-B discloses SEQ ID NOS 94-97, in order. FIGS. 36C and D exemplify SpeI-linearized plasmid pWUR704 (FIG. 36C) and pWUR705 (FIG. 36D) incubated with TtArgouaute-siDNA and TtArgonauteDM—siDNA complexes targeting both strands of the plasmid, and resolved on 0.8% agarose gets. LIN, linear; M1, 1 kb Generuler marker (Fermentas); M2, open circular and linearized pWUR704 (FIG. 36C), or open circular and linearized: pWUR705 (FIG. 36D); OC, open circular. FW guide: BG3466. RV guide; BG4017. High salt concentration (250 mM NaCl) in the reaction buffer cause the TtArgonaute-treated samples to run higher in the gel than M1 and M2. FIG. 36K exemplifies two-step plasmid cleavage. Target pWUR704 was first nicked by a TtArgonaute—siDNA complex targeting the first strand (FW guide, lane 1), after which a TtArgonaute—siDNA complex targeting the other strand was added (RV guide, lane 2). FW guide is still present, and its presence is therefore indicated as (+). LIN, linear; M1, 1 kb Generuler marker (Fermentas): OC open circular; SC, supercoiled. f, g, Nb. FIGS. 36F and 36G show BsmI-nicked plasmid pWUR704 (FIG. 36F) and pWUR705 (FIG. 36G) incubated with TtArgonaute—siDNA and TtArgonauteDM—siDNA complexes targeting the un-nicked strands of the plasmid (33 bp away from the nicking site), and resolved on 0.8% agarose gels. LIN, linear; M1, 1 kb Generuler marker (Fermentas); M2, open circular and linearized pWUR704, or open circular and linearized pWUR705; OC open circular. High salt concentrations (250 mM NaCl) in the reaction buffer cause the TtArgonaute-treated samples to run higher in the gel than M1 and M2. FIG. 36H shows TtArgonaute dsDNA cleavage site analysis, (i) Plasmid pWUR704 with TtArgonaute—siDNA target sequences. Predicted cleavage sites are indicated with black triangles, (ii) pWUR704 was linearized using TtArgonaute—siDNA complexes targeting the plasmid on both strands, (iii) The linearized plasmid was cleaved using either NheI (as shown) or XbaI (not shown), (iv) Restriction site overhangs and possible overhangs resulting from TtArgonaute—siDNA cleavage were filled using Klenow fragment, polymerase (Fermentas). (v) Blunt-end DNA. was ligated using T4 DNA ligase (Fermentas), after which the plasmid could be transformed and later sequenced to determine the cleavage site. Sequences revealed that TtArgonaute siDNA complexes indeed cleaved the target at the predicted locations (as shown in a), and are shown in more detail in FIG. 30B and FIG. 36A-B. Note that in this picture target sequences are displayed in reversed order compared with FIG. 30B and FIG. 36A, B, I. TtArgonaute prefers $Mn^{2+}$ over $Mg^{2+}$ as a divalent cation for cleavage, (i) 21-nucleotide DNA guide and 98-nucleotide ssDNA target used. The predicted cleavage site is indicated with a black triangle, (ii) 98-nucleotide ssDNA target cleavage reaction with TtArgonaute loaded with a 21-nucleotide siDNA in the presence of increasing concentrations of $Mg^{2+}$, as indicated on top of the gel. (iii) 98-nucleotide ssDNA target cleavage reaction with TtArgonaute loaded with a 21-nucleotide siDNA in the presence of increasing concentrations of $Mn^{2+}$, as indicated. Samples were resolved on 15% denaturing polyacrylamide gels. FIG. 36I discloses SEQ ID NOS 21 and 88, in order.

FIG. 37 depicts the expression profiles of *T. thermophilus* genes involved in competence and host defense.

FIG. 38 depicts mass spectrometry data of identified protein (SEQ ID NOS 98-111, in order) after Strep(II)-tag affinity purification.

FIG. 39 shows that TtAgo acquires designed nucleic acid-targeting nucleic acids from plasmid DNA.

Figures 40A, 40B:
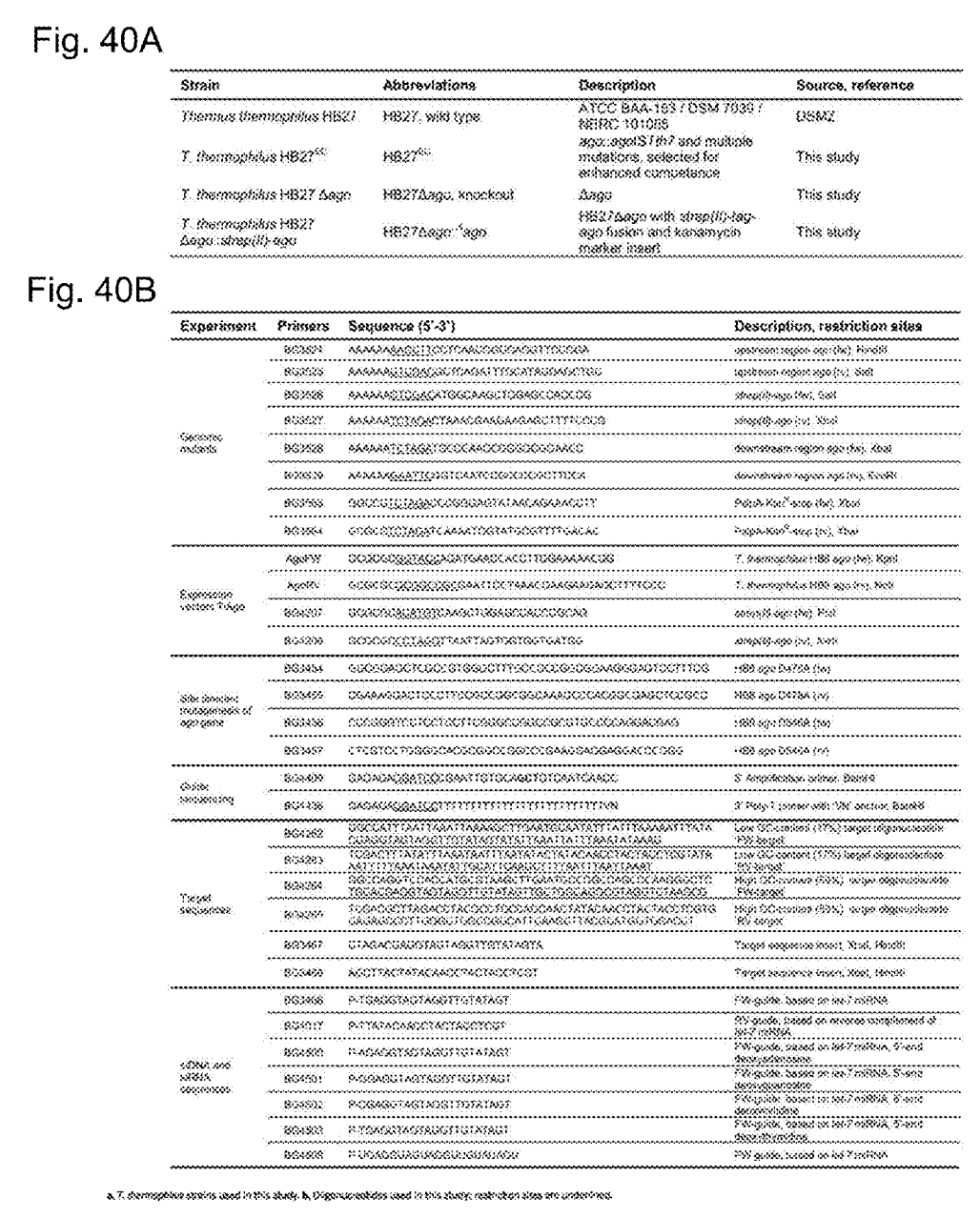

FIG. 40A and B list exemplary strains and oligonucleotides (SEQ ID NOS 1-12, 112, 14-16, 113-114, 17-20, 115-116, 21-22, 31, 92-93, 21 and 87, in order) used in the methods of the disclosure.

FIG. 41 lists exemplary plasmids used in the methods of the disclosure.

FIGS. 42A-H list exemplary sequences (SEQ ID NOS 117-124, in order) of Argonautes from exemplarly prokaryotes *Halogeometricum borinquense, Anoxybacillus flavithertmis, Archaeoglobus fulgidus, Pyrococcus furiosus, Aquifex acotieus, Thermus thermophilus.*

Figure 43:
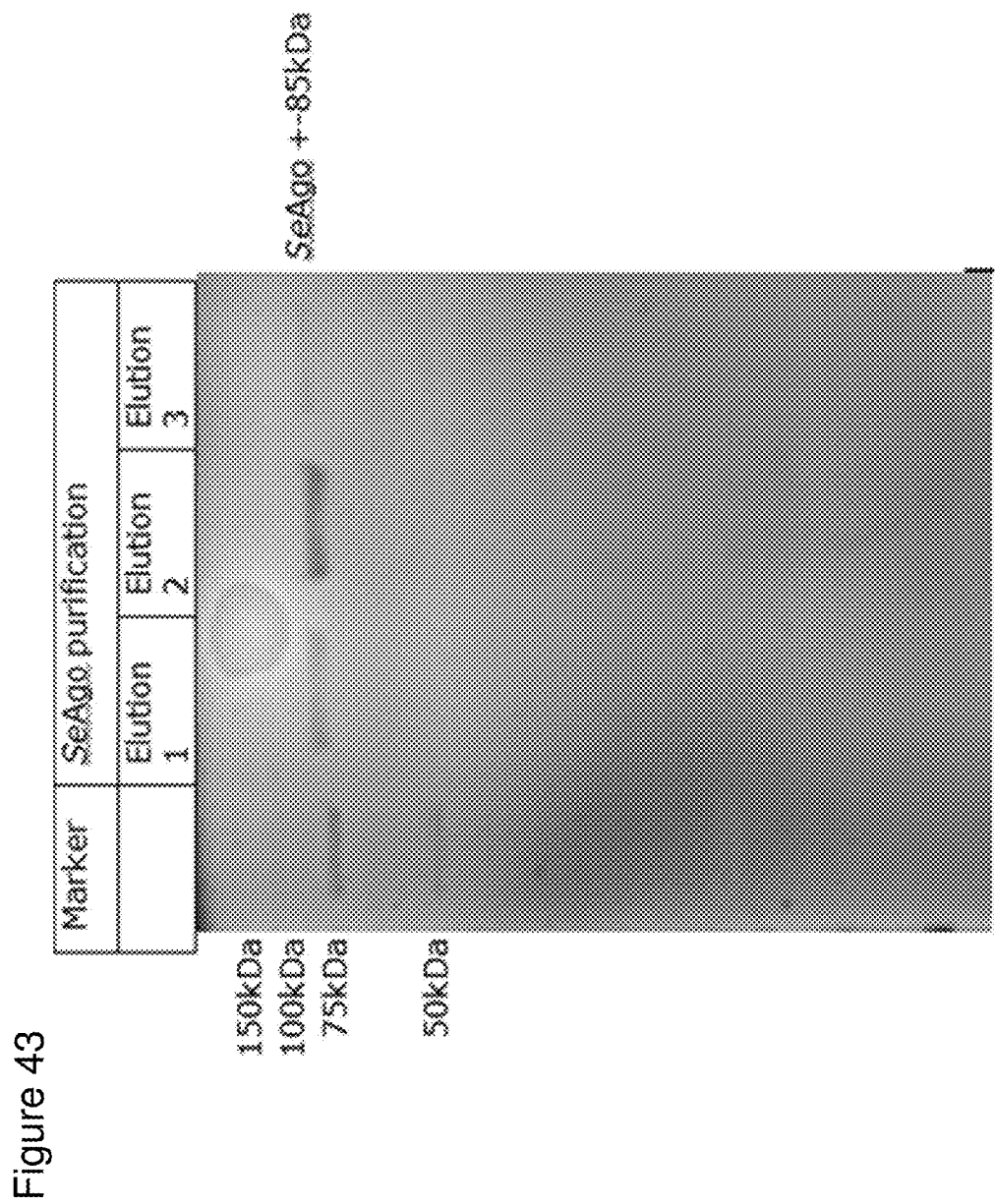

FIG. 43 depicts the results of affinity purification of *S. elongatus* Argonaute.

Figure 44:
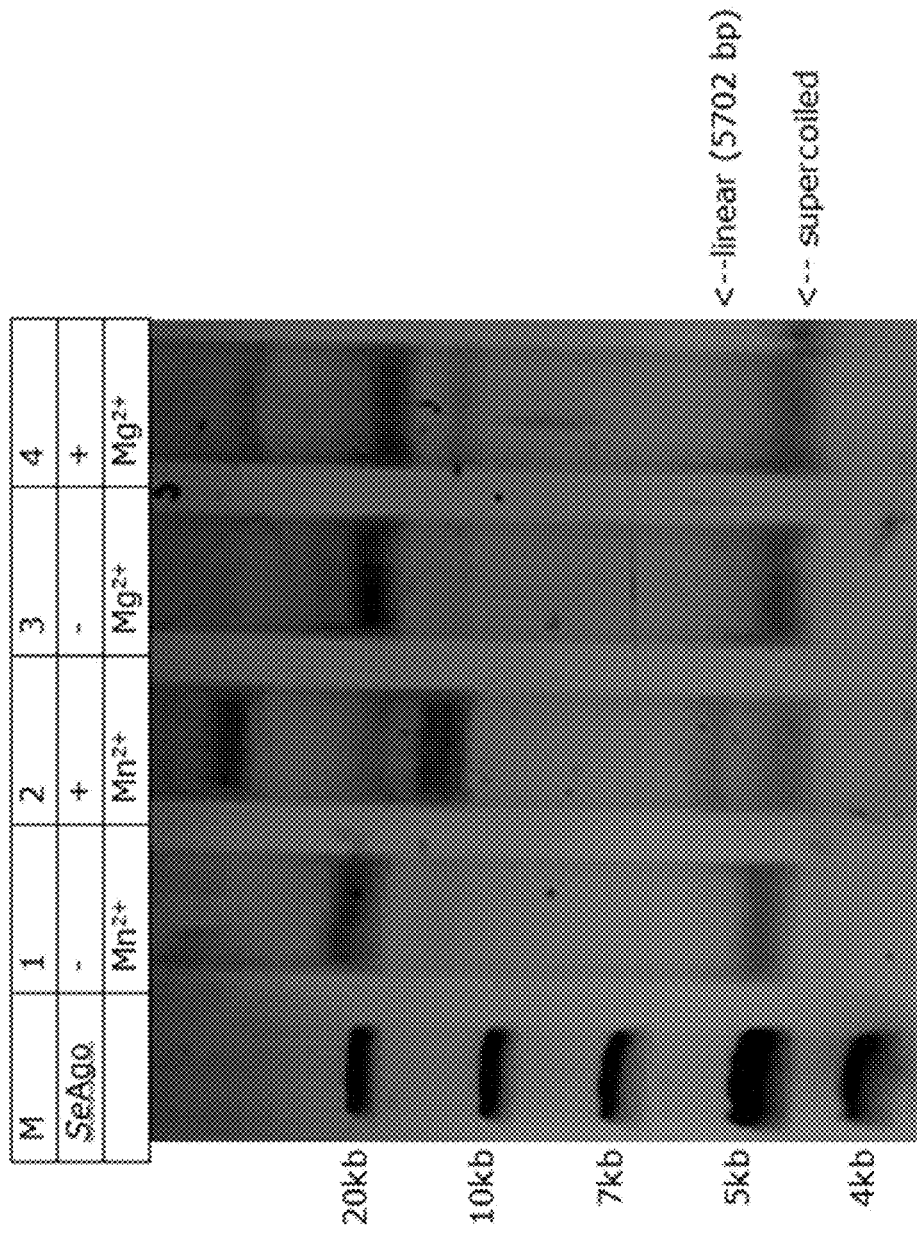

FIG. 44 illustrates activity analysis of S. elongatus Argonaute on a double-stranded DNA target.

Figure 45:
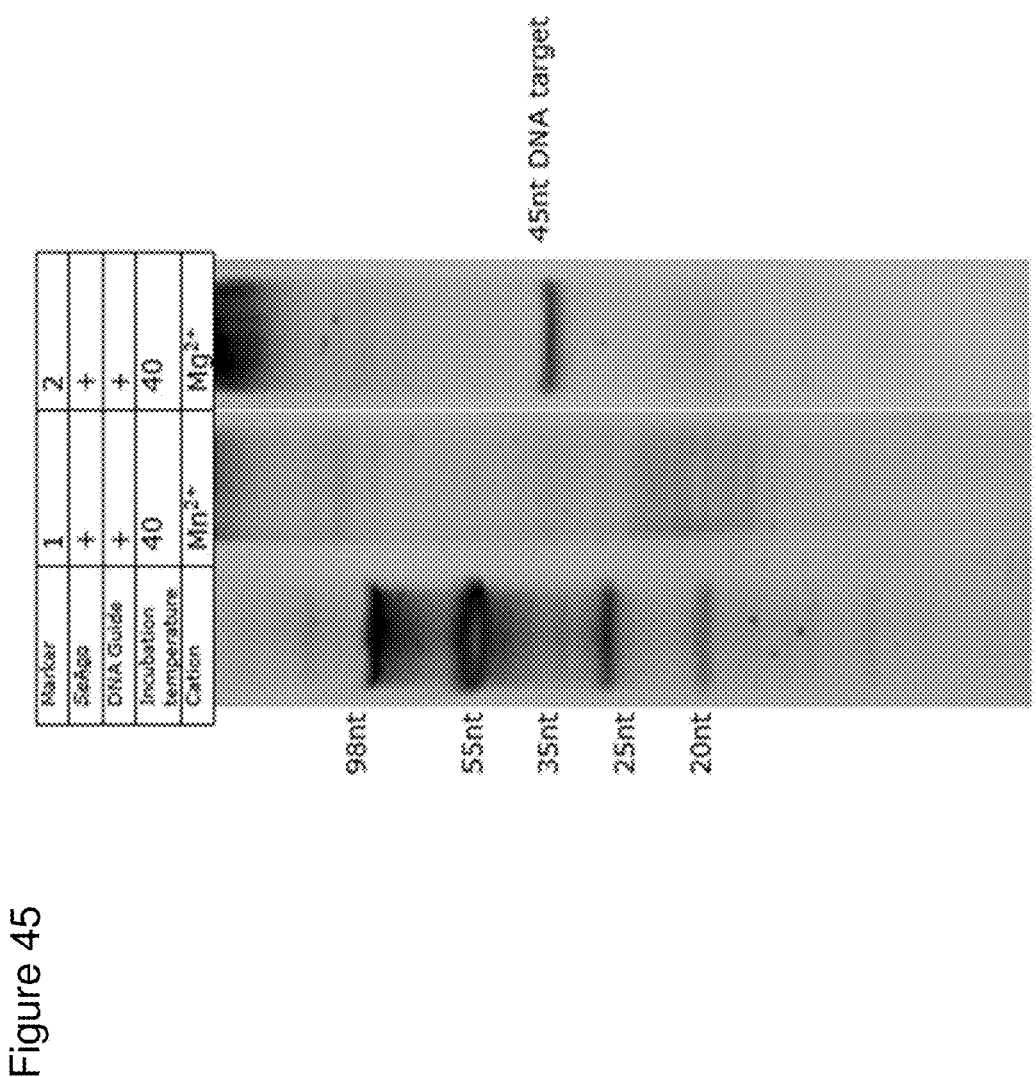

FIG. 45 illustrates activity analysis of S. elongatus Argonaute on a single-stranded DNA target.

FIG. 46 depicts an exemplary Argonaute sequence from S. elongatus. (SEQ ID NO: 125.)

DETAILED DESCRIPTION

Definitions

As used herein, unless otherwise specified, "Argonaute" and "pArgonaute" are interchangeable and can generally refer to a polypeptide with at least about 5%, 10%, 20%, 30%. 40%, 50%. 60%, 70%, 80%, 90%, 95%, or 100% sequence identity and/or sequence similarity to a wild type exemplary Argonaute polypeptide (e.g., Argonaute from *T. thermophilus* or *S. elongatus*, FIG. 42B, FIG. 46). Argonaute can generally refer to can refer to a polypeptide with at most about 5%, 10%, 20%, 30%, 40%, 50%, 60%, 70%, 80%, 90%, 95%, or 100% sequence identity and/or sequence .similarity to a wild type exemplary Argonaute polypeptide (e.g., e.g., Argonaute from *T. thermophilus* or *S. elongatus*, FIG. 42B, FIG. 46). Argonaute can refer to the wildtype or a modified form of the Argonaute protein that can comprise m amino acid change such as a deletion, insertion, substitution, variant, mutation, fusion, chimera, or any combination thereof.

An Argonaute can refer to any modified (e.g., shortened, mutated, lengthened) polypeptide sequence or homologue of the Argonaute. An Argonaute can be codon optimized. An Argonaute can be a codon-optimized homologue of an Argonaute. An Argonaute can be enzymatically inactive, partially active, constitutively active, fully active, inducibly active and/or more active, (e.g. more than the wild type homologue of the protein or polypeptide.). In some instances, the Argonaute (e.g., variant, mutated, and/or enzymatically inactive Argonaute) can target a target nucleic acid. The Argonaute (e.g., variant, mutated, and/or enzymatically inactive) can target doubles stranded DNA.

As used herein, "affinity tag" can refer to either a peptide affinity tag or a nucleic acid affinity tag. Affinity tag generally refer to a protein or nucleic acid sequence that can be bound to a molecule (e.g., bound by a small molecule, protein, covalent bond). An affinity tag can be a non-native sequence. A peptide affinity lag can comprise a peptide. A peptide affinity tag can be one that is able to be part of a split system (e.g., two inactive peptide fragments can combine together in trans to form an active affinity tag). A nucleic acid affinity tag can comprise a nucleic acid. A nucleic acid affinity tag can be a sequence that can selectively bind to a known nucleic acid sequence (e.g. through hybridization), A nucleic acid affinity tag can be a sequence that can selectively bind to a protein. An affinity tag can be fused to a native protein. An affinity tag can be fused to a nucleotide sequence. Sometimes, one, two, or a plurality of affinity tags can be fused to a native protein or nucleotide sequence. An affinity tag can be introduced into a designed nucleic acid-targeting nucleic acid using methods of in vitro or in vivo transcription. Nucleic acid affinity rags can include, for example, a chemical tag, an RNA-binding protein binding sequence, a DNA-binding protein binding sequence, a sequence hybridizable to an affinity-tagged polynucleotide, a synthetic RNA aptamer, a synthetic DNA aptamer, or an aptazyme. Examples of chemical nucleic acid affinity lags can include, but are not limited to, nucleotriphosphates containing biotin, fluorescent dyes, and digoxeginin. Examples of protein-binding nucleic acid affinity tags can include, but are not limited to, restriction endonuclease binding sequences, trancription factor binding sequences, zinc finger binding sequences, TALEN binding sequences, or any sequence recognized by a DNA binding protein. Examples of protein-binding nucleic acid affinity tags can include, but are not limited to, the MS2 binding sequence, the U1A binding sequence, stem-loop binding protein sequences, the boxB sequence, the eIF4A sequence, or any sequence recognized by an RNA binding protein. Examples of nucleic acid affinity-tagged oligonucleotides can include, but are not limited to, biotinylated oligonucleotides, 2,4-dinitrophenyl oligonucleotides, fluorescein oligonucleotides, and primary amine-conjugated oligonucleotides.

A nucleic acid affinity tag can. be an RNA/DNA aptamer. Aptamers can include, aptamers that bind to theophylline, streptavidin, dextran B512, adenosine, guanosine. guanine/xanthine, 7-methyl-GTP, amino acid aptamers such as aptamers that bind to arginine, citrulline, valine, tryptophan, cyanocobalamine, N-methylmesoporphyrin IX, flavin, NAD, and antibiotic aptamers such as aptamers that bind to tobramycin, neomycin, lividomycin, kanamycin, streptomycin, viomycin, and chloramphenicol.

A nucleic acid affinity tag can comprise a DNA sequence that can be bound by an Argonaute. The DNA sequence can be bound by a protein containing a zinc finger domain, a TALE domain, or any other DNA-binding domain.

A nucleic acid affinity tag can comprise a ribozyme sequence. Suitable ribozymes can include peptidyl transferase 23S rRNA, RnaseP, Group I introns. Group II introns, G1R1 branching ribozyme, Leadzyme, hairpin ribozymes, hammerhead ribozymes, HDV ribozymes, CPEB3 ribozymes, VS ribozymes, glmS ribozyme, CoTC ribozyme, and synthetic ribozymes.

Peptide affinity tags can comprise tags that can be used for tracking or purification (e.g., a fluorescent protein, green fluorescent protein (GFP), YFP, RFP, CFP, mCherry, tdTomato, a his tag, (e.g., a 6XHis tag) (SEQ ID NO: 23), a hemagglutinin (HA) tag, a FLAG tag, a Myc tag, a GST tag, a MBP tag, and chitin binding protein tag, a calmodulin tag, a V5 tag, a streptavidin binding tag, and the like).

Both nucleic acid and peptide affinity tags can comprise small molecule tags such as biotin, or digitoxin, fluorescent label tags, such as for example, fluoroscein, rhodamin, Alexa fluor dyes, Cyanine3 dye, Cyanine5 dye.

Nucleic acid affinity tags can be located 5' to a nucleic acid (e.g., a designed nucleic acid-targeting nucleic acid). Nucleic acid affinity tags can be located 3' to a nucleic acid. Nucleic acid affinity tags can be located 5' and 3' to a nucleic acid. Nucleic acid affinity tags can be located within a nucleic acid. Peptide affinity tags can be located N-terminal to a polypeptide sequence. Peptide affinity tags can be located C-terminal to a polypeptide sequence. Peptide affinity tags can be located N-terminal and C-terminal to a polypeptide sequence. A plurality of affinity tags can be fused to a nucleic acid and/or a polypeptide sequence.

As used herein, "capture agent" can generally refer to an agent that can purify a polypeptide and/or a nucleic acid. A capture agent can be a biologically active molecule or material (e.g. any biological substance found in nature or synthetic, and includes but is not limited to cells, viruses, subcellular particles, proteins, including more specifically antibodies, immunoglobulins, antigens, lipoproteins, glycoproteins, peptides, polypeptides, protein complexes, (strept) avidin-biotin complexes, ligands, receptors, or small molecules, aptamers, nucleic acids, DNA, RNA, peptidic nucleic acids, oligosaccharides, polysaccharides, lipopolysccharides, cellular metabllites, haptens, pharmacologically active substances, alkaloids, steroids, vitamins, amino acids, and sugures). In some embodiments, the capture agent can comprise an affinity tag. In some embodiments, a capture agent can preferentially bind to a target polypeptide or nucleic acid of interest. Capture agents can be free floating in a mixture. Capture agents can be bound to a particle (e.g. a bead, a microbead, a nanoparticle). Capture agents can be bound to a solid or semisolid surface. In some instances, capture agents are irreversibly bound to a target. In other instances, capture agents are reversibly bound to a target (e.g. if a target can be eluted, or by use of a chemical such as imidizole).

As used herein, a "cell" can generally refer to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatos, rice, cassava, sugarcane, pumpkin, hay, potatos, cotton, cannabis, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. Agardh*, and the like), seaweeds (e.g. kelp) a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not orginating from a natural organism (e.g. a cell can be a synthetically made, sometimes termed an artificial cell).

A cell can be in vitro. A cell can be in vivo. A cell can be an isolated cell. A cell can be a cell inside of an organism. A cell can be an organism. A cell can be a cell in a cell culture. A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell.

A cell can be a stem cell or progenitor cell. Cells can include stem cells (e.g., adult stem cells, embryonic stem cells, iPS cells) and progenitor cells (e.g., cardiac progenitor cells, neural progenitor cells, etc.). Cells can include mammalian stem cells and progenitor cells, including rodent stem cells, rodent progenitor cells, human stem cells, human progenitor cells, etc. Clonal cells can comprise the progeny of a cell. A cell can comprise a target nucleic acid. A cell can be in a living organism. A cell can be a genetically modified cell. A cell can be a host cell.

A cell can be a totipotent stem cell, however, in some embodiments of this disclosure, the term "cell" may be used but may not refer to a totipotent stem cell. A cell can be a plant cell, but in some embodiments of this disclosure, the term "cell" may be used but may not refer to a plant cell. A cell can be a pluripotent cell. For example, a cell can be a pluripotent hematopoietic cell that can differentiate into other cells in the hematopoietic cell lineage but may not be able to differentiate into any other non-hematopoetic cell. A cell may be able to develop into a whole organism. A cell may or may not be able to develop into a whole organism. A cell may be a whole organism.

A cell can be a primary cell. For example, cultures of primary cells can be passaged 0 times, 1 time, 2 times, 4 times, 5 times, 10 times, 15 times or more. Cells can be unicellular organisms. Cells can be grown in culture.

A cell can be a diseased cell. A diseased cell can have altered metabolic, gene expression, and/or morphologic features. A diseased cell can be a cancer cell, a a diabetic cell, and a apoptotic cell. A diseased cell can be a cell from a diseased subject. Exemplary diseases can include blood disorders, cancers, metabolic disorders, eye disorders, organ disorders, musculoskeletal disorders, cardiac disease, and the like.

If the cells are primary cells, they may be harvested from an individual by any method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

As used herein, "designed nucleic acid-targeting nucleic acid" or "designed nucleic acid-targeting nucleic acid" can refer to a nucleic acid that can bind an Argonaute protein of the disclosure and hybridize with a target nucleic acid. A designed nucleic acid-targeting nucleic acid can be RNA. A designed nucleic acid-targeting nucleic acid can be DNA. A designed nucleic acid-targeting nucleic acid can be single-stranded DNA. A designed nucleic acid-targeting nucleic acid can be double-stranded DNA. The designed nucleic acid-targeting nucleic acid can bind to a target nucleic acid site-specifically. A portion of the designed nucleic acid-targeting nucleic acid can be complementary to a portion of a target nucleic acid. A designed nucleic acid-targeting nucleic acid can comprise a segment that can be referred to as a "nucleic acid-targeting segment." A designed nucleic acid-targeting nucleic acid can comprise a segment that can be referred to as a "protein-binding segment." The nucleic acid-targeting segment and the protein-binding segment can be the same segment of the designed nucleic acid-targeting nucleic acid.

A designed nucleic acid-targeting nucleic acid can comprise one or more modifications (e.g., a base modification, a backbone modification), to provide the nucleic acid with a new or enhanced feature (e.g., improved stability). A designed nucleic acid-targeting nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming designed nucleic acid-targeting nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within designed nucleic acid-targeting nucleic acids, the phosphate groups can commonly be referred to as forming the internucleoside backbone of the designed nucleic acid-targeting nucleic acid. The linkage or backbone of the designed nucleic acid-targeting nucleic acid can be a 3' to 5' phosphodiester linkage.

A designed acid-targeting nucleic acid can comprise a modified backbone and/or modified internucleoside linkages. Modified backbones can include those that retain a phosphorus atom in the backbone and those that do not have a phosphorus atom in the backbone.

Suitable modified designed nucleic acid-targeting nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage. Suitable designed nucleic acid-targeting nucleic acids having inverted polarity can comprise a single 3' to 3' linkage at the 3'-most internucleotide linkage (i.e. a single inverted nucleoside residue in which the nucleobase is missing or has a hydroxyl group in place thereof). Various salts (e.g., potassium chloride or sodium chloride), mixed salts, and free acid forms can also be included.

A designed nucleic acid-targeting nucleic acid can comprise one or more phosphorothioate and/or heteroatom internucleoside linkages, in particular —$CH_2$—NH—O—$CH_2$—, —$CH_2$—N($CH_3$)—O—$CH_2$— (i.e. a methylene (methylimino) or MMI backbone), —$CH_2$—O—N($CH_3$)—$CH_2$—, —$CH_2$—N($CH_3$)—N($CH_3$) —$CH_2$— and —O—N($CH_3$)—$CH_2$—$CH_2$— (wherein the native phosphodiester internucleotide linkage is represented as —O—P(=O)(OH)—O—$CH_2$—).

A designed nucleic acid-targeting nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A designed nucleic acid-targeting nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A designed nucleic acid-targeting nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A designed nucleic acid-targeting nucleic acid can comprise linked morpholino units (i.e. morpholino nucleic acid) having heterocyclic bases attached to the morpholino ring Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of designed nucleic acid-targeting nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2—), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'- exonucleolytic degradation and good solubility properties.

A designed nucleic acid-targeting nucleic acid can comprise one or more substituted sugar moieties. Suitable polynucleotides can comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are O((CH2)nO) mCH$_3$, O(CH$_2$)$_n$OCH$_3$, O(CH$_2$)$_n$NH2, O(CH$_2$)$_n$CH$_3$, O(CH$_2$)$_n$ONH$_2$, and O(CH$_2$)$_n$ON((CH$_2$)$_n$ CH$_3$)$_2$, where n and m are from 1 to about 10. A sugar substituent group can be selected from: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an designed nucleic acid-targeting nucleic acid, or a group for improving the pharmacodynamic properties of an designed nucleic acid-targeting nucleic acid, and other substituents having similar properties. A suitable modification can include 2'-methoxyethoxy (2'—O—CH$_2$ CH$_2$OCH$_3$, also known as 2'—O—(2-methoxyethyl) or 2'- MOE i.e., an alkoxyalkoxy group). A further suitable modification can include 2'-dimethylaminooxyethoxy, (i.e., a O(CH$_2$)$_2$ON(CH$_3$)$_2$ group, also known as 2'-DMAOE), and 2'- dimethylaminoethoxyethoxy (also known as 2'—O-dimethyl-amino-ethoxy-ethyl or 2'-DMAEOE), i.e., 2'—O—CH2—O—CH$_2$—N(CH$_3$)$_2$.

Other suitable sugar substituent groups can include methoxy (—O—CH$_3$), aminopropoxy (—O CH$_2$ CH$_2$ CH$_2$NH$_2$), allyl (—CH$_2$—CH=CH$_2$), —O-allyl (—O—CH$_2$—CH=CH$_2$) and fluoro (F). 2'-sugar substituent groups may be in the arabino (up) position or ribo (down) position. A suitable 2'- arabino modification is 2'-F. Similar modifications may also be made at other positions on the oligomeric compound, particularly the 3' position of the sugar on the 3' terminal nucleoside or in 2'-5' linked nucleotides and the 5' position of 5' terminal nucleotide. Oligomeric compounds may also have sugar mimetics such as cyclobutyl moieties in place of the pentofuranosyl sugar.

A designed nucleic acid-targeting nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2- propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8- substituted adenines and guanines, 5-halo particularly 5-bromo, 5-trifluoromethyl and other 5- substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido (5,4-b)(1,4)benzothiazin-2(3H)-one), G-clamps such as a substituted phenoxazine cytidine (e.g. 9-(2-aminoethoxy)-H-pyrimido(5,4-b) (1,4) benzoxazin-2(3H)-one), carbazole cytidine (2H-pyrimido(4, 5-b)indo1-2-one), pyridoindole cytidine (Hpyrido(3',2':4,5) pyrrolo(2,3-d)pyrimidin-2-one).

Heterocyclic base moieties can include those in which the purine or pyrimidine base is replaced with other heterocycles, for example 7-deaza-adenine, 7-deazaguanosine, 2-aminopyridine and 2-pyridone. Nucleobases can be useful for increasing the binding affinity of a polynucleotide compound. These can include 5-substituted pyrimidines, 6-azapyrimidines and N-2, N-6 and O-6 substituted purines, including 2-aminopropyladenine, 5- propynyluracil and 5-propynylcytosine. 5-methylcytosine substitutions can increase nucleic acid duplex stability by 0.6-1.2° C. and can be suitable base substitutions (e.g., when combined with 2'-O-methoxyethyl sugar modifications).

A modification of a designed nucleic acid-targeting nucleic acid can comprise chemically linking to the designed nucleic acid-targeting nucleic acid one or more moieties or conjugates that can enhance the activity, cellular distribution or cellular uptake of the designed nucleic acid-targeting nucleic acid. These moieties or conjugates can include conjugate groups covalently bound to functional groups such as primary or secondary hydroxyl groups. Conjugate groups can include, but are not limited to, intercalators, reporter molecules, polyamines, polyamides, polyethylene glycols, polyethers, groups that enhance the pharmacodynamic properties of oligomers, and groups that can enhance the pharmacokinetic properties of oligomers. Conjugate groups can include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that can enhance the pharmacokinetic properties include groups that improve uptake, distribution, metabolism or excretion of a nucleic acid. Conjugate moieties can include but are not limited to lipid moieties such as a cholesterol moiety, cholic acid a thioether, (e.g., hexyl-S-tritylthiol), a thiocholesterol, an aliphatic chain (e.g., dodecandiol or undecyl residues), a phospholipid (e.g., di-hexadecyl-rac-glycerol or triethylammonium 1,2-di-O-hexadecyl-rac-glycero-3-H-phosphonate), a polyamine or a polyethylene glycol chain, or adamantanc acetic acid, a palmityl moiety, or an octadecylamine or hexylamino-carbonyl-oxycholesterol moiety.

A modification, may include a "Protein Transduction Domain" or PTD (i.e. a cell penetrating peptide (CPP)). The PTD can refer to a polypeptide, polynucleotide, carbohydrate, or organic or inorganic compound that facilitates traversing a lipid bilayer, micelle, cell membrane, organelle membrane, or vesicle membrane. A PTD can be attached to another molecule, which can range from a small polar molecule to a large macromolecule and/or a nanoparticle, and can facilitate the molecule traversing a membrane, for example going from extracellular space to intracellular space, or cytosol to within an organelle. A PTD can be covalently linked to the amino terminus of a polypeptide. A PTD can he covalently linked to the carboxyl terminus of a polypeptide. A PTD can be covalently linked to a nucleic acid. Exemplary PTDs can include, but are not limited to, a minimal peptide protein transduction domain; a polyarginine sequence comprising a number of arginines sufficient to direct entry into a cell (e.g., 3, 4, 5, 6, 7, 8,9, 10, or 10-50 arginines (SEQ ID NO: 25)), a VP22 domain, a *Drosophila* Antennapedia protein transduction domain, a truncated human calcitonin peptide, polylysine, and transportan, arginine homopolymer of from 3 arginine residues to 50 arginine residues (SEQ ID NO: 25). The PTD can be an activatable CPP (ACPP). ACPPs can comprise a polycationic CPP (e.g., Arg9 or "R9" (SEQ ID NO: 26)) connected via a cleavable linker to a matching polyanion (e.g., Glu9 or "E9" (SEQ ID NO: 27)), which can reduce the net charge to nearly zero and thereby inhibits adhesion and uptake into cells. Upon cleavage of the linker, the polyanion can he released, locally unmasking the polyarginine and its inherent adhesiveness, thus "activating" the ACPP to traverse the membrane.

As used herein, "donor polynucleotide" can refer to a nucleic acid that can be integrated into a site during genome engineering, target nucleic acid engineering, or during any other method of the disclosure.

As used herein, "endonuclease," "endonuclease domain" and "endonuclease activity" are interchangeable, unless otherwise specified.

As used herein, "fixative" or "cross-linker" can generally refer to an agent that can fix or cross-link cells. Fixed or cross-linking cells can stabilize protein-nucleic acid complexes in the cell. Suitable fixatives and cross-linkers can include, formaldehyde, glutaraldehyde, ethanol-based fixatives, methanol-based fixatives, acetone, acetic acid, osmium tetraoxide, potassium dichromate, chromic acid, potassium permanganate, mercurials, picrates, formalin, paraformaldehyde, amine-reactive NHS-ester crosslinkers such as bis[sulfosuccinimidyl] suberate (BS3), 3,3'-dithiobis [sulfosuccinimidylpropionate] (DTSSP), ethylene glycol bis [sulfosuccinimidylsuccinate (sulfo-EGS), disuccinimidyl glutarate (DSG), dithiobis[succinimidyl propionate] (DSP), disuccinimidyl suberate (DSS), ethylene glycol bis[succinimidylsuccinate] (EGS), NHS-ester/diazirine crosslinkers such as NHS-diazirine, NHS-LC-diazirine, NHS-SS-diazirine, sulfo-NHS-diazirine, sulfo-NHS-LC-diazirine, and sulfo-NHS-SS-diazirine.

As used herein, "fusion" can refer to a protein and/or nucleic acid comprising one or more non-native sequences (e.g., moieties). A fusion can comprise one or more of the same non-native sequences. A fusion can comprise one or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the Argonaute (e.g., a nuclear localization signal (NLS) for targeting to the nucleus, a mitochondrial localization signal for targeting to the mitochondria, a chloroplast localization signal for targeting to a chloroplast, an endoplasmic reticulum (ER) retention signal, and the like). A fusion can provide a non-native sequence (e.g., affinity tag) that can be used to track or purify. A fusion can be a small molecule such as biotin or a dye such as alexa fluor dyes, Cyanine3 dye, Cyanine5 dye. The fusion can provide for increased or decreased stability.

In some embodiments, a fusion can comprise a detectable label, including a moiety that can provide a detectable signal. Suitable detectable labels and/or moieties that can provide a detectable signal can include, but are not limited to, an enzyme, a radioisotope, a member of a specific binding pair; a fluorophore; a fluorescent protein; a quantum dot; and the like.

A fusion can comprise a member of a FRET pair. FRET pairs (donor/acceptor) suitable for use can include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5 and fluorescein/LC Red 705.

A fluorophore/quantum dot donor/acceptor pair can be used as a fusion. Suitable fluorophores ("fluorescent label") can include any molecule that may be detected via its inherent fluorescent properties, which can include fluorescence detectable upon excitation. Suitable fluorescent labels can include, but are not limited to, fluorescein, rhodamine, tetramethylrhodamine, eosin, erytkrosin, coumarin, methyl-coumarins, pyrene, Malacite green, stilbene, Lucifer Yellow, CASCADE BLUE™ label, Texas Red, IAEDANS, EDANS, BODIPY FL, LC Red 640, Cy 5, Cy 5.5, LC Red 705 and Oregon green.

A fusion can comprise an enzyme. Suitable enzymes can include, but are not limited to, horse radish peroxidase, luciferase, beta-galactosidase, and the like.

A fusion can comprise a fluorescent protein. Suitable fluorescent proteins can include, but are not limited to, a green fluorescent protein (GFP), (e.g., a GFP from *Aequoria victoria*, fluorescent proteins from *Anguilla japonica*, or a mutant or derivative thereof), a red fluorescent protein, a yellow fluorescent protein, any of a variety of fluorescent and colored proteins.

A fusion can comprise a nanoparticle. Suitable nanoparticles can include fluorescent or luminescent nanopartieles, and magnetic nanoparticles. Any optical or magnetic property or characteristic of the nanopartide(s) can be detected.

A fusion can comprise quantum dots (QDs). QDs can be rendered water soluble by applying coating layers comprising a variety of different materials. For example, QDs can be solubilized using amphiphilic polymers. Exemplary polymers that have been employed can include octylamine-modified low molecular weight polyacrylic acid, polyethylene-glycol (PEG)-derivatized phospholipids, polyanhydrides, block copolymers, etc. QDs can be conjugated to a polypeptide via any of a number of different functional groups or linking agents that can be directly or indirectly linked to a coating layer. QDs with a wide variety of absorption and emission spectra are commercially available, e.g., from Quantum Dot Corp. (Hayward Calif.; now owned by Invitrogen) or from Evident Technologies (Troy, N.Y.). For example, QDs having peak emission wavelengths of approximately 525, 535, 545, 565, 585, 605, 655, 705, and 800 nm are available. Thus the QDs can have a range of different colors across the visible portion of the spectrum and in some cases even beyond.

A fusion can comprise a radioisotope. Suitable radioisotopes can include, but are not limited to $^{14}C$, $^{3}H$, $^{32}P$, $^{33}P$, $^{35}S$, and $^{125}I$.

A fusion can comprise a helicase, a nuclease (e.g. FokI), a nuclease-helicase (e.g. Cas3), a DNA methyltransferase (e.g. Dam), or DNA demethylase, a histone methyltransferase, a histone demethylase, an acetylase, a deacetylase, a phosphatase, a kinase, a transcription (co-)activator, an RNA polymerase subunit, a transcription repressor, a DNA binding protein, a DNA structuring protein, a marker protein, a reporter protein, a fluorescent protein, a ligand binding protein (e.g. mCherry or a heavy metal binding protein), a signal peptide (e.g. Tat-signal sequence), a subcellular localisation sequence (e.g. nuclear localisation sequence), and/or an antibody epitope, or any combination thereof.

As used herein, "genetically modified cell" can generally refer to a cell that has been genetically modified. Some non-limiting examples of genetic modifications can include: insertions, deletions, inversions, translocations, gene fusions, or changing one or more nucleotides. A genetically modified cell can comprise a target nucleic acid with an introduced double strand break (e.g., DNA break). A genetically modified cell can comprise an exogenously introduced nucleic acid (e.g., a vector). A genetically modified cell can comprise an exogenously introduced polypeptide of the disclosure and/or nucleic acid of the disclosure. A genetically modified cell can comprise a donor polynucleotide. A genetically modified cell can comprise an exogenous nucleic acid integrated into the genome of the genetically modified cell. A genetically modified cell can comprise a deletion of DNA. A genetically modified cell can also refer to a cell with modified mitochondrial or chloroplast DNA.

As used herein, "genome engineering" can refer to a process of modifying a target nucleic acid. Genome engineering can refer to the integration of non-native nucleic acid into native nucleic acid. Genome engineering can refer to the targeting of an Argonaute and a designed nucleic acid-targeting nucleic acid to a target nucleic acid, without an integration or a deletion of the target nucleic acid. Genome engineering can refer to the cleavage of a target nucleic acid, and the rejoining of the target nucleic acid without an integration of an exogenous sequence in the target nucleic acid, or a deletion in the target nucleic acid. The native nucleic acid can comprise a gene. The non-native nucleic acid can comprise a donor polynucleotide. In the methods of the disclosure, Argonautes (e.g., Arg), or complexes thereof, can introduce double-stranded breaks in a nucleic acid, (e.g. genomic DNA). The double-stranded break can stimulate a cell's endogenous DNA-repair pathways (e.g. homologous recombination (HR) and/or non-homologous end joining (NHEJ), or A-NHEJ (alternative non-homologous end-joining)). Mutations, deletions, alterations, and integrations of foreign, exogenous, and/or alternative nucleic acid can be introduced into the site of the double-stranded DNA break.

As used herein, the term "isolated" can refer to a nucleic acid or polypeptide that, by the hand of a human, exists apart from its native environment and is therefore not a product of nature. Isolated can mean substantially pure. An isolated nucleic acid or polypeptide can exist in a purified form and/or can exist in a non-native environment such as, for example, in a transgenic cell.

As used herein, "non-native" can refer to a nucleic acid or polypeptide sequence that is not found in a native nucleic acid or protein. Non-native can refer to affinity tags. Non-native can refer to fusions. Non-native can refer to a naturally occurring nucleic acid or polypeptide sequence that comprises mutations, insertions and/or deletions. A non-native sequence may exhibit and/or encode for an activity (e.g., enzymatic activity, methyltransferase activity, acetyltransferase activity, kinase activity, ubiquitinating activity, etc.) that can also be exhibited by the nucleic acid and/or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid and/or polypeptide sequence encoding a chimeric nucleic acid and/or polypeptide. A non-native sequence can refer to a 3'0 hybridizing extension sequence.

As used herein, a "nucleic acid" can generally refer to a polynucleotide sequence, or fragment thereof A nucleic acid can comprise nucleotides. A nucleic acid can be exogenous or endogenous to a cell. A nucleic acid can exist in a cell-free environment. A nucleic acid can be a gene or fragment thereof A nucleic acid can be DNA. A nucleic acid can be RNA. A nucleic acid can comprise one or more analogs (e.g. altered backgone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine.

As used herein, a "nucleic acid sample" can generally refer to a sample from a biological entity. A nucleic acid sample can comprise nucleic acid. The nucleic acid from the nucleic acid sample can be purified and/or enriched. The nucleic acid sample may show the nature of the whole. Nucleic acid samples can come from various sources. Nucleic acid samples can come from one or more individuals. One or more nucleic acid samples can come from the same individual. One non limiting example would be if one sample came from an individual's blood and a second sample came from an individual's tumor biopsy. Examples of nucleic acid samples can include but are not limited to, blood, serum, plasma, nasal swab or nasopharyngeal wash, saliva, urine, gastric fluid, spinal fluid, tears, stool, mucus, sweat, earwax, oil, glandular secretion, cerebral spinal fluid, tissue, semen, vaginal fluid, interstitial fluids, including interstitial fluids derived from tumor tissue, ocular fluids, spinal fluid, throat swab, cheeck swab, breath, hair, finger nails, skin, biopsy, placental fluid, amniotic fluid, cord blood, emphatic fluids, cavity fluids, sputum, pus, micropiota, meconium, breast milk, buccal samples, nasopharyngeal wash, other excretions, or any combination thereof. Nucleic acid samples can originate from tissues. Examples of tissue samples may include but are not limited to, connective tissue, muscle tissue, nervous tissue, epithelial tissue, cartilage, cancerous or tumor sample, bone marrow, or bone. The nucleic acid sample may be provided from a human or animal. The nucleic acid sample may be provided from a mammal, vertebrate, such as murines, simians, humans, farm animals, sport animals, or pets. The nucleic acid sample may be collected from a living or dead subject. The nucleic acid sample may be collected fresh from a subject or may have undergone some form of pre-processing, storage, or transport.

A nucleic acid sample can comprise a target nucleic acid. A nucleic acid sample can originate from cell lysate. The cell lysate can originate from a cell.

"Nucleotide" can generally refer to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [$\alpha$S]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide may be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS).

Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]d-dTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g. biotin-11-dUTP, biotin-16-dUTP, biotin-20-dUTP).

As used here, "purified" can refer to a molecule (e.g., Argonaute, designed nucleic acid-targeting nucleic acid) that comprises at least 50, 60, 70, 80, 90, 95, 96, 97, 98, 99, or 100% of the composition. For example, a sample that comprises 10% of an Argonaute, but after a purification step comprises 60% of the Argonaute, then the sample can be said to be purified. A purified sample can refer to an enriched sample, or a sample that has undergone methods to remove particles other than the particle of interest.

As used herein, "recombinant" can refer to sequence that originates from a source foreign to the particular host (e.g., cell) or, if from the same source, is modified from its original form. A recombinant nucleic acid in a cell can include a nucleic acid that is endogenous to the particular cell but has been modified through, for example, the use of site-directed mutagenesis. The term can include non-naturally occuring multiple copies of a naturally occurring DNA sequence. Thus, the term can refer to a nucleic acid that is foreign or heterologous to the cell, or homologous to the cell but in a position or form within the cell in which the nucleic acid is not ordinarily found. Similarly, when used in the context of a polypeptide or amino acid sequence, an exogenous polypeptide or amino acid sequence can be a polypeptide or amino acid sequence that originates from a source foreign to the particular cell or, if from the same source, is modified from its original form.

As used herein, the term "specific" can refer to interaction of two molecules where one of the molecules through, for example chemical or physical means, specifically binds to the second molecule. Exemplary specific binding interactions can refer to antigen-antibody binding, avidin-biotin binding, carbohydrates and lectins, complementary nucleic acid sequences (e.g., hybridizing), complementary peptide sequences including those formed by recombinant methods, effector and receptor molecules, enzyme cofactors and enzymes, enzyme inhibitors and enzymes, and the like. "Non-specific" can refer to an interaction between two molecules that is not specific.

As used herein, "solid support" can generally refer to any insoluble, or partially soluble material. A solid support can refer to a test strip, a multi-well dish, and the like. The solid support can comprise a variety of substances (e.g., glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc. A solid support can be solid, semisolid, a bead, or a surface. The support can mobile in a solution or can be immobile. A solid support can be used to capture a polypeptide. A solid support can comprise a capture agent.

As used herein, "target nucleic acid" can generally refer to a target nucleic acid to be targeted in the methods of the disclosure. A target nucleic acid can refer to a chromosomal sequence or an extrachromosomal sequence, (e.g. an episomal sequence, a minicircle sequence, a mitochondrial sequence, a chloroplast sequence, etc.). A target nucleic acid can be DNA. A target nucleic acid can be single-stranded DNA. A target nucleic acid can be double-stranded DNA. A target nucleic acid can be RNA. A target nucleic acid can herein be used interchangeably with "polynucleotide", "nucleotide sequence", and/or "target polynucleotide".

In any of the embodiments of the methods, compositions, and kits of the disclosure the use of the singular can refer to the plural. In any of the embodiments of the methods, compositions, and kits of the disclosure the use of the plural can refer to the singular.

It must be noted that as used herein and in the appended claims, the singular forms "a," "an," and "the" include plural referents unless the context clearly dictates otherwise. Thus, for example, reference to "an Argonaute" can includs a plurality of such Argonautes. It is further noted that the plural forms of nouns such as "compositions," "kits," "methods," "vectors," and "genetically modified organisms," can refer to the singular form of the noun.

Argonautes

An Argonaute can be a polypeptide that can bind to a target nucleic acid. An Argonaute can be a nuclease. The Argonaute protein may be a prokaryotic Argonaute protein (pArgonaute). The pArgonaute may be derived from an archaea. The pArgonaute may be derived from a bacterium. The bacterium may be selected from a thermophilic bacterium and a mesophilic bacterium. The bacteria or archaea may be selected from *Aquifex aeolicus, Microsystis aeruginosa, Clostridium bartlettii, Exiguobacterium , Anoxybacillus flavithermus, Halogeometricum borinquense, Halorubrum lacusprofundi, Aromatoleum aromaticum, Thermus thermophilus, Synechococcus, Synechococcus elongatus*, and *Thermosynechococcus elogatus*, or any combination thereof The bacterium may be a thermophilic bacterium. The bacterium may be *Aquifex aeolicus*. The thermophilic bacterium may be *Thermus thermophilus* (*T.thermophilus*) (TtArgonaute). The Argonaute may be from a *Synechococ-* cus bacterium. The Argonaute may be from *Synechococcus elongatus*. The pArgonaute may be a variant pArgonaute of a wild-type pArgonaute.

In some embodiments, the Argonaute of the disclosure is a type I prokaryotic Argonaute. In some embodiments, the type I prokaryotic Argonaute carries a DNA nucleic acid-targeting nucleic acid. In some embodiments, the DNA nucleic acid-targeting nucleic acid targets one strand of a double stranded DNA (dsDNA) to produce a nick or a break of the dsDNA. In some embodiments, the nick or break triggers host DNA repair. In some embodiments, the host DNA repair is non-homologous end joining (NHEJ) or homologous directed recombination (HDR). In some embodiments, the dsDNA is selected from a genome, a chromosome and a plasmid. In some embodiments, the type I prokaryotic Argonaute is a long type I prokaryotic Argonaute. In some embodiments, the long type I prokaryotic Argonaute possesses an N-PAZ-MID-PIWI domain architecture. In some embodiments the long type I prokaryotic Argonaute possesses a catalytically active PIWI domain. In some embodiments, the long type I prokaryotic Argonaute possesses a catalytic tetrad encoded by aspartate-glutamate-aspartate-aspartate/histidine (DEDX). In some embodiments, the catalytic tetrad binds one or more Mg+ ions. In some embodiments, the catalytic tetrad does not bind Mg+ ions. In some embodiments, the catalytic tetrad binds one or more Mn+ ions. In some embodiments, the catalytically active PIWI domain is optimally active at a moderate temperature. In some embodiments, the moderate temperature is about 25° C. to about 45° C. In some embodiments, the moderate temperature is about 37° C. In some embodiments, the type I prokaryotic Argonaute anchors the 5' phosphate end of a DNA guide. In some embodiments, the DNA guide has a deoxy-cytosine at its 5' end. In some embodiments, the type I prokaryotic Argonaute is a *Thermus thermophilus* Ago (TtAgo). In some embodiments, the type I prokaryotic Argonaute is a *Synechococcus elongatus* Ago (SeAgo).

In some embodiments, the prokaryotic Argonaute is a type II pAgo. In some embodiments, the type II prokaryotic Argonaute carries an RNA nucleic acid-targeting nucleic acid. In some embodiments, the RNA nucleic acid-targeting nucleic acid targets one strand of a double stranded DNA (dsDNA) to produce a nick or a break of the dsDNA. In some embodiments, the nick or break triggers host DNA repair. In some embodiments, the host DNA repair is non-homologous end joining (NHEJ) or homologous directed recombination (HDR). In some embodiments, the dsDNA is selected from a genome, a chromosome and a plasmid. In some embodiments, the type II prokaryotic Argonaute is selected from a long type II prokaryotic Argonaute and a short type II prokaryotic Argonaute. In some embodiments, the long type II prokaryotic Argonaute has an N-PAZ-MID-PIWI domain architecture. In some embodiments, the long type II prokaryotic Argonaute does not have an N-PAZ-MID-PIWI domain architecture. In some embodiments, the short type II prokaryotic Argonaute has a MID and PIWI domain, but not a PAZ domain. In some embodiments, the short type II pAgo has an analog of a PAZ domain. In some embodiments the type II pAgo does not have a catalytically active PIWI domain. In some embodiments, the type II pAgo lacks a catalytic tetrad encoded by aspartate-glutamate-aspartate-aspartate/histidine (DEDX). In some embodiments, a gene encoding the type II prokaryotic Argonaute clusters with one or more genes encoding a nuclease, a helicase or a combination thereof. The nuclease or helicase may be natural, designed or a domain thereof. In some embodiments, the nuclease is selected from a Sir2, REI and TIR. In some embodiments, the type II pAgo anchors the 5' phosphate end of an RNA guide. In some embodiments, the RNA guide has a uracil at its 5' end. In some embodiments, the type II prokaryotic Argonaute is a *Rhodobacter sphaeroides* Argonaute (RsAgo).

In some embodiments, a pair of pAgos can carry RNA and/or DNA nucleic acid-targeting nucleic acid. A type I pAgo can carry an RNA nucleic acid-targeting nucleic acid, each capable of targeting one strand of a double stranded DNA to produce a double-stranded break in the double stranded DNA. In some embodiments, the pair of pAgos comprises two type I pAgos. In some embodiments, the pair of pAgos comprises two type II pAgos. In some embodiments, the pair of pAgos comprises a type I pAgo and a type II pAgo.

Argonaute Domains

The Argonaute protein may comprise one or more domains. The Argonaute protein may comprise a domain selected from a PAZ domain, a MID domain, and a PIWI domain or any combination thereof. The Argonaute protein may comprise a domain architecture of N-PAZ-MID-PIWI-C. The PAZ domain may comprise an oligonucleotide-binding fold to secure a 3' end of a designed nucleic acid-targeting nucleic acid. Release of the 3'-end of the designed nucleic acid-targeting nucleic acid from the PAZ domain may facilitate the transitioning of the pArgonaute ternary complex into a cleavage active conformation. The MID domain may bind a 5' phosphate and a first nucleotide of the designed nucleic acid-targeting nucleic acid. The target nucleic acid can remain bound to the Argonaute through many rounds of cleavage by means of anchorage of the 5' phosphate in the MID domain.

An Argonaute can comprise a nucleic acid-binding domain. The nucleic acid-binding domain can comprise a region that contacts a nucleic acid. A nucleic acid-binding domain can comprise a nucleic acid. A nucleic acid-binding domain can comprise a proteinaceous material. A nucleic acid-binding domain can comprise nucleic acid and a proteinaceous material. A nucleic acid-binding domain can comprise DNA. A nucleic acid-binding domain can comprise single-stranded DNA. Examples of nucleic acid-binding domains can include, but are not limited to, a helix-turn-helix domain, a zinc finger domain, a leucine zipper (bZIP) domain, a winged helix domain, a winged helix turn helix domain, a helix-loop-helix domain, a HMG-box domain, a Wor3 domain, an immunoglobulin domain, a B3 domain, and a TALE domain.

A nucleic acid-binding domain can be a domain of an Argonaute protein. An Argonaute protein can be a eukaryotic Argonaute or a prokaryotic Argonaute. An Argonaute protein can bind RNA or DNA, or both RNA and DNA. An Argonaute protein can cleave RNA, or DNA, or both RNA and DNA. In some instances, an Argonaute protein binds a DNA and cleaves the DNA. In some instances, the Argonaute protein binds a double-stranded DNA and cleaves a double-stranded DNA.

In some instances, two or more nucleic acid-binding domains can be linked together. Linking a plurality of nucleic acid-binding domains together can provide increased polynucleotide targeting specificity. Two or more nucleic acid-binding domains can be linked via one or more linkers. The linker can be a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length. Linkers can comprise at least 5%, 10%, 15%, 20%, 25%, 30%, 35%, 40%, 45%, 50%, 55%, 60%, 65%, 70%, 75%, 80%, 85%, 90%, 95%, or 100% glycine content. Linkers can comprise at most 5%, 10%, 15%, 20%, 25%, 30%, 35%, 40%, 45%, 50%, 55%, 60%, 65%, 70%, 75%, 80%, 85%, 90%, 95%, or 100% glycine content. Linkers can comprise at least 5%, 10%, 15%, 20%, 25%, 30%, 35%, 40%, 45%, 50%, 55%, 60%, 65%, 70%, 75%, 80%, 85%, 90%, 95%, or 100% serine content. Linkers can comprise at most 5%, 10%, 15%, 20%, 25%, 30%, 35%, 40%, 45%, 50%, 55%, 60%, 65%, 70%, 75%, 80%, 85%, 90%, 95%, or 100% serine content.

Linkers can be a nucleic acid linter which can comprise nucleotides. A nucleic acid linker can link two DNA-binding domains together. A nucleic acid linker can be at most 5, 10, 15, 20, 25, 30, 35, 40, 45, or 50 or more nucleotides in length. A nucleic acid linker can be at least 5, 10, 15, 20, 25, 30, 35, 40, 45, or 50 or more nucleotides in length.

Nucleic acid-binding domains can bind to nucleic acid sequences. Nucleic acid binding domains can bind to nucleic acids through hybridization. Nucleic acid-binding domains can be engineered (e.g. engineered to hybridize to a sequence in a genome). A nucleic acid-binding domain can be engineered by molecular cloning techniques (e.g., directed evolution, site-specific mutation, and rational mutagenesis).

An Argonaute can comprise a nucleic acid-cleaving domain. The nucleic acid-cleaving domain can be a nucleic acid-cleaving domain from any nucleic acid-cleaving protein. The nucleic acid-cleaving domain can originate from a nuclease. Suitable nucleic acid-cleaving domains include the nucleic acid-cleaving domain of endonucleases (e.g., AP endonuclease, RecBCD enonuclease, T7 endonuclease, T4 endonuclease IV, Bal 31 endonuclease, Endonucleasel (endo I), Micrococcal nuclease, Endonuclease II (endo VI, exo III)), exonucleases, restriction nucleases, endoribonucleases, exoribonucleases, RNases (e.g., RNAse I, II, or III). In some instances, the nucleic acid-cleaving domain can originate from the Fokl endonuclease. An Argonaute can comprise a plurality of nucleic acid-cleaving domains. Nucleic acid-cleaving domains can be linked together. Two or more nucleic acid-cleaving domains can be linked via a linker. In some embodiments, the linker can be a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length. In some embodiments, an Argonaute can comprise the plurality of nucleic acid-cleaving domains.

Argonautes can introduce double-stranded breaks or single-stranded breaks in nucleic acid, (e.g. genomic DNA). The double-stranded break can stimulate a cell's endogenous DNA-repair pathways (e.g. homologous recombination and non-homologous end joining (NHEJ) or alternative non-homologues end joining (A-NHEJ)). NHEJ can repair cleaved target nucleic acid without the need for a homologous template. This can result in deletions of the target nucleic acid. Homologous recombination (HR) can occur with a homologous template. The homologous template can comprise sequences that are homologous to sequences flanking the target nucleic acid cleavage site. After a target nucleic acid is cleaved by an Argonaute the site of cleavage can be destroyed (e.g., the site may not be accessible for another round of cleavage with the original nucleica acid-targeting nucleic acid and Argonaute).

In some cases, homologous recombination can insert an exogenous polynucleotide sequence into the target nucleic acid cleavage site. An exogenous polynucleotide sequence can be called a donor polynucleotide. In some instances of the methods of the disclosure the donor polynucleotide, a portion of the donor polynucleotide, a copy of the donor polynucleotide, or a portion of acopy of the donor polynucleotide can be inserted into the target nucleic acid cleavage site. A donor polynucleotide can be an exogenous polynucleotide sequence. A donor polynucleotide can be a sequence that does not naturally occur at the target nucleic acid cleavage site. A vector can comprise a donor polynucleotide. The modifications of the target DNA due to NHEJ and/or HR can lead to, for example, mutations, deletions, alterations, integrations, gene correction, gene replacement, gene tagging, transgene insertion, nucleotide deletion, gene disruption, and/or gene mutation. The process of integrating non-native nucleic acid into genomic DNA can be referred to as genome engineering.

In some cases, the Argonaute can comprise an amino acid sequence having at most 10%, at most 15%, at most 20%, at most 30%, at most 40%, at most 50%, at most 60%, at most 70%, at most 75%, at most 80%, at most 85%, at most 90%, at most 95%, at most 99%, or 100%, amino acid sequence identity to a wild type exemplary Argonaute (e.g,. Argonaute from T. thermophilus or S. elongatus, FIG. 42B, FIG. 46).

In some cases, the Argonaute can comprise an amino acid sequence having at least 10%, at least 15%, 20%, at least 30%, at least 40%, at least 50%, at least 60%, at least 70%, at least 75%, at least 80%, at least 85%, at least 90%, at least 95%, at least 99%, or 100%, amino acid sequence identity to a wild type exemplary Argonaute (e.g., Argonaute from T. thermophilus or S. elongatus, FIG. 42B, FIG. 46).

In some cases, the Argonaute can comprise an amino acid sequence having at most 10%, at most 15%, at most 20%, at most 30%, at most 40%, at most 50%, at most 60%, at most 70%, at most 75%, at most 80%, at most 85%, at most 90%, at most 95%, at most 99%, or 100%, amino acid sequence identity to the nuclease domain of a wild type exemplary Argonaute (e.g., Argonaute from T. thermophilus or S. elongatus, FIG. 42B, FIG. 46).

An Argonaute can comprise at least 70, 75, 80, 85, 90, 95, 97, 99, or 100% identity to wild-type Argonaute (e.g., Argonaute from T. thermophilus or S. elongatus, FIG. 42B, FIG. 46) over 10 contiguous amino acids of the MID domain. An Argonaute can comprise at most 70, 75, 80, 85, 90, 95, 97, 99, or 100% identity to wild-type Argonaute (e.g., Argonaute from T thermophilus or S. elongatus, FIG. 42B, FIG. 46) over 10 contiguous amino acids of the MID domain. An Argonaute can comprise at least 70, 75, 80, 85, 90, 95, 97, 99, or 100% identity to wild-type Argonaute (e.g., Argonaute from T. thermophilus or S. elongatus, FIG. 42B, FIG. 46) over 10 contiguous amino acids of the PAZ domain. An Argonaute can comprise at most 70, 75, 80, 85, 90, 95, 97, 99, or 100% identity to wild-type Argonaute (e.g., Argonaute from T. thermophilus or S. elongatus, FIG. 42B, and FIG. 46) over 10 contiguous amino acids of the PAZ domain. An Argonaute can comprise at least 70, 75, 80, 85, 90, 95, 97, 99, or 100% identity to wild-type Argonaute (e.g., Argonaute from T. thermophilus or S. elongatus, FIG. 42B, FIG. 46) over 10 contiguous amino acids of the PIWI domain. An Argonaute can comprise at most 70, 75, 80, 85, 90, 95, 97, 99, or 100% identity to wild-type Argonaute (e.g., Argonaute from T. thermophilus or S. elongatus, FIG. 42B, FIG. 46) over 10 contiguous amino acids of the PIWI domain.

The Argonaute can comprise a modified form of a wild type exemplary Argonaute. The modified form of the wild type exemplary Argonaute can comprise an amino acid change (e.g., deletion, insertion, or substitution) that reduces the nucleic acid-cleaving activity of the Argonaute. For example, the modified form of the wild type exemplary Argonaute can have less than less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary Argonaute (e.g., Argonaute from *T. thermophilus* or *S. elongatus*). The modified form of the Argonaute can have no substantial nucleic acid-cleaving activity. When an Argonaute is a modified form that has no substantial nucleic acid-cleaving activity, it can be referred to as "enzymatically inactive." In some instances, an enzymatically inactive Argonaute may not refer to an Argonaute from Rhodobacter sphaeroides.

Residues in the wild type exemplary *T. thermophilus* Argonaute polypeptide such as Asp478, and Asp 546 can be mutated to decrease the activity of an Argonaute. The residues to be mutated in an Argonaute protein can correspond to residues Asp478, and Asp 546 in the wild type exemplary *T. thermophilus* Argonaute polypeptide (e.g., as determined by sequence and/or structural alignment). Non-limiting examples of mutations can include D478A, and D546A. One skilled in the art will recognize that mutations other than alanine substitutions are suitable. In some instances, sequences can be inserted to an Argonaute protein to reduce its activity. Inserted sequences can comprise the ISTth7 sequence.

The modified form of the wild type exemplary Argonaute can have more than 90%, more than 80%, more than 70%, more than 60%, more than 50%, more than 40%, more than 30%, more than 20%, more than 10%, more than 5%, or more than 1% of the nucleic acid-cleaving activity of the wild-type exemplary Argonaute (e.g., Argonaute from *T. thermophilus* or *S. elongatus*).

The Argonaute proteins disclosed herein may comprise one or more modifications. The modification may comprise a post-translational modification. The modification of the target nucleic acid may occur at least 1, 2, 3, 4, 5, 6, 7, 8, 9, 10, 20, 30, 40, 50, 60, 70, 80, 90, 100 or more amino acids away from the either the carboxy terminus or amino terminus end of the Argonaute protein. The modification of the Argonaute protein may occur at most 1, 2, 3, 4, 5, 6, 7, 8, 9, 10, 20, 30, 40, 50, 60, 70, 80, 90, 100 or more amino acids away from the carboxy terminus or amino terminus end of the Argonaute protein. The modification may occur due to the modification of a nucleic acid encoding an Argonaute protein.

Exemplary modifications can comprise methylation, demethylation, acetylation, deacetylation, ubiquitination, deubiquitination, deamination, alkylation, depurination, oxidation, pyrimidine dimer formation, transposition, recombination, chain elongation, ligation, glycosylation. Phosphorylation, dephosphorylation, adenylation, deadenylation, SUMOylation, deSUMOylation, ribosylation, deribosylation, myristoylation, remodelling, cleavage, oxidoreduction, hydrolation, and isomerization.

The Argonaute protein may comprise one or more mutations. The Argonaute protein may comprise amino acid modifications (e.g., substitutions, deletions, additions, etc., and combinations thereof). The Argonaute protein may comprise one or more non-native sequences (e.g., a fusion). The amino acid modifications may comprise one or more non-native sequences (e.g., a fusion, an affinity tag). The amino acid modifications may not substantially alter the activity of the endonuclease. The Argonaute comprising amino acid modifications and/or fusions may retain at least about 75%, at least about 80%, at least about 85%, at least about 90%, at least about 95%, at least about 97% or 100% activity of the wild-type Argonaute.

Modifications (e.g., mutations) of the disclosure can be produced by site-directed mutation. Mutations can include substitutions, additions, and deletions, or any combination thereof In some instances, the mutation converts the mutated amino acid to alanine. In some instances, the mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). The mutation can convert the mutated amino acid to a non-natural amino acid (e.g., selenomethionine). The mutation can convert the mutated amino acid to amino acid mimics (e.g.,phosphomimics). The mutation can be a conservative mutation. For example, the mutation can convert the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation).

In some instances, the Argonaute (e.g., variant, mutated, and/or enzymatically inactive) can target nucleic acid. The Argonaute (e.g., variant, mutated, and/or enzymatically inactive) can target DNA.

The Argonauts can comprise one or more non-native sequences (e.g., a fusion). In some instances, the non-native sequence of the Argonaute comprises a moiety that can alter transcription. Transcription can be increased or decreased. Transcription can be altered by at least about 1-fold, 2-fold, 3-fold, 4-fold, 5-fold, 10-fold, 15-fold, or 20-fold or more. Transcription can be altered by at most about 1-fold, 2-fold, 3-fold, 4-fold, 5-fold, 10 fold, 15-fold, or 20-fold or more. The moiety can be a transcription factor. When an Argonaute is a fusion Argonaute comprising a non-native sequence that can alter transcription the Argonaute may comprise reduced enzymatic activity as compared to a wild-type Argonaute (e.g., Argonaute from *T. thermophilus* or *S. elongatus*).

The Argonaute of the disclosure may be thermo-sensitive (e.g., may be active or inactive at different temperatures). The Argonaute may be active at a temperature of about 37° C. The pArgonaute may be active at a temperature above 37° C. The Argonaute may be active at a temperature of at least about 35, 40, 45, 50, 55, 60, 65, 70, 75, 80, 85, 90, or 95 or more degrees celsius. The Argonauts may be active at a temperature of at most about 35, 40, 45, 50, 55, 60, 65, 70, 75, 80, 85, 90, or 95 or more degrees celsius. The Argonaute may be active at a temperature of about 55-75° C. The Argonaute may be active at a temperature of about 75° C. The Argonaute may be active at a temperature of about 20 to 25° C. or above.

The Argonaute of the disclosure may be modified to be active at a desired temperature. For example, an Argonaute that is active at an elevated temperature (e.g., 50° C.) may be engineered such that it is active at a reduced temperature (e.g., 37° C.). An Argonaute that is active at a low temperature (e.g., 20° C.) may be engineered such that it is active at an elevated temperature (e.g., 37° C.).

Activity of Argonaute

By way of non-limiting example, Argouaute may bind a designed nucleic acid-targeting nucleic acid (e.g., single-stranded DNA, single-stranded RNA) that guides it to a target nucleic acid that is complementary to the designed nucleic acid-targeting nucleic acid, wherein the target nucleic acid comprises a dsDNA (e.g., such as a plasmid), and thereby carries out site specific cleavage within the target nucleic acid.

Argonaute may introduce double-stranded breaks or single-stranded breaks in the target nucleic acid, (e.g.

genomic DNA). The double-stranded break can stimulate a cell's endogenous DNA-repair pathways (e.g. homologous recombination and non-homologous end joining (NHEJ) or alternative non-homologues end-joining (A-NHEJ)). NHEJ can repair cleaved target nucleic acid without the need for a homologous template. This can result in deletions of the target nucleic acid. Homologous recombination (HR) can occur with a homologous template. The homologous template can comprise sequences that are homologous to sequences flanking the target nucleic acid cleavage site. After a target nucleic acid is cleaved by an Argonaute the site of cleavage can he destroyed (e.g., the site may not be accessible for another round of cleavage with the original nucleic acid-targeting nucleic acid and Argonaute).

Argonaute proteins which can function as endonueleases can comprise three key functional domains: a PIWI endonuclease domain, a PAZ domain, and a MID domain. The PIWI domain may resemble a nuclease. The nuclease may be an RNase H or a DNA-guided ribonuclease. The PIWI domain may share a divalent cation-binding motif for catalysis exhibited by other nucleases that can cleave RNA and DNA. The divalent cation-binding motif may contain four negatively charged, evolutionary conserved amino acids. The four negatively charged evolutionary conserved amino acids may be aspartate-glutamate-aspartate-aspartate (DEDD) (SEQ ID NO: 28). The four negatively charged evolutionary conserved amino acids may form a catalytic tetrad that binds two $Mg^{2+}$ ions and cleaves a target nucleic acid into products bearing a 3' hydroxyl and 5' phosphate group The PIWI domain may further comprise one or more amino acids selected from a basic residue. The PIWI domain may further comprise one or more amino acids selected from histidine, arginine, lysine and a combination thereof The histidine, arginine and/or lysine may play an important, role in catalysis and/or cleavage. Cleavage of the target nucleic acid by Argonaute can occur at a single phosphodiester bond.

In some instances, one or more magnesium and/or manganese cations can facilitate target nucleic acid cleavage, wherein a first cation can nucleophilically attack and activate a water molecule and a second cation can stabilize the transition state and leaving group.

The MID domain can bind the 5' phosphate and first nucleotide of the designed nucleic acid-targeting nucleic acid. The PAZ domain can use its oligonucleotide-binding fold to secure the 3' end of the designed nucleic acid-targeting nucleic acid.

An Argonaute can comprise an amino acid sequence comprising at least 30% amino acid identity to an Argonaute from a prokaryote (e.g., *T. thermophilus* or *S. elongatus*).

An Argonaute can comprise an amino acid sequence comprising at least 30% amino acid identity to an Argonaute from a prokaryote (e.g., *T. thermophilus*), and a nucleic acid cleaving domain, wherein the nucleic acid cleaving domain comprise at least 70% amino acid identity to a nuclease domain from an Argonaute from a prokaryote (e.g., *T. thermophilus* or *S. elongatus*).

An Argonaute can comprise an amino acid sequence comprising at least 30% amino acid identity to an Argonaute from a prokaryote (e.g., *T. thermophilus* or *S. elongatus*), a nucleic acid cleaving domain, comprising at least 70% amino acid identity to a nuclease domain from an Argonaute from a prokaryote (e.g., *T. thermophilus*), and a linker linking the Argonaute to a non-native sequence.

An Argonaute can comprise an amino acid sequence comprising at least 30% amino acid identity to an Argonaute from a prokaryote (e.g., *T. thermophilus* or *S. elongatus*), a nucleic acid cleaving domain, comprising at least 70% amino acid identity to a nuclease domain from an Argonaute from a prokaryote (e.g., *T. thermophilus* or *S. elongatus*), wherein the Argonaute comprises a mutation in the nucleic acid cleaving domain that reduces the cleaving activity of the nuclease domains by at least 50%.

Zinc Finger Nucleases

A "DNA binding zinc finger domain" (ZFD) or binding domain can be a protein, or a domain within a larger protein, that can bind DNA in a sequence-specific-manner through one or more zinc fingers, which can be regions of amino acid sequence within the binding domain whose structure can be stabilized through coordination of a zinc ion. The term zinc finger DNA binding protein can often be abbreviated as zinc finger protein or ZFP. Thus, as used herein, "zinc finger protein," "zinc finger polypeptide," or "ZFP" can refer to a polypeptide having nucleic acid (e.g., DNA, binding domains that are stabilized by zinc). The individual DNA binding domains can typically be referred to as "fingers," such that a zinc finger protein or polypeptide can have at least one finger, two fingers, three fingers, or even four or five fingers, to at least six or more fingers. Each finger can bind from two to four base pairs of DNA. A ZFP can bind to a target nucleic acid. Each finger can comprise a zinc-chelating, DNA-binding subdomain comprising approximately 30 amino acids. A zinc fingerprotein can comprise at least two DNA-binding domains, one of which is a zinc finger polypeptide, linked to the other domain via a flexible linker. The two domains can be identical or different. Both domains can be zinc finger proteins, either identical or different zinc finger domains.

Zinc finger binding domains can be engineered to bind to a sequence of choice. An engineered zinc finger binding domain can have a novel binding specificity compared to a naturally occurring zinc finger protein. Engineering methods can include, but are not limited to, rational design and various types of selection. Rational design can include, for example, using databases comprising triplet (or quadruplet) nucleotide sequences and individual zinc-finger amino acid sequences, in which each triplet or quadruplet nucleotide sequence is associated with one or more amino acid sequences of zinc-fingers which can bind the particular triplet or quadruplet sequence.

Zinc finger nucleases (ZFNs) can be enzymes comprising a DNA cleavage domain and a DNA binding zinc finger domain. ZFNs can be powerful tools for genome editing and can be assembled to induce double strand breaks (DSBs) site-specifically into genomic DNA. ZFNs can allow specific gene disruption. For example, during DNA repair the targeted genes can be disrupted via non-homologous end joint (NHEJ) or modified via homologous recombination (HR) if a closely related DNA template is supplied.

In some embodiments, the zinc finger nucleases can have altered catalytic activity. The DNA-cleaving domain of zinc finger nucleases can be inactivated. Inactivation can be introduced through techniques in directed evolution, site-specific mutation, rational mutagenesis, and photo-activatable caging. A ZFN can be conditionally enzymatically inactive.

In some instances, the zinc finger protein (naturally occurring, or engineered) is not fused to a DNA cleavage domain.

In some instances, the zinc finger protein can comprise one or more non-native sequences (e.g., a fusion).

TALE-Nucleases

Transcription activator-like effector (TALE) nucleases or TALEs can be programmable and can recognize a nucleic-acid target sequence in a highly specific manner. TALEs can be proteins secreted by *Xanthomonas* bacteria via their type III secretion system when they infect various plant species. These proteins can bind promoter sequences in the host and activate the expression of host genes that aid bacterial infection. These proteins are interesting both for their role in disease, for example of important crop species, and the relative ease of retargeting them to bind new DNA sequences. Similar proteins can be found in the pathogenic bacteria *Ralstonia solanacearum*. One distinctive characteristic of TALE proteins is a central repeat domain containing between 1.5 and 33.5 repeats that are usually 34 residues in length (the C-terminal repeat is generally shorter and referred to as a "half repeat"). A typical repeat sequence is LTPEQVVAIASHDGGKQALETVQRLLPVLCQAHG (SEQ ID NO 29), but the residues at the 12th and $13^{th}$ positions can be hypervariable (these two amino acids are also known as the repeat variable diresidue or RVD). It has been shown that there can be a simple relationship between the identity of these two residues in sequential repeats and sequential DNA bases in the TALE effector's target site. There can be a one-to-one correspondence between the identity of two critical amino acids in each repeat and each DNA base in the target sequence. TAL effectors can be engineered and generated for the purpose of binding to particular nucleotide sequences.

The site-directed polypeptide can include TAL effector DNA binding domains and non -TALE endonuclease domains. Thus, nucleic acids encoding such site-directed polypeptides can include a nucleotide sequence from a sequence-specific TAL effector linked to a nucleotide sequence from a nuclease.

In some embodiments, the TALE-nucleases can have altered catalytic activity. The DNA-cleaving domain of TALE-nucleases can be inactivated. Inactivation can be introduced through techniques in directed evolution, site-specific mutation, rational mutagenesis, and photo-activatable caging.

In some instances, the TALE-nuclease protein (naturally occurring, or engineered) is not fused to a DNA cleavage domain.

In some instances, the TALE-nuclease protein can comprise one or more non-native sequences (e.g., a fusion).

Designed Nucleic Acid-Targeting Nucleic Acids (Designed Nucleic Acid-Targeting Nucleic Acids)

Disclosed herein are designed nucleic acid-targeting nucleic acids (designed nucleic acid-targeting nucleic acids) that can direct the activities of an associated polypeptide (e.g., Argonaute protein) to a specific target sequence within a target nucleic acid. The designed nucleic acid-targeting nucleic acid can comprise nucleotides. The designed nucleic acid-targeting nucleic acid may be a single stranded DNA (ssDNA). The designed nucleic acid-targeting nucleic acid may comprise double-stranded DNA. The designed nucleic acid-targeting nucleic acid may be RNA.

The designed nucleic acid-targeting nucleic acid can be at least about 5, 6, 7, 8, 9, 10, 11, 12, 13, 14, 15, 16, 17, 18, 19, 20, 21, 22, 23, 24, 25, 25, 27, 28, 29, or 30 or more nucleotides in length. The designed nucleic acid-targeting nucleic acid can be at most about 5, 6, 7, 8, 9, 10, 11, 12, 13, 14, 15, 16, 17, 18, 19, 20, 21, 22, 23, 24, 25, 25, 27, 28, 29, or 30 or more nucleotides in length. In some instances, the designed nucleic acid-targeting nucleic acid is 21 nucleotides in length.

The designed nucleic acid-targeting nucleic acid can comprise a 5' deoxycytosine. The designed nucleic acid-targeting nucleic acid can comprise a deoxycytosine-deoxyadenosine at the 5' end of the designed nucleic acid-targeting nucleic acid. In some embodiments, any nucleotide can be present at the 5' end. The designed nucleic acid-targeting nucleic acid may comprise a 5' phosphorylated end.

The designed nucleic acid-targeting nucleic acid can be fully complementary to the target nucleic acid (e.g., hybridizable). The designed nucleic acid-targeting nucleic acid can be partially complementary to the target nucleic acid. For example, the designed nucleic acid-targeting nucleic acid can be at least 30, 40, 50, 60, 70, 80, 90, 95, or 100% complementary to the target nucleic acid over the region of the designed nucleic acid-targeting nucleic acid. The designed nucleic acid-targeting nucleic acid can be at most 30, 40, 50, 60, 70, 80, 90, 95, or 100% complementary to the target nucleic acid over the region of the designed nucleic acid-targeting nucleic acid.

A stretch of nucleotides of the designed nucleic acid-targeting nucleic acid can be complementary to the target nucleic acid (e.g., hybridizable). A stretch of at least 2, 3, 4, 5, 6, 7, 8, 9, 10, 11, 12, 13, 14, 15, 16, 17, 18, 19, 20, 21, 22, 23, 24, 25, 25, 27, 28, 29, or 30 contiguous nucleotides can be complementary to target nucleic acid. A stretch of at most 2, 3, 4, 5, 6, 7, 8, 9, 10, 11, 12, 13, 14, 15, 16, 17, 18, 19, 20, 21, 22, 23, 24, 25, 25, 27, 28, 29, or 30 contiguous nucleotides can be complementary to target nucleic acid.

A portion of the designed nucleic acid-targeting nucleic acid which is fully complementary to the target nucleic acid may extend from at least nucleotide 2, to nucleotide 17 (as counted from the 5' end of the designed nucleic acid-targeting nucleic acid). A portion of the designed nucleic acid-targeting nucleic acid which is fully complementary to the target nucleic acid may extend from at least nucleotide 3 to nucleotide 20, nucleotide 4 to nucleotide 18, nucleotide 5 to nucleotide 16, nucleotide 6 to nucleotide 14, nucleotide 7 to nucleotide 12, nucleotide 6 to nucleotide 16, nucleotide 6 to nucleotide 18, or nucleotide 6 to nucleotide 20.

The designed nucleic acid-targeting nucleic acid can hybridize to a target nucleic acid. The designed nucleic acid-targeting nucleic acid can hybridize with a mismatch between the designed nucleic acid-targeting nucleic acid and the target nucleic acid (e.g., a nucleotide in the designed nucleic acid-targeting nucleic acid may not hybridize with the target nucleic acid). A designed nucleic acid-targeting nucleic acid can comprise at least 1, 2, 3, 4, 5, 6, 7, 8, 9, or 10 or more mismatches when hybridized to a target nucleic acid. A designed nucleic acid-targeting nucleic acid can comprise at most 1, 2, 3, 4, 5, 6, 7, 8, 9, or 10 or more mismatches when hybridized to a target nucleic acid.

The designed nucleic acid-targeting nucleic acid may direct cleavage of the target nucleic acid at the bond between the $1^{st}$ and $2^{nd}$, $2^{nd}$ and $3^{rd}$, $3^{rd}$ and $4^{th}$, $4^{th}$ and $5^{th}$, $5^{th}$ and $6^{th}$, $6^{th}$ and $7^{th}$, $7^{th}$ and $8^{th}$, $8^{th}$ and $9^{th}$, $9^{th}$ and $10^{th}$, $10^{th}$ and $11^{th}$, $11^{th}$ and $12^{th}$, $12^{th}$ and $13^{th}$, $13^{th}$ and $14^{th}$, $14^{th}$ and $15^{th}$, $15^{th}$ and $16^{th}$, $16^{th}$ and $17^{th}$, $17^{th}$ and $18^{th}$, $18^{th}$ and $19^{th}$, $19^{th}$ and $20^{th}$, $20^{th}$ and $21^{st}$, $21^{st}$ and $22^{nd}$, $22^{nd}$ and $23^{rd}$ $23^{rd}$ and $24^{th}$, or $24^{th}$ and $25^{th}$ nucleotides relative to the 5'-end of the designed nucleic acid-targeting nucleic acid. The designed nucleic acid-targeting nucleic acid may direct cleavage of the target nucleic acid at the bond between the 10th and 11th nucleotides (t10 and t11) relative to the 5'-end of the designed nucleic acid-targeting nucleic acid. The precise design for optimum cleavage of the target nucleic acid cleavage site may be determined by preliminary tests with plasmid targets incorporating the cleavage site.

Target Nucleic Acid

The target nucleic acid may comprise one or more sequences that is at least partially complementary to one or more designed nucleic acid-targeting nucleic acids. The target nucleic acid can be part or all of a gene, a 5' end of a gene, a 3' end of a gene, a regulatory element (e.g. promoter, enhancer), a pseudogene, non-coding DNA, a microsatellite, an intron, an exon, chromosomal DNA, mitrochondrial DNA, sense DNA, antisense DNA, nucleoid DNA, chloroplast DNA, or RNA among other nucleic acid entities. The target nucleic acid can be part or all of a plasmid DNA. The plasmid DNA or a portion thereof may be negatively supercoiled. The target nucleic acid can be in vitro or in vivo.

The target nucleic acid may comprise a sequences within a low GC content region. The target nucleic acid may be negatively supercoiled. Thus, by non-limiting example, the target nucleic acid may comprise a GC content of at least about 5, 10, 15, 20, 25, 30, 35, 40, 45, 50, 55, 60, or 65% or more. The target nucleic acid may comprise a GC content of at most about 5, 10, 15, 20, 25, 30, 35, 40, 45, 50, 55, 60, or 65% or more.

A region comprising a particular GC content may be the length of the target nucleic acid that hybridizes with the designed nucleic acid-targeting nucleic acid. The region comprising the GC content may be longer or shorter than the length of the region that hybridizes with the designed nucleic acid-targeting nucleic acid. The region comprising the GC content may be at least 30, 40, 50, 60, 70, 80, 90 or 100 or more nucleotides longer or shorter than the length of the region that hybridizes with the designed nucleic acid-targeting nucleic acid. The region comprising the GC content may be at most 30, 40, 50, 60, 70, 80, 90 or 100 or more nucleotides longer or shorter than the length of the region that hybridizes with the designed nucleic acid-targeting nucleic acid.

Complex of a Designed Nucleic Acid-Targeting Nucleic Acid and an Argonaute

A designed nucleic acid-targeting nucleic acid (designed nucleic acid-targeting nucleic acid) and an Argonaute protein (Argonaute) can form a complex, wherein the designed nucleic acid-targeting nucleic acid provides targeting specificity to the complex by comprising a nucleotide sequence that can hybridize to a sequence of a target nucleic acid. The Argonaute may be guided to the target nucleic acid sequence by its association with at least the protein-binding segment of the designed nucleic acid-targeting nucleic acid. Thus, the designed nucleic acid-targeting nucleic acid may direct the activity of the Argonaute protein. The designed nucleic acid-targeting nucleic acid may direct the activity of an enzymatically active Argonaute protein. The designed nucleic acid-targeting nucleic acid may direct the activity of an enzymatically inactive Argonaute protein.

In some instances, the Argonaute-designed nucleic acid-targeting nucleic acid complex comprises an Argonaute protein comprising at least 30% amino acid identity to an Argonaute (e.g., from *T. thermophilus* or *S. elongatus*) and a designed nucleic acid-targeting nucleic acid comprising at least 15 nucleotides.

In some instances, the Argonaute-designed nucleic acid-targeting nucleic acid complex comprises an Argonaute protein comprising at least 30% amino acid identity to an Argonaute (e.g., from *T. thermophilus* or *S. elongatus*) and a designed nucleic acid-targeting nucleic acid comprising at least 15 nucleotides, wherein at least 30% of the designed nucleic acid-targeting nucleic acid is complementary to the target nucleic acid over the length of the designed nucleic acid-targeting nucleic acid.

Any designed nucleic acid-targeting nucleic acid of the disclosure, Argonaute of the disclosure, effector protein, donor polynucleotide, reporter element, genetic element of interest, component of a split system and/or any nucleic acid or proteinaceous molecule necessary to carry out the embodiments of the methods of the disclosure may be recombinant, purified and/or isolated.

A complex of the disclosure can comprise an Argonaute comprising an amino acid sequence comprising at least 30% amino acid identity to an Argonaute from a prokaryote (e.g., *T. thermophilus* or *S. elongatus*), and a designed nucleic acid-targeting nucleic acid, wherein the designed nucleic acid-targeting nucleic acid is from 9-25 nucleotides in length and comprises a cytosine at its 5' end.

A complex of the disclosure can comprise an Argonaute can comprise an amino acid sequence comprising at least 30% amino acid identity to an Argonaute from a prokaryote (e.g., *T. thermophilus* or *S. elongatus*), a nucleic acid cleaving domain, wherein the nucleic acid cleaving domain comprise at least 70% amino acid identity to a nuclease domain from an Argonaute from a prokaryote (e.g., *T. thermophilus* or *S. elongatus*); and a designed nucleic acid-targeting nucleic acid, wherein the designed nucleic acid-targeting nucleic acid is from 9-25 nucleotides in length and comprises a cytosine at its 5' end.

A complex of the disclosure can comprise an Argonaute can comprise an amino acid sequence comprising at least 30% amino acid identity to an Argonaute from a prokaryote (e.g., *T. thermophilus* or *S. elongatus*), a nucleic acid cleaving domain, comprising at least 70% amino acid identity to a nuclease domain from an Argonaute from a prokaryote (e.g., *T. thermophilus* or *S. elongatus*), a linker linking the Argonaute to a non-native sequence, and a designed nucleic acid-targeting nucleic acid, wherein the designed nucleic acid-targeting nucleic acid is from 9-25 nucleotides in length and comprises a cytosine at its 5' end.

A complex of the disclosure can comprise an Argonaute can comprise an amino acid sequence comprising at least 30% amino acid identity to an Argonaute from a prokaryote (e.g., *T. thermophilus* or *S. elongatus*), a nucleic acid cleaving domain, comprising at least 70% amino acid identity to a nuclease domain from an Argonaute from a prokaryote (e.g., *T. thermophilus* or *S. elongatus*), wherein the Argonaute comprises a mutation in the nucleic acid cleaving domain that reduces the cleaving activity of the nuclease domains by at least 50%, and a designed nucleic acid-targeting nucleic acid, wherein the designed nucleic acid-targeting nucleic acid is from 9-25 nucleotides in length and comprises a cytosine at its 5' end.

Nucleic Acids Encoding a Designed Nucleic Acid-Targeting Nucleic Acid and/or an Argonaute The present disclosure provides for a nucleic acid comprising a nucleotide sequence encoding a designed nucleic acid-targeting nucleic acid of the disclosure, an Argonaute of the disclosure, an effector protein, a donor polynucleotide, a multiplexed genetic targeting agent, a tandem fusion polypeptide, a reporter element, a genetic element of interest, a component of a split system and/or any nucleic acid or proteinaceous molecule necessary to carry out the embodiments of the methods of the disclosure. In some embodiments, the nucleic acid encoding a designed nucleic acid-targeting nucleic acid of the disclosure, an Argonaute of the disclosure, an effector protein, a donor polynucleotide, a multiplexed genetic targeting agent, a tandem fusion polypeptide, a reporter element, a genetic element of interest, a component of a split system and/or any nucleic acid or proteinaceous molecule necessary to carry out the embodiments of the methods of the disclosure can be a vector (e.g., a recombinant expression vector).

In some embodiments, the recombinant expression vector can be a viral construct, (e.g., a recombinant adeno-associated virus construct), a recombinant adenoviral construct, a recombinant lentiviral construct, a recombinant retroviral construct, etc.

Suitable expression vectors can include, but are not limited to, viral vectors (e.g. viral vectors based on vaccinia virus, poliovirus, adenovirus, adeno-associated virus, SV40, herpes simplex virus, human immunodeficiency virus, a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus), plant vectors (e.g., T-DNA vector), and the like. The following vectors can be provided by way of example, for eukaryotic host cells: pXT1, pSG5, pSVK3, pBPV, pMSG, and pSVLSV40 (Pharmacia). Other vectors may be used so long as they are compatible with the host cell.

In some instances, the vector can be a linearized vector. The linearized vector can comprise an Argonaute and/or a designed nucleic acid-targeting nucleic acid. The linearized vector may not be a circular plasmid. The linearized vector can comprise a double-stranded break. The linearized vector may comprise a sequence encoding a fluorescent protein (e.g., orange fluorescent protein (OFP)). The linearized vector may comprise a sequence encoding an antigen (e.g., CD4). The linearized vector can be linearized (e.g., cut) in a region of the vector encoding parts of the designed nucleic acid-targeting nucleic acid. For example the linearized vector can be linearized (e.g., cut) in a 5' region of the designed nucleic acid-targeting nucleic acid. The linearized vector can be linearized (e.g., cut) in a 3' region of the designed nucleic acid-targeting nucleic acid. In some instances, a linearized vector or a closed supercoiled vector comprises a sequence encoding an Argonaute (e.g., Argonaute), a promoter driving expression of the sequence encoding the Argonaute (e.g., CMV promoter), a sequence encoding a marker, a sequence encoding an affinity tag, a sequence encoding portion of a designed nucleic acid-targeting nucleic acid, a promoter driving expression of the sequence encoding a portion of the designed nucleic acid-targeting nucleic acid, and a sequence encoding a selectable marker (e.g., ampicillin), or any combination thereof The vector can comprise a transcription and/or translation control element. Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a designed nucleic acid-targeting nucleic acid of the disclosure, an Argonaute of the disclosure, an effector protein, a donor polynucleotide, a multiplexed genetic targeting agent, a tandem fusion polypeptide, a reporter element, a genetic element of interest, a component of a split system and/or any nucleic acid or proteinaceous molecule necessary to carry out the embodiments of the methods of the disclosure can be operably linked to a control element (e.g., a transcriptional control element), such as a promoter. The transcriptional control element may be functional in a eukaryotic cell, (e.g., a mammalian cell), and/or a prokaryotic cell (e.g,. bacterial or archaeal cell). In some embodiments, a nucleotide sequence encoding a designed nucleic acid-targeting nucleic acid of the disclosure, an Argonaute of the disclosure, an effector protein, a donor polynucleotide, a multiplexed genetic targeting agent, a tandem fusion polypeptide, a reporter element, a genetic element of interest, a component of a split system and/or any nucleic acid or proteinaceous molecule necessary to carry out the embodiments of the methods of the disclosure can be operably linked to multiple control elements. Operable linkage to multiple control elements can allow expression of the nucleotide sequence encoding a designed nucleic aeid-targeting nucleic acid of the disclosure, an Argonaute of the disclosure, an effector protein, a donor polynucleotide, a reporter element, a genetic element of interest, a component of a split system and/or any nucleic acid or proteinaceous molecule necessary to carry out the embodiments of the methods of the disclosure in either prokaryotic or eukaryotic cells.

Non-limiting examples of suitable eukaryotic promoters (i.e. promoters functional in a eukaryotic cell) can include those from cytomegalovirus (CMV) immediate early; herpes simplex vims (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-active promoter (CAG), murine stem cell virus promoter (MSCV), phosphoglycerate kinase-1 locus promoter (PGK) and mouse metallothionein-I. The promoter can be a fungi promoter. The promoter can be a plain promoter. A database of plant promoters can be found (e.g., PlantProm) The expression vector may also contain a ribosome binding site for translation initiation and a transcription terminator. The expression vector may also include appropriate sequences for amplifying expression. The expression vector may also include nucleotide sequences encoding non-native tags (e.g., a 6xHis tag (SEQ ID NO: 23), hemagglutinin tag, green fluorescent protein, etc.) that are fused to the Argonaute, thus resulting in a fusion protein.

In some embodiments, a nucleotide sequence or sequences encoding a designed nucleic acid-targeting nucleic acid of the disclosure, an Argonaute of the disclosure, an effector protein, a donor polynucleotide, a multiplexed genetic targeting agent, a tandem fusion polypeptide, a reporter element, a genetic element of interest, a component of a split system and/or any nucleic acid or proteinaceous molecule necessary to carry out the embodiments of the methods of the disclosure can be operably linked to an inducible promoter (e.g., heat shock promoter, tetracycline-regulated promoter, steroid-regulated promoter, metal-regulated promoter, estrogen receptor-regulated promoter, etc.). In some embodiments, a nucleotide sequence encoding a designed nucleic acid-targeting nucleic acid of the disclosure, an Argonaute of the disclosure, an effector protein, a donor polynucleotide, a multiplexed genetic targeting agent, a tandem fusion polypeptide, a reporter element, a genetic element of interest, a component of a split system and/or any nucleic acid or proteinaceous molecule necessary to carry out the embodiments of the methods of the disclosure can be operably linked to a constitutive promoter (e.g., CMV promoter, UBC promoter). In some embodiments, the nucleotide sequence can be operably linked to a spatially restricted and/or temporally restricted promoter (e.g., a tissue specific promoter, a cell type specific promoter, etc.).

A nucleotide sequence or sequences encoding a designed nucleic acid-targeting nucleic acid of the disclosure, an Argonaute of the disclosure, an effector protein, a donor polynucleotide, a multiplexed genetic targeting agent, a tandem fusion polypeptide, a reporter element, a genetic element of interest, a component of a split system and/or any nucleic acid or proteinaceous molecule necessary to carry out the embodiments of the methods of the disclosure can be packaged into or on the surface of biological compartments for delivery to cells. Biological compartments can include, but are not limited to, viruses (lentivirus, adenovirus), nanospheres, liposomes, quantum dots, nanoparticles, polyethylene glycol particles, hydrogels, and micelles.

Introduction of the complexes, polypeptides, and nucleic acids of the disclosure into cells can occur by viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Donor Polynucleotides

A donor polynucleotide can refer to any polynucleotide suitable for insertion into a cleaved target nucleic acid. The donor polynucleotide may be a double-stranded target nucleic acid (e.g. dsDNA). A donor polynucleotide can be a naturally occuring nucleic acid. A donor polynucleotide can be a non-naturally occurring nucleic acid. A donor polynucleotide can comprise both a naturally occurring nucleic acid and a non-naturally occurring nucleic acid. A donor polynucleotide can comprise regions of homology with a target nucleic acid.

A donor polynucleotide can comprise regions of homology to the cleaved target nucleic acid. The regions of homology can be useful for integrating the donor polynucleotide into the cleaved target nucleic acid by homologous recombination. The regions of homology can be at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 or more nucleotides in length. The regions of homology can be at most about 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 or more nucleotides in length.

The regions of homology can have at least 5, 10, 15, 20, 25, 30, 35, 40, 45, 50, 55, 60, 65, 70, 75, 80, 85, 90, 95, or 100% homology to the cleaved target nucleic acid. The regions of homology can have at most 5, 10, 15, 20, 25, 30, 35, 40, 45, 50, 55, 60, 65, 70, 75, 80, 85, 90, 95, or 100% homology to the cleaved target nucleic acid.

A donor polynucleotide can be an oligonucleotide. A donor polynucleotide can be at least 5, 10, 15, 20, 25, 30, 35, 40, 45, 50, 55, 60, 65, 70, 75, 80, 85, 90, 95, or 100 or more nucleotides in length. A donor polynucleotide can be at most 5, 10, 15, 20, 25, 30, 35, 40, 45, 50, 55, 60, 65, 70, 75, 80, 85, 90, 95, or 100 or more nucleotides in length.

A donor polynucleotide can be a gene (e.g., transgene). A donor polynucleotide can be a cDNA. A donor polynucleotide can comprise genomic DNA. A donor polynucleotide can comprise introns. A donor polynucleotide can comprise a plurality of genes. A donor polynucleotide can be at least 1, 2, 3, 4, 5, 6, 7, 8, 9, 10 or more kilobases in length. A donor polynucleotide can be at most 1, 2, 3, 4, 5, 6, 7, 8, 9, 10 or more kilobases in length.

In some instances, a donor polynucleotide can comprise an artificial chromosome (e.g., bacterial artificial chromosome, yeast artificial chromosome).

The donor polynucleotide can comprise a sequence encoding for, for example, antibodies, antigens, enzymes, receptors (cell surface or nuclear), hormones, lymphokines, cytokines, reporter polypeptides, growth factors, insect resistant, transcription factors and functional fragments of any of the above. The coding sequences may be, for example, cDNAs.

For example, the donor polynucleotide may comprise a sequence encoding a polypeptide that is lacking or non-functional in the subject having a genetic disease, including but not limited to any of the following genetic diseases: achondroplasia, achromatopsia, acid maltase deficiency, adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, and Wiskott-Aldrich syndrome.

In some embodiments, the donor polynucleotide can comprise an agronomic gene or nucleotide sequence encoding a polypeptide of interest may include, for example and without limitation: a gene that confers resistance to a pests or disease; a gene that encodes a *Bacillus thuringiensis* protein, a derivative thereof, or a synthetic polypeptide modeled thereon; a gene that encodes a lectin; a gene that encodes a vitamin-binding protein; a gene encoding an insect-specific hormone or pheromone, e.g., an ecdysteroid or juvenile hormone, a variant thereof, a mimetic based thereon, or an antagonist or agonist thereof; a gene encoding an insect-specific peptide or neuropeptide that, upon expression, disrupts the physiology of the affected pest; a gene encoding an insect-specific venom produced in nature by a snake, a wasp, or other organism; a gene encoding an enzyme responsible for a hyperaccumulation of a monoterpene, a sesquiterpene, a steroid, hydroxamic acid, a phenylpropanoid derivative or other molecule with insecticidal activity; a gene encoding an enzyme involved in the modification, including the post-translational modification, of a biologically active molecule, e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, whether natural or synthetic; a gene encoding a molecule that stimulates signal transduction; a gene that encodes an insect-specific antibody or immunotoxin derived therefrom; a gene encoding a virus-specific antibody; a gene encoding a developmental-arrestive protein produced in nature by a pathogen or a parasite; a gene encoding a developmental-arrestive protein produced in nature by a plant. In some embodiments, donor polynucleotides can comprise an agronomic gene or nucleotide sequence encoding a polypeptide such as genes that confer resistance to an herbicide, such as an herbicide that inhibits the growing point or meristem, for example, an imidazolinone or a sulfonylurea; glyphosate resistance as conferred by, e.g., mutant 5-enolpyruvylshikimate-3-phosphate synthase (EPSPs) genes (via the introduction of recombinant nucleic acids and/or various forms of in vivo mutagenesis of native EPSPs genes); aroA genes and glyphosate acetyl transferase (GAT) genes, respectively); other phosphono compounds, such as glufosinate phosphinothricin acetyl transferase (PAT) genes from *Streptomyces* species, including *Streptomyces hygroscopicus* and *Streptomyces viridichromogenes*); and pyridinoxy or phenoxy proprionic acids and cyclohexones (ACCase inhibitor-encoding genes).

Codon-Optimization

A polynucleotide encoding an Argonaute and/or an endoribonuclease can be codon-optimized. This type of optimization can entail the mutation of foreign-derived (e.g., recombinant) DNA to mimic the codon preferences of the intended host organism or cell while encoding the same protein. Thus, the codons can be changed, but the encoded protein remains unchanged. For example, if the intended target cell was a human cell, a human codon-optimized polynucleotide could be used for producing a suitable Argonaute. As another non-limiting example, if the intended host cell were a mouse cell, then a mouse codon-optimized polynucleotide could be a suitable Argonaute. A polynucleotide encoding an Argonaute can be codon optimized for many host cells of interest. A host cell can be a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens C. Agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), etc. Codon optimization may not be required. In some instances, codon optimization can be preferable.

Transgenic Cells and Organisms

The disclosure provides for transgenic cells and organisms. The nucleic acid of a genetically modified host cell and/or transgenic organism can be targeted for genome engineering.

Exemplary cells that can be used to generate transgenic cells according to the methods of the disclosure can include, but are not limited to, HeLa cell, Chinese Hamster Ovary cell, 293-T cell, a pheochromocytoma, a neuroblastomas fibroblast, a rhabdomyosarcoma, a dorsal root ganglion cell, a NSO cell, Tobacco BY-2, CV-I (ATCC CCL 70), COS-I (ATCC CRL 1650), COS-7 (ATCC CRL 1651), CHO- K1 (ATCC CCL 61), 3T3 (ATCC CCL 92), NIH/3T3 (ATCC CRL 1658), HeLa (ATCC CCL 2), C 1271 (ATCC CRL 1616), BS-C-I (ATCC CCL 26), MRC-5 (ATCC CCL 171), L-cells, HEK-293 (ATCC CRL1573) and PC 12 (ATCC CRL- 1721), HEK293T (ATCC CRL-11268), RBL (ATCC CRL- 1378), SH-SY5Y (ATCC CRL-2266), MDCK (ATCC CCL-34), SJ-RH30 (ATCC CRL-2061), HepG2 (ATCC HB-8065), ND7/23 (ECACC 92090903), CHO (ECACC 85050302), Vera (ATCC CCL 81), Caco-2 (ATCC HTB 37), K562 (ATCC CCL 243), Jurkat (ATCC TIB- 152), Per.Co, Huvec (ATCC Human Primary PCS 100-010, Mouse CRL 2514, CRL 2515, CRL 2516), HuH-7D12 (ECACC 01042712), 293 (ATCC CRL 10852), A549 (ATCC CCL 185), IMR-90 (ATCC CCL 186), MCF-7 (ATC HTB-22), U-2 OS (ATCC HTB-96), and T84 (ATCC CCL 248), or any cell available at American Type Culture Collection (ATCC), or any combination thereof.

Organisms that can be transgenic can include bacteria, archaea, single-cell eukaryotes, plants, algae, fungi (e.g., yeast), invertebrates (e.g., fruit fly, cnidarian, echinoderm, nematode, etc), vertebrates (e.g., fish, amphibian, reptile, bird, mammal), mammals mammal (e.g., a pig, a cow, a goat, a sheep, a rodent, a rat, a mouse, a non-human primate, a human, etc.), etc.

Transgenic organisms can comprise genetically modified cells. Transgenic organisms and/or genetically modified cells can comprise organisms and/or cells that have been genetically modified with an exogenous nucleic acid comprising a nucleotide sequence encoding a designed nucleic acid-targeting nucleic acid of the disclosure, an Argonaute of the disclosure, an effector protein, a donor polynucleotide, a reporter element, a genetic element of interest, a component of a split system and/or any nucleic acid or proteinaceous molecule necessary to carry out the embodiments of the methods of the disclosure, or any combination thereof.

A genetically modified cell can comprise an exogenous Argonaute and/or an exogenous nucleic acid comprising a nucleotide sequence encoding an Argonaute. Expression of the Argonaute in the cell may take 0.1, 0.2, 0.5, 1, 2, 3, 4, 5, 6, or more days. Cells, introduced with the Argonaute, may be grown for 0.1, 0.2, 0.5, 1, 2, 3, 4, 5, 6, 7, 8, 9, 10 or even more days before the cells can be removed from cell culture and/or host organism.

Subjects

The disclosure provides for performing the methods of the disclosure in a subject. A subject can be a human. A subject can be a mammal (e.g., rat, mouse, cow, dog, pig, sheep, horse). A subject can be a vetebrate or an invertebrate. A subject can be a laboratory animal. A subject can be a patient. A subject can be suffering from a disease. A subject can display symptoms of a disease. A subject may not display symptoms of a disease, but still have a disease. A subject can be under medical care of a caregiver (e.g., the subject is hospitalized and is treated by a physician). A subject can be a plant or a crop. A subject can be in a clinical trial.

Kits

The present disclosure provides kits for carrying out the methods of the disclosure. A kit can include one or more of: a designed nucleic acid-targeting nucleic acid of the disclosure, a polynucleotide encoding a designed nucleic acid-targeting nucleic acid, an Argonaute protein of the disclosure, a polynucleotide encoding an Argonaute protein, an effector protein, a polynucleotide encoding an effector protein, a donor polynucleotide, a multiplexed genetic targeting agent of the disclosure, a polynucleotide endcoding a multiplexed genetic targeting agent of the disclosure, a tandem fusion polypeptide, a polynucleotide encoding a tandem fusion polypeptide, a reporter element, a genetic element of interest, a component of a split system and/or any nucleic acid or proteinaceous molecule necessary to carry out the embodiments of the methods of the disclosure, or any combination thereof.

A designed nucleic acid-targeting nucleic acid of the disclosure, a polynucleotide encoding a designed nucleic acid-targeting nucleic acid, an Argonautc protein of the disclosure, a polynucleotide encoding an Argonautc protein, an effector protein, a polynucleotide encoding an effector protein, a donor polynucleotide, a multiplexed genetic targeting agent of the disclosure, a polynucleotide endcoding a multiplexed genetic targeting agent of the disclosure, a tandem fusion polypeptide, a polynucleotide encoding a tandem fusion polypeptide, a reporter element, a genetic element of interest, a component of a split system and/or any nucleic acid or proteinaceous molecule necessary to carry out the embodiments of the methods of the disclosure are described in detail above.

The kit may further comprise a $Mn^{2+}$-containing buffer or $Mn^{2+}$. The kit may further comprise a $Mg^{2+}$-containing buffer or $Mg^{2+}$.

A kit can comprise: (1) a vector comprising a nucleotide sequence encoding a designed nucleic acid-targeting nucleic acid, and (2) a vector comprising a nucleotide sequence encoding an Argonaute protein and (3) a reagent for reconstitution and/or dilution of the vectors.

A kit can comprise; (1) a vector comprising (i) a nucleotide sequence encoding a designed nucleic acid-targeting nucleic acid, and (ii) a nucleotide sequence encoding an Argonaute protein and (2) a reagent for reconstiiution and/or dilution of the vector.

A kit can comprise: (1) a vector comprising a nucleotide sequence encoding a designed nucleic acid-targeting nucleic acid, (2) a vector comprising a nucleotide sequence encoding an Argonaute protein, (3) a vector comprising a nucleotide sequence encoding an effector protein, a donor polynucleotide, a reporter element, a genetic element of interest, a component of a split system and/or any nucleic acid or proteinaceous molecule necessary to carry out the embodiments of the methods of the disclosure, and (4) a reagent for rcconstitution and/or dilution of the vectors.

A kit can comprise: (1) a vector comprising (i) a nucleotide sequence encoding a designed nucleic acid-targeting nucleic acid, (ii) a nucleotide sequence encoding the an Argonaute protein, (2) a vector comprising a nucleotide sequence encoding an effector protein, a donor polynucleotide, a reporter element, a genetic element of interest, a component of a split system and/or any nucleic acid or proteinaceous molecule necessary to carry out the embodiments of the methods of the disclosure, and (3) a reagent for reconstitution and/or dilution of the recombinant expression vectors.

A kit can comprise an Argonaute comprising an amino acid sequence comprising at least 30% amino acid identity to an Argonaute from a prokaryote (e.g., *T. thermophilus*), and a designed nucleic acid-targeting nucleic acid, wherein the designed nucleic acid-targeting nucleic acid is from 9-25 nucleotides in length and comprises a cytosine at its 5' end.

A kit can comprise an Argonaute can comprise an amino acid sequence comprising at least 30% amino acid identity to an Argonaute from a prokaryote (e.g., *T. thermophilus*), a nucleic acid cleaving domain, wherein the nucleic acid cleaving domain comprise at least 70% amino acid identity to a nuclease domain from an Argonaute from a prokaryote (e.g., *T. thermophilus*); and a designed nucleic acid-targeting nucleic acid, wherein the designed nucleic acid-targeting nucleic acid is from 9-25 nucleotides in length and comprises a cytosine at its 5' end.

A kit can comprise an Argonaute can comprise an amino acid sequence comprising at least 30% amino acid identity to an Argonaute from a prokaryote (e.g., *T. thermophilus*), a nucleic acid cleaving domain, comprising at least 70% amino acid identity to a nuclease domain from an Argonaute from a prokaryote (e.g., *T thermophilus*), a linker linking the Argonaute to a non-native sequence, and a designed nucleic acid-targeting nucleic acid, wherein the designed nucleic acid-targeting nucleic acid is from 9-25 nucleotides in length and comprises a cytosine at its 5' end.

A kit can comprise an Argonaute can comprise an amino acid sequence comprising at least 30% amino acid identity to an Argonaute from a prokaryote (e.g., *T. thermophilus*), a nucleic acid cleaving domain, comprising at least 70% amino acid identity to a nuclease domain from an Argonaute from a prokaryote (e.g., *T. thermophilus*), wherein the Argonaute comprises a mutation in the nucleic acid cleaving domain that reduces the cleaving activity of the nuclease domains by at least 50%, and a designed nucleic acid-targeting nucleic acid, wherein the designed nucleic acid-targeting nucleic acid is from 9-25 nucleotides in length and comprises a cytosine at its 5' end.

In some embodiments of any of the above kits, the kit can further comprise a donor polynucleotide, or a polynucleotide sequence encoding the donor polynucleotide, to effect the desired genetic modification. Components of a kit can be in separate containers; or can be combined in a single container.

A kit described above further comprise one or more additional reagents, where such additional reagents can be selected from: a buffer, a buffer for introducing the a polypeptide or polynucleotide item of the kit into a cell, a wash buffer, a control reagent, a control vector, a control RNA and/or DNA polynucleotide, a reagent for in vitro production of the polypeptide from DNA, adaptors for sequencing and the like. A buffer can be a stabilization buffer, a reconstituting buffer, or a diluting buffer.

In some instances, the buffer in the kit may comprise manganese and/or magnesium ions. The buffer may comprise manganese and/or magnesium ions at a concentration of at least about 1, 2, 3, 4, 5, 6, 7, 8, 9, 10, 15, 20, 25, 30, 35, 40, 45, 50 or 55 or more micromolar. The buffer may comprise manganese and/or magnesium ions at a concentration of at most about 1, 2, 3, 4, 5, 6, 7, 8, 9, 10, 15, 20, 25, 30, 35, 40, 45, 50 or 55.

In some instances, a kit can comprise one or more additional reagents specific for plants and/or fungi. One or more additional reagents for plants and/or fungi can include, for example, soil, nutrients, plants, seeds, spores, Agrobacterium, T-DNA vector, and a pBINAR vector.

In addition to above-mentioned components, a kit can further include instructions for using the components of the kit to practice the methods. The instructions for practicing the methods are generally recorded on a suitable recording medium. For example, the instructions may be printed on a substrate, such as paper or plastic, etc. The instructions may be present in the kits as a package insert, in the labeling of the container of the kit or components thereof (i.e., associated with the packaging or subpackaging) etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this embodiment is a kit that includes a web address where the instructions can be viewed and/or from which the instructions can be downloaded. As with the instructions, this means for obtaining the instructions can be recorded on a suitable substrate.

In some embodiments, a kit can comprise a linearized vector. A linearized vector can comprise a plasmid comprising an Argonaute and/or a designed nucleic acid-targeting nucleic acid that is linearized (e.g., it is not circular). A linearized vector can be stored in a buffer comprising 10 mM Tris-HCl, pH 8.0 and 1mM EDTA, pH 8.0. A kit can comprise about 20 microliters of the linearized vector. In some embodiments, a kit can comprise one or more circular vectors.

In some embodiments a kit can comprise an oligonucleotide annealing buffer. An oligonucleotide annealing buffer can be a buffer used to anneal DNA oligos together to generate a double-stranded DNA that encode a designed nucleic acid-targeting nucleic acid. A oligonucleotide annealing buffer can be at least about, 1, 2, 3, 4, 5, 6, 7, 8, 9, or 10 or more concentrated than the concentration of use. An oligonucleotide annealing buffer can be 10 times more concentrated than the concentretion when used. An oligonucleotide annealing buffer can comprise 100 mM Tris-HCl, pH 8.0, 10mM EDTA, pH 8.0 and 1M NaCl. A kit can comprise 250 microliters of the oligonucleotide annealing buffer.

A kit can comprise DNase-free water. A kit can comprise RNAse-free water. A kit can comprise at least 1.5 milliliters of RNase-free and/or DNAse-free water.

A kit can comprise a ligation buffer. A ligation buffer can be used to ligate oligonucleotides to the linearized vector. A ligation buffer can be at least about, 1, 2, 3, 4, 5, 6, 7, 8, 9, or 10 or more concentrated than the concentration of use. A ligation buffer can be 5 times as concentrated as the concentration of use. A 5× ligation buffer can comprise 250 mM Tris-HCl, pH 7.6, 50 mM $MgCl_2$, 5 mM ATP, 5 mM DTT, and 25% (w/v) polyethylene glycol-8000. A kit can comprise about 80 microliters of a ligation buffer.

A kit can comprise a DNA ligase. A DNA ligase can be used to ligate the oligonucleotides to the linearized vector. A DNA ligase can comprise 10 mM Tris-HC1, pH 7.5, 50 mM KCl, 1 mM DTT, and 50% (v/v) glycerol. A kit can comprise 20 microliters of a DNA ligase.

A kit can comprise a sequencing primer. The sequencing primer can be used to sequence the vector once the oligonucleotides have been ligated into a linearized vector. A sequencing primer can be diluted in Tris-EDTA buffer pH 8.0. A kit can comprise 20 microliters of a sequencing primer.

A kit can comprise a control oligonucleotide. A control oligonucleotide can be an oligonucleotide to be ligated into a linearized vector but does not encode for a designed nucleic acid-targeting nucleic acid. A control oligonucleotide can be diluted in 1× concentration of the oligonucleotide annealing buffer. A kit can comprise 10 microliters of a control oligonucleotide.

In some instances, a kit can comprise a linearized vector comprising an Argonaute and a designed nucleic acid-targeting nucleic acid, an oligonucleotide annealing buffer, DNAse/RNAse free water, a ligation buffer, a ligase enyzme, a sequencing primer and a control oligonucleotide, or any combination thereof.

Pharmaceutical Compositions

Molecules, such as a designed nucleic acid-targeting nucleic acid of the disclosure as described herein, a polynucleotide encoding a designed nucleic acid-targeting nucleic acid, an Argonaute of the disclosure, a polynucleotide encoding an Argonaute, an effector protein, a polynucleotide encoding an effector protein, a donor polynucleotide, a reporter element, a genetic element of interest, a component of a split system and/or any nucleic acid or proteinaceous molecule necessary to carry out the embodiments of the methods of the disclosure, can be formulated in a pharmaceutical composition.

A pharmaceutical composition can comprise a combination of any molecules described herein with other chemical components, such as carriers, stabilizers, diluents, dispersing agents, suspending agents, thickening agents, and/or excipients. The pharmaceutical composition can facilitate administration of the molecule to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration.

A pharmaceutical composition can be administered in a local or systemic manner, for example, via injection of the molecule directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the molecules with pharmaceutically-acceptable carriers or excipients. Such carriers can be used to formulate tablets, powders, pills, dragees, capsules, liquids, gels, syrups, elixirs, slurries, suspensions and the like, for oral ingestion by a subject.

Pharmaceutical preparations for oral use can be obtained by mixing one or more solid excipient with one or more of the molecules described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally can include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can comprise the active ingredients in admixture with filler such as lactose, binders such as starches, and/or lubricants such as talc or magnesium stearate and, stabilizers. In soft capsules, the molecule can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parental injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration can include aqueous solutions of the active compounds in water-soluble form.

Suspensions of molecules can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the molecules to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can comprise solubilizers, stabilizers, tonicity enhancing agents, buffers and preservatives.

Formulations suitable for transdermal administration of the molecules can employ transdermal delivery devices and transdermal delivery patches, and can be lipophilic emulsions or buffered aqueous solutions, dissolved and/or dispersed in a polymer or an adhesive. Such patches can be constructed for continuous, pulsatile, or on demand delivery of molecules. Transdermal delivery can be accomplished by means of iontophoretic patches and the like. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin.

For administration by inhalation, the molecule can be in a form as an aerosol, a mist, or a powder. Pharmaceutical compositions can be delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The molecules can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of the disclosure, therapeutically-effective amounts of the compounds described herein can be administered in pharmaceutical compositions to a subject having a disease or condition to be treated. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the molecule into preparations that can be used pharmaceutically. Formulation can be modified depending upon the route of administration chosen. Pharmaceutical compositions comprising a molecule described herein can be manufactured, for example, by mixing, dissolving, granulating, dragee-making, levigating, emulsifying, encapsulating, entrapping, or compression processes.

The pharmaceutical compositions can include at least one pharmaceutically acceptable carrier, diluent, or excipient and molecule described herein as free-base or pharmaceutically-acceptable salt form. The methods and pharmaceutical compositions described herein include the use crystalline forms (also known as polymorphs), and active metabolites of these compounds having the same type of activity.

Methods for the preparation of compositions comprising the compounds described herein can include formulating the molecule with one or more inert, pharmaceutically-acceptable excipients or carriers to form a solid, semi-solid, or liquid composition. Solid compositions can include, for example, powders, tablets, dispersible granules, capsules, cachets, and suppositories. Liquid compositions can include, for example, solutions in which a compound is dissolved, emulsions comprising a compound, or a solution containing liposomes, micelles, or nanoparticles comprising a compound as disclosed herein. Semi-solid compositions can include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms can include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, and nutraceuticals, or any combination thereof Non-limiting examples of pharmaceutically-acceptable excipients can include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material, and spheronization agents, or any combination thereof.

A composition can be, for example, an immediate release form or a controlled release formulation. An immediate release formulation can be formulated to allow the molecules to act rapidly. Non-limiting examples of immediate release formulations can include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations can include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, granular masses, and the like.

A controlled release formulation can be a delayed release form. A delayed release form can be formulated to delay a molecule's action for an extended period of time. A delayed release form can be formulated to delay the release of an effective dose of one or more molecules, for example, for about 4, about 8, about 12, about 16, or about 24 hours.

A controlled release formulation can be a sustained release form. A sustained release form can be formulated to sustain, for example, the molecule's action over an extended period of time. A sustained release form can be formulated to provide an effective dose of any molecule described herein (e.g., provide a physiologically-effective blood profile) over about 4, about 8, about 12, about 16 or about 24 hours.

Methods of Administration and Treatment Methods

Pharmaceutical compositions containing molecules described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Amounts effective for this use can vary based on the severity and course of the disease or condition, previous therapy, the subject's health status, weight, and response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The molecules can be packed together or separately, in a single package or in a plurality of packages. One or all of the therapeutic agents can be given in multiple doses. If not simultaneous, the timing between the multiple doses may vary to as much as about a month.

Molecules described herein can be administered before, during, or after the occurrence of a disease or condition, and the timing of administering the composition containing a compound can vary. For example, the pharmaceutical compositions can be used as a prophylactic and can be administered continuously to subjects with a propensity to conditions or diseases in order to prevent the occurrence of the disease or condition. The molecules and pharmaceutical compositions can be administered to a subject during or as soon as possible after the onset of the symptoms. The administration of the molecules can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A molecule can be administered as soon as is practicable after the onset of a disease or condition is detected or suspected, and for a length of time necessary for the treatment of the disease, such as, for example, from about 1 month to about 3 months. The length of treatment can vary for each subject.

A molecule can be packaged into a biological compartment. A biological compartment comprising the molecule can be administered to a subject. Biological compartments can include, but are not limited to, viruses (lentivirus, adenovirus), nanospheres, liposomes, quantum dots, nanoparticles, microparticles, nanocapsules, vesicles, polyethylene glycol particles, hydrogels, and micelles.

For example, a biological compartment can comprise a liposome. A liposome can be a self-assembling structure comprising one or more lipid bilayers, each of which can comprise two monolayers containing oppositely oriented amphipathic lipid molecules. Amphipathic lipids can comprise a polar (hydrophilic) headgroup covalently linked to one or two or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups can be oriented towards the bilayer's surface and acyl chains are oriented towards the interior of the bilayer, effectively shielding the acyl chains from contact with the aqueous environment.

Examples of preferred amphipathic compounds used in liposomes can include phosphoglycerides and sphingolipids, representative examples of which include phosphatidylcholine, phosphatidylethanolamine, phosphatidylserine, phosphatidylinositol, phosphatidic acid, phoasphatidylglycerol, palmitoyloleoyl phosphatidylcholine, lysophosphatidylcholine, lysophosphatidylethanolamine, dimyristoylphosphatidylcholine (DMPC), dipalmitoylphosphatidylcholine (DPPC), dioleoylphosphatidylcholine, distearoylphosphatidylcholine (DSPC), dilinoleoylphosphatidylcholine and egg sphingomyelin, or any combination thereof.

A biological compartment can comprise a nanoparticle. A nanoparticle can comprise a diameter of from about 40 nanometers to about 1.5 micrometers, from about 50 nanometers to about 1.2 micrometers, from about 60 nanometers to about 1 micrometer, from about 70 nanometers to about 800 nanometers, from about 80 nanometers to about 600 nanometers, from about 90 nanometers to about 400 nanometers, from about 100 nanometers to about 200 nanometers.

In some instances, as the size of the nanoparticle increases, the release rate can be slowed or prolonged and as the size of the nanoparticle decreases, the release rate can be increased.

The amount of albumin in the nanoparticles can range from about 5% to about 85% albumin (v/v), from about 10% to about 80%, from about 15% to about 80%, from about 20% to about 70% albumin (v/v), from about 25% to about 60%, from about 30% to about 50%, or from about 35% to about 40%. The pharmaceutical composition can comprise up to 30, 40, 50, 60, 70 or 80% or more of the nanoparticle. In some instances, the nucleic acid molecules of the disclosure can be bound to the surface of the nanoparticle.

A biological compartment can comprise a virus. The virus can be a delivery system for the pharmaceutical compositions of the disclosure. Exemplary viruses can include lentivirus, retrovirus, adenovirus, herpes simplex virus I or II, parvovirus, reticuloendotheliosis virus, and adeno-associated virus (AAV). Pharmaceutical compositions of the disclosure can be delivered to a cell using a virus. The virus can infect and transduce the cell in vivo, ex vivo, or in vitro. In ex vivo and in vitro delivery, the transduced cells can be administered to a subject in need of therapy.

Pharmaceutical compositions can be packaged into viral delivery systems. For example, the compositions can be packaged into virions by a HSV-1 helper virus-free packaging system.

Viral delivery systems (e.g., viruses comprising the pharmaceutical compositions of the disclosure) can be administered by direct injection, stereotaxic injection, intracerebroventricularly, by minipump infusion systems, by convection, catheters, intravenous, parenteral, intraperitoneal, and/or subcutaenous injection, to a cell, tissue, or organ of a subject in need. In some instances, cells can be transduced in vitro or ex vivo with viral delivery systems. The transduced cells can be administered to a subject having a disease. For example, a stem cell can be transduced with a viral delivery system comprising a pharmaceutical composition and the stem cell can be implanted in the patient to treat a disease. In some instances, the dose of transduced cells given to a subject can be about $1\times10^5$ cells/kg, about $5\times10^5$ cells/kg, about $1\times10^6$ cells/kg, about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $5\times10^7$ cells/kg, about $1\times10^8$ cells/kg, or more in one single dose.

Pharmaceutical compositions in biological compartments can be used to treatinflammatory diseases such as arthritis, cancers, such as, for example, bone cancer, breast cancer, skin cancer, prostate cancer, liver cancer, lung cancer, throat cancer and kidney cancer, bacterial infections, to treat nerve damage, lung, liver and kidney diseases, eye treatment, spinal cord injuries, heart disease, arterial disease.

Introduction of the biological compartments into cells can occur by viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Dosage

Pharmaceutical compositions described herein can be in unit dosage forms suitable for single administration of precise dosages. In unit dosage form, the formulation can be divided into unit doses containing appropriate quantities of one or more compounds. The unit dosage can be in the form of a package containing discrete quantities of the formulation. Non-limiting examples can include packaged tablets or capsules, and powders in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A molecule described herein can be present in a composition in a range of from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A molecule described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

A molecule (e.g., Argonaute, designed nucleic acid-targeting nucleic acid and/or complex of an Argonaute and a designed nucleic acid-targeting nucleic acid) described herein can be present in a composition that provides at least 0.1, 0.5, 1, 1.5, 2, 2.5 3, 3.5, 4, 4.5, 5, 5.5, 6, 6.5, 10 or more units of activity/mg molecule. In some embodiments, the total number of units of activity of the molecule delivered to a subject is at least 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190, 000, 200,000, 210,000, 220,000, 230,000, or 250,000 or more units. In some embodiments, the total number of units of activity of the molecule delivered to a subject is at most 25,000, 30,000, 35,000, 40,000, 45,000, 50,000, 60,000, 70,000, 80,000, 90,000, 110,000, 120,000, 130,000, 140, 000, 150,000, 160,000, 170,000, 180,000, 190,000, 200,000, 210,000, 220,000, 230,000, or 250,000 or more units.

In some embodiments, at least about 10,000 units of activity is delivered to a subject, normalized per 50 kg body weight. In some embodiments, at least about 10,000, 15,000, 25,000, 30,000, 35,000, 40,000, 45,000, 50,000, 60,000, 70,000, 80,000, 90,000, 110,000, 120,000, 130,000, 140, 000, 150,000, 160,000, 170,000, 180,000, 190,000, 200,000, 210,000, 220,000, 230,000, or 250,000 units or more of activity of the molecule is delivered to the subject, normalized per 50 kg body weight. In some embodiments, a therapeutically effective dose comprises at least $5\times10^5$, $1\times10^6$, $2\times10^6$, $3\times10^6$, 4, $10^6$, $5\times10^6$, $6\times10^6$, $7\times10^6$, $8\times10^6$, $9\times10^6$, $1\times10^7$, $1.1\times10^7$, $1.2\times10^7$, $1.5\times10^7$, $1.6\times10^7$, $1.7\times10^7$, $1.8\times10^7$, $1.9\times10^7$, $2\times10^7$, $2.1\times10^7$, or $3\times10^7$ or more units of activity of the molecule. In some embodiments, a therapeutically effective dose comprises at most $5\times10^5$, $1\times10^6$, $2\times10^6$, $3\times10^6$, 4, $10^6$, $5\times10^6$, $6\times10^6$, $7\times10^6$, $8\times10^6$, $9\times10^6$, $1\times10^7$, $1.1\times10^7$, $1.2\times10^7$, $1.5\times10^7$, $1.6\times10^7$, $1.7\times10^7$, $1.8\times10^7$, $1.9\times10^7$, $2\times10^7$, $2.1\times10^7$, or $3\times10^7$ or more units of activity of the molecule.

In some embodiments, a therapeutically effective dose is at least about 10,000, 15,000, 20,000, 22,000, 24,000, 25,000, 30,000, 40,000, 50,000, 60,000, 70,000, 80,000, 90,000, 100,000, 125,000, 150,000, 200,000, or 500,000 units/kg body weight. In some embodiments, a therapeutically effective dose is at most about 10,000, 15,000, 20,000, 22,000, 24,000, 25,000, 30,000, 40,000, 50,000, 60,000, 70,000, 80,000, 90,000, 100,000, 125,000, 150,000, 200, 000, or 500,000 units/kg body weight.

In some embodiments, the activity of the molecule delivered to a subject is at least 10,000, 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, or 50,000 or more U/mg of molecule. In some embodiments, the activity of the molecule delivered to a subject is at most 10,000, 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, or 50,000 or more U/mg of molecule.

Pharmacokinetic and Pharmacodynamic Measurements

Pharmacokinetic and pharmacodynamic data can be obtained by various experimental techniques. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean can be determined by calculating the average of all subject's measurements for each parameter measured. A dose can be modulated to achieve a desired pharmacokinetic or pharmacodynamics profile, such as a desired or effective blood profile, as described herein.

The pharmacokinetic parameters can be any parameters suitable for describing a molecule. For example, the $C_{max}$ can be, for example, not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; or any other $C_{max}$ appropriate for describing a pharmacokinetic profile of a molecule described herein.

The $T_{max}$ of a molecule described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of a molecule described herein.

The $AUC_{(0-inf)}$ of a molecule described herein can be, for example, not less than about 50 ng/hr/mL, not less than about 100 ng/hr/mL, not less than about 150 ng/hr/mL, not less than about 200 ng/hr/mL, not less than about 250 ng/hr/mL, not less than about 300 ng/hr/mL, not less than about 350 ng/hr/mL, not less than about 400 ng/hr/mL, not less than about 450 ng/hr/mL, not less than about 500 ng/hr/mL, not less than about 600 ng/hr/mL, not less than about 700 ng/hr/mL, not less than about 800 ng/hr/mL, not less than about 900 ng/hr/mL, not less than about 1000 ng/hr/mL, not less than about 1250 ng/hr/mL, not less than about 1500 ng/hr/mL, not less than about 1750 ng/hr/mL, not less than about 2000 ng/hr/mL, not less than about 2500 ng/hr/mL, not less than about 3000 ng/hr/mL, not less than about 3500 ng/hr/mL, not less than about 4000 ng/hr/mL, not less than about 5000 ng/hr/mL, not less than about 6000 ng/hr/mL, not less than about 7000 ng/hr/mL, not less than about 8000 ng/hr/mL, not less than about 9000 ng/hr/mL, not less than about 10,000 ng/hr/mL, or any other $AUC_{(0-inf)}$ appropriate for describing a pharmacokinetic profile of a molecule described herein.

The plasma concentration of a molecule described herein about one hour after administration can be, for example, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a molecule described herein.

The pharmacodynamic parameters can be any parameters suitable for describing pharmaceutical compositions of the disclosure. For example, the pharmacodynamic profile can exhibit decreases in factors associated with inflammation after, for example, about 2 hours, about 4 hours, about 8 hours, about 12 hours, or about 24 hours.

Pharmaceutically-Acceptable Salts

The disclosure provides the use of pharmaceutically-acceptable salts of any molecule described herein. Pharmaceutically-acceptable salts can include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt, or any combination thereof.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine, or any combination thereof In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt, or any combination thereof.

Acid addition salts can arise from the addition of an acid to a molecule of the disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid, or any combination thereof.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt, or any combination thereof.

Engineered Argonautes

General Overview

The disclosure describes methods, compositions, systems, and/or kits for modifying Argonaute proteins (Argonautes) (e.g. prokaryotic Argonautes (pArgonautes)) and/or related enzymes. Modifications may include any covalent or non-covalent modification to Argonaute proteins. In some cases, this may include chemical modifications to one or more regions of the Argonaute protein. In some cases, modifications may include conservative or non-conservative amino acid substitutions of the Argonaute protein. In some cases, modifications may include the addition, deletion or substitution of any portion of the Argonaute protein with amino acids, peptides, or domains that are not found in the native Argonaute protein. In some cases, one or more non-native domains may be added, deleted or substituted in the Argonaute protein. In some cases the Argonaute protein may exist as a fusion protein.

In some cases, the present disclosure provides for the engineering of Argonaute proteins to recognize a desired target nucleic acid sequence with desired enzyme specificity and/or activity. Modifications to an Argonaute protein can be performed through protein engineering. Protein engineering can include fusing functional domains to such engineered Argonaute protein which can be used to modify the functional state of the overall Argonaute protein or the actual target nucleic acid sequence of an endogenous cellular locus. The Argonaute protein of the disclosure can be used to regulate endogenous gene expression, both through activation and repression of endogenous gene transcription.

The Argonaute protein-fusions can also be linked to other regulatory or functional domains, for example nucleases, transposases or methylases, to modify endogenous chromosomal sequences. In some cases, the Argonaute protein may be linked to at least one or more regulatory domains, described herein. Non-limiting examples of regulatory or functional domains include transcription factor repressor or activator domains such as KRAB and VP16, co-repressor and co-activator domains, DNA methyl transferases, histone acetyltransferases, histone deacetylases, and DNA cleavage domains such as the cleavage domain from the endonuclease FokI.

In some instances, one or more specific domains, regions or structural elements of the Argonaute protein can be modified together. Modifications to the Argonaute protein may occur, but are not limited to Argonaute protein elements such as regions that recognize or bind to the target nucleic acid, and/or regions that bind or recognize the designed nucleic acid-targeting nucleic acid. Such binding or recognition elements may include a MID domain, a PAZ domain, one or more nuclease domains, such as a PIWI domain. Modifications may be made to additional domains, structural elements, sequence or amino acids within the Argonaute protein.

Modifications to one or more regions of the Argonaute protein may be performed to alter various properties of the Argonaute protein. In some cases, modifications may alter binding recognition for certain nucleic acid target sequences. This may include but is not limited to increasing binding affinity and/or specificity to certain sequences or preferentially targeting of certain target nucleic acid sequences/recognition elements. In some cases, modifications may be used to alter native nuclease function. In some cases, modifications to the Argonaute protein may alter target nucleic acid specificity and/or designed nucleic acid-targeting nucleic acid specificity.

Described herein are also compositions and methods including fusion proteins comprising an Argonaute protein (e.g., pArgonaute from $T.$ $thermophilus$) and one or more domains or regions engineered for genomic editing (e.g., cleaving of genes; alteration of genes, for example by cleavage followed by insertion (physical insertion or insertion via homology-directed repair) of an exogenous sequence and/or cleavage followed by NHEJ; partial or complete inactivation of one or more genes; generation of alleles with altered functional states of endogenous genes, insertion of regulatory elements; etc.) and alterations of the genome which are carried into the germline. Also disclosed are methods of making and using these compositions (i.e. reagents), for example to edit (i.e. alter) one or more genes in a target cell. Thus, the methods and compositions described herein provide highly efficient methods for targeted gene alteration (e.g., knock-in) and/or knockout (partial or complete) of one or more genes and/or for randomized mutation of the sequence of any target allele, and, therefore, allow for the generation of animal models of human diseases. One skilled in the art will recognize that although the term "genome engineering" or "genomic editing" is often used to describe the methods herein, the methods and compositions described herein can also be used to alter any target nucleic acid that may not be strictly speaking in the genome of a cell (e.g. can be used on a synthetic nucleic acid, a plasmid, a vector, a viral nucleic acid, a recombinant nucleic acid, etc.).

The methods and compositions described herein allow for novel therapeutic applications, (e.g., prevention and/or treatment of: genetic diseases, cancer, fungal, protozoal, bacterial, and viral infection, ischemia, vascular disease, arthritis, immunological disorders, etc.), novel diagnostics (e.g. prediction and/or diagnosis of a condition) as well as providing for research tools (e.g. kits, functional genomics assays, and generating engineered cell lines and animal models for research and drug screening), and means for developing plants with altered phenotypes, including but not limited to, increased disease resistance, and altering fruit ripening characteristics, sugar and oil composition, yield, and color. The methods and compositions described herein allow for novel epigenetic studies.

Protein Modifications and Engineering

Amino Acid Alterations

Argonaute proteins, as disclosed herein, can be modified. The modification can comprise modifications to an amino acid of the Argonaute protein. The modifications can alter the primary amino acid sequence and/or the secondary, tertiary, and quaternary amino acid structure. In some cases some amino acid sequences of Argonaute protein of the invention can be varied without a significant effect on the structure or function of the protein. The type of mutation may be completely unimportant if the alteration occurs in some regions (e.g. a non-critical) region of the protein. In some cases, depending upon the location of the replacement, the mutation may not have a major effect on the biological properties of the resulting variant. For example, properties and functions of the Argonaute variants can be of the same type as wild-type Argonaute. In some caess, the mutation can critically impact the structure and/or function of the Argonaute protein.

The location of where to modify the Argonaute protein (e.g., a Argonaute variant) can be determined using sequence and/or structural alignment. Sequence alignment can identify regions of a polypeptide that similar and/or disimliar (e.g., conserved, not conserved, hydrophobic, hydrophilic, etc). In some instances, a region in the sequence of interest that is similar to other sequences is suitable for modification. In some instances, a region in the sequence of interest that is disimilar from other sequences is suitable for modification. For example, sequence alignment can be performed by database search, pairwise alignment, multiple sequence alignment, genomic analysis, motif finding, benchmarking, and/or programs such as BLAST, CS-BLAST, HHPRED, psi-BLAST, LALIGN, PyMOL, and SEQALN. Structural alignment can be performed by programs such as Dali, PHYRE, Chimera, COOT, O, and PyMOL. Alignment can be performed by database search, pairwise alignment, multiple sequence alignment, genomic analysis, motif finding, or bench marking, or any combination thereof An Argonaute protein can be modified to increase binding specificity to a designed nucleic acid-targeting nucleic acid and/or a target nucleic acid. An Argonaute protein can be modified to increase binding to specific regions of a designed nucleic acid-targeting nucleic acid and/or a target nucleic acid.

In some cases, the modification can comprise a conservative modification. A conservative amino acid change can involve substitution of one of a family of amino acids which are related in their side chains (e.g, cysteine/serine).

In some cases amino acid changes in the Argonaute protein disclosed herein are non-conservative amino acid changes, (i.e., substitutions of disimiliar charged or uncharged amino acids). A non-conservative amino acid change can involve substitution of one of a family of amino acids which may be unrelated in their side chains or a substitution that alters biological activity of the Argonaute protein.

The mutation may result in a change that may comprise a change in $K_d$ of binding between a mutated Argonaute protein and a target nucleic acid. The change in $K_d$ of binding between a mutated Argonaute protein and a target nucleic acidmay be more than 1000-fold, more than 500-fold, more than 100-fold, more than 50-fold, more than 25-fold, more than 10-fold, more than 5-fold, more than 4-fold, more than 3-fold, more than 2-fold higher or lower than the $K_d$ of binding between a non-mutated Argonaute protein and a target nucleic acid. The change in $K_d$ of binding between a mutated Argonaute protein and a target nucleic acid may be less than 1000-fold, less than 500-fold, less than 100-fold, less than 50-fold, less than 25-fold, less than 10-fold, less than 5-fold, less than 4-fold, less than 3-fold, less than 2-fold higher or lower than the $K_d$ of binding of binding between a non -mutated Argonaute protein and a target nucleic acid.

The mutation may result in a change that may comprise a change in $K_d$ of the binding between a mutated Argonaute protein and a designed nucleic acid-targeting nucleic acid. The change in $K_d$ of binding between a mutated Argonaute protein and a designed nucleic acid-targeting nucleic acid may be more than 1000-fold, more than 500-fold, more than 100-fold, more than 50-fold, more than 25-fold, more than 10-fold, more than 5-fold, more than 4-fold, more than 3-fold, more than 2-fold higher or lower than the $K_d$ of binding between a wild-type Argonaute protein (e.g, Argonaute from *T. thermophilus* or *S. elongatus*) and a designed nucleic acid-targeting nucleic acid. The change in $K_d$ of binding between a mutated Argonaute protein and a designed nucleic acid-targeting nucleic acid may be less than 1000-fold, less than 500-fold, less than 100-fold, less than 50-fold, less than 25-fold, less than 10-fold, less than 5-fold, less than 4-fold, less than 3-fold, less than 2-fold higher or lower than the $K_d$ of binding between a wild-type Argonaute protein (e.g, Argonaute from *T. thermophilus* or *S. elongatus*) and a designed nucleic acid-targeting nucleic acid.

The mutation of an Argonaute protein can also change the kinetics of the enzymatic action of the Argonaute protein. The mutation may result in a change that may comprise a change in the $K_m$ of the mutated Argonaute protein. The change in $K_m$ of the mutated Argonaute protein may be more than 1000-fold, more than 500-fold, more than 100-fold, more than 50-fold, more than 25-fold, more than 10-fold, more than 5-fold, more than 4-fold, more than 3-fold, more than 2-fold higher or lower than the $K_m$ of a wild-type Argonaute protein (e.g, Argonaute from *T. thermophilus* or *S. elongatus*). The change in $K_m$ of a mutated Argonaute protein may be less than 1000-fold, less than 500-fold, less than 100-fold, less than 50-fold, less than 25-fold, less than 10-fold, less than 5-fold, less than 4-fold, less than 3-fold, less than 2-fold higher or lower than the $K_m$ of a wild-type Argonaute protein (e.g, Argonaute from *T. thermophilus* or *S. elongatus*).

The mutation of an Argonaute protein may result in a change that may comprise a change in the turnover of the Argonaute protein. The change in the turnover of the mutated Argonaute protein may be more than 1000-fold, more than 500-fold, more than 100-fold, more than 50-fold, more than 25-fold, more than 10-fold, more than 5-fold, more than 4-fold, more than 3-fold, more than 2-fold higher or lower than the turnover of a wild-type Argonaute protein (e.g, Argonaute from *T. thermophilus* or *S. elongatus*). The change in the turnover of a mutated Argonaute protein may be less than 1000-fold, less than 500-fold, less than 100-fold, less than 50-fold, less than 25-fold, less than 10-fold, less than 5-fold, less than 4-fold, less than 3-fold, less than 2-fold higher or lower than the turnover of a wild-type Argonaute protein (e.g, Argonaute from *T. thermophilus* or *S. elongatus*).

The mutation may result in a change that may comprise a change in the AG of the enzymatic action of the Argonaute protein. The change in the AG of the mutated Argonaute protein may be more than 1000-fold, more than 500-fold, more than 100-fold, more than 50-fold, more than 25-fold, more than 10-fold, more than 5-fold, more than 4-fold, more than 3-fold, more than 2-fold higher or lower than the AG of a wild-type Argonaute protein (e.g, Argonaute from *T. thermophilus* or *S. elongatus*). The change in the turnover of a mutated Argonaute protein may be less than 1000-fold, less than 500-fold, less than 100-fold, less than 50-fold, less than 25-fold, less than 10-fold, less than 5-fold, less than 4-fold, less than 3-fold, less than 2-fold higher or lower than the AG of a wild-type Argonaute protein (e.g, Argonaute from *T. thermophilus* or *S. elongatus*).

The mutation may result in a change that may comprise a change in the $V_{max}$ of the enzymatic action of the Argonaute protein. The change in the $V_{max}$ of the mutated Argonaute protein may be more than 1000-fold, more than 500-fold, more than 100-fold, more than 50-fold, more than 25-fold, more than 10-fold, more than 5-fold, more than 4-fold, more than 3-fold, more than 2-fold higher or lower than the $V_{max}$ of a wild-type Argonaute protein (e.g, Argonaute from *T. thermophilus* or *S. elongatus*). The change in the turnover of a mutated Argonaute protein may be less than 1000-fold, less than 500-fold, less than 100-fold, less than 50-fold, less than 25-fold, less than 10-fold, less than 5-fold, less than 4-fold, less than 3-fold, less than 2-fold higher or lower than the $V_{max}$ of a wild-type Argonaute protein (e.g, Argonaute from *T. thermophilus* or *S. elongatus*).

The mutation may result in a change that may comprise a change in any kinetic parameter of the Argonaute protein. The mutation may result in in a change that may comprise a change in any thermodynamic parameter of the Argonaute protein. The mutation may result in in a change that may comprise a change in the surface charge, surface area buried, and/or folding kinetics of the Argonaute protein and/or enzymatic action of the Argonaute protein.

Amino acids in the Argonaute protein of the present invention that are essential for function can be identified by methods such as site-directed mutagenesis, alanine-scanning mutagenesis, protein structure analysis, nuclear magnetic resonance, photoaffinity labeling, and electron tomography, high-throughput screening, ELISAs, biochemical assays, binding assays, cleavage assays (e.g., Surveyor assay), reporter assays, and the like.

Other amino acid alterations may also include amino acids with glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue. In some cases mutated Argonaute proteins may also include allelic variants and species variants.

Truncations of regions which do not affect functional activity of the Argonaute protein may be engineered. Truncations of regions which do affect functional activity of the Argonaute protein may be engineered. A truncation may comprise a truncation of less than 5, less than 10, less than 15, less than 20, less than 25, less than 30, less than 35, less than 40, less than 45, less than 50, less than 60, less than 70, less than 80, less than 90, less than 100 or more amino acids. A truncation may comprise a truncation of more than 5, more than 10, more than 15, more than 20, more than 25, more than 30, more than 35, more than 40, more than 45, more than 50, more than 60, more than 70, more than 80, more than 90, more than 100 or more amino acids. A truncation may comprise truncation of about 5%, 10%, 15%, 20%, 25%, 30%, 35%, 40%, 45%, 50%, 55%, 60%, 65%, 70%, 75%, 80%, 85%, 90%, 95% or 100% of the Argonaute protein.

Deletions of regions which do not affect functional activity of the Argonaute proteins may be engineered. Deletions of regions which do affect functional activity of the Argonaute protein may be engineered. A deletion can comprise a deletion of less than 5, less than 10, less than 15, less than 20, less than 25, less than 30, less than 35, less than 40, less than 45, less than 50, less than 60, less than 70, less than 80, less than 90, less than 100 or more amino acids. A deletion may comprise a deletion of more than 5, more than 10, more than 15, more than 20, more than 25, more than 30, more than 35, more than 40, more than 45, more than 50, more than 60, more than 70, more than 80, more than 90, more than 100 or more amino acids. A deletion may comprise deletion of about 5%, 10%, 15%, 20%, 25%, 30%, 35%, 40%, 45%, 50%, 55%, 60%, 65%, 70%, 75%, 80%, 85%, 90%, 95% or 100% of the Argonaute protein. A deletion can occur at the N-terminus, the C-terminus, or at any region in the polypeptide chain.

Screens

The disclosure provides for methods for engineering an Argonaute protein. Screens can be used to engineer the Argonaute protein. For example, a screen can be set up to screen for the effect of mutations in a region of the Argonaute protein. For example, a screen can be set up to test modifications of the highly basic patch on the affinity for RNA structure (e.g., designed nucleic acid-targeting nucleic acid structure), or processing capability (e.g., target nucleic acid cleavage). Exemplary screeing methods can include but are not limited to, cell sorting emthods, mRNA display, phage display, and directed evolution.

Fusions

In some instances, the Argonaute protein is modified such that it comprises a non-native sequence (i.e. the polypeptide has a modification that alters it from the allele or sequence it was derived from) (e.g., the polypeptide can be referred to as a fusion). The non-native sequence can also include one or more additional proteins, protein domains, subdomains or polypeptides. For example. Argonaute may be fused with any suitable additional nonnative nucleic acid binding proteins and/or domains, including but not limited to transcription factor domains, nuclease domains, nucleic acid polymerizing domains. The non-native sequence can comprise a sequence of Argonaute and/or an Argonaute-homologue.

The non-native squence can confer new functions to the fusion protein. These functions can include for example, DNA methylation, DNA damage, DNA repair, modification of a target polypeptide associated with target DNA (e.g., a histone, a DNA-binding protein, etc.), leading to, for example, histone methylation, histone acetylation, histone ubiquitination, and the like. Other functions conferred by a fusion protein can include methyltransferase activity, demethylase activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, and demyristoylation activity, or any combination thereof.

Modifications to the PIWI Domain

The PIWI domain of Argonaute may be modified. In some cases, the PIWI domain may share at least 5%, 10%, 15%, 20%, 25%, 30%, 35%, 40%, 45%, 50%, 55%, 60%, 65%, 70%. 75%, 80%. 85%, 90%, 95%, 98%, 99%, or 100% amino acid identity with the PIWI domain of an exemplary wild-type Argonaute (e.g., from *T. thermophilus* or *S. elongatus*). The PIWI domain may share at most 5%, 10%, 15%, 20%, 25%, 30%, 35%. 40%, 45%, 50%, 55%, 60%. 65%, 70%, 75%, 80%, 85%, 90%, 95%, 98%, 99%, or 100% amino acid identity with the PIVVI domain of an exemplary wild-type Argonauie (e.g.. from *T. thermophilus* or *S. elongatus*).

In some cases, modifications to the PIWI domain may include but are not limited to individual amino acid modifications, as described herein. In some cases, modification to the PIWI domain may include but are not limited to insertions, deletions or substitution of individual amino acids, or polypeptides, such as other protein elements (e.g domains, structural motifs, proteins).

Modifications may include modifications to at least 1, 2, 3, 4, 5, 6, 7, 8, 9, 10, 11, 12, 13, 14, 15, 16, 17, 18, 19, 20 or more amino acids of PIWI domain. Modifications may include modifications to at most 1, 2, 3, 4, 5, 6, 7, 8, 9, 10, 11, 12, 13, 14, 15, 16, 17, 18, 19, 20 or more amino acids of the PIWI domain. Modifications may also include at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the PIWI domain. Modifications may also include at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the PIWI domain.

In some cases, modifications to the Argonaute protein PIWI domain sequences may include particular polypeptide structural motifs, including but not limited to alpha helix, beta strand, beta sheet, 310-helix, pi-helix, polyproline I motif, polyproline II motif, polyproline III motif, beta turn, alpha-turn-alpha, or helix kinks or hinges. For example, substitutions to the Argonaute protein PIWI domain may include substitution or addition with one or more proline amino acid residues. Insertion of proline residues may introduce kinks in the PIWI domain which may alter the binding specificity of the PIWI domain for the target nucleic acid. Substitution or addition may include one or more glycine amino acid residues. Insertion or substitution of glycine residues may introduce increased flexibility in the bridge helix, or "hinges" which may also alter the binding specificity of the PIWI domain for the target nucleic acid. Altering binding specificity may or may not affect enzymatic activity of the Argonaute protein.

In some cases, modifications to Argonaute protein PIWI domain sequences may include deletion of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the PIWI domain. In some cases, modifications to Argonaute protein PIWI domain sequences may include deletion of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the PIWI domain.

In some cases, modifications to Argonaute protein PIWI domain sequences may include addition or substitution of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Argonaute protein PIWI domain. In some cases, modifications to Argonaute protein PIWI domain sequences may include addition or substitution of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Argonaute protein PIWI domain.

The PIWI domain may be substituted or inserted with a PIWI domain, or fragment thereof, derived from another Argonaute enzyme from a different species. Non-native PIWI domains may be derived from any suitable organism. In some cases, the Argonaute protein and PIWI domain may be derived from prokaryotic organisms, including but not limited to archea, bacteria, protists (e.g., *E. coli, S. pyogenes, S. thermophilus, P. furiosus, T. thermophilus*, etc.).

In some instances, an Argonaute protein comprises an amino acid sequence comprising at least 50% amino acid identity to an exemplary wild-type Argonaute (e.g., from *T. thermophilus* or *S. elongatus*), and a modified PIWI domain.

Modifications to the MID Domain

The MID domain of Argonaute may be modified. In some cases, the MID domain may share at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% amino acid identity with the MID domain of an exemplary wild-type Argonaute (e.g., from *T. thermophilus* or *S. elongatus*). The MID domain may share at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% amino acid identity with the MID domain of an exemplary wild-type Argonaute (e.g., from *T. thermophilus* or *S. elongatus*).

In some cases, modifications to the MID domain may include but are not limited to individual amino acid modifications, as described herein. In some cases, modification to the MID domain may include but are not limited to insertions, deletions or substitution of individual amino acids, or polypeptides, such as other protein elements (e.g domains, structural motifs, proteins).

Modifications may include modifications to at least 1, 2, 3, 4, 5, 6, 7, 8, 9, 10, 11, 12, 13, 14, 15, 16, 17, 18, 19, 20 or more amino acids of MID domain. Modifications may include modifications to at most 1, 2, 3, 4, 5, 6, 7, 8, 9, 10, 11, 12, 13, 14, 15, 16, 17, 18, 19, 20 or more amino acids of the MID domain. Modifications may also include at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the MID domain. Modifications may also include at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the MID domain.

In some cases, modifications to the Argonaute protein MID domain sequences may include particular polypeptide structural motifs, including but not limited to alpha helix, beta strand, beta sheet, 310-helix, pi-helix, polyproline I motif, polyproline II motif, polyproline III motif, beta turn, alpha-turn-alpha, or helix kinks or hinges. For example, substitutions to the Argonaute protein MID domain may include substitution or addition with one or more proline amino acid residues. Insertion of proline residues may introduce kinks in the MID domain which may alter the binding specificity of the MID domain for the target nucleic acid. Substitution or addition may include one or more glycine amino acid residues. Insertion or substitution of glycine residues may introduce increased flexibility in the bridge helix, or "hinges" which may also alter the binding specificity of the MID domain for the target nucleic acid. Altering binding specificity may or may not affect enzymatic activity of the Argonaute protein.

In some cases, modifications to Argonaute protein MID domain sequences may include deletion of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the MID domain. In some cases, modifications to Argonaute protein MID domain sequences may include deletion of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the MID domain.

In some cases, modifications to Argonaute protein MID domain sequences may include addition or substitution of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Argonaute protein MID domain. In some cases, modifications to Argonaute protein MID domain sequences may include addition or substitution of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Argonaute protein MID domain.

The MID domain may be substituted or inserted with a MID domain, or fragment thereof, derived from another Argonaute enzyme from a different species. Non-native MID domains may be derived from any suitable organism. In some cases, the Argonaute protein and MID domain may be derived from prokaryotic organisms, including but not limited to archea, bacteria, protists (e.g., *E. coli, S. pyogenes, S. thermophilus, P. furiosus, T. thermophilus*,etc.).

In some instances, an Argonaute protein comprises an amino acid sequence comprising at least 50% amino acid identity to a Argonaute from T.thermophilus, and a modified MID domain.

Modifications to the PAZ Domain

The PAZ domain of Argonaute may be modified. In some cases, the PAZ domain may share at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% amino acid identity with the PAZ domain of an exemplary wild-type Argonaute (e.g., from *T. thermophilus* or *S. elongatus*). The PAZ domain may share at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% amino acid identity with the PAZ domain of an exemplary wild-type Argonaute (e.g., from *T. thermophilus* or *S. elongatus*).

In some cases, modifications to the PAZ domain may include but are not limited to individual amino acid modifications, as described herein. In some cases, modification to the PAZ domain may include but are not limited to insertions, deletions or substitution of individual amino acids, or polypeptides, such as other protein elements (e.g domains, structural motifs, proteins).

Modifications may include modifications to at least 1, 2, 3, 4, 5, 6, 7, 8, 9, 10, 11, 12, 13, 14, 15, 16, 17, 18, 19, 20 or more amino acids of PAZ domain. Modifications may include modifications to at most 1, 2, 3, 4, 5, 6, 7, 8, 9, 10, 11, 12, 13, 14, 15, 16, 17, 18, 19, 20 or more amino acids of the PAZ domain. Modifications may also include at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the PAZ domain. Modifications may also include at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the PAZ domain.

In some cases, modifications to the Argonaute protein PAZ domain sequences may include particular polypeptide structural motifs, including but not limited to alpha helix, beta strand, beta sheet, 310-helix, pi-helix, polyproline I motif, polyproline II motif, polyproline III motif, beta turn, alpha-turn-alpha, or helix kinks or hinges. For example, substitutions to the Argonaute protein PAZ domain may include substitution or addition with one or more proline amino acid residues. Insertion of proline residues may introduce kinks in the PAZ domain which may alter the binding specificity of the PAZ domain for the target nucleic acid. Substitution or addition may include one or more glycine amino acid residues. Insertion or substitution of glycine residues may introduce increased flexibility in the bridge helix, or "hinges" which may also alter the binding specificity of the PAZ domain for the target nucleic acid. Altering binding specificity may or may not affect enzymatic activity of the Argonaute protein.

In some cases, modifications to Argonaute protein PAZ domain sequences may include deletion of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the PAZ domain. In some cases, modifications to Argonaute protein PAZ domain sequences may include deletion of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the PAZ domain.

In some cases, modifications to Argonaute protein PAZ domain sequences may include addition or substitution of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Argonaute protein PAZ domain. In some cases, modifications to Argonaute protein PAZ domain sequences may include addition or substitution of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Argonaute protein PAZ domain.

The PAZ domain may be substituted or inserted with a PAZ domain, or fragment thereof, derived from another Argonaute enzyme from a different species. Non-native PAZ domains may be derived from any suitable organism. In some cases, the Argonaute protein and PAZ domain may be derived from prokaryotic organisms, including but not limited to archea, bacteria, protists (e.g., *E. coli, S. pyogenes, S. thermophilus, P. furiosus, T. thermophilus, S. elongatus* etc.).

In some instances, an Argonaute protein comprises an amino acid sequence comprising at least 50% amino acid identity to a Argonaute from *T. thermophilus*, and a modified PAZ domain.

Modifications to Alter Designed Nucleic Acid-Targeting Nucleic Acid Specificity

In some instances, the Argonaute protein can recognize a designed nucleic acid-targeting nucleic acid. The Argonaute protein can be modified to alter designed nucleic acid-targeting nucleic acid specificity. For example, the Argonaute protein can be modified such that prior to the modifying the polypeptide targets a first a designed nucleic acid-targeting nucleic acid and after the modifying the Argonaute protein targets a second a designed nucleic acid-targeting nucleic acid. In some instances, altered designed nucleic acid-targeting nucleic acid specificity can comprise a change in binding specificity (e.g., increased binding, decreased binding), and/or a change in the binding constant (e.g., increase Kd, decrease Kd).

The Argonaute protein can be modified such that the Argonaute protein can recognize a new type of a designed nucleic acid-targeting nucleic acid different from the the type the wild-type Argonaute protein recognizes. Any region of the Argonaute protein can be engineered alter specificity according to the methods of the disclosure.

In some instances, the Argonaute protein comprises an amino acid sequence comprising at least 50% amino acid identity to a Argonaute from *T. thermophilus* and a modification, wherein prior to introduction of the modification the Argonaute protein is adapted to bind a first a designed nucleic acid-targeting nucleic acid and after introduction of the modification, the Argonaute protein is adapted to bind to a different a designed nucleic acid-targeting nucleic acid.

Modifications to Alter Hybridization Requirements
Insertions

The Argonaute protein can be modified to increase binding specificity to a target nucleic acid. A sequence may be inserted into the Argonaute protein. In some instances, a PIWI, PAZ, and/or MID domain may be inserted in the Argonaute protein. The insertion may take place at any location in the Argonaute protein. The inserted PIWI, PAZ, and/or MID domain may comprise a mutation. The inserted PIWI, PAZ, and/or MID domain may comprise a mutation that reduces the nuclease activity of the domain.

The Argonaute protein can be modified to increase binding specificity to a designed nucleic acid-targeting nucleic acid. A sequence may be inserted into the Argonaute protein. A PIWI, PAZ, and/or MID domain may be inserted in the Argonaute protein. The non-native sequence (e.g., PIWI, PAZ, and/or MID domain) may originate from any species. The insertion may take place at any location in the Argonaute protein. The insertion may occur in tandem (e.g., adjacent) to the native PIWI, PAZ, and/or MID domain of the Argonaute protein. The inserted PIWI, PAZ, and/or MID domain may comprise a mutation. The inserted PIWI, PAZ, and/or MID domain may be comprise a mutation that reduces the nuclease activity of the domain.

The Argonaute protein can be engineered to comprise a polypeptide domain that can bind to double-stranded DNA (e.g., domains comprising helix-turn-helix motifs, domains comprising leucine zipper motifs, domains comprising helix-loop-helix motifs, domains comprising zinc finger motifs). For example, the Argonaute protein can be engineered to comprise a helix-turn-helix motif. Non-limiting exemplary helix-turn-helix motifs include those from dnaB, TetR, MuB, P2R, CysB, BirA, the bacteriophage lambda repressor, Engrailed, Myb, LuxR, MarR, ETS, ZNF10a, Kox-1. The helix-loop-helix motif can be di-helical, tri-helical, tetrahelical, a winged helix-turn-helix, or other modified helix-loop-helix. The inserted domain may be comprise a mutation. The inserted domain may be comprise a mutation that reduces the nuclease activity of the domain.

In some instances, an Argonaute protein can be engineered such that it can target a double-stranded target nucleic acid (e.g., DNA) and cleave both strands of the double-stranded target nucleic acid. The cleavage of both strands of the double-stranded target nucleic acid can occur simulatenously (e.g., one Argonaute protein is sufficient to cleave both strands of the target nucleic acid).

Compensatory Mutations

The Argonaute protein can comprise a mutation and/or be engineered such that it may preferentially bind to a mutated and/or engineered designed nucleic acid-targeting nucleic acid. Such mutation of the Argonaute protein and designed nucleic acid-targeting nucleic acid pair can be referred to as a compensatory mutation. For example, the Argonaute protein can be engineered such PIWI, PAZ, and/or MID domain is replaced by a nucleic acid binding domain. The Argonaute protein can be engineered such that a nucleic acid binding domain is inserted into the Argonaute protein. The resulting Argonaute protein can bind to a designed nucleic acid-targeting nucleic acid that is mutated and/or engineered to comprise a nucleic acid binding domain binding site (e.g., binding site for Argonaute nucleic acid binding domains).

In some instances, the Argonaute protein comprises an amino acid sequence comprising at least 50% amino acid identity to an Argonaute from *T. thermophilus*, and a compensatory mutation, in which the Argonaute protein is such that it can bind to an engineered designed nucleic acid-targeting nucleic acid but not an unmodified designed nucleic acid-targeting nucleic acid.

Methods to Cleave Target Nucleic Acid
General Overview

Figure 1:
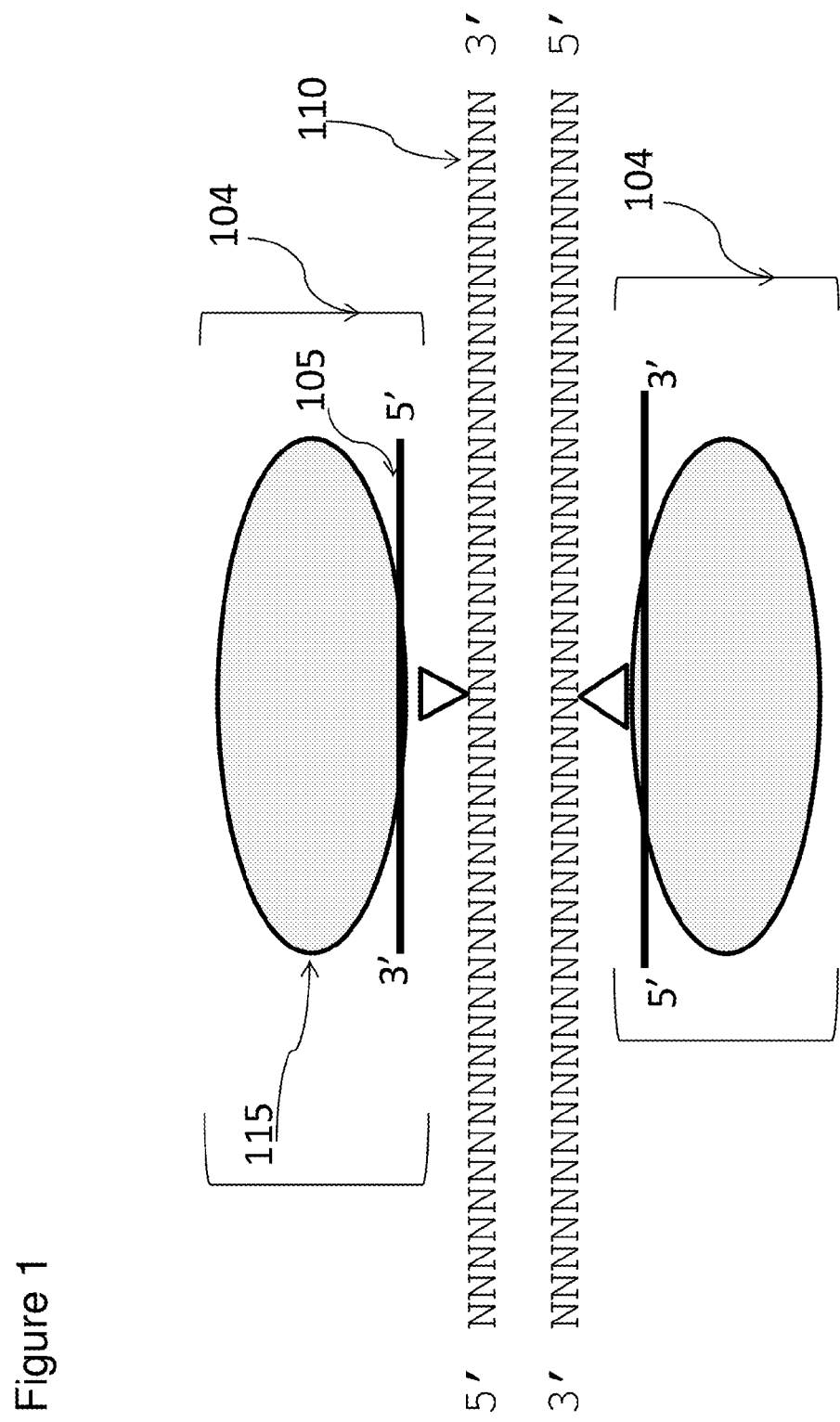
FIG. 1 depicts an exemplary embodiment of a method of the disclosure for generating a blunt end double-stranded break.

The disclosure provides for a method to generate a double-stranded break in a double-stranded target nucleic acid using complexes comprising an Argonaute protein and a designed nucleic acid-targeting nucleic acid. FIG. 1 depicts an exemplary embodiment of the method for generating a blunt end cut in a double-stranded target nucleic acid. A double-stranded target nucleic acid 110 can be contacted with two complexes 104, each complex comprising an Argonaute protein 115 and a designed nucleic acid-targeting nucleic acid 105. One complex targets a region of a first strand of the double-stranded target nucleic acid 110. One complex targets a region of the second strand of the double-stranded target nucleic acid 110. The targeted region of the first strand of the double-stranded target nucleic acid 110 and the targeted region of the second strand of the double-stranded target nucleic acid 110 can be complementary to each other. In some instances the targeted region of the first strand of the double-stranded target nucleic acid 110 and the targeted region of the second strand of the double-stranded target nucleic acid 110 can overlap (e.g., be complementary) such that the cleavage of the Argonaute protein 115 of each strand of the double-stranded target nucleic acid results in a blunt end double-stranded break of the target nucleic acid 110.

Figure 2:
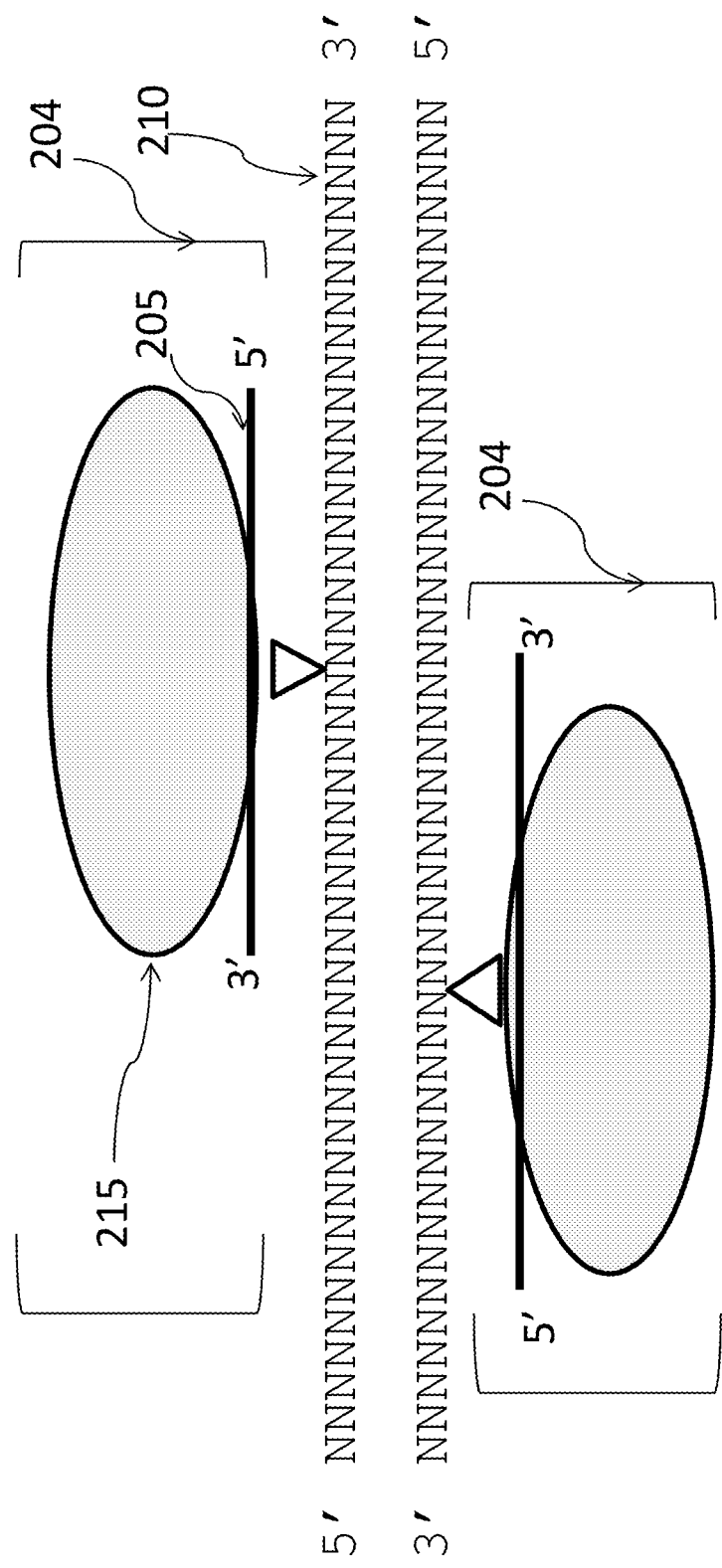
FIG. 2 depicts an exemplarly embodiment of a method for the disclosure for generating a staggard double-stranded break.

In some embodiments, the targeted regions of the first strand of the target nucleic acid and the second strand of the target nucleic acid may partially overlap, thereby promoting generation of sticky ends after cleavage. FIG. 2 depicts an exemplary embodiment of the generation of sticky ends by the Argonaute-designed nucleic acid-targeting nucleic acid complexes of the disclosure. A double-stranded target nucleic acid 210 can be contacted with two complexes 204, each complex comprising an Argonaute protein 215 and a designed nucleic acid-targeting nucleic acid 205. One complex targets a region of a first strand of the double-stranded target nucleic acid 210. One complex targets a region of the second strand of the double-stranded target nucleic acid 210. A portion, or none, of the targeted region of the first strand of the double-stranded target nucleic acid 210 and the targeted region of the second strand of the double-stranded target nucleic acid 210 can be complementary to each other (e.g., overlap). In some instances the targeted region of the first strand of the double-stranded target nucleic acid 210 and the targeted region of the second strand of the double-stranded target nucleic acid 210 can partially overlap (e.g., be partially complementary) such that the cleavage of the Argonaute protein 215 of each strand of the double-stranded target nucleic acid results in a sticky end double-stranded break of the target nucleic acid 210.

The method can be performed using any of the Argonaute proteins, designed nucleic acid-targeting nucleic acids, and complexes of Argonaute proteins and designed nucleic acid-targeting nucleic acids as described herein.

In some instances, the double-stranded break in the target nucleic acid can be introduced by a first complex comprising an Argonaute and a designed nucleic acid-targeting nucleic acid cleaving a first strand of the double-stranded target nucleic acid and a second complex comprising an Argonaute and a designed nucleic acid-targeting nucleic acid cleaving a second strand of a the double-stranded larger nucleic acid.

The method can introduce a blunt end cut into a double-stranded target nucleic acid. A blunt cut can be introduced when a first designed nucleic acid-targeting nucleic acid cleaves at the same spot on a first strand of a double-stranded target nucleic acid as a second designed nucleic acid-targeting nucleic acid which is designed to cleave at the same spot on the other strand of the double-stranded target nucleic acid.

The method may comprise introducing a staggered cut (e.g., sticky end cut) into the double-stranded target nucleic acid. A staggard cut can be introduced when a first designed nucleic acid-targeting nucleic acid cleaves at a different spot on a first strand of a double-stranded target nucleic acid as a second designed nucleic acid-targeting nucleic acid which is designed to hybridize to the other strand as the first designed nucleic acid-targeting nucleic acid.

A staggard cuts can result in sticky ends. Sticky ends can be at least about 1, 2, 3, 4, 5, 6, 7, 8, 9, 10, 20, 30, 40, 50, 60, 70, 80, 90 or 100 or more nucleotides in length. Sticky ends can be at most about 1, 2, 3, 4, 5, 6, 7, 8, 9, 10, 20, 30, 40, 50, 60, 70, 80, 90 or 100 or more nucleotides in length.

The method may comprise contacting the target nucleic acid (e.g., double stranded target nucleic acid) with a plurality of complexes comprising art Argonauie and a designed nucleic acid-targeting nucleic acid. A target nucleic acid can be contacted with at least about 1, 2, 3, 4, 5, 6, 7, 8, or 9 or more complexes. A target nucleic acid can be contacted with at most about 1, 2, 3, 4, 5, 6, 7, 8, or 9 or more complexes. The Argonautes of the complexes may be the same. The Argonautes of the complexes may be different.

The designed nucleic acid-targeting nucleic acids of the complexes may be the same. The designed nucleic acid-targeting nucleic acids of the complex may be different. The designed nucleic acid-targeting nucleic acids of the complexes (e.g., 2 complexes) may differ by at least 1, 2, 3, 4, 5, 6, 7, 8, 9, or 10 or more nucleotides. The designed nucleic acid-targeting nucleic acids of the complexes (e.g., 2 complexes) may differ by at most 1, 2, 3, 4, 5, 6, 7, 8, 9, or 10 or more nucleotides.

The designed nucleic acid-targeting nucleic acids of the complexes may be fully complementary to each other. The designed nucleic acid-targeting nucleic acids of the complexes may be partially complementary to each other. The designed nucleic acid-targeting nucleic acids may be complementary to each other over at least 1, 2, 3, 4, 5, 6, 7, 8, 9, 10, 11, 12, 13, 14, 15, 16, 17, 18, 19, 20, or 21 or more consecutive nucleotides. The designed nucleic acid-targeting nucleic acids may be complementary to each other over at most 1, 2, 3, 4, 5, 6, 7, 8, 9, 10, 11, 12, 13, 14, 15, 16, 17, 18, 19, 20, or 21 or more consecutive nucleotides. Nucleic acid-targeting nucleic acids can be fully or partially complementary to each other when they are designed to target overlapping regions on each strand of a double-stranded target nucleic acid.

In some instances, a plurality of complexes can target a plurality of locations on the same strand of the double-stranded target nucleic acid. For example, a first complex comprising an Argonaute and a first designed nucleic acid-targeting nucleic acid can be contacted to a first strand of a double-stranded target nucleic acid, and a second complex comprising an Argonaute an a second designed nucleic acid-targeting nucleic acid can be contacted to a different location on the same first strand as the first complex. This can result in excision of a portion of one strand of a double-stranded target nucleic acid. The method can be useful for engineering single nucleotide polymorphisms, and introducing non-natural nucleotides (e.g., that may form wobble pairs, or be modified with a reactive moiety). In some instances, when a portion of one strand of the double-stranded target nucleic acid is removed, the region of nucleic acid can be filled in by a polymerase (e.g., Klenow fragment). Synthesis of the excised strand can comprise introducing non-natural nucleotides into the double-stranded target nucleic acid.

The two Argonaute proteins may be the same Argonaute protein. The two Argonaute proteins may be different Argonaute proteins. When the two Argonaute proteins are different, they may differ by at least 1, 2, 3, 4, 5, 6, 7, 8, 9, 10, 20, 30, 40, 50, 60, 70, 80, 90 or 100%. When the two Argonaute proteins are different, they may differ in the PAZ, MID, and/or PIWI domain. When the two Argonaute proteins are different, they may be fused to different non-native sequences.

In some instances, the two complexes targeted to the target nucleic acid can comprise two different proteins. For example, a first complex can comprise an Argonaute protein and a second complex can comprise a Cas9 protein. In some instances, the Argonaute protein can be bound to a DNA nucleic acid-targeting nucleic acid and the Cas9 protein can be bound to an RNA nucleic acid-targeting nucleic acid. Both the DNA and RNA nucleic acid-targeting nucleic acids can target the target nucleic acid.

Cas9

Cas9 can comprise two or more nuclease domains. Cas9 can comprise a HNH or HNH-like nuclease domain and/or a RuvC or RuvC-like nuclease domain. HNH or HNH-like domains can comprise a McrA-like fold. HNH or HNH-like domains can comprise two antiparallel 0-strands and an a-helix. HNH or HNH-like domains can comprise a metal binding site (e.g., divalent cation binding site). HNH or HNH-like domains can cleave one strand of a target nucleic acid (e.g., complementary strand of the crRNA targeted strand). Proteins that comprise an HNH or HNH-like domain can include endonucleases, clicins, restriction endonucleases, transposases, and DNA packaging factors.

RuvC or RuvC-like domains can comprise an RNaseH or RNaseH-like fold. RuvC/RNaseH domains can be involved in a diverse set of nucleic acid-based functions including acting on both RNA and DNA. The RNaseH domain can comprise 5 β-strands surrounded by a plurality of α-helices. RuvC/RNaseH or RuvC/RNaseH-like domains can comprise a metal binding site (e.g., divalent cation binding site). RuvC/RNaseH or RuvC/RNaseH-like domains can cleave one strand of a target nucleic acid (e.g., non-complementary strand of the crRNA targeted strand). Proteins that comprise a RuvC, RuvC-like, or RNaseH-like domain can include RNaseH, RuvC, DNA transposases, retroviral integrases, and Argonaut proteins).

Cas9 can introduce double-stranded breaks or single-stranded breaks in nucleic acid, (e.g. genomic DNA). The double-stranded break can stimulate a cell's endogenous DNA-repair pathways (e.g. homologous recombination and non-homologous end joining (NHEJ) or alternative non-homologues end joining (A-NHEJ)). NHEJ can repair cleaved target nucleic acid without the need for a homologous template. This can result in deletions of the target nucleic acid. Homologous recombination (HR) can occur with a homologous template. The homologous template can comprise sequences that are homologous to sequences flanking the target nucleic acid cleavage site. After a target nucleic acid is cleaved by a site-directed polypeptide the site of cleavage can be destroyed (e.g., the site may not be accessible for another round of cleavage with the original nucleica acid-targeting nucleic acid and site-directed polypeptide).

In some cases, Cas9 can comprise an amino acid sequence having at most 10%, at most 15%, at most 20%, at most 30%, at most 40%, at most 50%, at most 60%, at most 70%, at most 75%, at most 80%, at most 85%, at most 90%, at most 95%, at most 99%, or 100%, amino acid sequence identity to a wild type exemplary Cas9 (e.g,. Cas9 from *S. pyogenes*).

In some cases, Cas9 can comprise an amino acid sequence having at least 10%, at least 15%, 20%, at least 30%, at least 40%, at least 50%, at least 60%, at least 70%, at least 75%, at least 80%, at least 85%, at least 90%, at least 95%, at least 99%, or 100%, amino acid sequence identity to a wild type exemplary Cas9 (e.g., Cas9 from *S. pyogenes*).

In some cases, Cas9 can comprise an amino acid sequence having at most 10%, at most 15%, at most 20%, at most 30%, at most 40%, at most 50%, at most 60%, at most 70%, at most 75%, at most 80%, at most 85%, at most 90%, at most 95%, at most 99%, or 100%, amino acid sequence identity to the nuclease domain of a wild type exemplary Cas9 (e.g,. Cas9 from *S. pyogenes*).

A Cas9 can comprise at least 70, 75, 80, 85, 90, 95, 97, 99, or 100% identity to wild-type Cas9 (e.g., Cas9 from *S. pyogenes*) over 10 contiguous amino acids. A Cas9 can comprise at most 70, 75, 80, 85, 90, 95, 97, 99, or 100% identity to Cas9 (e.g., Cas9 from *S. pyogenes*) over 10 contiguous amino acids. A Cas9 can comprise at least 70, 75, 80, 85, 90, 95, 97, 99, or 100% identity to a wild-type Cas9 (e.g., Cas9 from *S. pyogenes*) over 10 contiguous amino acids in a HNH nuclease domain of the Cas9. A Cas9 can comprise at most 70, 75, 80, 85, 90, 95, 97, 99, or 100% identity to a wild-type Cas9 (e.g., Cas9 from *S. pyogenes*) over 10 contiguous amino acids in a HNH nuclease domain of the Cas9. A Cas9 can comprise at least 70, 75, 80, 85, 90, 95, 97, 99, or 100% identity to a wild-type Cas9 (e.g., Cas9 from *S. pyogenes*) over 10 contiguous amino acids in a RuvC nuclease domain of the Cas9. A Cas9 can comprise at most 70, 75, 80, 85, 90, 95, 97, 99, or 100% identity to a wild-type Cas9 (e.g., Cas9 from *S. pyogenes*) over 10 contiguous amino acids in a RuvC nuclease domain of the Cas9.

In some cases, the Cas9 can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100%, amino acid sequence identity to the nuclease domain of a wild type exemplary Cas9 (e.g., Cas9 from *S. pyogenes*).

The Cas9 can comprise a modified form of a wild type exemplary Cas9. The modified form of the wild type exemplary Cas9 can comprise an amino acid change (e.g., deletion, insertion, or substitution) that reduces the nucleic acid-cleaving activity of the Cas9. For example, the modified form of the wild type exemplary Cas9 can have less than less than 90%, less than 80%, less than 70%, less than 60%, less than 50%, less than 40%, less than 30%, less than 20%, less than 10%, less than 5%, or less than 1% of the nucleic acid-cleaving activity of the wild-type Cas9 (e.g., Cas9 from *S. pyogenes*). The modified form of the Cas9 can have no substantial nucleic acid-cleaving activity. When a Cas9 is a modified form that has no substantial nucleic acid-cleaving activity, it can be referred to as "enzymatically inactive."

The modified form of the wild type exemplary Cas9 can have more than 90%, more than 80%, more than 70%, more than 60%, more than 50%, more than 40%, more than 30%, more than 20%, more than 10%, more than 5%, or more than 1% of the nucleic acid-cleaving activity of the wild-type exemplary Cas9 (e.g., Cas9 from *S. pyogenes*).

The modified form of the Cas9 can comprise a mutation. The modified form of the Cas9 can comprise a mutation such that it can induce a single stranded break (SSB) on a target nucleic acid (e.g., by cutting only one of the sugar-phosphate backbones of the target nucleic acid). The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type Cas9 (e.g., Cas9 from *S. pyogenes*). The mutation can result in one or more of the plurality of nucleic acid-cleaving domains retaining the ability to cleave the complementary strand of the target nucleic acid but reducing its ability to cleave the non-complementary strand of the target nucleic acid. The mutation can result in one or more of the plurality of nucleic acid-cleaving domains retaining the ability to cleave the non-complementary strand of the target nucleic acid but reducing its ability to cleave the complementary strand of the target nucleic acid. For example, residues in the wild type exemplary *S. pyogenes* Cas9 polypeptide such as Asp10, His840, Asn854 and Asn856 can be mutated to inactivate one or more of the plurality of nucleic acid-cleaving domains (e.g., nuclease domains). The residues to be mutated can correspond to residues Asp10, His840, Asn854 and Asn856 in the wild type exemplary *S. pyogenes* Cas9 polypeptide (e.g., as determined by sequence and/or structural alignment). Non-limiting examples of mutations can include D10A, H840A, N854A or N856A. One skilled in the art will recognize that mutations other than alanine substitutions are suitable.

A D10A mutation can be combined with one or more of H840A, N854A, or N856A mutations to produce a Cas9 substantially lacking DNA cleavage activity. A H840A mutation can be combined with one or more of D10A, N854A, or N856A mutations to produce a Cas9 substantially lacking DNA cleavage activity. A N854A mutation can be combined with one or more of H840A, D10A, or N856A muiations to produce a Cas9 substantially lacking DNA cleavage activity. A N856A mutation can be combined with one or more of H840A, N854A, or D10A mutations to produce a Cas9 substantially lacking DNA cleavage activity. Cas9 that comprise one substantially inactive nuclease domain can be referred to as a nickase.

Methods for Enrichment and Sequencing of Target Nucleic Acids

General Overview

Sequencing can be useful for diagnosing disease by identifying mutations and/or other sequence variants (e.g., polymorphisms). The methods of the disclosure provide for methods, kits, and compositions for enriching a target nucleic acid sequence without the use of amplification methodologies. A target nucleic acid can be enriched with, the use of the Argonaute protein and a designed nucleic acid-targeting nucleic acid.

Figure 3:
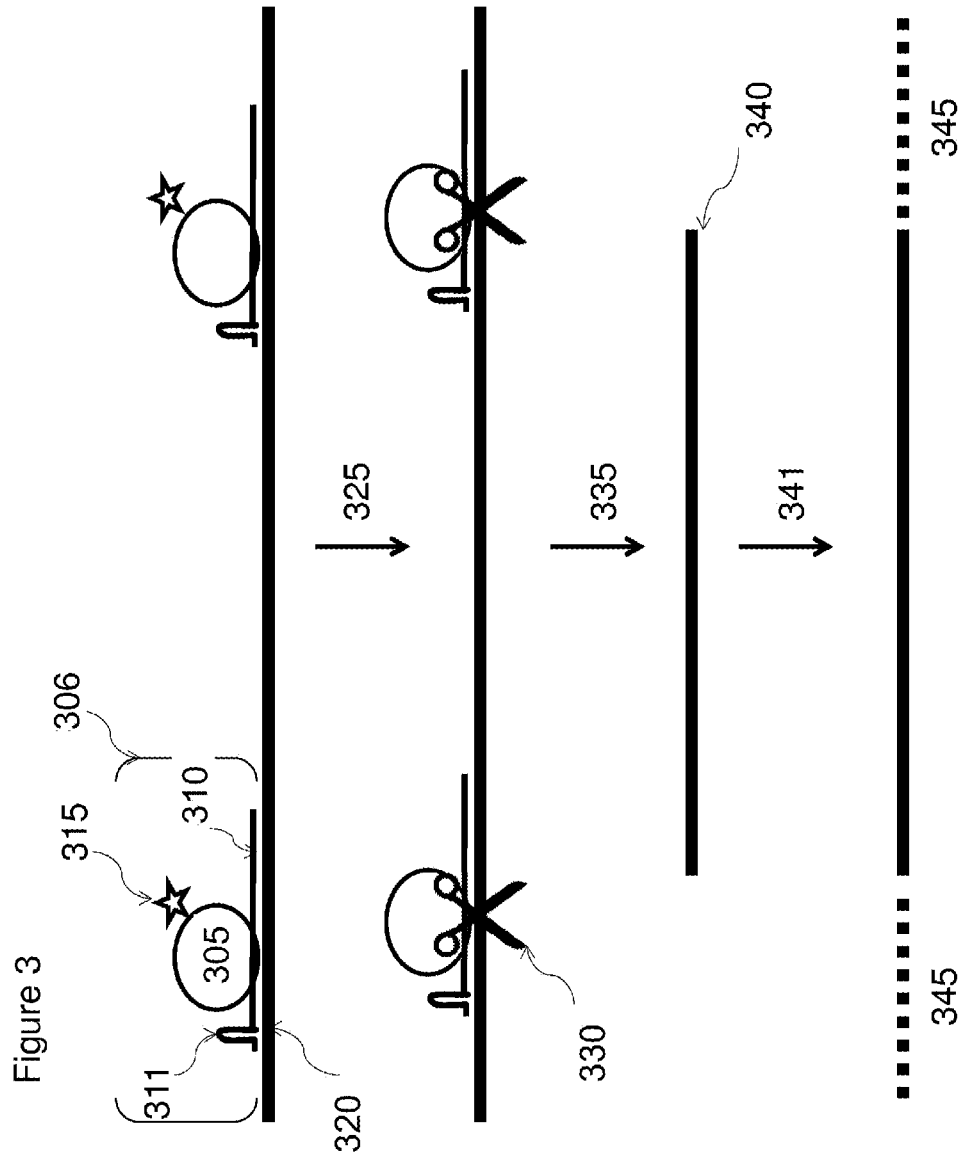
FIG. 3 depicts an exemplary embodiment of a sequence enrichment method of the disclosure utilizing target nucleic acid cleavage.

FIG. 3 depicts an exemplary embodiment of the methods of the disclosure. An Argonaute protein 305 can bind a designed nucleic acid-targeting nucleic acid 310, thereby forming a complex 306. The designed nucleic acid-targeting nucleic acid 310 can comprise a nucleic acid affinity tag 311. The Argonaute protein 305 can comprise a nuclease domain. The Argonaute protein 305 can be enzymatically active. The Argonaute protein 305 can comprise an affinity tag 315. The designed nucleic acid-targeting nucleic acid 310 can hybridize to a target nucleic acid 320. In some embodiments, a plurality of complexes 306 can hybridize to a plurality of locations within a target nucleic acid 320. In a cleavage step 325, the nuclease domain of an Argonaute protein 305 can cleave, or cut 330 the target nucleic acid 320. The excised target nucleic acid 340 can be purified in a purification step 335. Adaptors 345 can be ligated to the excised target nucleic acid. The adaptors can facilitate sequencing of the excised target nucleic acid.

Figure 4:
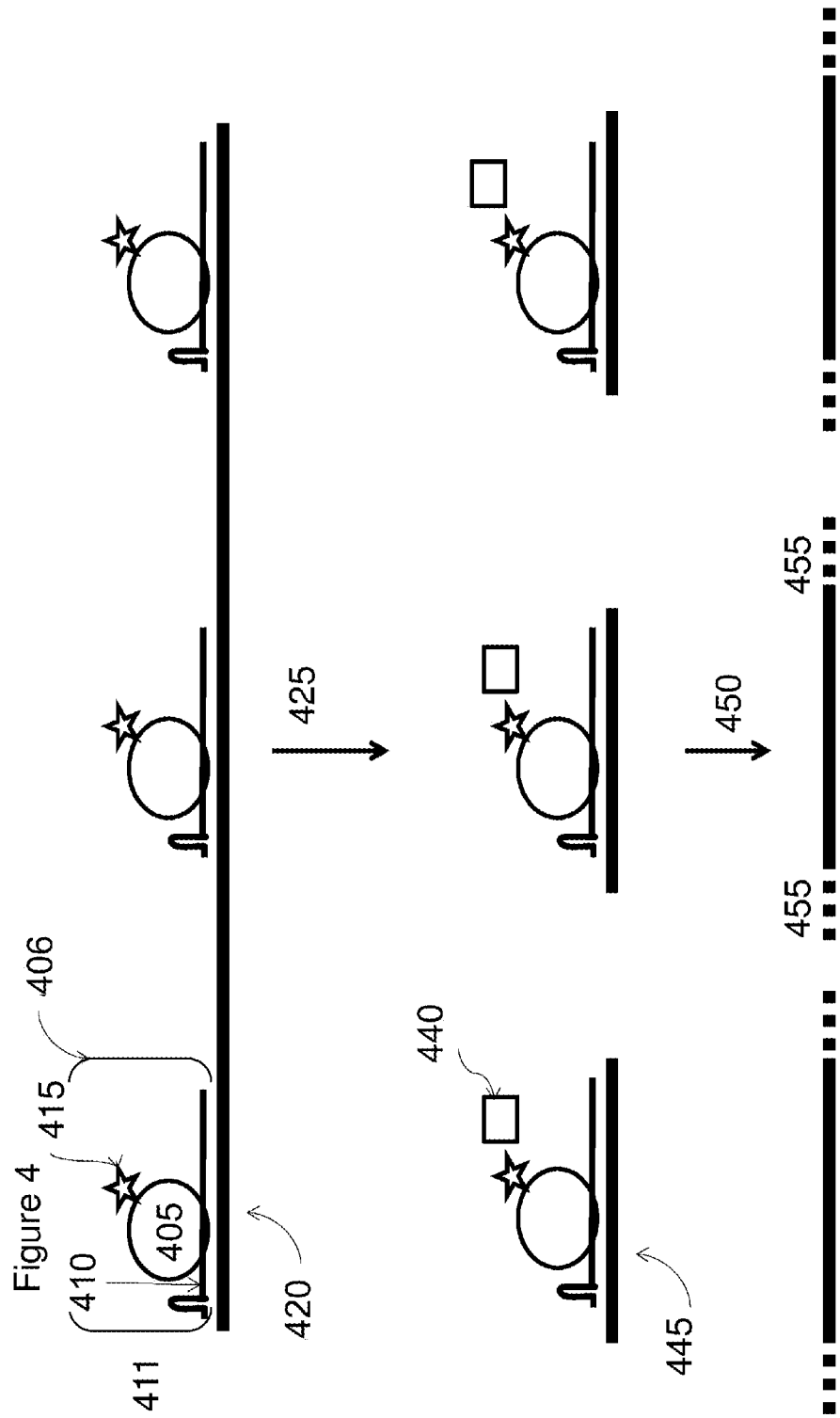
FIG. 4 depicts an exemplary embodiment of a sequence enrichment method of the disclosure utilizing target nucleic acid enrichment.

FIG. 4 depicts an exemplary embodiment of the methods of the disclosure. An Argonaute protein 405 can interact with a designed nucleic acid-targeting nucleic acid 410, thereby forming a complex 406. The Argonaute protein 405 can comprise a nuclease domain. In some embodiments, the nuclease domain of the Argonaute protein 405 can be enzymatically inactive. The Argonaute protein 405 can comprise an affinity tag 415. The designed nucleic acid-targeting nucleic acid 410 can hybridize to a target nucleic acid 420. The designed nucleic acid-targeting nucleic acid 410 can comprise a nucleic acid affinity tag 411. The affinity tag 411 of the designed nucleic acid-targeting nucleic acid can comprise a hairpin structure. A plurality of complexes 406 can hybridize to a plurality of locations within a target nucleic acid 420. In a fragmenting step 425, the target nucleic acid 420 can be fragmented into target nucleic acid fragment 445 (also herein referred to as a "target nucleic acid"). The Argonaute protein 405 can be purified by a capture agent 440 that can bind to the affinity tag 415 of the Argonaute protein 405. The fragmented target nucleic acid 445 can be eluted from the complex 406 in a purification step 450. In the same step, or optionally, in a different step, adaptors 455 can be ligated to the target nucleic acid. The adaptors can facilitate sequencing of the target nucleic acid.

Complex of a Designed Nucleic Acid-Targeting Nucleic Acid and an Argonaute Protein The designed nucleic acid-targeting nucleic acid can interact with the Argonaute protein (e.g., a nucleic acid-guided nuclease, e.g. Argonaute), thereby forming a complex. The designed nucleic acid-targeting nucleic acid can guide the Argonaute protein to a target nucleic acid.

In some embodiments, a designed nucleic acid-targeting nucleic acid can be engineered such that the complex can bind inside of the cleavage site of the site-directed polpeptide. In this case, the target nucleic acid can interact with the complex and the target nucleic acid can be bound (e.g., bound to the complex).

The designed nucleic acid-targeting nucleic acid can be engineered in such a way that the complex (e.g., comprising the Argonaute protein and/or the designed nucleic acid-targeting nucleic acid) can hybridize to a plurality of locations within a nucleic acid sample.

A plurality of complexes can be contacted to a nucleic acid sample. The plurality of complexes can comprise designed nucleic acid-targeting nucleic acids engineered to hybridize to the same sequence. The plurality of complexes can comprise designed nucleic acid-targeting nucleic acids engineered to hybridize to the different sequences.

The sequences can be at different locations within a target nucleic acid. The locations can comprise the same, or similar, target nucleic acid sequences. The locations can comprise different target nucleic acid sequences. The locations can be a defined distance from each other. The locations can be less than 10 kilobases (Kb) apart, less than 8 Kb apart, less than 6 Kb apart, less than 4 Kb apart, less than 2 Kb apart, less than 1 Kb apart, less than 900 nucleotides apart, less than 800 nucleotides apart, less than 700 nucleotides apart, less than 600 nucleotides apart, less than 500 nucleotides apart, less than 400 nucleotides apart, less than 300 nucleotides apart, less than 200 nucleotides apart, less than 100 nucleotides apart.

The complexes can cleave the target nucleic acid which can result in an excised target nucleic acid that can be less than 10 kilobases (Kb) long, less than 8 Kb long, less than 6 Kb long, less than 4 Kb long, less than 2 Kb long, less than 1 Kb long, less than 900 nucleotides long, less than 800 nucleotides long, less than 700 nucleotides long, less than 600 nucleotides long, less than 500 nucleotides long, less than 400 nucleotides long, less than 300 nucleotides long, less than 200 nucleotides long, less than 100 nucleotides long.

The complexes can be bound to a fragmented target nucleic acid that can be be less than 10 kilobases (Kb) long, less than 8 Kb long, less than 6 Kb long, less than 4 Kb long, less than 2 Kb long, less than 1 Kb long. less than 900 nucleotides long, less than 800 nucleotides long, less than 700 nucleotides long, less than 600 nucleotides long, less than 500 nucleotides long, less than 400 nucleotides long, less than 300 nucleotides long, less than 200 nucleotides long, less than 100 nucleotides long.

Methods for Detecting Off-Target Binding Sites of Argonaute Proteins

General Overview

This disclosure describes methods, compositions, systems, and/or kits for determining off target binding sites of Argonaute proteins. In some embodiments of the disclosure the Argonaute protein can comprise a designed nucleic acid-targeting nucleic acid, thereby forming a complex. The complex can be contacted with a target nucleic acid. The target nucleic acid can be captured with capture agents that can bind to the affinity tags of the complex. The identity of the target nucleic acid can be determined through sequencing. Sequencing (e.g., high throughput sequencing, e.g., Illumina, Ion Torrent) can also identify the frequency of off-target binding sites of the Argonaute protein and/or complex, by counting the number of times a particular binding site is read. The methods, compositions, systems, and/or kits of the disclosure can facilitate the development of more accurately and specifically targeted Argonaute proteins.

Figure 5:
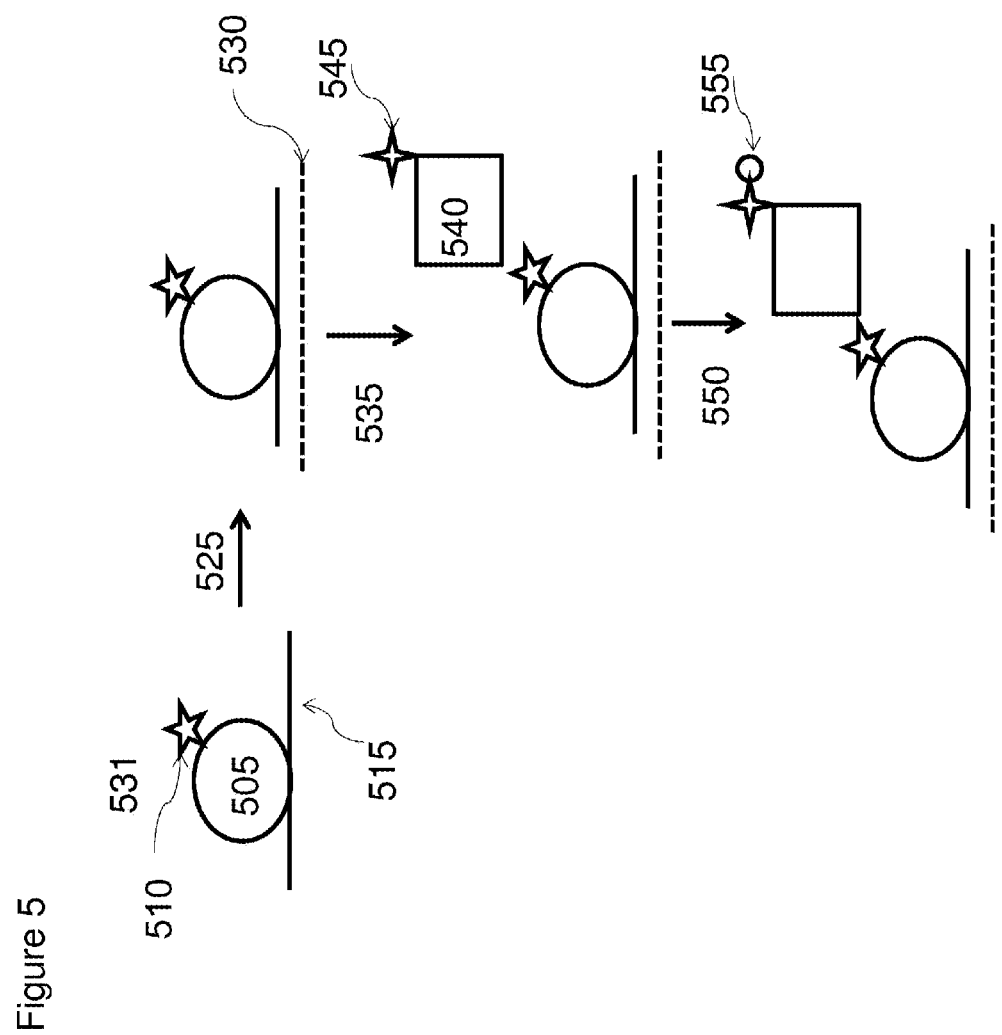
FIG. 5 depicts an exemplary embodiment of a method of the disclosure tor determining off-target binding sites of an Argonaute utilizing purification of the Argonaute.

FIG. 5 depicts an exemplary embodiment of the methods of the disclosure. An Argonaute protein 505 can comprise an affinity tag 510. The Argonaute protein can comprise a nucleic acid-binding domain 515. The nucleic acid-binding domain 515 can be a nucleic acid. In some embodiments, the nucleic acid-binding domain 515, and the Argonaute protein 505 form a complex 531. The complex 531 can be contacted 525 with a target nucleic acid 530. In a preferred embodiment, the target nucleic acid 530 is DNA (e.g. genomic DNA or gDNA). The complex can be affinity purified 535 with a capture agent 540. The capture agent 540 can bind to the affinity tag 510 from the Argonaute protein 505. The capture agent 540 can comprise a second affinity tag 545. The capture agent 540 can be affinity purified 550 by binding to a solid support 555. In some embodiments, the solid support 555 is a bead coated with an affinity reagent that cars bind to the affinity tag 545 of the capture agent. Optionally, the solid support 555 can bind to the affinity tag 510 of the Argonaute protein 505 to facilitate purification. In some embodiments, one or more rounds of purification can occur. Each round can comprise contacting a solid support 555 with the affinity tags of the Argonaute protein 510 and/or the capture agent 545. The affinity purified complex can be eluted from the target nucleic acid 530. The target nucleic acid can subsequently be prepared for further processing. Processing can include downstream analysis methods, e.g. sequencing.

Figure 6:
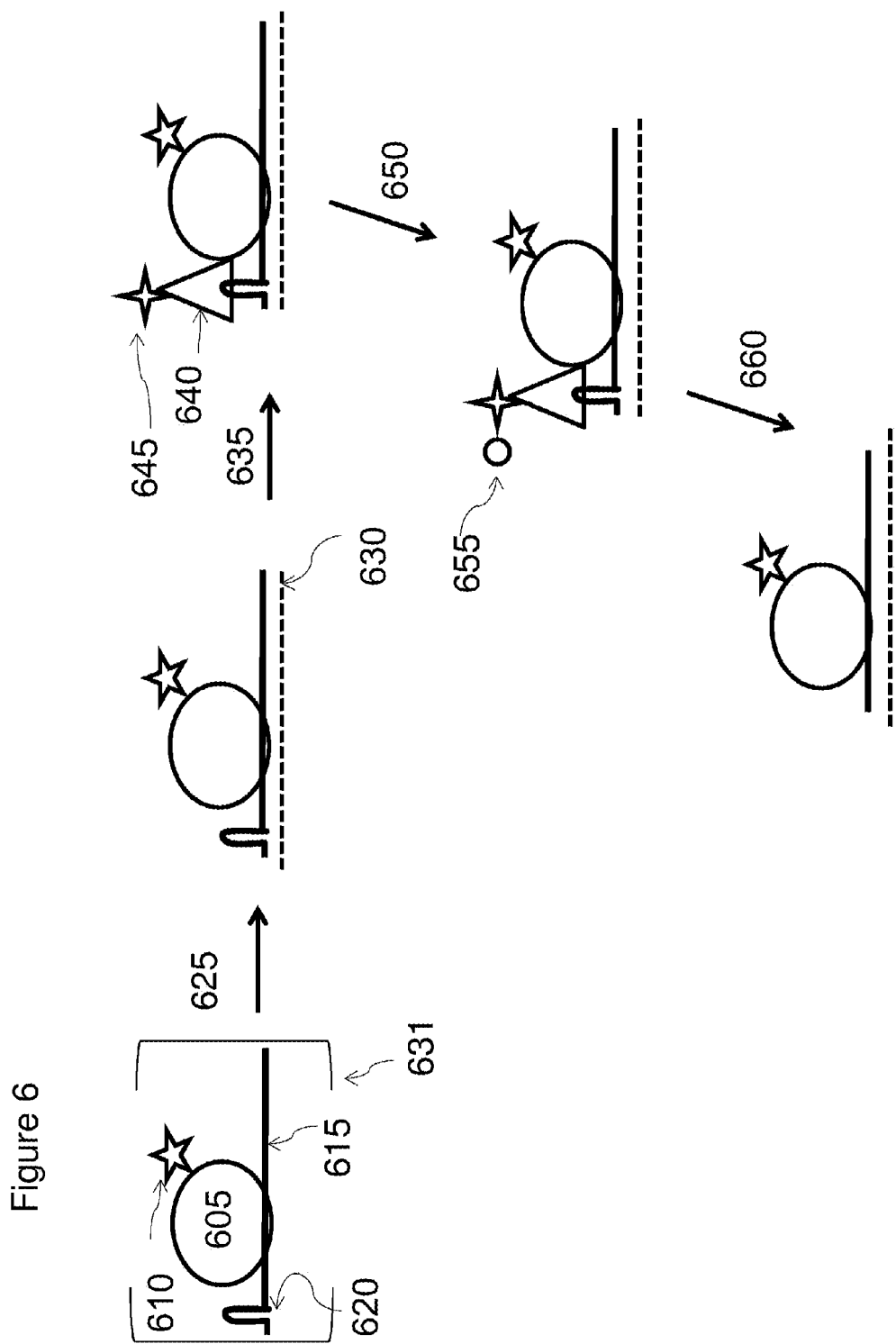
FIG. 6 depicts an exemplary embodiment of a method of the disclosure for determining off-target binding sites of an Argonaute utilizing purification of the designed nucleic acid-targeting nucleic acid.

FIG. 6 depicts an exemplary embodiment of the methods of the disclosure. An Argonaute protein 605 can comprise an affinity tag 610. The Argonaute protein 60S can comprise a nucleic acid-binding domain 615. The nucleic acid-binding domain 615 can be a nucleic acid. In some embodiments, the nucleic acid-binding domain 615 can comprise an affinity tag 620. In some embodiments, the nucleic acid-binding domain 615 and the Argonaute protein 605 can form a complex 631. The complex 631 may be contacted 625 with a target nucleic acid 630. In a preferred embodiment, the target nucleic acid 630 is DNA. The complex 631 can be affinity purified 635 with a capture agent 640. The capture agent 640 can bind to the affinity tag 620. The capture agent 640 can comprise an affinity tag 645. The capture agent 640 can be affinity purified 650 by binding to a solid support 655. In some embodiments, the solid support is a bead coated with an affinity reagent that can bind to the affinity tag 645 of the capture agent 640. Optionally, the solid support 655 can bind to the affinity tag 610 of the Argonaute protein 605 to facilitate purification. In some embodiments, two rounds of purification can occur, each comprising contacting a solid support 655 with the affinity tags of the Argonaute protein 610 and/or the capture agent 640. Cleavage of the affinity tag 620 can facilitate elation 660 of the target nucleic acid 630 from the solid support 655. The target nucleic acid 630 can subsequently be prepared for further downstream analysis methods such as sequencing.

Methods

The disclosure provides methods for nuclease immunoprecipitation and sequencing (NIP-Seq). In some embodiments, the method can comprise a) contacting a nucleic acid sample (e.g. nucleic acids comprising a target nucleic acid) with a complex comprising an engymatically inactive Argonaute protein, an Argonautc protein, and/or a designed nucleic acid-targeting nucleic acid (e.g. Argonaute-designcd nucleic acid-targeting nucleic acid complex). The complex can hybridize to the target nucleic acid. The complex can be captured with a capture agent, producing a captured complex, and the target nucleic acid bound to the captured complex can be sequenced. In some embodiments, the method can further comprise determining the identity of the off-target binding site. The method can be performed using any of the Argonaute proteins, designed nucleic acid-targeting nucleic acids, and complexes of Argonaute proteins and designed nucleic acid-targeting nucleic acids as described herein.

The methods can be performed outside of a cell. For example, a sample can comprise purified genomic DNA, cell lysate, homogenized tissue, plasma, and the like. The methods can be performed in cells (e.g., in vivo, in situ).

The captured complexes can be fixed or cross-linked. The cells can be crosslinked before they are lysed. Fixed or cross-linking cells can stabilize protein-DNA complexes in the cell. Suitable fixatives and cross-linkers can include, formaldehyde, glutaraldehyde, ethanol-based fixatives, methanol-based fixatives, acetone, acetic acid, osmium tetraoxide, potassium dichromate, chromic acid, potassium permanganate, mercurials, picrates, formalin, paraformaldehyde, amine-reactive NHS-ester crosslinkers such as bis[sulfosuccinimidyl] suberate (BS3), 3,3'-dithiobis[sulfosuccinimidylpropionate] (DTSSP), ethylene glycol bis[sulfosuccinimidylsuccinate (sulfo-EGS), disuccinimidyl glutarate (DSG), dithiobis[succinimidyl propionate] (DSP), disuccinimidyl suberate (DSS), ethylene glycol bis[succinimidylsuccinate] (EGS), NHS-ester/diazirine crosslinkers such as NHS-diazirine, NHS-LC-diazirine, NHS-SS-diazirine, sulfo-NHS-diazirine, sulfo-NHS-LC-diazirine, and sulfo-NHS-SS-diazirine.

The nucleic acid sample (e.g., genomic DNA) can be treated to fragment the nucleic acid before affinity purification. Fragmentation can be performed through physical, mechanical or enzymatic methods. Physical fragmentation can include exposing a target polynucleotide to heat or to ultraviolet (UV) light. Mechanical disruption may be used to mechanically shear a target polynucleotide into fragments of the desired range. Mechanical shearing may be accomplished through a number of methods such as repetitive pipetting of the target polynucleotide, sonication and nebulization. Target polynucleotides may also be fragmented using enzymatic methods. In some cases, enzymatic digestion may be performed using enzymes such as using restriction enzymes. Restriction enzymes may be used to perform specific or non-specific fragmentation of target polynucleotides. The methods may use one or more types of restriction enzymes, generally described as Type I enzymes, Type II enzymes, and/or Type III enzymes. Type II and Type III enzymes are generally commercially available. Type II and Type III enzymes can recognize specific sequences of nucleotide nucleotides within a double stranded polynucleotide sequence (a "recognition sequence" or "recognition site"). Upon binding and recognition of these sequences, Type II and Type III enzymes can cleave the polynucleotide sequence. In some cases, cleavage can result in a polynucleotide fragment with a portion of overhanging single stranded DNA, called a "sticky end." In other cases, cleavage may not result in a fragment with an overhang, creating a "blunt end." The methods may comprise use of restriction enzymes that generate either sticky ends or blunt ends.

Fragments of nucleic acids can also be generated via amplification techniques (e.g. polymerase chain reaction, long range polymerase chain reaction, linear polymerase chain reaction, and etc.).

Once fragmented, the captured complexes comprising the Argonaute protein can be purified by incubation with a solid support. For example, if the Argonaute protein comprises a biotin tag, the solid support can be coated with avidin or streptavidin to bind to the biotin tag.

In some embodiments, once fragmented, the captured complexes comprising the Argonaute protein, the target nucleic acid, and/or the designed nucleic acid-targeting nucleic acid are purified by incubation with a capture agent. A capture agent can refer to any agent that can bind to an affinity tag fused to the Argonaute protein. Exemplary capture agents can include, biotin, streptavidin, and antibodies. For example, if the affinity tag fused to the Argonaute protein is a FLAG tag, then the capture agent will be an anti-FLAG-tag antibody. In some embodiments, the capture agent cancomprise an affinity tag (e.g., biotin, streptavidin).

In some instances, the capture agent is a DNA-binding protein. In some instances, the capture agent is nuclease. In some instances, the capture agent is an enzymatically inactive nuclease. Nucleases can include, for example, Type I endonucleases, Type II endo nucleases, Type III endonucleases, restriction endonucleases, AP endonuclease, and the like.

The capture agent can be purified with a solid support. For example, if the capture agent comprises a biotin tag, the bead can be coated with avidin or streptavidin to bind the biotinylated capture agent.

In some embodiments of the method, two or more rounds of purification can be performed. At least 1, 2, 3, 4, 5, 6, 7 or more rounds of purification can be performed. At most 1, 2, 3, 4, 5, 6, 7 or more rounds of purification can be performed. A first round of purification can comprise purification with a solid support that can bind to the affinity tag of the capture agent and/or the affinity tag of the designed nucleic acid-targeting nucleic acid and a second round of purification can comprise purification with a solid support that can bind to the affinity tag of the Argonaute protein. A first round of purification can comprise purification with a solid support that can bind to the affinity tag of the Argonaute protein and a second round of purification can comprise purification with a solid support that will bind to the affinity tag of the capture agent and/or the affinity tag of the designed nucleic acid-targeting nucleic acid. The method can be used to optimize the binding specificity of the Argonaute protein by performing the method more than once.

The captured complex can comprise the Argonaute protein and the target nucleic acid. The target nucleic acid can be eluted from the captured complex by methods such as high salt washing, ethanol precipitation, boiling, and gel purification.

The eluted target nucleic acid can be prepared for sequencing analysis (e.g., shearing, ligation of adaptors). Preparation for sequencing analysis can include the generation of sequencing libraries of the eluted target nucleic acid. Sequencing analysis can determine the identity and frequency of off-target binding sites of Argonaute proteins. Sequence determination can also be performed using methods that determine many (typically thousands to billions) nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLID™ technology, Life Technology, Inc., Carlsbad, Calif.); sequencing by synthesis using modified nucleotides (such as commercialized in TRUSEQ™ and HiSEQ™ systems by Illumina, Inc.. San Diego, Calif, HELISCOPE™ system by Helicos Biosciences Corporation. Cambridge, Mass., and PacBio RS by Pacific Biosciences of California. Inc., Menlo Park, Calif.), sequencing by ion detection technologies (Ion Torrent. Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and other known highly parallelized sequencing methods.

In some embodiments, the method further comprises collecting data and storing data. The data can be machiene readable and can be stored and/or collected on. a computer server (e.g. FIG. 17 and Example 32).

Methods for Detecting Sequence Variants in Nucleic Acids

General Overview

Figure 7:
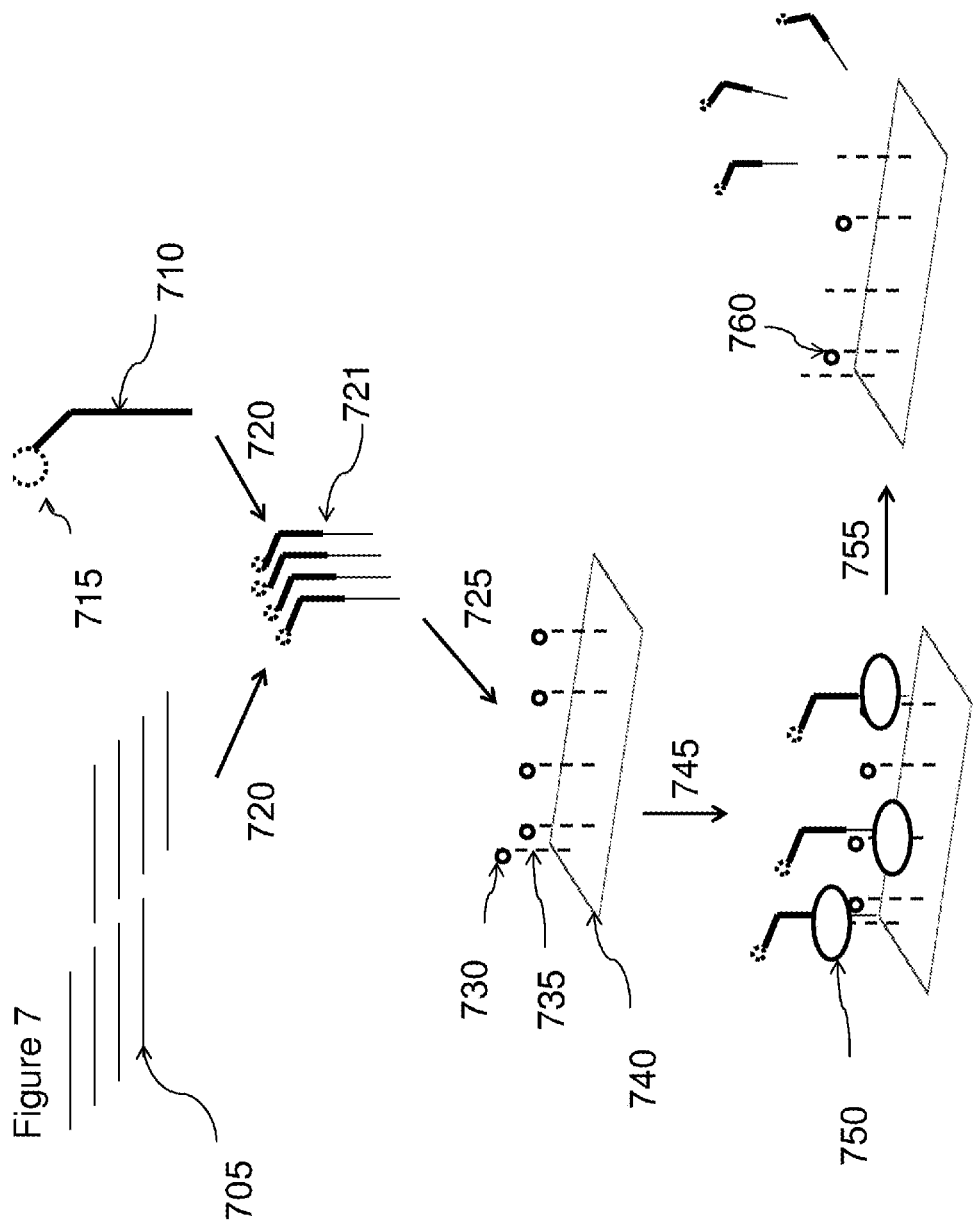
FIG. 7 illustrates an exemplary embodiment for an array-based sequencing method using an Argonaute of the disclosure.

In some embodiments, the methods of the disclosure provide for detecting sequence variants in nucleic acids. The method can be performed using any of the Argonaute proteins, designed nucleic acid-targeting nucleic acids, and complexes of Argonaute proteins and designed nucleic acid-targeting nucleic acids as described herein. As depicted in FIG. 7, a nucleic acid sample 705 can he ligated 720 with a nucleic acid tag 710. The nucleic acid tag can comprise a detectable label 715. Together, the nucleic acid sample 705 ligated to the nuclei acid tag 710 can be referred to as a tagged test sample 721. The tagged test sample 721 can be contacted 725 to an array 740 comprising immobilized oligonucleotides 735. The immobilized oligonucleotides 735 can be referred to as a nucleic acid library. The oligonucleotides 735 can be double stranded DNA. The oligonucleotides 735 can comprise a detectable label 730. The individual members of the tagged test sample 721 can hybridize 745 to the oligonucleotides 735 to which, they share enough complementarity to facilitate hybridization. The amount of hybridization can be quantified by comparing the intensities of the two detectable labels 715 and 730. For example, hybridized oligonucleotides can display two detectable labels. Unhybridized oligonucleotides can display one detectable label 730. The hybridized sample can be contacted with the Argonauts protein 750 The Argonaute protein can cleave 755 the oligonucleotides 735 in the array 740 that have hybridized with members of the tagged test sample 721. Cleavage by the Argonaute protein can allow the hybridized members of the tagged test sample 721 to be removed. After cleavage by the Argonaute protein 750, only unhybridized oligonucleotide delectable labels 760 will remain on the array The remaining detectable label 760 can be quantified The quantification of the remaining detectable labels 760 can be correlated to which sequences were represented in the nucleic acid sample 705 and which were not. Oligonucleotides that do not display a remaining detectable label 760 correspond to sequences that were represented in the nucleic acid sample 705 Oligonucleotides that display a remaining detectable label 760 correspond to sequences that were not represented in the nucleic acid sample 705.

Figure 8:
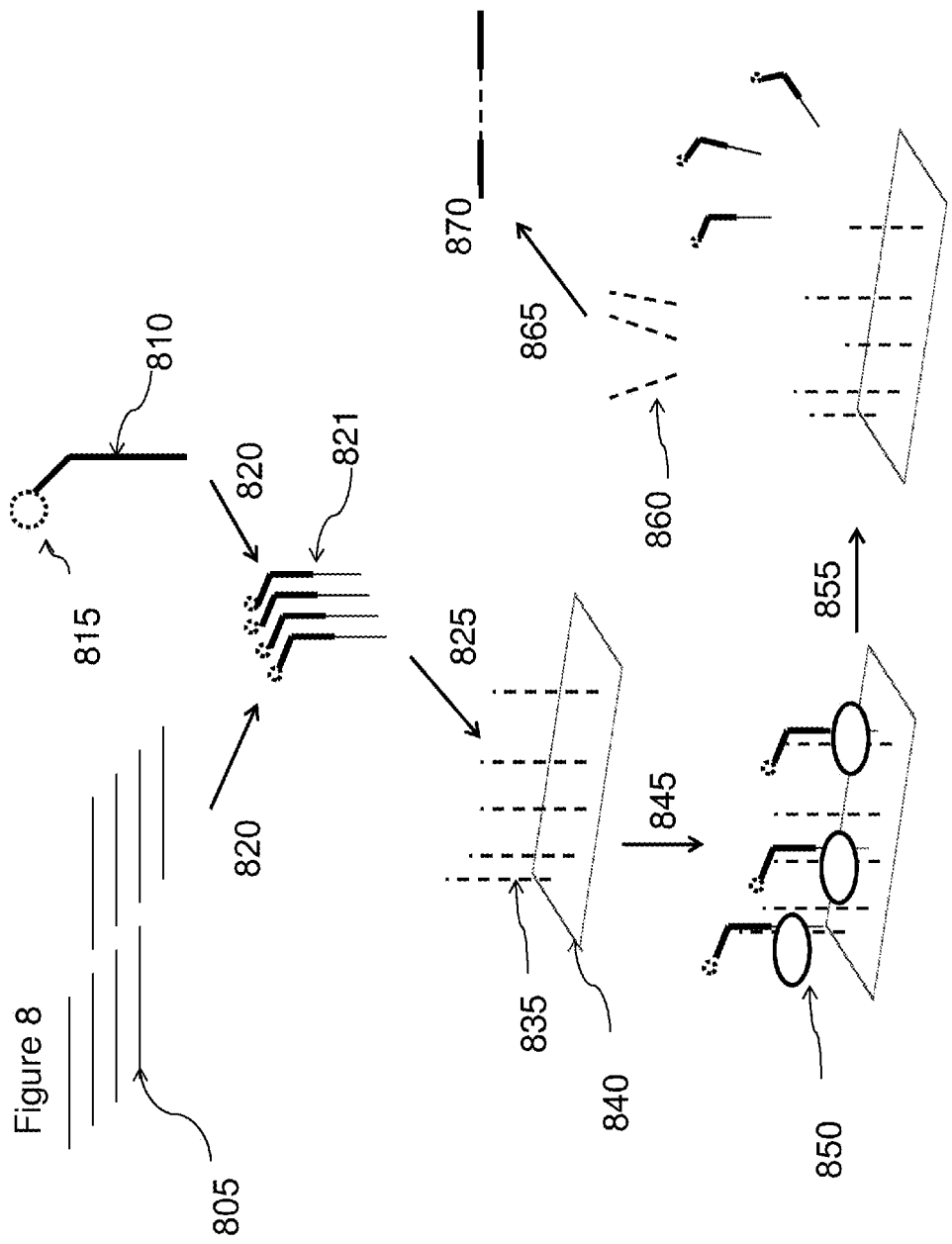
FIG. 8 illustrates aw exemplary embodiment for an array-based sequencing method using an Argonaute of the disclosure, wherein cleaved products are sequenced.

In some embodiments, in reference to FIG. 8, a nucleic acid sample 805 can be ligated 820 with a nucleic acid tag 810. The nucleic acid tag can be a designed nucleic acid-targeting nucleic acid. The nucleic acid tag can comprise a detectable label 815. Together, the nucleic acid sample ligated to the nuclei acid tag can be referred to as a tagged test sample 821. The tagged test sample 821 can be contacted 825 to an array 840 comprising immobilized oligonucleotides 835. The immobilized oligonucleotides can be referred to as a nucleic acid library. The oligonucleotides 835 can be double stranded DNA. The individual members of the tagged test sample 821 can hybridize 845 to the oligonucleotides 835 to which they share enough complementarity to facilitate hybridization. The hybridized sample can be contacted with an Argonaute protein 850. The Argonaute protein can cleave 855 the oligonucleotides 835 in the array 840 that have hybridized with members of the tagged test sample 821. Cleavage by the Argonaute protein 850 can allow the hybridized members of the tagged test sample 821 to be removed. Cleavage by the Argonaute protein 850 can allow a portion of the immobilized olignucleotide to be cleaved and separated from the array 860. The separated cleaved oligonucleotides 860 can be ligated 865 to appropriate adaptors 870 for sequencing Sequencing of the cleaved oligonucleotides 860 can determine the sequences represented in the nucleic acid sample 805.

Figure 9:
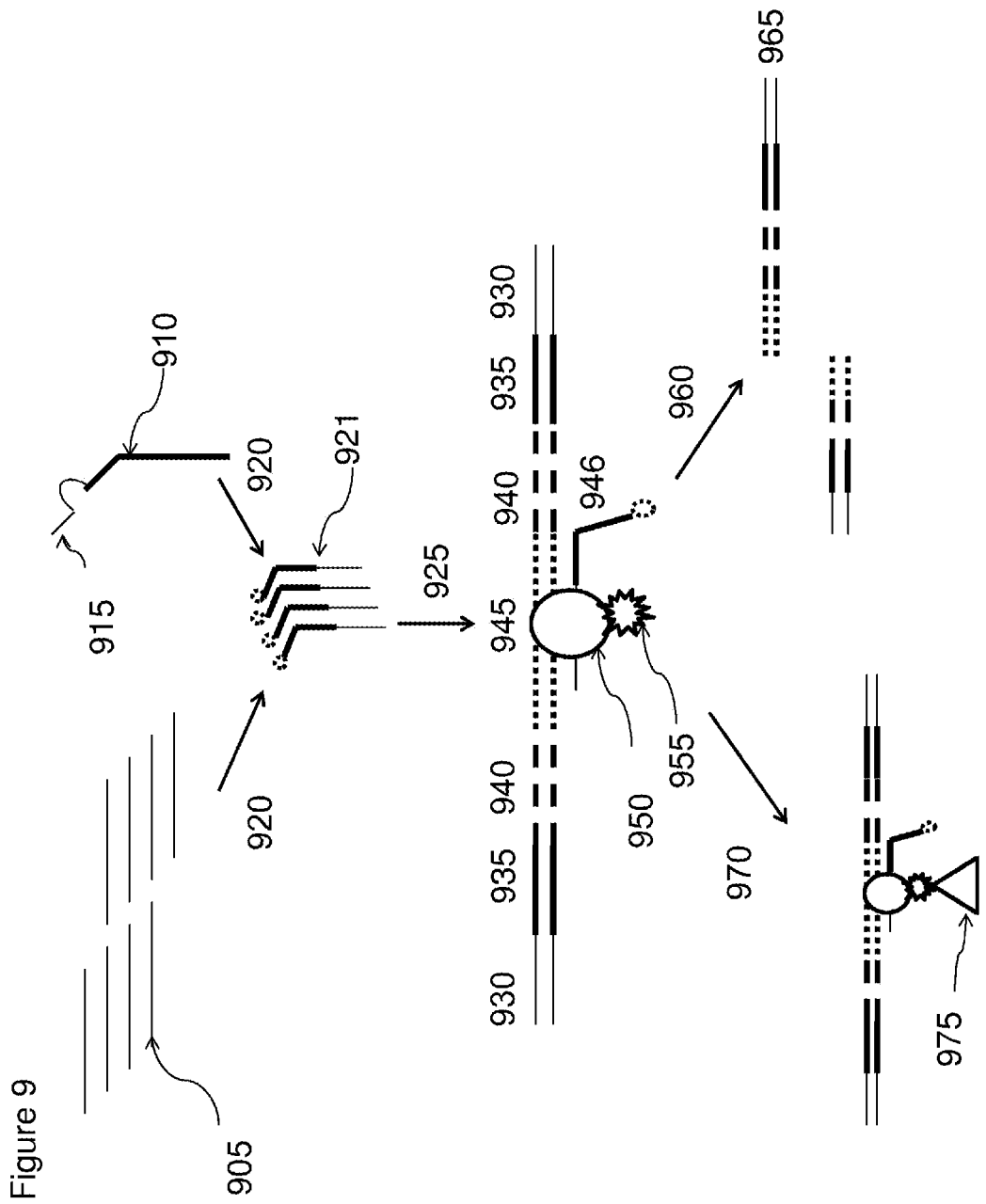
FIG. 9 illustrates an exemplary embodiment for a next-generation sequencing-based method using an Argonaute of the disclosure.

In some embodiments, a nucleic acid library can be generated for sequencing analysis using commercially available high throughput sequencing platforms. In FIG. 9, the library can comprise nucleic acids that can comprise one or more sequencing tags 930 and a target sequence 945, The target sequence 945 can be a sequence that may be represented in a nucleic acid sample 905. Optionally, nucleic acids in a nucleic acid library can comprise one or more identifying polynucleotide sequences 935. and one or more, extension sequences 940. In this embodiment, a nucleic acid sample 905 can be ligated 920 with a nucleic acid tag 910, The nucleic acid tag can be a designed nucleic acid-targeting nucleic acid. Optionally, the nucleic acid tag can comprise an affinity lag 915. Together, the nucleic acid sample ltgated to the nuclei acid tag can be referred to as a tagged test sample 921. The tagged test sample 921 can be contacted 925 to a nucleic acid library. The tagged test sample 921 can hybridize to a nucleic acid in the nucleic acid library, forming a complex 946. The hybridized tagged test sample and nucleic acid library can be contacted with an Argonaute protein 950. The Argonaute protein 950 can cleave the hybridized nucleic acid library members. The cleaved nucleic acid library members 965 can be separated from the uncleaved members. The uncleaved members can be subjected to sequencing analysis. Sequencing analysis can determine which sequences were represented in the nucleic acid sample 905. For example, the sequences of the uncleaved members can correspond to sequences that were not represented in the nucleic acid sample 905. These sequences can be removed from the known sequences in the nucleic acid library. The resulting sequences can be the sequences of the cleaved members 965 of the nucleic acid library which can correspond to sequences that were represented in the nucleic acid sample 905.

The Argonaute protein 950 can comprise an affinity tag 955. Optionally, the Argonaute protein 950 can be an enzymatically inactive variant of an Argonaute protein. In some embodiments, an enzymatically inactive Argonaute protein can be contacted to a hybridized nucleic acid library (e.g., complex 946). The Argonaute protein can bind but cannot cleave the hybridized nucleic acid library members. The Argonaute protein can be affinity purified 970 with a capture agent 975 that can bind to the affinity tag 955. Optionally, the complex 946 can be affinity purified with a capture agent that can bind to the affinity tag 915. The affinity purified nucleic acid library members can be subjected to sequencing analysis. In this embodiment, the sequenced nucleic acid library members can. correspond to sequences that are represented in the nucleic acid sample 905.

Sequencing

Methods for detecting sequence variants can comprise sequencing the variants. Sequence determination can be performed using methods that determine many (typically thousands to billions) nucleic acid sequences in an intrinsically parallel manner, where many sequences are read out preferably in parallel using a high throughput serial process. Such methods can include but are not limited to pyrosequencing (for example, as commercialized by 454 Life Sciences, Inc., Branford, Conn.); sequencing by ligation (for example, as commercialized in the SOLID™ technology, Life Technology, Inc.. Carlsbad, Calif.); sequencing by synthesis using modified nucleotides (such as commercialized in TRUSEQ™ and HISEQ™ systems by Ulumina, inc., San Diego, Calif., HELISCOPE™ system by Helicos Biosciences Corporation. Cambridge, Mass., and PacBio RS by Pacific Biosciences of California, Inc., Menio Park, Calif.); sequencing by ion detection technologies (Ion Torrent, Inc., South San Francisco, Calif.); sequencing of DNA nanobalis (Complete Genomics, Inc., Mountain View, Calif.); nanopore-based sequencing technologies (for example, as developed by Oxford Nanopore Technologies, LTD. Oxford, UK); capillary sequencing (eg, such as commercialized in MegaBACE by Molecular Dynamics), electronic sequencing; single molecule sequencing (e.g.. such as commercialized in SMRT™ technology by Pacific Biosciences, Menlo Park, Calif.); droplet microfluidic sequencing; sequencing by hybridization (such as commercialized by Asymetrix, Santa Clara, Calif.); bisulfate sequencing; and other known highly parallelized sequencing methods.

Real Time PCR

Methods for delecting sequence variants can comprise delecting the variants using real time PCR. Sequence determination am be performed by real time polymerase chain reaction (RT-PCR, also referred to as quanlitative-PCR (QPCR)) can detect an amount of ampiifiahle nucleic acid present in a sample. QPCR is a technique based on the polymerase chain reaction, and can be used to amplify and simultaneously quantify a target nucleic acid. QPCR can allow for both detection and quantification of a specific sequence in a target nucleic acid sample. The procedure can follow the general principle of polymerase chain reaction, with the additional feature that the amplified target nucleic acid can be quantified as it accumulates in the reaction in real time after each amplification cycle. Two methods of quantification can be: (1) use of fluorescent dyes that intercalate with double-stranded target nucleic acid, and (2) modified DNA oligonucleotide probes that fluoresce when hybridised with a complementary target nucleic acid. In the first method, a target nucleic acid-binding dye can bind to all double-stranded (ds) nucleic acid in PCR, resulting in fluorescence of the dye. An increase in nucleic acid product during PCR therefore can lead to an increase in fluorescence intensity and can be measured at each cycle, thus allowing nucleic acid concentrations to be quantified. The reaction can be prepared similarly to a standard PCR reaction, with the addition of fluorescent (ds) nucleic acid dye. The reaction can be run in a thermocyeicr, and after each cycle, the levels of fluorescence can be measured with a detector; the dye can only fluoresce when bound to the (ds)nucleic acid (i.e.., the PCR product). With reference to a standard dilution, the (ds) nucleic acid concentration in the PCR can be determined. The values obtained can not have absolute units associated with it. A comparison of a measured DNA/RNA sample to a standard dilution can give a fraction or ratio of the sample relative to the standard, allowing relative comparisons between different tissues or experimental conditions. To ensure accuracy in the quantification, the expression of a target gene can be normalized to a stably expressed gene. This can allow for correction of possible differences in nucleic acid quantity or quality across samples. The second method can use a sequence-specific RNA or DNA-based probe to quantify only the nucleic acid containing the probe sequence; therefore, use of the reporter probe can increase specificity, and can allow quantification even in the presence of some non-specific nucleic acid amplification. This can allow for multiplexing, (i.e., assaying for several genes in the same reaction by using specific probes with differently colored labels), provided that all genes are amplified with similar efficiency. This method can be carried out with a nucleic acid-based probe with a fluorescent reporter (e.g. 6-carboxyfluorescein) at one end and a quencher (e.g., 6-carboxy-tetramethylrhodamine) of fluorescence at the opposite end of the probe. The close proximity of the reporter to the quencher can prevent detection of its fluorescence. Breakdown of the probe by the 5' to 3' exonuclease activity of a polymerase (e.g., Taq polymerase) can break the reporter-quencher proximity and thus can allow unquenched emission of fluorescence, which can be detected. An increase in the product targeted by the reporter probe at each PCR cycle can result in a proportional increase in fluorescence due to breakdown of the probe and release of the reporter The reaction can be prepared similarly to a standard PCR reaction, and the reporter probe can be added. As the reaction commences, during the annealing stage of the PCR both probe and primers can anneal to the target nucleic acid. Polymerization of a new DNA strand can be initiated from the primers, and once the polymerase reaches the probe, its 5'-3'-exonuclease can degrade the probe, physically separating the fluorescent reporter from the quencher, resulting in an increase in fluorescence. Fluorescence can be detected and measured in a real-time PCR thermocycler, and geometric increase of fluorescence can correspond to exponential increase of the product is used to determine the threshold cycle in each reaction. Relative concentrations of DNA present during the exponential phase of the reaction can be determined by plotting fluorescence against cycle number on a logarithmic scale (so an exponentially increasing quantity can give a straight line). A threshold for detection of fluorescence above background can be determined. The cycle at which the fluorescence from a sample crosses the threshold can be called the cycle threshold, Ct. Since the quantity of DNA can double every cycle during the exponential phase, relative amounts of DNA can be calculated, (e.g. a sample with a Ct of 3 cycles earlier than another has 23=8 times more template). Amounts of nucleic acid (e.g., RNA or DNA) can be determined by comparing the results to a standard curve produced by a real-time PCR of serial dilutions (e.g. undiluted, 1:4, 1:16, 1:64) of a known amount of nucleic acid. The QPCR reaction can invoke a dual fluorophore approach that takes advantage of fluorescence resonance energy transfer (FRET), (e.g., LIGHTCYCLER hybridization, probes, where two oligonucleotide probes can anneal to the amplicon). The oligonucleotides can be designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: SCORPIONS probes. Sunrise (or AMPUFLOUR) primers, and LUX primers and MOLECULAR BEACONS probes. The QPCR reaction can use fluorescent Taqman methodology and an instrument capable of measuring fluorescence in real time (eg., ABI Prism 7700 Sequence Detector). The Taqman reaction, can use a hybridization probe labeled with two- different fluorescent dyes. One dye can be a reporter dye (6-carboxyfluorescein), the other can be a quenching dye (6-carboxy-tetramethylrhodamine). When the probe is intact, fluorescent energy transfer can occur and the reporter dye fluorescent emission can be absorbed by the quenching dye. During the extension phase of the PCR cycle, the fluorescent hybridization probe can be cleaved by the 5'-3' nucleolytic activity of the DNA polymerase. On cleavage of the probe, the reporter dye emission can no longer transferred efficiently to the quenching dye, resulting in an increase of the reporter dye fluorescent emission spectra. Any nucleic acid quantification, method, including real-time methods or single-point detection methods can be use to quantify the amount of nucleic acid in the sample. The detection can be performed several different methodologies (e.g., staining, hybridization with a labeled probe; incorporation of biotinylatcd primers followed by avidin-enzyme conjugate detection; incorporation of 32P-labeled deoxymicleotide triphosphates, such as dCTP or dATP, into the amplified segment. The quantification can or can not include an amplification step. The quantitation can not be experimental.

Microarray

Methods for detecting sequence variants can comprise sequencing and/or detecting the variants using a microarray. Microarrays can be used for determining the expression level of a plurality of genes in a nucleic acid sample. Microarrays can be used for determining sequence identity of a plurality of sequences in a nucleic acid sample.

A microarray can comprise a substrate. Substrates can include, but are not limited to, glass and modified or functionahzed glass, plastics (including acrylics, polystyrene and copolymers of styrene and other materials, polypropylene, polyethylene, polybutylene, polyurethanes, TEFLON™ polymer, and the like), polysaccharides, nylon or nitrocellulose, resins, silica or silica-based materials including silicon and modified silicon, carbon, metals, inorganic glasses, and plastics.

Microarrays can comprise a plurality of polynucleotide probes. A microarray can comprise about 1, 10, 100, 1000, 5000, 10000, 20000, 30000, 40000, 50000, 60000, 70000, 80000, 90000, 100000, 110000, 120000 or more probes.

Probes can be can be at least 10, 20, 30, 40, 50, 60, 70, 80, 90, 100, 110, 120, 130, 140 nucleotides or more in length.

In some embodiments, probes can comprise sequence information for a specific set of genes and/or species. A probe can be complementary to a nucleic acid sequence encoding a host protein. A probe can be complementary to a non-coding nucleic acid sequence. A probe can be complementary to a DNA sequence. A probe can be complementary to an RNA sequence.

Probes can be immobilized on a microarray. The immobilization of polynucleotides on a solid substrate can be achieved by direct synthesis (e.g., photolithographic synthesis) of polynucleotides on a solid substrate or by immobilization (spotting) of previously synthesized polynucleotides on predetermined regions of a solid substrate. Polynucleotides can be immobilized on a microarray substrate by activating a surface of a solid substrate with a nucleophilic functional group (e.g., an amino group), coupling biomolecules (e.g., polynucleotides) activated with a good leaving group to the surface-activated solid substrate, and removing unreacted reactants. Probes can be immobilized to a bead further conjugated through a covalent or ionic attachment to a solid support. Probes can be immobilized onto a substrate using a specific film having a low conductivity and a low melting temperature, namely a gold film. An applied electromagnetic radiation can melt and can ablate the film at the impingement site. The film can be in contact with a colloidal dispersion and upon melting can generate a convective flow at the reaction site, thereby leading to adhering of an insoluble particle in the dispersion to the specifically melted site.

A microarray can analyze a nucleic acid sample comprising nucleic acids of unknown identity (e.g., test sample) by comparing the nucleic acid sample of unknown identity with a reference sample. A nucleic acid sample can be prepared from DNA (e.g., isolated DNA, genomic DNA, extrachromasomal DNA). A nucleic acid sample can be prepared from RNA. RNA can be reverse transcribed into DNA with a gene-specific primer or a univerisal primer. The reverse transcribed DNA (e.g., cDNA), can be treated with Rnase or base (e.g., NaOH) to hydrolyze the RNA. The cDNA can be labelled with a dye (e.g, Cy3, Cy5) with N-hydroxysuccinimide chemistry or similar labeling chemistries. Suitable fluorescent dyes can include a variety of commercial dyes and dye derivatives such as those that are denoted Alexa, Fluorescein, Rhodamine, FAM, TAMRA, Joe, ROX, Texas Red, BODIPY, FITC, Oregon Green, Lissamine and others. The reference sample can be labeled with a different dye than the test sample.

The test sample and the reference sample can be applied to a microarray to contact multiple spots simultaneously. The test sample and the reference sample can be applied to the microarray under hybridizing conditions that can allow the nucleic acids in the nucleic acid sample to bind to a complement probe on the microarray. Various reaction steps can be performed with the bound molecules in the microarray, including exposure of bound reactant molecules to washing steps. The progress or outcome of the reaction can be monitored at each spot (e.g., probe) in the microarray in order to characterize the nucleic acid sample immobilized on the chip. Microarray analysis usually can require an incubation period that can range from minutes to hours. The duration of the incubation period can be assay dependent and can be determined by a variety of factors, such as the type of reactant, degree of mixing, sample volume, target copy number, and density of the array. During the incubation period, nucleic acids in the nucleic acid sample can be in intimate contact with the microarray probes.

Detection can be performed using a confocal scanning instrument with laser excitation and photomultiplier tube detection, such as the ScanArray 3000 provided by GSI Lumonics (Bellerica, Mass.). Confocal and non-confocal fluorescent detection systems can be used to implement the method such as those provided by Axon Instruments (Foster City, Calif.), Genetic MicroSystems (Santa Clara, Calif.), Molecular Dynamics (Sunnyvale, Calif.) and Virtek (Woburn, Mass.). Alternative detection systems can include scanning systems that use gas, diode and solid state lasers as well as those that use a variety of other types of illumination sources such as xenon and halogen bulbs. In addition to photomultiplier tubes, detectors can include cameras that use charge coupled device (CCD) and complementary metal oxide silicon (CMOS) chips.

The ratio of the intensities of the two dyes from the test sample and the reference sample can be compared for each probe. The strength of the signal detected from a given microarray spot can be directly proportional to the degree of hybridization of a nucleic acid in the sample to the probe at a given spot (e.g., a spot comprises a probe). Analysis of the fluorescence intensities of hybridized microarrays can include spot segmentation, background determination (and possible subtraction), elimination of bad spots, followed by a method of normalization to correct for any remaining noise. Normalization techniques can include global normalization on all spots or a subset of the spots such as housekeeping genes, prelog shifting to obtain better baseline matches, or in the case of two (or more) channel hybridizations finding the best fit that helps to give an M vs. A plot that is centered about M=0 and/or that helps to give a log(Red) vs. log(Green) plot that is centered about the diagonal with the smallest spread. The M vs. A plot can also be referred to as the R vs. I plot, where R is a ratio, such as R=$\log_2$(Red/Green) and I is an intensity, such as I=log VRed* Green.

Scaling, shifting, best fits through scatter plots, etc. can be techniques utilized to normalize microarray datasets and to give better footing for subsequent analysis. Most of these normalization methods can have some underlying hypothesis behind them (such as "most genes within the study do not vary much").

Tagged Designed Nucleic Acid-Targeting Nucleic Acids

Figure 10:
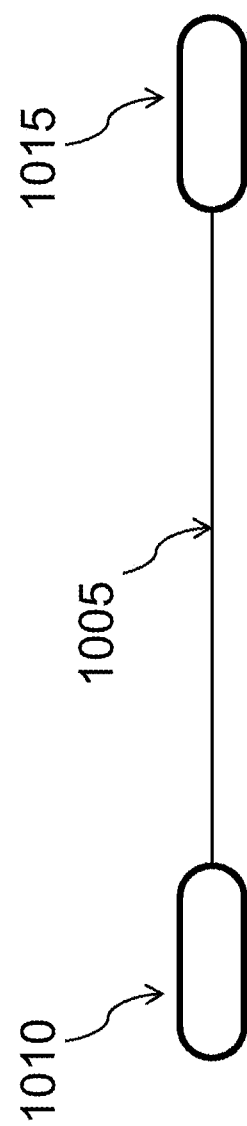
FIG. 10 depicts an exemplary tagged designed nucleic acid-targeting nucleic acid.

The disclosure provides for kits, methods, and compositions for tagged nucleic acid-targeting nucleic acids, as described herein. FIG. 10 depicts an exemplary embodiment of nucleic acid-targeting nucleic acid 1005 of the disclosure. A designed nucleic acid-targeting nucleic acid can comprise one or more non-native sequences (e.g., tags) 1010/1015. A designed nucleic acid-targeting nucleic acid can comprise a non-native sequence 1010/1015 at either the 3' end, the 5' end, or both the 3' and 5' end of the nucleic acid-targeting nucleic acid.

In some instances, a designed nucleic acid-targeting nucleic acid can be designed nucleic acid-targeting nucleic acids as described herein, and comprise one or more non-native sequences, such as either at the 3'end, the 5'end or both the 3' and 5' ends of the designed nucleic acid-targeting nucleic acid.

The non-native sequence can be at least 5, 10, 15, 20, 25, 30, 35, 40, 45, 50, 55, 60, 65, 70, 75, 80, 85, 90, 95, or 100 or more nucleotides in length. The non-native sequences can be at most 5, 10, 15, 20, 25, 30, 35, 40, 45, 50, 55, 60, 65, 70, 75, 80, 85, 90, 95, or 100 or more nucleotides in length. The non-native sequence can be DNA-binding protein binding sequence. The non-native sequence may be cleavable sequence. The non-native sequence can be a genetic element, such as, for example, a promoter, a transcription terminator, an enhancer, a coding nucleic acid, a non-coding nucleic acid, a ribosome binding site, and a internal ribosome entry site.

Detecting Genetic Mobility Events

Figure 11:
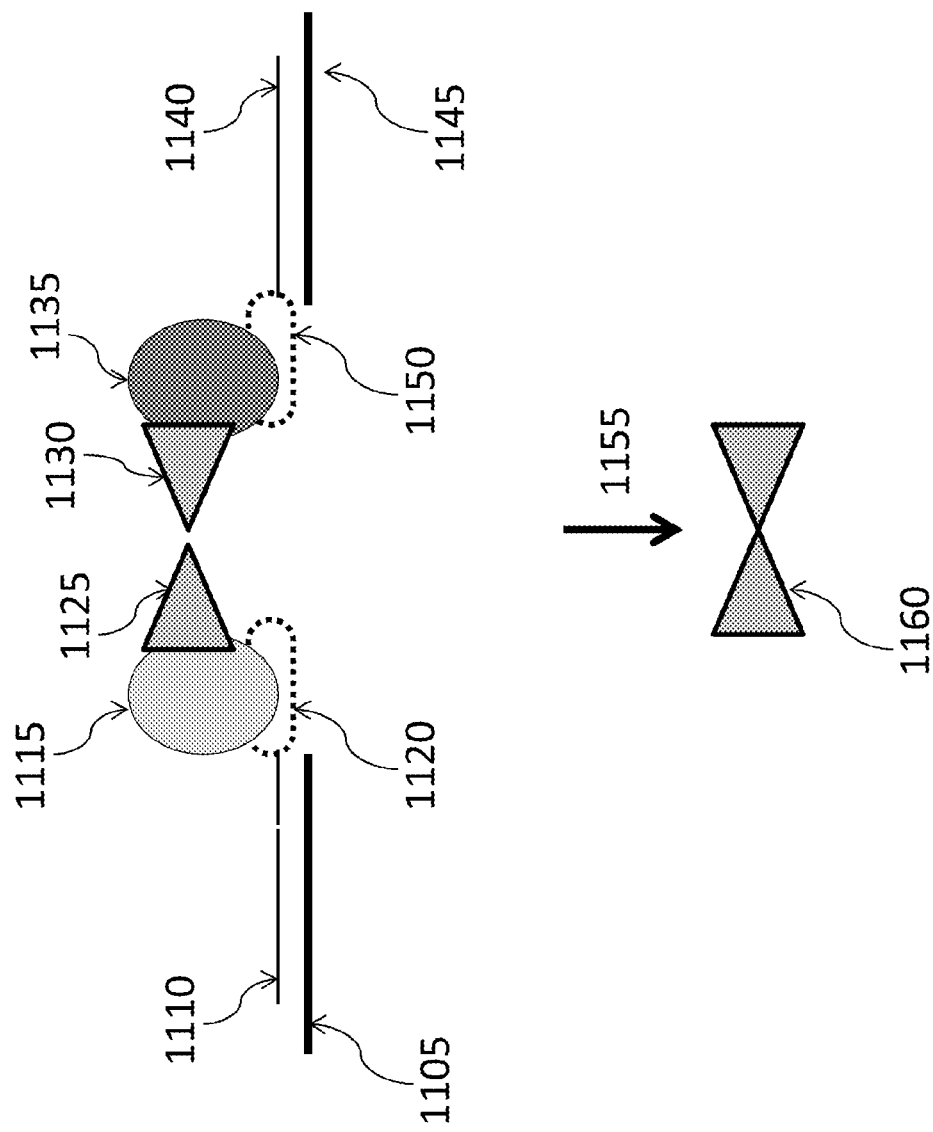
FIG. 11 illustrates an exemplary embodiment of a method of using a tagged designed nucleic acid-targeting nucleic acid with a split system (e.g., split fluorescent system).

The disclosure provides for methods of use of tagged designed nucleic acid-targeting nucleic acids. The method can be performed using any of the Argonautes, designed nucleic acid-targeting nucleic acids, and complexes of Argonautes and designed nucleic acid-targeting nucleic acids as described herein. In some instances, a plurality of tagged designed nucleic acid-targeting nucleic acids can be contacted to a plurality of target nucleic acids. FIG. 11 depicts an exemplary method of use for tagged designed nucleic acid-targeting nucleic acids. A tagged designed nucleic acid-targeting nucleic acid 1110 can hybridize with a target nucleic acid 1105. The designed nucleic acid-targeting nucleic acid can comprise a non-native sequence (e.g., tag) 1120. The non-native sequence 1120 can be bound by a DNA-binding protein 1115. The DNA-binding protein 1115 can comprise a non-native sequence 1125 (e.g., a fusion, i.e., the DNA-binding protein 1115 can be a fusion polypeptide). The non-native sequence (e.g., fusion) 1125 can alter the transcription of the target nucleic acid and/or an exogenous nucleic acid. The non-native sequence (e.g., fusion) 1125 can comprise a first portion of a split system.

In some embodiments, a second nucleic acid-targeting nucleic acid, comprising a second spacer 1140 that can hybridize to a second target nucleic acid 1145, can comprise a second non-native sequence (e.g., tag) 1150. The second non-native sequence (e.g., tag) 1150 can be a DNA-binding protein binding sequence. The second non-native sequence 1150 can be bound by a DNA-binding protein 1135. The DNA-binding protein can comprise a non-native sequence 1130 (e.g., fusion, i.e., the DNA-binding protein 1135 can be a fusion). The non-native sequence 1130 (e.g., fusion) can be a second portion of a split system.

In some instances, the first portion of the split system 1125 and the second portion of the split system 1130 can be close together in space, such that the first portion of the split system 1125 and the second portion of the split system 1130 interact 1155 to form an active split system 1160. An active split system 1160 can refer to an unsplit system, wherein the first portion and the second portion form a whole piece of the split system. Activation of the split system can indicate that two target nucleic acids 1105/1145 are close together in space.

The disclosure provides for methods for contacting a target nucleic acid with a complex comprising an Argonaute protein and a designed nucleic acid-targeting nucleic acid, and introducing one or more effector proteins, wherein the one or more effector proteins comprises a non-native sequence and can bind to the designed nucleic acid-targeting nucleic acid and/or Argonaute protein. An effector protein can refer to any protein with a functional effect. For example, an effector protein can comprise enzymatic activity, remodel biological molecules (e.g., folding chaperones), be a scaffolding protein, and/or bind a small molecule or metabolite. The effector protein can modify the target nucleic acid (e.g., cleavage, enzymatic modification, transcriptional modification). The methods of the disclosure provide for using the compositions of the disclosure as biosensors. For example, the complexes (e.g., comprising the designed nucleic acid-targeting nucleic acid, the Argonaute protein and/or the effector protein) can be used to monitor genetic mobility events, sense when sequences are close together in three-dimensional space, and conditionally alter transcription.

Genetic Mobility Event

The disclosure provides for methods for determining the occurance of a genetic mobility event. The method can be performed using any of the Argonaute proteins, designed nucleic acid-targeting nucleic acids, and complexes of Argonaute proteins and designed nucleic acid-targeting nucleic acids as described herein. A genetic mobility event can comprise, for example, a translocation, a recombination, an integration, a transposition, a horizontal gene transfer event, a transformation, a transduction, a conjugation, a gene conversion event, a duplication, a translocation, an inversion, a deletion, a substitution, or any combination thereof A genetic mobility event can comprise a recombination between genes. The recombination can lead to deleterious gene products (e.g., the BCR-ABL recombination which can contribute to breast cancer). Recombination can include, for example, homologous recombination, non-homologous recombination (e.g., non-homologous end joining), and V(D)J recombination. Recombination can refer to chromosomal crossover. Recombination can occur during prophase I of meiosis (e.g., synapsis). Recombination can comprise double-stranded breakage of nucleic acid strands of DNA, followed by formation of a holliday junction by recombinases which can catalyze swapping of the DNA strands.

Genetic mobility events can cause disease. For example, chronic myelogenous leukemia can result from a genetic mobility event. Translocation between chromosome 9 and 22 can result in a fusion BCR-Abl1 gene, which can result in the lengthening of one chromosome (e.g., 9), and the shortening of another chromosome (e.g., 22, i.e., Philadelphia chromosome). The BCR-Abll translocation can lead to the production of a BCR-Abl fusion protein which can interact with receptors (e.g., interleukin-3 receptor) to promote cell division, leading to chronic myelogenous leukemia (CML). Other non-limiting exemplary genetic mobility events include BRD3-NUT, BRD4-NUT, KIAA1549-BRAF, Figure/GOPC-ROS1, ETV6-NTRK3, BCAS4-BCAS3, TBL1XR1-RGS17, ODZ4-NRG1, MALAT1-TFEB, APSCR1-TFE3, PRCC-TFE3, CLTC-TFE3, NONO-TFE3, SFPQ-TFE3, ETV6-NRTK3, EML4-ALK, EWSR1-ATF1, MN1-ETV6, CTNNB1-PLAG1, LIFR-PLAG1, TCEA1 -PLAG1, FGFrl-PLAG1, CHCHD7-PLAG1, HMGA2-FHIT, HMGA-NFIB, CRTC1-MAM12, CRCT3-MAML2, EWSR1-POUF5F1, TMPRSS1-ERG, TMPRSS2-ETV4, TMPRSS2-ETV5, HNRNPA2B1-ETV1, HERV-K-ETV1, C15ORF21-ETV1, SLC45A3-ETV1, SLC45A3-ETV5, SLC45A3-ELK4, KLK2-ETV4, CANT1-ETV4, RET-PTC1/CCDC6, RET-PTC2/PRKAR1A, RET-PTC3,4/NCOA4, RET-PTC5/GOLGA5, RET-PTC6/TRIM24, RET-PTC7/TRIM33, RET-PTC8/KTN1, RET-PTC9/RFG9, RET-PTCM1, TFG-NTRK1, TPM3-NRTK1, TPR-NRTK1, RET-D10S170, ELKS-RET, HOOKS3-RET, RFP-RET, AKAP9-BRAF, and PAX8-PPARG.

Diseases that can be caused by genetic mobility events can include Charcot-Marie-Tooth disease type 1A (CMT1A), juvenile nephronophtisis (NPH), X-linked icthyosis, familial growth hormone deficiency type 1A, fascioscapulohumeral muscular dystrophy (FSHD), α-thalassemia, hemophilia A, Hunter syndrome (i.e., mucopolysaccharidosis II), Emery-Dreifuss musclar dystrophy, Hemoglobin Lepore, steroid 21-hydroxylase deficiency, glucocorticoid-suppressible hyperaldosteronism (GSH), color-blindness (e.g., visual dichromacy), autosomal recessive spinal muscular atrophy (SMA), cancer, T-cell acute lymphoblastic leukemia (T-ALL), aggressive midline carcinoma, Astrocytoma, Secretory breast carcinoma, Breast cancer, Kidney carcinoma, Mesoblastic nephroma, Lung adenocarcinoma, Melanoma, Meningioma, pleomorphic adenoma, mucoepidermoid cancer, Prostate carcinoma, Thyroid carcinoma, and acute promyelocytic leukemia.

The methods of the disclosure provide for determining the occurrence of a genetic mobility event in which a target nucleic acid can be contacted with two complexes, each complex comprising the Argonaute protein and a designed nucleic acid-targeting nucleic acid, and two or more effector proteins can be introduced, wherein the two or more effector proteins can bind to the designed nucleic acid-targeting nucleic acids, wherein one of the two or more effector proteins comprises a non-native sequence that is a first piece of a split system and one of the two or more effector proteins comprises a non-native sequence that is a second piece of the split system. A split system can refer to a protein complex composed of two or more protein fragments that individually are not fluorescent, but, when formed into a complex, result in a functional (that is, fluorescing) fluorescent protein complex. Individual protein fragments of a split system (e.g., split fluorescent protein) can be referred to as "complementing fragments" or "complementary fragments". Complementing fragments which can spontaneously assemble into a functional fluorescent protein complex can be known as self-complementing, self-assembling, or spontaneously-associating complementing fragments. For example, a split system can comprise GFP. In a GFP split system, complementary fragments are derived from the three dimensional structure of GFP, which includes eleven anti-parallel outer beta strands and one inner alpha strand. A first fragment can comprise one of the eleven beta-strands of the GFP molecule (e.g., GFP S11), and a second fragment can comprise the remaining strands (e.g., GFP S1-10). In some instances, a split system can refer to a chemical inducible system (e.g., estrogen-receptor-alpha inducible chemical system), and any bi-partite transcriptional activation system (e.g., yeast two-hybrid system, e.g., LexA-B42, GAL4-UAS, bait-prey system), or a split enzyme (e.g., split-ubiquitin system).

Prior to the genetic mobility event the target nucleic acid sequence targetable by one complex can be far apart from the target nucleic acid sequence targetable by another sequence. The distance between the two target nucleic acid sequences can comprise at least about 0.1, 0.5, 1, 2, 3, 4, 5, 6, 7, 8, 9, 10 or more Kb. The distance between the two target nucleic acid sequences can comprise at most about 0.1, 0.5, 1, 2, 3, 4, 5, 6, 7, 8, 9, 10 or more Kb. The two target nucleic acid sequences can be located on different chromosomes. The two target nucleic acid sequences can be located on the same chromosome.

Prior to the genetic mobility event the effector proteins that comprise pieces of the split system may not be able to interact with each other (e.g., the split system can be inactive). After the genetic mobility event, the target nucleic acid sequence targetable by one complex may be located in close proximity to the target nucleic acid sequence targetable by the other complex. After the genetic mobility event, the effector proteins that comprise pieces of the split system may be able to interact with each other, thereby activating the split system.

The activated split system can indicate the occurance of the genetic mobility event. For example, if the activated split system is a fluorescent protein split system, then prior to the genetic mobility event fluorescence may not be detected in the sample. In some instances, the levels of fluorescence of the inactive split system (e.g., background levels) may be 0.01, 0.05, 0.1, 0.5, 1, 1.5, 2, 2.5, 3, 3.5 or more fold less fluorescent compared to a control sample (e.g., cell) that does not comprise the split system. In some instances, the levels of fluorescence of the inactive split system (e.g., background level) may be 0.01, 0.05, 0.1, 0.5, 1, 1.5, 2, 2.5, 3, 3.5 or more fold more fluorescent than a control sample (e.g., cell) that does not comprise the split system.

After the genetic mobility event, the two split pieces can unite to form an active fluorescent protein, and fluorescence can be detected in the sample. An active split system can result in at least about a 0.1, 0.5, 1, 2, 3, 4, 5, 6, 7, 8, 9, 10 or more fold increase in fluorescence. An active split system can result in at most about a 0.1, 0.5, 1, 2, 3, 4, 5, 6, 7, 8, 9, 10 or more fold increase in fluorescence.

Detection of a genetic mobility can be used to genotype a subject (e.g., a patient). A genotype can be indicative of a disease. The detection of a genetic mobility event can be used to diagnose a subject. The genetic and diagnostic information obtained from the methods described herein can be communicated to a subject. The genetic and diagnostic information obtained from the methods described herein can be used to develop a subject-specific treatment plan. For example, if the data obtained from the methods of the disclosure indicate that a patient has a genotype that makes them resistant to a particular therapeutic regimen, a new treatment plan can be made for the subject.

Altering Transcription

The methods of the disclosure can provide for altering the transcription of a nucleic acid. The method can be performed using any of the Argonaute proteins, designed nucleic acid-targeting nucleic acids, and complexes of Argonaute proteins and designed nucleic acid-targeting nucleic acids as described herein. The methods provide for contacting the target nucleic acid with two complexes, each complex comprising the Argonaute protein and the designed nucleic acid-targeting nucleic acid, and introducing two or more effector proteins, wherein the two or more effector proteins can bind to the designed nucleic acid-targeting nucleic acids,wherein the one of the two or more effector proteins comprises a non-native sequence that is a first piece of a split transcripition factor system and one of the two or more effector proteins comprises a non-native sequence that is a second piece of the split transcription factor system, and wherein an interaction between the first piece and the second piece of the split transcription factor system forms a transcription factor that alters transcription of the nucleic acid.

The transcription factor can alter transcription levels of a nucleic acid and/or a target nucleic acid. Altered transcription can include increased transcription levels and/or decreased transcription levels. A transcription factor can alter transcription levels more than 2-fold, 3-fold, 5-fold, 10-fold, 50-fold, 100-fold, 1000-fold or more higher or lower than unaltered transcription levels. A transcription factor can alter transcription levels less than 2-fold, 3-fold, 5-fold, 10-fold, 50-fold, 100-fold, 1000-fold or more higher or lower than unaltered transcription levels.

The transcription factor can alter the transcription of the target nucleic acid and/or an exogenous nucleic acid. The target nucleic acid can be the nucleic acid that is contacted by the complex comprising the Argonaute protein and the designed nucleic acid-targeting nucleic acid. An exogenous nucleic acid can comprise a donor polynucleotide, a plasmid, and/or the target nucleic acid.

An exogenous nucleic acid can comprise a polynucleotide encoding genes involved in apoptosis. Suitable genes involved in apoptosis can include tumor necrosis factor (TNF), TNF-R1, TNF-R2, TNF receptor-associated death domain (TRADD), Fas receptor and Fas ligand, caspases (e.g., caspase-3, caspase-8, caspase-10), APAF-1, FADD, and apoptosis inducing factor (AIF). An exogenous nucleic acid can comprise a polynucleotide encoding genes that result in cell lysis. Suitable genes can include the Adenovirus death protein (ADP), defensins, membrane-permeabilizing lytic peptides derived from c-FLIP, procaspases, cell-penetrating peptides e.g. HIV TAT. An exogenous nucleic acid can comprise a polynucleotide encoding an antigen that can result in recruitment of immune cells to the cell location (e.g., MHC class peptides). An exogenous nucleic acid can comprise a polynucleotide encoding a nucleic-acid targeting nucleic acid that targets sequences that occur many times within the genome (e.g., microsatellites, tandem repeats), resulting in large scale genome fragmentation and cell-death.

Modification of Target Nucleic Acid

The disclosure provides for methods to modify a target nucleic acid using the designed nucleic acid-targeting nucleic acid of the disclosure. The method can be performed using any of the Argonaute proteins, designed nucleic acid-targeting nucleic acids, and complexes of Argonaute proteins and designed nucleic acid-targeting nucleic acids as described herein. For example, a target nucleic acid can be contacted with a complex comprising the Argonaute protein, a tagged designed nucleic acid-targeting nucleic acid, and one or more effector proteins, wherein the one or more effector proteins comprises a non-native sequence and can bind to the tag of the tagged designed nucleic acid-targeting nucleic acid. For example, a tagged designed nucleic acid-targeting nucleic acid can comprise a zinc finger binding site, which can be bound by a zinc finger protein, wherein the zinc finger protein is fused to a non-native sequence such as a transcription factor. The non-native sequence of the effector protein can confer an enzymatic activity and/or transcriptional activity of the effector protein can modify the target nucleic acid. For example, if the effector protein comprises a non-native sequence corresponding to a methyltransferase, then the methyltransferase may be able to methylate the target nucleic acid. The modification of the target nucleic acid may occur at least 1, 2, 3, 4, 5, 6, 7, 8, 9, 10, 20, 30, 40, 50, 60, 70, 80, 90, 100 or more nucleotides away from the either the 5' or 3' end of the target nucleic acid. The modification of the target nucleic acid may occur at most 1, 2, 3, 4, 5, 6, 7, 8, 9, 10, 20, 30, 40, 50, 60, 70, 80, 90, 100 or more nucleotides away from the either the 5' or 3' end of the target nucleic acid. The modification can occur on a separate nucleic acid that does not comprise the target nucleic acid (e.g., another chromosome).

Exemplary modifications can comprise methylation, demethylation, acetylation, deacetylation, ubiquitination, deubiquitination, deamination, alkylation, depurination, oxidation, pyrimidine dimer formation, transposition, recombination, chain elongation, ligation, glycosylation.

Phosphorylation, dephosphorylation, adenylation, deadenylation, SUMOylation, deSUMOylation, ribosylation, deribosylation, myristoylation, remodelling, cleavage, oxidoreduction, hydrolation, and isomerization.

Determining a Genotype and Treatment

The disclosure provides for methods for treating a disease using the designed nucleic acid-targeting nucleic acid of the disclosure. The method can be performed using any of the Argonaute proteins, designed nucleic acid-targeting nucleic acids, and complexes of Argonaute proteins and designed nucleic acid-targeting nucleic acids as described herein. For example, using the split system described herein, the presence of two or more target nucleic acids close together in space (e.g., in a genetic mobility event, in chromatin structure, or on a linear nucleic acid) can be indicative of a genotype (e.g,. of a subject). A genotype can refer to the presence or absence of a particular sequence of nucleic acid, a nucleotide polymorphism (i.e., either a single nucleotide polymorphism, or a multi-nucleotide polymorphism), an allelic variant, or any other indication of the sequence of a nucleic acid. The genotype can indicate whether a patient suffers from a disease and/or is predisposed to contract a disease.

Determining a genotype can include, for example, determining if a subject comprises a mutant sequence (e.g., nucleic acid sequence comprising a mutation). In some instances, a first designed nucleic acid-targeting nucleic acid comprising the appropriate components as described herein to comprise a first part of a split system can be designed to target a region near a predicted mutant sequence. In some instances, a second designed nucleic acid-targeting nucleic acid comprising the appropriate components as described herein to comprise a second part of the split system can be designed to target a region comprising the predicted mutant sequence. If the mutant sequence does exist, the second designed nucleic acid-targeting nucleic acid can bind to it, and the two parts of the split system can interact. The interaction can generate a signal which can be indicative of the presence of a mutant sequence.

A genotype can be identified by a biomarker. A biomarker can be indicative of any physiological process. A biomarker can serve as a indicator of efficacy of a treatment (e.g., drug treatment). A biomarker can be a nucleic acid, a polypeptide, an analyte, a solute, a small molecule, an ion, an atom, a modification to a nucleic acid and/or polypeptide, and/or a degradation product. A biomarker can refer to relative expression levels of a nucleic acid and/or a polypeptide.

A subject-specific treatment plan may be identified from determining the genotype of the subject using the methods of the disclosure. For example, if a subject comprises a certain genotype known to be unresponsive to a particular therapy, then the subject can be treated with a different therapy. Determining of genotype can allow a subject to be selected or deselected for a clinical trial.

Determination of the genotype can be communicated from a caregiver to a subject (e.g., from a doctor to a patient, or from a person performing the genotype analysis to a customer). The communication can occur in person (e.g., in a doctor's office), over the phone, in writing, or electronically. The communication can further inform the subject of a subject-specific treatment regimen determined from the genotype of the subject.

The method can be performed more than once (e.g., iteratively) in a subject. For example, the genotype of a subject can be determined, a course of treatment can be prescribed for the subject, the genotype of the subject can be determined again. The two genotypes can be compared to determine the effectiveness of the course of treatment. The treatment plan can be altered based on the comparision of the genotypes.

Location of Sequences in Three-Dimensional Space

In some instances, the disclosure provide for a method for determining the location of sequences in three-dimensional space in a cell. The method can be performed using any of the Argonaute proteins, designed nucleic acid-targeting nucleic acids, and complexes of Argonaute proteins and designed nucleic acid-targeting nucleic acids as described herein. Determining the three-dimensional organization of chromatin and nucleic acid can be important for understanding gene regulation such as transcriptional activation and/or repression of genes. In some instances, the method comprises contacting a target nucleic acid with two complexes, wherein each complex binds to a cognate target nucleic acid. The complexes can comprise any Argonaute protein and designed nucleic acid-target nucleic acid of the disclosure. Two or more effector proteins can be introduced, wherein the each of the two or more effector proteins binds to a complex. The effector proteins can be similar to the split system described above, wherein each effector protein can comprise an inactive fragment of a whole polypeptide. When the effector proteins are far apart in space, the effector proteins are inactive (e.g., no signal is detected). When the effector proteins are close enough in space to interact, they can form a detectable active polypeptide.

The effector proteins can be part of a split affinity tag system. In a split affinity tag system, the two inactive polypeptide fragments of the system can correspond to two inactive fragments of an affinity tag. When the two fragments bind together, the whole affinity tag is restored, such that the affinity tag can be detectable by a binding agent. A binding agent can refer to a molecule that can bind and purify the affinity tag. Examples of binding agents can include antibodies, antibody-conjugated beads, and small-molecule conjugated beads.

Introduction of the complexes and polypeptides of the disclosure can occur by viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticlemediated nucleic acid delivery, and the like.

The cells can be cultured with the complexes for at least 1, 2, 3, 4, 5, 6, 7, 8, 9, 10 or more days. The cells can be cultured with the complexes for at most 1, 2, 3, 4, 5, 6, 7, 8, 9, 10 or more days. After an appropriate period of time (e.g,. a period of time to allow the complexes to bind to their target nucleic acid), the cells can be lysed.

The cells can be crosslinked before they are lysed. Fixed or cross-linking cells can stabilize protein-DNA complexes in the cell. Suitable fixatives and cross-linkers can include, formaldehyde, glutaraldehyde, ethanol-based fixatives, methanol-based fixatives, acetone, acetic acid, osmium tetraoxide, potassium dichromate, chromic acid, potassium permanganate, mercurials, picrates, formalin, paraformaldehyde, amine-reactive NHS-ester crosslinkers such as bis [sulfosuccinimidyl] suberate (BS3), 3,3'-dithiobis[sulfosuccinimidylpropionate] (DTSSP), ethylene glycol bis [sulfosuccinimidylsuccinate (sulfo-EGS), disuccinimidyl glutarate (DSG), dithiobis[succinimidyl propionate] (DSP), disuccinimidyl suberate (DSS), ethylene glycol bis[succinimidylsuccinate] (EGS), NHS-ester/diazirine crosslinkers such as NHS-diazirine, NHS-LC-diazirine, NHS-SS-diazirine, sulfo-NHS-diazirine, sulfo-NHS-LC-diazirine, and sulfo-NHS-SS-diazirine.

Lysed cells can be contacted with a binding agent (e.g, an antibody) that is directed to bind to the affinity tag. The contacting can occur in a test-tube. The contacting can occur in a chromatographic setting (e.g., an affinity chromatograhy column). Contacting with the binding agent can occur for at least 1 minute, 5 minutes, 10 minutes, 15 minutes, 20 minutes, 25 minutes, 30 minutes, 1 hour, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 or more hours. Contacting with the binding agent can occur for at most 1 minute, 5 minutes, 10 minutes, 15 minutes, 20 minutes, 25 minutes, 30 minutes, 1 hour, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 or more hours. In some instances, contacting with a binding agent occurs prior to cell lysis.

The complexes can be purified with the binding agent. The purified complexes can be subjected to nucleic acid purification techniques to separate the target nucleic acid from the complexes. Nucleic acid purification techniques can include spin column separation, precipitation, and electrophoresis.

The target nucleic acid (e.g., nucleic acid comprising the target nucleic acid) can be subjected to sequencing methodologies. The target nucleic acid can be prepared for sequencing analysis by ligation of one or more adaptors. Sequenced nucleic acids can be analyzed to identify polymorphisms, diagnose a disease, determine a course of treatment for a disease, and/or determine the three-dimensional structure of the genome.

Stoichiometric Delivery of Nucleic Acids

General Overview

Figure 12:
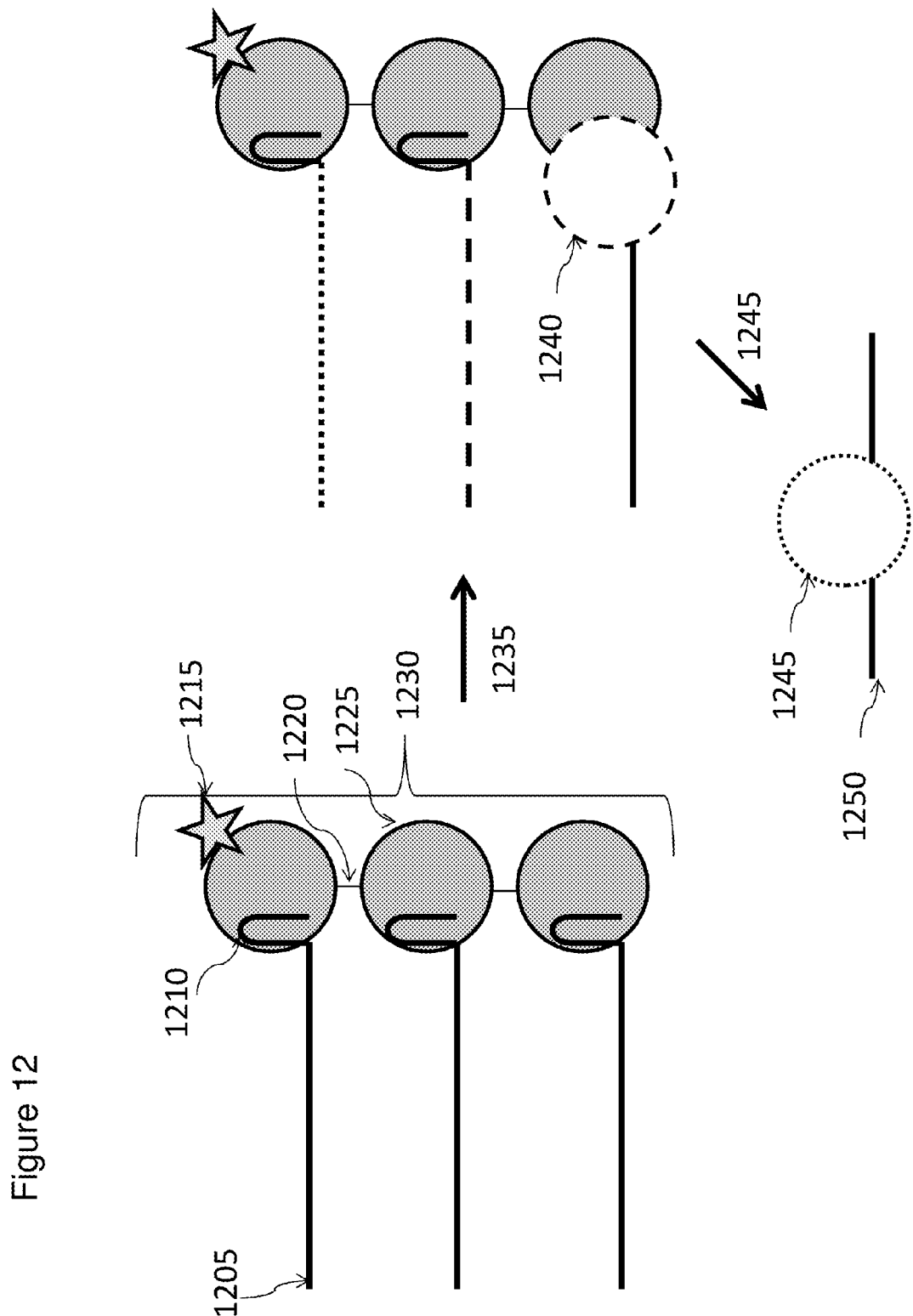
FIG. 12 depicts an exemplary embodiment of a method of the disclosure for stoichiometric delivery of designed nucleic acid-targeting nucleic acids.

The disclosure provides for compositions, methods, and kits for stoichiometric delivery of a nucleic acid to a cell and/or subcellular localization. The stoichiometric delivery may be mediated by a complex. FIG. 12 depicts an exemplary complex for stoichiometric delivery of a plurality of nucleic acids to a cell and/or subcellular location. The complex can comprise a plurality of nucleic acids 1205. Each nucleic acid can comprise a nucleic acid-binding protein binding site 1210. The nucleic acid-binding protein binding sites 1210 can all be the same sequences, different sequences, or some can be same sequences and some can be different sequences. In some embodiments, the nucleic acid-binding protein binding sites can bind a DNA-binding protein. The complex can comprise a tandem fusion polypeptide 1230. The tandem fusion polypeptide can comprise DNA-binding proteins 1225 fused together in tandem. The nucleic acid-binding proteins can be separated by a linker 1220. The nucleic acid-binding proteins 1225 can be the same protein, can be different proteins, or some can be the same proteins and some can be different proteins. The nucleic acid-binding proteins 1225 can bind the nucleic acid-binding protein binding site 1210 on the nucleic acid 1205. The tandem fusion polypeptide 1230 can comprise a non-native sequence 1215. In some instances, the non-native sequence is a subcellular (e.g., nuclear) localization sequence. In some embodiments, the nucleic acid 1205 can encode a non-native sequence (e.g. a subcellular, (e.g., nuclear) localization sequence). The complex can be introduced 1235 into cells, wherein one or more of the nucleic acids 1205 can be translated into polypeptides 1240. A translated polypeptide 1240 can bind and cleave the nucleic acid-binding protein binding site 1210 on the nucleic acid 1205. The cleavage 1245 can liberate the nucleic acid 1250 which can be a designed nucleic acid-targeting nucleic acid. The liberated nucleic acid 1250 can bind to a translated polypeptide 1245 (e.g., an Argonaute polypeptide), thereby forming a unit. The translated polypeptide 1245 can comprise a nuclear localization signal. The unit can translocate to the nucleus, wherein the unit can be guided to a target nucleic acid hybridizable with the spacer of the liberated nucleic acid 1250. The unit can be hybridized to a target nucleic acid. The Argonaute of the unit can cleave the target nucleic acid. The cleavage of the target nucleic acid can be referred to as genome engineering. The method can be performed using any of the Argonautes polypeptides, designed nucleic acid-targeting nucleic acids, and complexes of Argonautes polypeptides and designed nucleic acid-targeting nucleic acids as described herein.

Methods

The disclosure provides for methods for stoichiometric delivery of nucleic acids to a cell (e.g., stoichiometrically deliverable nucleic acids). The method can comprise binding a tandem fusion polypeptide to a plurality of stoichiometrically deliverable nucleic acids, thereby forming a complex. The complex can comprise stoichiometric amounts of the nucleic acids (e.g., the complex can comprise the plurality of nucleic acids in a prescribed ratio and/or amount). 1, 2, 3, 4, 5, 6, 7, 8, 9, 10 or more nucleic acids can be stoichiometrically delivered. In some instances, 3 stoichiometrically deliverable nucleic acids can be stoichiometrically delivered. In some instances, 4 stoichiometrically deliverable nucleic acids can be stoichiometrically delivered.

The stoichiometrically deliverable nucleic acid can encode for a polypeptide or a non-coding DNA. The polypeptide may be an Argonaute polypeptide. The polypeptide may be a nuclease. The stoichiometrically deliverable nucleic acid can encode for more than one polypeptide. The stoichiometrically deliverable nucleic acid can comprise a plurality of stoichiometrically deliverable nucleic acids (e.g., in an array). The stoichiometrically deliverable nucleic acid can encode for a non-coding DNA (e.g., a designed nucleic acid-targeting nucleic acid), and/or a coding DNA (e.g., coding for a gene). A stoichiometrically deliverable nucleic acid can encode a donor polynucleotide.

The stoichiometrically deliverable nucleic acid can encode for a non-native sequence. In some instances, the stoichiometrically deliverable nucleic acid encodes for a non-native sequence such that when a polypeptide is translated from a stoichiometrically deliverable nucleic acid encoding a polypeptide, the polypeptide is fused to the non-native sequence (e.g., thereby generating a fusion protein). The non-native sequence can be a peptide affinity tag. The non-native sequence (e.g., peptide affinity tag) can be located at the N-terminus of the polypeptide, the C-terminus of the polypeptide, or any location within the polypeptide (e.g., a surface accessible loop). In some embodiments, the non-native sequence is a nuclear localization signal (NLS). A NLS can be monopartite or bipartite sequence. The NLS can be recognised by nuclear import machinery (e.g., importins). A NLS can be a small peptide (e.g., PKKKRKV (SEQ ID NO: 30) of the SV40 large t-antigen). A NLS can be a polypeptide domain (e.g., acidic M9 domain of hnRNP A1).

The non-native sequence can be a nucleic acid affinity tag (e.g., nucleic acid localization signal). For example, a stoichiometrically deliverable nucleic acid encoding a DNA. (e.g., a donor polynucleotide) can comprise a nucleic acid localization signal which can localize the DNA to the nucleus. Such nucleic acid localization signals can include, tor example, peplide-nucleic acid (PNA) sequences.

The stoichiometrically deliverable nucleic acids can comprise regulatory sequences that can allow for appropriate translation or amplification of the nucleic acid. For example, an nucleic acid can comprise a promoter, a TATA box, an enhancer element a transcription termination element, a DNA liability element, a ribosome-binding site, a 3' un-translated region, a 5' un-translated region, a 5' cap sequence, a 3' poly adenylation sequence, an RNA stability clement, and the like.

The nucleic acid can comprise a nucleic acid-binding protein binding site. The nucleic acid-binding protein binding site can be bound by an nucleic acid-binding protein. The nucleic acid-binding protein binding site can be bound by a DNA polypeptide (e.g., a nuclease). Some examples of nucleic acid-binding protein binding sites can include, for example, sequences that can be bound by DNA-binding proteins such as zinc fingers, a helix-turn-helix domain, a zinc finger domain, a leucine zipper (bZIP) domain, a winged helix domain, a winged helix turn helix domain, a helix-loop-helix domain, a HMG-box domain, a Wor3 domain, an immunoglobulin domain, a B3 domain, a TALE domain, and the like. Some examples of nucleic acid-binding protein binding sites can include, for example, sequences that can be bound by RNA-binding proteins such as the MS2 binding sequence, the U1A binding sequence, the boxB sequence, the eIF4A sequence, hairpins, sequences that can be bound by RNA recognition motif (RRM) domains (e.g., U1A), sequences that can be bound by double stranded RNA binding domains (dsRBD) (e.g., Staufen), sequences that can be bound PAZ domains, sequences that can be bound by PIWI domains, and the like.

The nucleic acid can comprise one or more nucleic acid-binding protein binding sites. The nucleic acid can comprise 1, 2, 3, 4, 5, 6, 7, 8, 9, 10 or more nucleic acid-binding protein binding sites. The one or more nucleic acid-binding protein binding sites may be the same. The one or more nucleic acid-binding protein binding sites may be different. For example, the nucleic acid can comprise a Zinc finger binding site and a transcription factor binding site. In some instances, the nucleic acid can comprise a RNA-binding protein binding site (e.g., MS2, Csy4). The one or more nucleic acid-binding protein binding sites can be separated by 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 450, 500 or more nucleotides. In some embodiments, the 3'-most nucleic acid-binding protein binding site can be bound by a tandem fusion polypeptide of the disclosure.

Tandem Fusion Polypeptide

In some embodiments, the method of the disclosure provides for binding a plurality of nucleic acids to a tandem fusion polypeptide. A tandem fusion polypeptide can comprise a plurality of nucleic acid binding proteins fused together in one polypeptide chain. A tandem fusion polypeptide can comprise 1, 2, 3, 4, 5, 6, 7, 8, 9, 10 or more nucleic acid-binding proteins. Nucleic acid-binding proteins of the tandem fusion polypeptide can bind to the nucleic acid-binding protein binding sites of the nucleic acids of the disclosure. In some embodiments, the nucleic acid-binding protein is a DNA-binding protein (e.g., a zinc finger, TALEN). In some instances, the nucleic acid can comprise a RNA-binding protein binding site (e.g., MS2, Csy4). In some instances, the nucleic acid-binding proteins are separated by a linker. A linker can comprise about 1, 2, 3, 4, 5, 6, 7, 8, 9, 10, 20, 30, 40, 50, 60, 70, 80, 90, 100 or more amino acids.

A tandem fusion polypeptide can comprise a non-native sequence (e.g., peptide affinity tag). The non-native sequence can comprise a nuclear localization signal (NLS) that can direct the tandem fusion polypeptide to a subcellular location (e.g., nucleus).

Each nucleic acid-binding protein of the tandem fusion polypeptide can comprise its own non-native sequence. The non-native sequence of each nucleic acid-binding protein can be the same. The non-native sequence of each nucleic acid-binding protein can be different. The non-native sequence of some of the nucleic acid-binding proteins of the tandem fusion polypeptide can be the same and the non-native sequence of some of the nucleic acid-binding proteins of the tandem fusion polypeptide can be different.

In some instances, the methods of the disclosure can provide for forming a complex comprising a tandem fusion polypeptide and a plurality of nucleic acids of the disclosure. Formation of the complex can comprise the nucleic acid-binding proteins of the tandem fusion polypeptide binding to their cognate nucleic acid-binding protein binding sequence in the nucleic acids of the disclosure. For example, a stoichiometrically deliverable nucleic acid comprising a TALEN binding site, can bind to the TALEN protein subunit in the tandem fusion protein. The complex can be formed outside of cells (e.g., in vitro). The complex can be formed in cells (e.g., in vivo). When a complex is formed in vitro it can be introduced into a cell by, for example, transfection, transformation, viral transduction, electroporation, injection, and the like.

The methods of the disclosure provide for therapeutic delivery of multiple nucleic acids both in vivo, in vitro, and ex vivo. The delivered nucleic acids can be used to treat a disease. For example, the delivered nucleic acids can be used in gene therapy and/or can integrate into the genome of the cell, thereby providing a therapeutic outcome. A therapeutic outcome can refer to increase or decrease in the levels of a protein, nucleic acid, or any biological molecule related to a disease such as a degradation product, small molecule, and/or ion. For example, a therapeutic outcome can comprise increasing the levels of an anti-inflammatory gene, or decreasing the levels of a protein in a pathway related to a disease. A therapeutic outcome can refer to a physiological effect. Physiological effects can include, morphological changes, metabolic changes, and/or structural changes in a cell. A therapeutic outcome can refer to changes in the modifications of a protein and/or nucleic acid, such as glycosylation, acetylation, methylation, demethylation, depurination, ubiquitinylation, and the like.

A therapeutic outcome can be measured by changes in the genetic makeup of the cell, the levels of bio-molecules of interest in the cell, and/or the physiological changes in the cell. Measurements can be made using molecular biology techniques such as spectroscopy, spectrometry sequencing. ELISA, microscopy, and/or x-ray crystallograhpy. Measurements can be made using animal models, such as mouse, rats, dogs, and primates. For example, genetically modified cells of the disclosure can be introduced into mice and assessed for biological and physiological changes such ast for example, the ability to metastasize and/or differentiate.

Multiplexed Genetic Targeting Agents

General Overview

This disclosure describes methods, compositions, systems, and/or kits for muliplexed genome engineering. In some embodiments of the disclosure a site-directed polypeptide can comprise a nucleic acid-targeting nucleic acid, thereby forming a complex. The complex can be contacted with a target nucleic acid. The target nucleic acid can be cleaved, and/or modified by the complex. The methods, compositions, systems, and/or kits of the disclosure can be useful in modifying multiple target nucleic acids quickly, efficiently, and/or simultaneously. The method can be performed using any of the site-directed polypeptides, nucleic acid-targeting nucleic acids, and complexes of site-directed polypeptides and nucleic acid-targeting nucleic acids as described herein.

Figure 13:
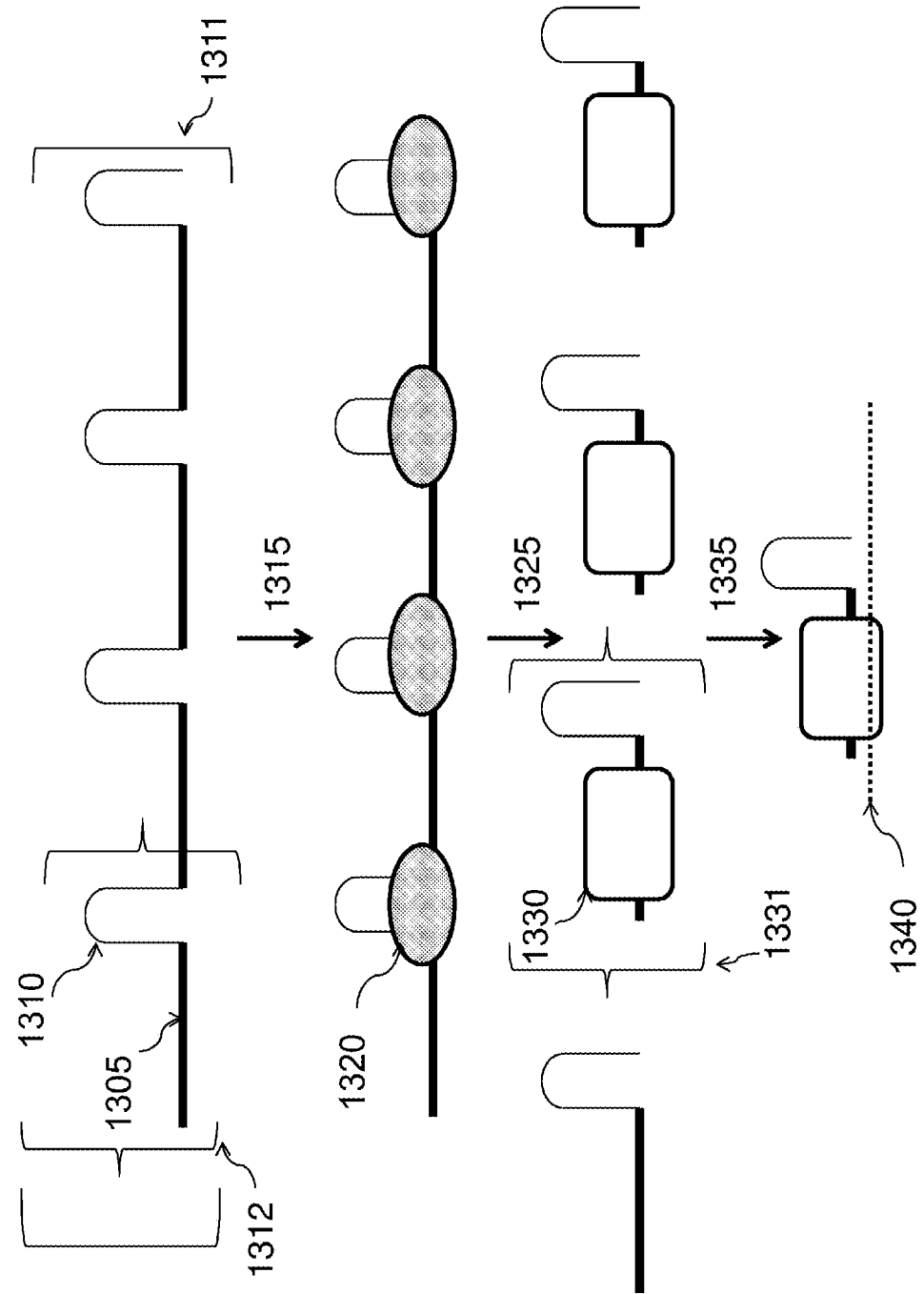
FIG. 13 depicts an exemplary embodiment of a method of multiplexed target nucleic acid cleavage.

FIG. 13 depicts an exemplary embodiment of the methods of the disclosure. A nucleic acid (e.g., a designed nucleic acid-targeting nucleic acid) 1305 can be fused to a non-native sequence (e.g., a moiety, an nuclease binding sequence, a DNA-protein binding sequence) 1310. thereby forming a nucleic acid module 1312. The nucleic acid module 1312 (e.g., comprising the nucleic acid fused to a non-native sequence) can be conjugated in tandem, thereby forming a multiplexed genetic targeting agent (e.g., poly-module, e.g., array) 1311. The multiplexed genetic targeting agent 1311 can comprise DNA, The multiplexed genetic targeting agent can be contacted 1315 with one or more nucleases 1320. The nucleases can bind to the non-native sequence 1310. The bound nuclease can cleave a nucleic acid module 1.312 of the multiplexed genetic targeting agent 1311 at a prescribed location defined by the non-native sequence 1310. The cleavage 1325 can process (e.g., liberate) individual nucleic acid modules 1312. In some embodiments, the processed nucleic acid modules 1312 can comprise all. some, or none, of the non-native sequence 1310. The processed nucleic acid modules 1312 can be bound by an Argonaute polypeptide 1330, thereby forming a complex 1331. The complex 1331 can be targeted 1335 to a target nucleic acid 1340, The target nucleic acid 1340 can by cleaved and/or modified by the complex 1331.

Multiplexed Genetic Targeting Agents

A multiplexed genetic targeting agent can be used in modifying multiple target nucleic acids at the same time, and/or in stoichiometric amounts. A multiplexed genetic targeting agent can be any nucleic acid-targeting nucleic acid as described herein in tandem. A multiplexed genetic targeting agent can refer to a continous nucleic acid molecule comprising one or more nucleic acid modules. A nucleic acid module can comprise a nucleic acid and a non-native sequence (e.g., a moiety, nuclease binding sequence, a DNA-binding sequence). The nucleic acid can be non-coding DNA or a coding DNA. The nucleic acid can comprise a gene, a transcriptional modulator element (terminator, promoter, IRES, ribosome binding site, enhancer). In some embodiments, the nucleic acid can be a designed nucleic acid-targeting nucleic acid.

The non-native sequence can be located at the 3' end of the nucleic acid module. The non-native sequence can be located at the 5' end of the nucleic acid module. The non-native sequence can be located at both the 3' end and the 5' end of the nucleic acid module. The non-native sequence can comprise a sequence that can bind to a nuclease (e.g., nuclease binding sequence). The non-native sequence can be a sequence that is sequence-specifically recognized by an nuclease (e.g., the non-native sequence can comprise GAATTC, which can be recognized by an EcoRI restriction nuclease). The non-native sequence can be a sequence that is structurally recognized by an nuclease (e.g., hairpin structure, single-stranded-double stranded junctions).

In some embodiments, wherein the non-native sequence comprises an nuclease binding sequence, the nucleic acid modules can be bound by the same nuclease. The nucleic acid modules may not comprise the same nuclease binding sequence. The nucleic acid modules may comprise different nuclease binding sequences. The different nuclease binding sequences can be bound by the same nuclease. In some embodiments, the nucleic acid modules can be bound by different nucleases.

The nucleic acids of the nucleic acid modules of the multiplexed genetic targeting agent can be identical. The nucleic acid modules can differ by 1, 2, 3, 4, 5, 6, 7, 8, 9, 10, 15, 20, 25, 30, 35, 40, 45, 50 or more nucleotides. For example, different nucleic acid modules can differ in the region of the nucleic acid module that hybridizes to the target nucleic acid, thereby targeting the nucleic acid module to a different target nucleic acid. In some instances, different nucleic acid modules can differ in the spacer region of the nucleic acid module, yet still target the same target nucleic acid. The nucleic acid modules can target the same target nucleic acid. The nucleic acid modules can target one or more target nucleic acids.

A nucleic acid module can comprise a regulatory sequence that can allow for appropriate translation or amplification of the nucleic acid module. For example, an nucleic acid module can comprise a promoter, a TATA box, an enhancer element, a transcription termination element, a ribosome-binding site, a 3' un-translated region, a 5' un-translated region, a 5' cap sequence, a 3' poly adenylation sequence, an RNA stability element, and the like.

Methods

The disclosure provides for methods for the modification of multiple target nucleic acids, simulataneously, through the use of a multiplexed genetic targeting agent. An Argonaute, an nuclease, and a multiplexed genetic targeting agent can be introduced into a host cell. A vector of the disclosure (e.g., comprising a multiplexed genetic targeting agent, an nuclease and/or an Argonaute polypeptide) can be introduced into a host cell. In some instances, more than one nuclease and/or multiplexed genetic targeting agent can be introduced into cells. If a multiplexed genetic targeting agent comprises different types of non-native sequences, where the non-native sequences are different nuclease binding sequences, then one or more nucleases corresponding to the types of binding sequences in the multiplexed genetic targeting agent may be introduced into cells.

Introduction can occur by any means to introduce a nucleic acid into a cell such viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. The vector can be transiently expressed in the host cell. The vector can be stably expressed in the host cell (e.g., by stably integrating into the genome of the host cell).

In instances where a non-native sequence comprises an nuclease binding sequence, an nuclease can be expressed and can bind to the nuclease binding site on the multiplexed genetic targeting agent. The nuclease can cleave the multiplexed genetic targeting agent into individual nucleic acid modules.

In instances where a moiety comprises a a catalytic DNA (e.g., self-cleaving DNA), an nuclease may not be required to be expressed in a host cell. The catalytic DNA can cleave itself, thereby resulting in cleavage of the multiplexed genetic targeting agent into individual nucleic acid modules.

Individual (e.g., cleaved) nucleic acid modules can comprise all, some, or none, of the moiety (e.g., nuclease binding sequence). For example, the liberated (e.g., processed) nucleic acid module can be subjected to exonuclease trimming and/or degradation that may result in removal of the 5' and/or 3' end of the nucleic acid module. In such instances, exonuclease trimming and/or degradation may result in the removal of all, part, or none of the non-native sequence (e.g., nuclease binding sequence, catalytic DNA sequence).

The liberated (e.g., processed) nucleic acid module can bind to an Argonaute thereby forming a complex. The complex can be guided to a target nucleic acid by the nucleic acid-targeting nucleic acid which can hybridize with the target nucleic acid in a sequence-specific manner. Once hybridized, the Argonaute of the complex can modify the target nucleic acid (e.g., cleave the target nucleic acid). In some instances, the modification comprises introduction of a double-stranded break in the target nucleic acid. In some instances, the modification comprises introduction of a single-stranded break in the target nucleic acid.

In some embodiments, one or more donor polynucleotides and/or vectors encoding the same can introduced into the cell. One or more donor polynucleotides can be incorporated into the modified (e.g., cleaved) target nucleic acids, thereby resulting in an insertion. The same donor polynucleotide can be incorporated into multiple cleavage sites of target nucleic acids. One or more donor polynucleotides can be incorporated into one or more cleavage sites of target nucleic acids. This can be referred to as multiplex genome engineering. In some instances, no donor polynucleotide and/or vector encoding the same may be introduced into the cells. In these instances, the modified target nucleic acid can comprise a deletion.

Seamless Reporter Selection
General Overview

This disclosure describes methods, compositions, systems and kits for genetic modification of cells and selection of such genetically modified cells by seamless incorporation, detection and excision of a reporter element. In some embodiments of the disclosure, a donor polynucleotide can comprise a nucleic acid to be introduced to a cell genome (here called the genetic element of interest) as well as a nucleic acid sequence encoding a reporter element (e.g. GFP), an Argonaute protein, and two designed nucleic acid-targeting nucleic acids. The donor polynucleotide may comprise one or more designed nucleic acid-targeting nucleic acids. Either the Argonaute protein and/or the designed nucleic acid-targeting nucleic acids, may be controlled by an inducible promoter. The Argonaute protein and the designed nucleic acid-targeting nucleic acid may form a complex which can target a site in the cell genome by hybridization of the designed nucleic acid-targeting nucleic acid to a target nucleic acid in the genome. The Argonaute protein of the complex may cleave the target nucleic acid. The donor polynucleotide can be inserted into the cleaved target nucleic acid. The donor polynucleotide may comprise cleavage sites for the Argonaute protein. After introduction of a double strand break (or single strand break) at the target nucleic acid in the presence of the donor polynucleotide, the population of recipient cells may be screened for the presence of the reporter molecule as a proxy for the presence of the genetic element of interest. After isolation of reporter molecule-containing cells, the reporter element can be excised by induction of Argonaute. The method can he performed using any of the Argonaute proteins, designed nucleic acid-targeting nucleic acids, and complexes of Argonaute proteins and designed nucleic acid-targeting nucleic acids as described herein.

Figure 14:
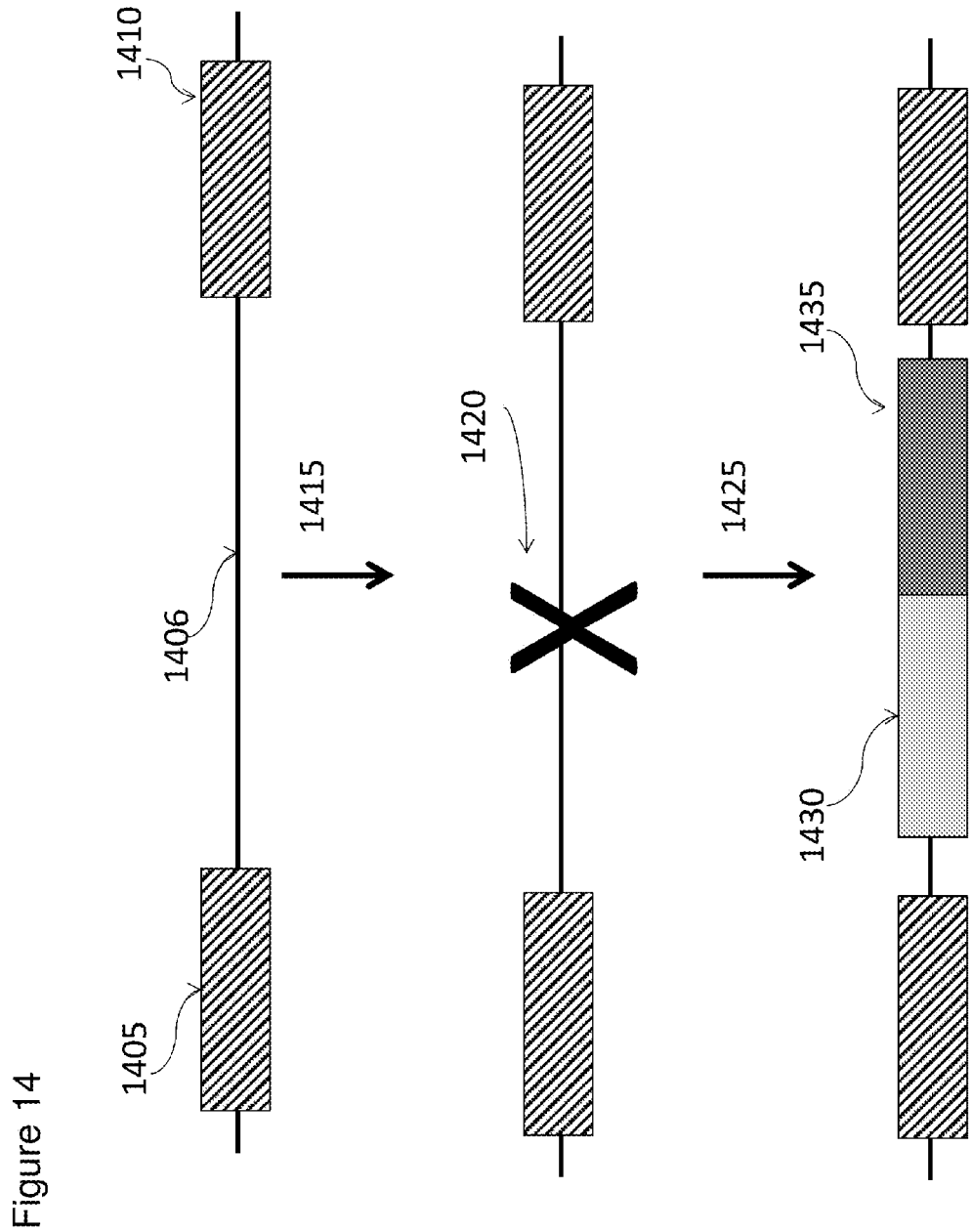
FIG. 14 depicts an exemplary embodiment of seamless insertion of a reporter element into a target nucleic acid using an Argonaute of the disclosure.

FIG. 14 depicts an exemplary embodiment of the methods of the disclosure. A nucleic acid can comprise a plurality of genetic elements 1405/1410. The genetic elements 1405 and 1410 can be, for example, genes, non-coding nucleic acids, introns, exons, DNA and/or UNA. The genetic elements 1405 and 1410 can be parts of the same gene. In between the genetic elements can be a target nucleic acid 1406 suitable for genetic engineering. An Argonaute protein and a designed nucleic acid-targeting nucleic acid of the disclosure can form a complex which can target 1415 the target nucleic acid 1406. One or more Argonaute proteins of one or more complexes can cleave 1420 the target nucleic acid 1406. A donor polynucleotide can be inserted 1425 into the cleaved target nucleic acid 1406. The donor polynucleotide can comprise a genetic element of interest 1430. The genetic element of interest 1430 can be a gene. The donor polynucleotide can also comprise a reporter element 1435. Insertion of the donor polynucleotide into the target nucleic acid 1406 can result in the expression of the reporter element 1435. The reporter element 1435 can be used as a way to select ceils that comprise the donor polynucleotide.

Figure 15:
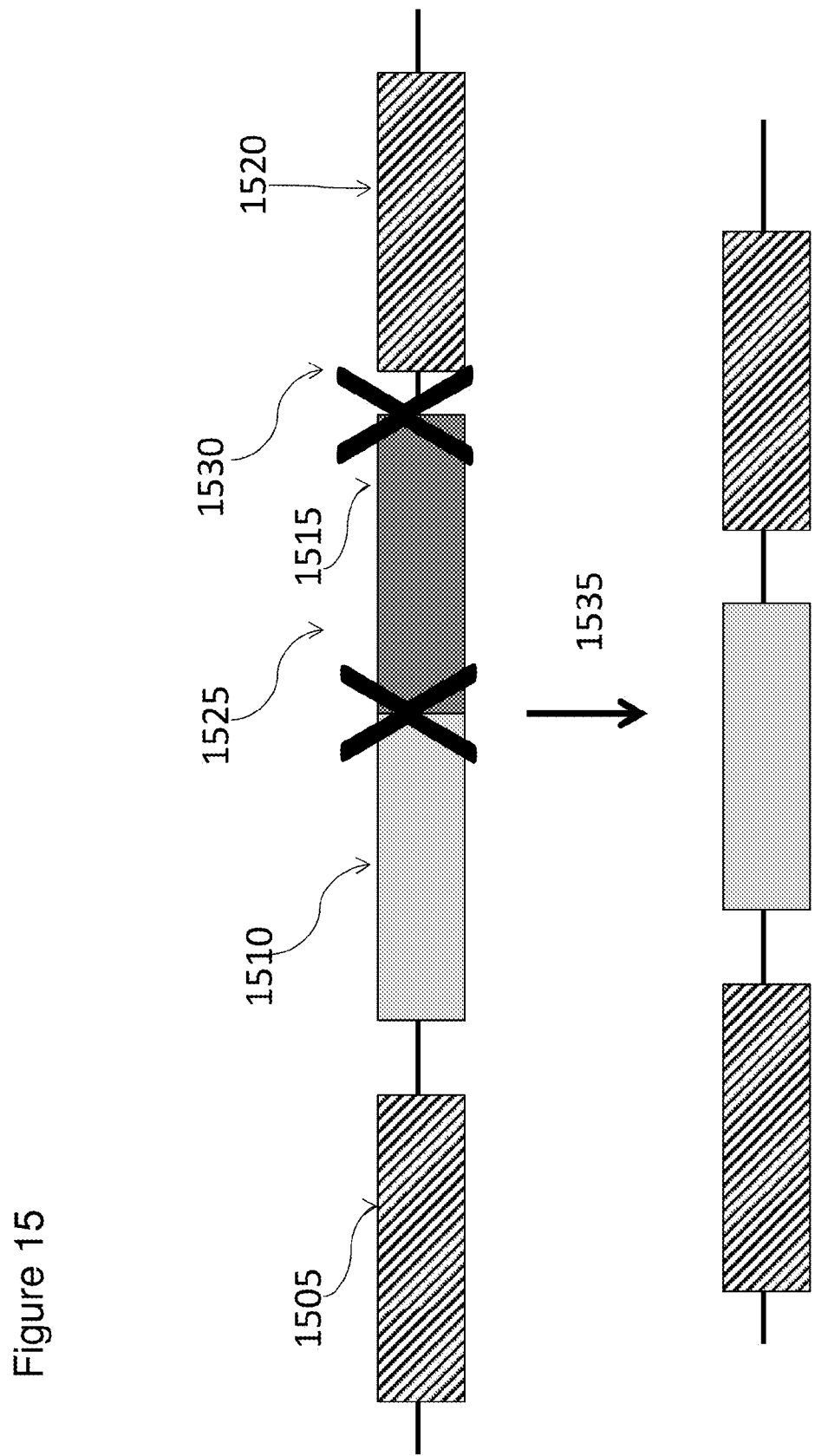
FIG. 15 depicts an exemplary embodiment for removing a reporter element from a target nucleic acid.

FIG. 15 depicts an exemplary embodiment for the removal of the reporter element 1515 from the target nucleic acid. A target nucleic acid can comprise a plurality of genetic elements 1505/1520. The reporter element 1515 can be fused to a genetic element of interest 1510. Expression, of the reporter gene 1515 can be induced which can result in the production of an Arganaute and one or more designed nucleic acid-targeting nucleic acids. The Argonaute protein can be operably linked to an inducible promoter. The Argonaute protein can bind sites near and/or in the reporter element. The Argonaute protein may bind a designed nucleic acid-targeting nucleic acid that can target 1525 the 5' end of the reporter element 1515 and 1530 the 3' end of the reporter element 1515. The targeted endsof the reporter element 1515 can be cleaved by one or more Argonaute proteins, thereby excising 1535 the reporter element 1515. The resulting target nucleic acid can comprise the genetic element of interest 1510 portion of the donor polynucleotide. The donor polynucleotide can be designed such that the donor polynucleotide is excised (including the genetic element of interest).

Methods

The present disclosure provides for methods of selecting cells using a reporter element and excision of the reporter element. An Argonaute, a designed nucleic acid targeting nucleic acid, and/or a donor polynucleotide can be introduced into a cell. The donor polynucleotide may include one or more genetic elements of interest. The donor polynucleotide may include one or more reporter elements. The donor polynucleotide includes one or more genetic elements of interest and one or more reporter elements. More than one Argonaute protein, donor polynucleotide and and/or designed nucleic acid-targeting nucleic acid can be introduced into a cell. In some instances, the cell already expresses an Argonaute protein, and/or a designed nucleic acid-targeting nucleic acid. In some instances, the Argonaute protein, and/or designed nucleic acid-targeting nucleic acid are encoded on a plasmid. In some instances, the Argonaute protein, and/or designed nucleic acid-targeting nucleic acid is encoded on more than one plasmid. In some instances, more than one Argonaute protein or designed nucleic acid encoding an Argonaute is introduced into the cell. In some instances, the cell is a cell lysate.

Introduction can occur by any means to introduce a nucleic acid into a cell such as viral or bacteriophage infection, transfection, conjugation, protoplast fusion, lipofection, electroporation, calcium phosphate transfection, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. The vector can be transiently expressed in the host cell. The vector can be stably expressed in the host cell (e.g., by stably integrating into the genome of the host cell).

A designed nucleic acid-targeting nucleic acid can bind to a target nucleic acid characterized by a particular target sequence and/or any sequence homologous to a particular sequence. The target sequence can be part or all of a gene, a 5' end of a gene, a 3' end of a gene, a regulatory element (e.g. promoter, enhancer), a pseudogene, non-coding DNA, a microsatellite, an intron, an exon, chromosomal DNA, mitrochondrial DNA, sense DNA, antisense DNA, nucleoid DNA, chloroplast DNA or RNA among other nucleic acid entities.

The Argonaute protein can cleave the target nucleic acid bound by a designed nucleic acid targeting nucleic acid. A donor polynucleotide can be incorporated in the target nucleic acid at the site where it was cleaved.

Excision

The methods disclosed herein may further comprise excision of all, some or none of the reporter element. A first designed nucleic acid-targeting nucleic acids of the reporter element can target the 5' end of the reporter element. A second designed nucleic acid-targeting nucleic acids of the reporter element can target the 3' end of the reporter element. A designed nucleic acid-targeting nucleic acid can target both the 5' and 3' ends of the reporter element. A designed nucleic acid-targeting nucleic acid can target two sequences in the reporter element and/or donor polynucleotide. The two target sequences can be at least about 70, 75, 80, 85, 90, 91, 92, 93, 94, 95, 96, 97, 98, 99 or 100% identical. The two target sequences can be at most about 70, 75, 80, 85, 90, 91, 92, 93, 94, 95, 96, 97, 98, 99 or 100% identical. When the designed nucleic acid-targeting nucleic acids of the reporter element are expressed, they may form a complex with the Argonaute protein and target the 5' and 3' ends of the reporter element by hybridizing to a complementary region on the 5' and 3' ends of the reporter element. Hybridization of the complex with the reporter element can result in cleavage of all, some or none of the reporter element. The cleaved nucleic acid can be rejoined by, for example, non-homologous end-joining. The rejoined nucleic acid may not introduce a deletion or insertion. The rejoined nucleic acid may introduce a deletion or insertion. The cleaved nucleic acid can be rejoined by, for example, homologous recombination. Homologous recombination can be used to rejoin a cleaved nucleic acid when the target nucleic acid sites are substantially identical.

Screening

Screening may be performed after introduction of the donor polynucleotide comprisng the reporter element and the genetic element of interest and/or after excising the reporter element from a selected cell. Screening may comprise screening for the absence of all or some of the reporter element. Screening can include fluorescence activate cell-sorting (FACS), wherein cells expressing a fluorescent protein encoded for by the reporter element are separated from cells that do not express a fluorescent protein. Cells may be contacted with fluorescent protein, fluorescent probe or fluorochrome conjugated antibodies that bind proteins encoded for by the reporter element or genetic element and subsequently selected by FACS. Fluorochromes can include but are not limited to Cascade Blue, Pacific Blue, Pacific Orange, Lucifer yellow, NBD, R-Phycoerythrin (PE), PE-Cy5 conjugates, PE-Cy7 conjugates, Red 613, PerCP, Tru-Red, FluorX, Fluorescein, BODIPY-FL, TRITC, Texas Red, Allophycocyanin, APC-Cy7 conjugates (PharRed), various Alexa Fluor dyes, Cy2, Cy3, Cy3B, Cy3.5, Cy5, Cy5.5, Cy7, various DyLights, Y66H, Y66F, EBFP, EBFP2, Azurite, GFPuv, T-Sapphire, TagBFP, Cerulean, mCFP, ECFP, CyPet, Y66W, dKeima-Red, mKeima-Red, TagCFP, AmCyan1, mTFP1, S65A, Midoriishi-Cyan, GFP, Turbo GFP, TagGFP, TagGFP2, AcGFP1, S65L, Emerald, S65T, S65C, EGFP, Azami-Green, ZaGreen1, Dronpa-Green, TagYFP, EYFP, Topaz, Venus, mCitirine, YPet, Turbo YFP, PhiYFP, PhiYFPm, ZaYellow1, mBanana, Kusabira-Orange, mOrange, mOrane2, mKO, TurboRFP, tdTomato, DsRed-Express2, TagRFP, DsRed monomer, DsRed2, mStrawberry, Turbo FP602, AsRed2, mRFP1, J-Red, mCherry, HcRedl, mKate2, Katushka, mKate, TurboFP635, mPlum, mRaspberry, mNeptune, E2-Crimson.

Cells may be contacted with antibodies that bind peptide affinity tags encoded for by the reporter element or genetic element and subsequently can be selected by immunomagnetic beads which recognize the antibodies. Screening may comprise staining cells by adding X-gal when the reporter element or genetic element encodes b-galactosidase. Screening may comprise manual sorting (e.g. diluting cell suspensions) and microscopy (e.g. fluorescence microscopy). Screening may comprise high-content screening.

Reporter elements may encode drug resistance genes, thereby allowing for selection of cells containing the reporter element by the addition of drugs, the drugs killing the cells that do not express the reporter element. Such drug can include, but are not limited to erythromycin, clindamycin, chloramphenicol, gentamicin, kanamycin, streptomycin, tetracycline, the combination quinupristin-dalfopristin, enrofloxacin, vancomycin, oxacillin, penicillin, sulfonamide sulfisoxazole, trimethoprim, methoinine sulphoximine, methotrexate, puromycine, blasticidin, histidinol, hygromycin, zeocin, bleomycin and neomycin.

Libraries

The present disclosure provides for a library of expression vectors comprising donor polynucleotides. In some embodiments, the library can comprise expression vectors comprising polynucleotide sequences encoding for differing genetic elements of interest but the same reporter elements. In some embodiments, the library can comprise expression vectors comprising polynucleotide sequences encoding for differing genetic elements of interest and differing reporter elements. Reporter elements may differ in their nucleic acid targeting sequences. Reporter elements may differ in their reporter genes (e.g. genes encoding fluorescent proteins). The present disclosure provides for methods of using the library to generate a plurality of genetically modified cells. The present disclosure provides for methods of using the library for a high throughput genetic screen. These libraries can allow for analyzing large numbers of individual genes to infer gene function. Libraries can comprise from about 10 individual members to about $10^{12}$ individual members; e.g. a library can comprise from about 10 individual members to about $10^2$ individual members, from about $10^2$ individual members to about $10^3$ individual members, from about $10^3$ individual members to about $10^5$ individual members, from about $10^5$ individual members to about $10^7$ individual members, from about 10$^7$ individual members to about 10$^9$ individual members, or from about 10$^9$ individual members to about 10$^{12}$ individual members.

Moding Cells (Transfection/Infection)

Methods for introducing a nucleic acid into a cell can include viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. In some embodiments, contacting the target nucleic acid or introducing into the cell (or a population of cells) one or more nucleic acids may not comprise viral infection. In some embodiments, contacting the target nucleic acid or introducing into the cell (or a population of cells) one or more nucleic acids may not comprise bacteriophage infection. In some embodiments, contacting the target nucleic acid or introducing into the cell (or a population of cells) one or more nucleic acids may not comprise transfection.

Methods for the Generation of Tagged Cell Lines Using a Designed Nucleic Acid-Targeting Nucleic Acid The methods of the disclosure provide for tagging a cell with a donor polynucleotide, wherein the donor polynucleotide can divide and/or differentiate, and the donor polynucleotide can be transmitted to each daughter cell during cell division. The method can be performed using any of the Argonautes, designed nucleic acid-targeting nucleic acids, and complexes of Argonaute proteins and designed nucleic acid-targeting nucleic acids as described herein.

A tagged cell can be generated by contacting the cell with a donor polynucleotide, and a complex comprising an Argonaute protein and a designed nucleic acid-targeting nucleic acid. The donor polynucleotide can be inserted into the cleaved target nucleic acid, thereby generating a tagged cell. The tagged cell can be propagated such as in a cell line, or to produce a propagated population of cells.

A donor polynucleotide can be introduced into the cut site by use of a donor cassette for homologous recombination that comprises ends homologous to sequences on either side of the double-strand break. The donor polynucleotide can comprise an additional sequence between the two ends. The additional sequence can be a nucleic acid sequence. The additional sequence can encode for a gene. The additional sequence can encode for a non-coding nucleic acid element.

The donor polynucleotide (e.g., the additional sequence of a donor polynucleotide between two homologous ends) can comprise a marker. A marker can comprise a visualization marker (e.g., a fluorescent marker such as GFP). A marker can comprise a random polynucleotide sequence (e.g., such as a random hexamer sequence). A marker can be a barcode.

NHEJ can introduce unique sequence signature at each cut site. The repair mechanism can result in the introduction of insertions (e.g., insertion of a donor polynucleotide), deletions or mutations into a cut site. A cell that undergoes NHEJ to repair a double-strand break can comprise a unique sequence after repair has taken place (e.g., a unique sequence can be inserted into the double-strand break). If more than one site is cut within a cell, repair can introduce the donor polynucleotide at each site, thereby adding sequence diversity to that cell. The repaired site can provide a unique barcode sequence to the cell that can be preserved during cell division and passed on to all progeny of the modified cell. A donor polynucleotide can be inserted into at least about 1, 2, 3, 4, 5, 6, 7, 8, 9 or 10 or more sites (e.g., cleaved target nucleic acids). A donor polynucleotide can be inserted into at most about 1, 2, 3, 4, 5, 6, 7, 8, 9 or 10 or more sites (e.g, cleaved target nucleic acids).

Homologous recombination (HR) can be used to introduce barcode sequences into a cell and/or a cell population (e.g., a human cell, a mammalian cell, a yeast, a fungi, a protozoa, an archaea). A library of donor plasmids (e.g., comprising the donor polynucleotide) can be prepared with randomized sequences in the donor cassette. The library can be made from oligonucleotides, a piece of double-stranded DNA, a plasmid, and/or a minicircle.

Donor polynucleotide sequences can be introduced into the genomes of individual cells for the purpose of tracking cell lineage. Sites can be chosen for modification in silent or "safe-harbor" regions of the genome, distant from genes and regulatory elements, to minimize potentially deleterious effects on cellular function. Sites within functional genetic elements can also be used to track cell fate.

For example, donor polynucleotides can be introduced into stem cell and/or stem cell populations. The methods of the disclosure can be used for tracking cell lineage development in animal models. For example, cell fate development and/or differentiation in hematopoesis can be tracked using the methods of the disclosure. The methods of the disclosure can be used for therapeutic cell engineering-based therapies. For example, a cell can be tagged with a donor polynucleotide encoding a therapeutic protein. The cell can be propagated. The propagated cell can be introduced into a subject. As another example, a differentiated cell can be removed from a subject. The differentiated cell can be tagged with two markers: one expressed when the cell is differentiated, one expressed when the cell is de-differentiated. Identifying the markers can be useful in determining differentiation events. In another example, a differentiated cell can be obtained from a subject. The differentiated cell can be de-differentiated into a pluripotent cell. The pluripotent cell can be tagged with a donor polynucleotide encoding a therapeutic protein. The cell can be re-differentiated into a new cell type while expressing the therapeutic protein, thereby creating a patient-specific therapeutic cell. Tagged cells can divide and differentiate, and the modification(s) to their genome can be transmitted to each daughter cell during cell division.

In some instances, two cells can be tagged with two different donor polynucleotide markers. The two cells can be combined. The combined mixture can be assayed simuntaneously. The donor polynucleotides can allow the multiplex analysis of the two cells because the donor polynucleotide can be used to distinguish the two cells.

A cell population can be chosen for introducing double-stranded breaks, or generating cellular signatures. Cells may be purified or selected. For example, a population of hematopoetic stem cells (CD45positive) may be selected by FACS or magnetic bead purification. Bone marrow may be treated ex vivo with the nuclease. Cells may be targeted in vivo by the use of viruses with a particular tropism. Cells may be selected by using viruses engineered to target cells bearing a particular receptor.

Tagged cells can be analyzed by high-throughput sequencing either at the population level or at the single-cell level. At the population level, a collection of cells can be lysed. The genomic DNA can be extracted. PCR primers can be designed to amplify the genomic region that has been modified by the nuclease. Sequences can be enriched by hybridization. A sequence library can be prepared from the genomic DNA and enriched. The region of interest can be enriched, and a sequence library can be prepared. A sequence library can be prepared simultaneously during enrichment using primers comprising appropriate sequence tags to be used with nucleic acid sequencing technologies. If the double-stranded break is made within a region that can be transcribed, RNA can be used to prepare sequence libraries.

Once nucleic acid sequence data has been obtained, the sequences can be analyzed to determine the clonal structure. This can be carried out by gathering common sequences together and counting those sequences.

Cells can be sub-selected by sorting schemes based on cell surface markers using flow cytometry or affinity purification methods. Cell surface markers can be used to define cell states, and by comparing cell states with clonal structure, the fate of modified cell populations can be determined.

At the single-cell level, cells can be isolated. PCR products can be generated from each individual cell. This can be achieved in microwell arrays, microfluidic devices, and/or emulsions. Where more than one genomic modification is carried out per cell, PCR products can be coupled together, either physically, or chemically, to ensure their relationship to the parent cell.

Methods for Quantifying Genome-Editing Events

For endonucleases, such as Argonaute, the nucleic acid recognition functionality and nuclease activities can be linked. In some instances, nucleic acid recognition functionality and nuclease activities may not be linked. The nuclease sites can be located within the specific sequence recognized by the nuclease.

Non-Homologous End-Joining can be an imperfect repair process that can result in the insertion of multiple bases at the site of the double stranded break. NHEJ can result in the introduction of insertions, deletions and/or mutations into a cut site. NHEJ can significantly disrupt the original sequence. The disruption of the native sequence as a consequence of repair mechanisms can be used to assess the efficiency of genome editing approaches.

Homologous recombination can enable more complete repair of the target nucleic acid break by exchanging nucleotide sequences between similar or identical molecules of nucleic acid. An additional sequence can be introduced into the target nucleic acid at the cut site by use of a donor cassette (e.g., donor polynucleotide) that comprises ends homologous to sequences either side of the double-strand break and additional sequence between the two ends.

This disclosure describes an approach for assessing double-stranded break activity and NHEJ-mediated insertions/deletions introduced by nucleic acid-dependent nucleases, such as Argonaute. The method takes advantage of the fact that the sites in a target nucleic acid recognized by Argonaute during the initial nuclease recognition and nucleic acid cleavage activity can be destroyed during the NHEJ process, either by the introduction of insertions or deletions.

In some instances, the method provides for the design of a designed nucleic acid-targeting nucleic acid to target a site of interest in a target nucleic acid (e.g., genome). A nucleic acid template encoding the designed nucleic acid-targeting nucleic acid can be designed with a promoter sequence appended at the 5' end of the designed nucleic acid-targeting nucleic acid to enable in vitro synthesis of the designed nucleic acid-targeting nucleic acid.

Primers can be designed at positions that flank the cleavage site. The cleavage site (and/or nucleic acid regions around the cleavage site) can be amplified (e.g., from genomic nucleic acid), thereby generating a product (e.g., amplified PCR product). The product (e.g., amplified PCR product) can be at least about 100, 200, 300, 400, 500, 600, 700, 800, 900, 1000, 1100, 1200 or more bases in length. The product (e.g., amplified PCR product) can be at most about 100, 200, 300, 400, 500, 600, 700, 800, 900, 1000, 1100, 1200 or more bases in length. The product (e.g., amplified PCR product) can be about 200-600 base pairs in length.

The products can be purified. The products can be incubated with a nuclease (e.g. Argonaute) and the designed nucleic acid-targeting nucleic acid. Those molecules that have been amplified from genomic nucleic acid that have not be modified by NHEJ can comprise the correct sequence that can be recognized and cleaved by Argonaute. The molecules that have been amplified from genomic nucleic acid that has been modified by NHEJ may not comprise sites that can be recognized and/or cut by Argonaute.

The digested products can then be analyzed by methods such as gel electrophoresis, capillary electrophoresis, high-throughput sequencing and/or quantitative PCR (e.g., qPCR). In the case of gel electrophoresis, a gel can be imaged. Once a gel has been imaged, the percentage of cells modified by NHEJ can be estimated by measuring the intensity of bands corresponding to digested products, and comparing to the intensity of bands corresponding to undigested products.

Methods for Delivering Donor Polynucleotide to a Double-Stranded Break for Insertion into the Double-Stranded Break This disclosure describes methods for bringing a donor polynucleotide into close proximity to a site-directed target nucleic acid break to enhance insertion (e.g., homologous recombination) of the donor polynucleotide into the site of the double-stranded break. The method can be performed using any of the Argonaute proteins, designed nucleic acid-targeting nucleic acids, and complexes of Argonautes and designed nucleic acid-targeting nucleic acids as described herein.

In some instances, the methods of the disclosure provide for bringing a donor polynucleotide in close proximity to the site of a double-stranded break in a target nucleic acid, by binding it to the nuclease that generates the double-stranded break (e.g., Argonaute).

Figure 16:
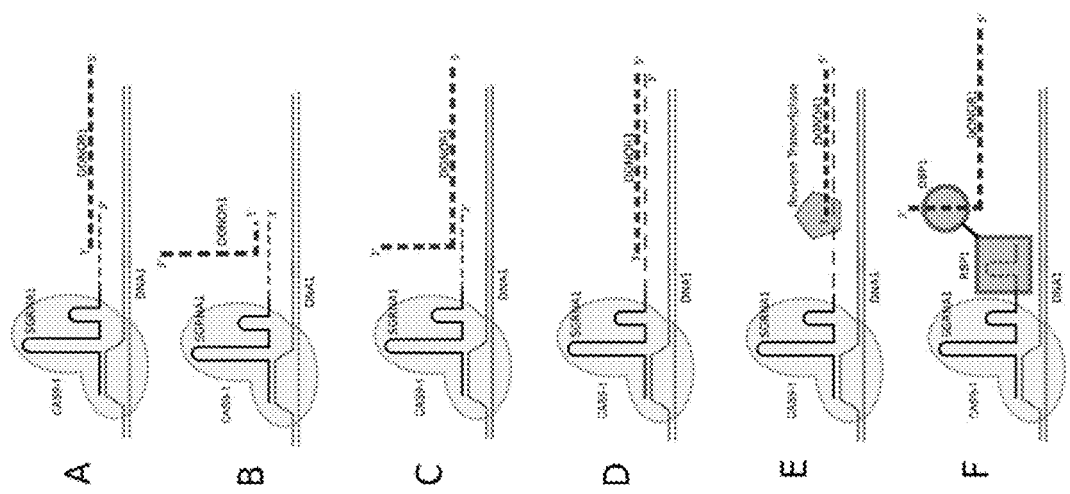
FIG. 16 A-F depict exemplary methods of the disclosure of bringing a donor polynucleotide to a modification site in a target nucleic acid.

A complex comprising an Argonaute protein, a designed nucleic acid-targeting nucleic acid, and a donor polynucleotide can be delivered to a target nucleic acid. FIG. 16 illustrates exemplary methods for bringing a donor polynucleotide into proximity to the site of a double-stranded break in a target nucleic acid. For example, a designed nucleic acid-targeting nucleic acid can comprise a non-native sequence such as a 3' hybridizing extension sequence (shown in the light dotted line attached to the designed nucleic acid-targeting nucleic acid). A 3' hybridizing extension sequence can be a non-native sequence. FIG. 16A illustrates that the 3' end of the designed nucleic acid-targeting nucleic acid can include a 3' hybridizing extension sequence that can hybridize to an end of the donor polynucleotide (e.g., the 3' end) (the donor polynucleotide is shown in bold thicker dashed line). The 3' hybridizing extension sequence can be at least about 1, 2, 3, 4, 5, 6, 7, 8, 9, or 10 or more nucleotides in length. The 3' hybridizing extension sequence can be at most about 1, 2, 3, 4, 5, 6, 7, 8, 9, or 10 or more nucleotides in length. The 3' hybridizing sequence can hybridize to at least about 1, 2, 3, 4, 5, 6, 7, 8, 9, or 10 or more nucleotides of the donor polynucleotide. The 3' hybridizing sequence can hybridize to at most about 1, 2, 3, 4, 5, 5, 6, 7, 8, 9, or 10 or more nucleotides of the donor polynucleotide. The 3' hybridizing sequence can hybridize to the donor polynucleotide with at least 1, 2, 3, 4, 5, 6, 7, 8, 9, or 10 or more mismatches. The 3' hybridizing sequence can hybridize to the donor polynucleotide with at most 1, 2, 3, 4, 5, 6, 7, 8, 9, or 10 or more mismatches.

The 3' hybridizing extension can hybridize to the 3' end of the donor polynucleotide. The 3' hybridizing extension can hybridize to at least the 1, 2, 3, 4, 5, 6, 7, 8, 9, or 10 or more 3' most nucleotides of the donor polynucleotide. The 3' hybridizing extension can hybridize to at most the 1, 2, 3, 4, 5, 6, 7, 8, 9, or 10 or more 3' most nucleotides of the donor polynucleotide.

As depicted in FIG. 16B, the 3' hybridizing extension sequence can include a sequence that can hybridize to the 5' end of the donor DNA. The 3' hybridizing extension can hybridize to at least the 1, 2, 3, 4, 5, 6, 7, 8, 9, or 10 or more 5' most nucleotides of the donor polynucleotide. The 3' hybridizing extension can hybridize to at most the 1, 2, 3, 4, 5, 6, 7, 8, 9, or 10 or more 5' most nucleotides of the donor polynucleotide.

The 3' hybridizing extension sequence can include a sequence that can hybridize to a region between the 3' end and 5' end of the donor polynucleotide, as shown in FIG. 16C. The 3' hybridizing extension can hybridize to at least 1, 2, 3, 4, 5, 6, 7, 8, 9, or 10 or more nucleotides between the 3' and 5' end of the donor polynucleotide. The 3' hybridizing extension can hybridize to at most the 1, 2, 3, 4, 5, 6, 7, 8, 9, or 10 or more nucleotides between the 3' and 5' end of the donor polynucleotide.

The 3' hybridizing extension sequence can include a sequence that can hybridize along the full length of the donor polynucleotide, as shown in FIG. 16D. The designed nucleic acid-targeting nucleic acid can hybridize along at least about 20, 30, 40, 50, 60, 70, 80, 90, or 100% of the donor polynucleotide. The designed nucleic acid-targeting nucleic acid can hybridize along at most about 20, 30, 40, 50, 60, 70, 80, 90, or 100% of the donor polynucleotide. The 3' hybridizing extension sequence can hybridize along the full length of the donor polynucleotide with at least about 1, 2, 3, 4, 5, 6, 7, 8, 9 or 10 or more mismatches. The 3' hybridizing extension sequence can hybridize along the full length of the donor polynucleotide with at most about 1, 2, 3, 4, 5, 6, 7, 8, 9 or 10 or more mismatches.

The 3' hybridizing extension sequence can comprise a sequence that can be used as a template and converted by, for example, a transcriptase (e.g., Klenow fragment) to generate hybrid nucleic acid (e.g., the resulting nucleic acid is an DNA-DNA hybrid, wherein the newly transcribed nucleic acid can be DNA), as shown in FIG. 16E. The transcriptase can extend the donor polynucleotide sequence from the 3' hybridizing extension template.

The 3' hybridizing extension sequence can incorporate a nucleic acid sequence that can binds a nucleic acid bindng protein (NBP). The NBP can be a DNA binding protein (DBP). The NBP can be fused to a DNA binding protein (DBP), as shown in FIG. 16F. The DNA-binding protein can bind to the donor polynucleotide.

The sequences used to bring the donor polynucleotide into close proximity with a double-stranded break can be appended to the 5' end of the designed nucleic acid-targeting nucleic acid. The sequences sequences used to bring the donor polynucleotide into close proximity with a double-stranded break can be appended to both the 5' end and the 3' end of the designed nucleic acid-targeting nucleic acid.

The nuclease used in the methods of the disclosure (e.g., Argonaute) can comprise nickase activity in which the nuclease can introduce single-stranded breaks in a target nucleic acid. Pairs of nucleases with nickase activity can be targeted to regions in close proximity to each other. A first Argonaute can bind to a first designed nucleic acid-targeting nucleic acid that can interact with a first single-stranded donor polynucleotide. A second Argonaute can bind to a second designed nucleic acid-targeting nucleic acid that can interact with a second single-stranded donor polynucleotide. The first and second single-stranded donor polynucleotides can be designed to hybridize with each other to make a double-stranded donor polynucleotide. Two separate donor polynucleotides can be brought to the nuclease site.

In some embodiments, the donor polynucleotide can be single stranded. In some embodiments, the donor polynucleotide can be double stranded. In some embodiments, the donor DNA can be a minicircle. In some embodiments, the donor polynucleotide can be a plasmid. In some embodiments, the plasmid can be supercoiled. In some embodiments, the donor polynucleotide can be methylated. In some embodiments, the donor polynucleotide can be unmethylated. The donor polynucleotide can comprise a modification. Modifications can include those described here including, but not limited to, biotinylation, chemical conjugate, and synthetic nucleotides.

Methods for Cloning and Expressing a Vector Comprising an Argonaute Protein and a Designed Nucleic Acid-Targeting Nucleic Acid The disclosure provides for methods for cloning a designed nucleic acid-targeting nucleic acid into a vector (e.g., a linearized vector). The method can be performed using any of the Argonaute proteins, designed nucleic acid-targeting nucleic acids, and complexes of Argonaute proteins and designed nucleic acid-targeting nucleic acids as described herein.

A user (e.g., a scientist) can design single-stranded DNA oligonucleotides. The single-stranded DNA oliognucleotides can target a target nucleic acid. The single-stranded DNA olignonucleotides can be at least about 5, 10, 15, 20, 25, 30 or more nucleotides in length. The single-stranded DNA olignonucleotides can be at most about 5, 10, 15, 20, 25, 30 or more nucleotides in length. The single-stranded DNA oligonucleotides can be 19-20 nucleotides in length.

A single-stranded DNA oligonucleotide can be designed such that it can hybridize to a target nucleic acid or a portion thereof. The DNA oligonucleotide can encode a sequence corresponding to the sense or antisense strand of the target nucleic acid sequence.

The single-stranded oligonucleotides can comprise a first portion that can hybridize and/or is complementary to a target nucleic acid. The single-stranded oligonucleotides can comprise a first portion that can hybridize and/or is complementary another single-stranded oligonucleotide. The single-stranded oligonuclotide can comprise a second portion that can hybridize to a sequence in the linearized vector. In other words, a pair of single-stranded oligonucleotides can comprise a first portion that hybridizes to each other and a second portion that comprise single-stranded overhangs, wherein the overhangs can hybridize to sticky ends in the linearized vector. In some instances, an overhang comprises 5'-GTTTT-3'. In some instances, an overhang comprises 5'-CGGTG-3'

The single stranded DNA nucleotides can be annealed together to generate a double-stranded oligonucleotide. The single-stranded DNA nucleotides can be annealed together in an oligonucleotide annealing buffer (e.g., comprising Tris-HCl, EDTA and NaCl). The double-stranded oligonucleotide can be diluted to a working concentration (e.g., a concentration suitable for ligation into a linearized plasmid). The diluted double-stranded oligonucleotide can be ligated into a linearized vector. Ligation can be performed in a ligation buffer (e.g., comprising Tris-HCl, MgCl$_2$, ATP) and with a ligase (e.g., T4 DNA ligase). The double-stranded oligonucleotide can be ligated into a linearized vector at a region within the sequence encoding the designed nucleic acid-targeting nucleic acid. In other words, the linearized vector can be linearized at a point within the region encoding the designed nucleic acid-targeting nucleic acid, wherein the linearization generates sticky ends that are complementary to the sticky ends of the double-stranded oligonucleotide. When the double-stranded oligonucleotide is ligated into the vector, it can generate a sequence encoding for a designed nucleic acid-targeting nucleic acid comprising a spacer sequence corresponding to the double-stranded oligonucleotide sequence.

The ligated vector can be transformed into chemically competent cells (e.g., DH5-alpha, Top10) and selected for expression of the correctly ligated vector (e.g., by antibotic screening). The selected transformants can be analyzed for the presence of an insert by sequencing. Sequencing can be perfomed using a sequencing primer that can hybridize to a portion of the vector.

Correctly ligated vector can be prepared (e.g., by large scale DNA preparation, maxiprep), and purified. The vector, comprising an Argonaute, a designed nucleic acid-targeting nucleic acid, wherein the designed nucleic acid-targeting nucleic acid comprise the double-stranded DNA oligonucleotides can be introduced (e.g., transfected) into a cell line of choice (e.g., mammalian cell line).

Light Inducible Enzymatically Active and/or Inactive Argonaute

The disclosure provides for compositions and methods for generating a conditionally enzymatically inactive and/or active Argonaute. The Argonaute can comprise a switch. The term "switch" as used herein can refer to a system or a set of components that act in a coordinated manner to affect a change, such as activation, repression, enhancement or termination of that function. A switch can refer to a genetic switch, which can comprise the basic components of gene regulatory proteins and the specific DNA sequences that these proteins recognize. Switches can relate to inducible and repressible systems used in gene regulation. The term "inducible" as used herein may encompass all aspects of a switch irrespective of the molecular mechanism involved (e.g., inducible or repressible). Exemplary switches can include, but are not limited antibiotic based inducible systems, electromagnetic energy based inducible systems, small molecule based inducible systems, nuclear receptor based inducible systems, hormone based inducible systems, a tetracycline (Tet)/DOX inducible system, a light inducible systems, a Abscisic acid (ABA) inducible system, a cumate repressor/operator system, a 40HT/estrogen inducible system, an ecdysone-based inducible systems and/or a FKBP12/FRAP (FKBP12-rapamycin complex) inducible system.

A switch may be associated with an Argonaute of the disclosure wherein the activity of the Argonaute of the disclosure can be controlled by contact with at least one inducer energy source as to the switch. The term "contact" as used herein can refer to any associative relationship between the switch and the inducer energy source, which may be a physical interaction with a component (as in molecules or proteins which bind together) or being in the path or being struck by energy emitted by the energy source (as in the case of absorption or reflection of light, heat or sound). The contact of the switch with the inducer energy source can be brought about by application of the inducer energy source. Contact can occur via passive feedback systems. A passive regulation mechanism by which the Argonaute of the disclosure activity is controlled by contact with an inducer energy source that is already present and hence does not need to be applied. For example this energy source may be a molecule or protein already existent in the cell or in the cellular environment. Interactions which bring about contact passively may include but are not limited to receptor/ligand binding, receptor/chemical ligand binding, receptor/protein binding, antibody/protein binding, protein dimerization, protein heterodimerization, protein multimerization, nuclear receptor/ligand binding, post-translational modifications such as phosphorylation, dephosphorylation, ubiquitination or deubiquitination.

Inducible effectors can be used for in vitro or in vivo application in which temporally or spatially specific gene expression control is desired. In vitro examples: temporally precise induction/suppression of developmental genes to elucidate the timing of developmental cues, spatially controlled induction of cell fate reprogramming factors for the generation of cell-type patterned tissues. In vivo examples: combined temporal and spatial control of gene expression within specific brain regions.

The inducible effector can be a Light Inducible Transcriptional Effector (LITE). The modularity of the LITE system can allow for one or more effector domains to be employed for transcriptional modulation. An inducible effector can comprise an Argonaute of the disclosure and the activation domain VP64.

LITEs can be designed to modulate or alter expression of individual endogenous genes in a temporally and spatially precise manner. Each LITE may comprise a two component system consisting of a modified Argonaute protein and a designed nucleic acid-targeting nucleic acid, a light-responsive cryptochrome heterodimer from Arabadopsis thaliana, and a transcriptional activation/repression domain. The Argonaute and designed nucleic acid-targeting nucleic acid can be designed to bind to the promoter sequence of a gene of interest. The Argonaute protein can be fused to one half of the cryptochrome heterodimer (cryptochrome-2 or CIB1), while the remaining cryptochrome partner can be fused to a transcriptional effector domain. Effector domains may be either activators, such as VP16, VP64, or p65, or repressors, such as KRAB, EnR, or SID.

In a LITE'S unstimulated state, the Argonaute-cryptochrome2 protein (e.g., comprising a designed nucleic acid-targeting nucleic acid bound to the Argonaute) can localize to the promoter of the gene of interest, but may not bound to the CIB1-effector protein. Upon stimulation of a LITE with blue spectrum light, cryptochrome-2 can become activated, undergo a conformational change, and reveal its binding domain. CIB1 can bind to cryptochrome-2 resulting in localization of the effector domain to the gene of interest and initiating gene overexpression or silencing.

Light responsiveness of a LITE can achieved via the activation and binding of cryptochrome-2 and CIB1. Blue light stimulation can induce an activating conformational change in cryptochrome-2, resulting in recruitment of its binding partner CIB1. The binding can be fast and reversible, achieving saturation in less than 15 seconds following pulsed stimulation and returning to baseline less than 15 min after the end of stimulation. Crytochrome-2 activation can allow for the use of low light intensity stimulation and mitigating the risks of phototoxicity.

Activator and repressor domains may selected on the basis of species, strength, mechanism, duration, size, and/or any number of other parameters. Effector domains can include, but are not limited to, a transposase domain, integrase domain, recombinase domain, resolvase domain, invertase domain, protease domain, DNA methyltransferase domain, DNA demethylase domain, histone acetylase domain, histone deacetylases domain, nuclease domain, repressor domain, activator domain, nuclear-localization signal domains, transcription-protein recruiting domain, cellular uptake activity associated domain, nucleic acid binding domain or antibody presentation domain.

Gene targeting in a LITE or in any other inducible effector may be achieved via the specificity of the designed nucleic acid-targeting nucleic acid bound to the modified Argonaute. For example, a target sequence in the promoter region of the gene of interest can be selected and a designed nucleic acid-targeting nucleic acid can be customized to target (e.g., hybridize) to this sequence.

The methods provided herein use isolated, non-naturally occurring, and recombinant or engineered Argonautes and/or designed nucleic acid-targeting nucleic acids that enable the targeting of nucleic acid sequences.

The activity mediated by the effector domain can be a biological activity. For example, in some embodiments the effector domain can a transcriptional inhibitor (i.e., a repressor domain), such as an mSin interaction domain (SID). SID4X domain or a Kruppel-associated box (KRAB) or fragments of the KRAB domain. In some embodiments the effector domain can be an enhancer of transcription (i.e. an activation domain), such as the VP 16, VP64 or p65 activation domain.

In some embodiments, an effector domain can include but is not limited to transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease.

In some instances, the conditionally active and/or inactive Argonaute can be controlled by a chemical inducible system. A chemical inducible system can include, for example, the estrogen receptor (ER) based system inducible by 4-hydroxytamoxifen (4OHT), thyroid hormone receptor, retinoic acid receptor, estrogen-related receptor, glucocorticoid receptor, progesterone receptor, androgen receptor may be used in inducible systems analogous to the ER based inducible system.

A chemical inducible system can comprise Transient receptor potential (TRP) ion channel based system inducible by energy, heat or radio-wave. TRP family proteins can respond to different stimuli, including light and heat. When this protein is activated by light or heat, the ion channel can open and allow the entering of ions such as calcium into the plasma membrane. This influx of ions can bind to intracellular ion interacting partners linked to an Argonaute of the disclosure, and the binding can induce the change of subcellular localization of the polypeptide, leading to the entire polypeptide entering the nucleus of cells. Once inside the nucleus, the TALE protein linked to the effector domains will be active and modulating target gene expression in cells.

In some instances, other methods of energy activation, in addition or instead of light, can be used such as for example, electric field energy and/or ultrasound. Electric field energy can be administered using one or more electric pulses of from about 1 Volt/cm to about 10 kVolts/cm under in vivo conditions. The electric field may be delivered in a continuous manner. The electric pulse may be applied for between 1 and 500 milliseconds or between 1 and 100 milliseconds. The electric field may be applied continuously or in a pulsed manner for 5 about minutes.

The electric field can have a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. The electric field has a strength of from about 1 V/cm to about 10 kV/cm under in vivo conditions. The electric pulse can be delivered as a waveform selected from an exponential wave form, a square wave form, a modulated wave form and a modulated square wave form.

Ultrasound can be administered at a power level of from about 0.05 $W/cm^2$ to about 100 $W/cm^2$. Diagnostic or therapeutic ultrasound may be used, or combinations thereof. As used herein, the term "ultrasound" can refer to a form of energy which consists of mechanical vibrations the frequencies of which are so high they are above the range of human hearing. Lower frequency limit of the ultrasonic spectrum may generally be taken as about 20 kHz. Diagnostic applications of ultrasound can employ frequencies in the range 1 and 15 MHz.

The exposure to an ultrasound energy source can be at a frequency of from about 0.015 to about 10.0 MHz. The exposure to an ultrasound energy source can be at a frequency of from about 0.02 to about 5.0 MHz or about 6.0 MHz. The ultrasound can be applied at a frequency of 3 MHz.

Thhe exposure can be for periods of from about 10 milliseconds to about 60 minutes. The exposure can be for periods of from about 1 second to about 5 minutes. The ultrasound can be applied for about 2 minutes. Depending on the particular target cell to be disrupted, however, the exposure may be for a longer duration, for example, for 15 minutes.

Non-Homology Driven Donor Polynucleotide Insertion into a Target Nucleic Acid

Described herein are methods of targeted insertion of any polynucleotides for insertion into a chosen location without the use of homology. Polynucleotides for insertion can also be referred to as "exogenous" polynucleotides, "donor" polynucleotides or molecules or "transgenes."

Donor nucleotides (e.g., plasmids) without homology arms (e.g., flanking the exogenous sequence) can be effectively integrated into a selected target region of the genome of cell following in vivo cleavage of the double-stranded donor. The donor polynucleotides can include one or more nuclease binding sites for cleavage of the donor in vivo (in the cell). The donor polynucleotide can include two nuclease binding sites. One or more of the nucleases (e.g., Argonaute) used to cleave the target nucleic acid may also be used to cleave the donor polynucleotide.

In certain embodiments, the donor polynucleotide can includes sequences (e.g., coding sequences, also referred to as transgenes) greater than 1 kb in length, for example between 2 and 200 kb, between 2 and 10 kb (or any value therebetween). The donor polynucleotide can also includes at least one nuclease target site. The donor polynucleotide can include at least 2 target sites, for example for a pair of ZFNs, TALENs, Argonautes, and Cas9's. The one or more nuclease target site can be located outside the transgene sequences, for example, 5' and/or 3' to the transgene sequence, for cleavage of the transgene. The one or more nuclease cleavage site may be for any number of nucleases. The one or more nuclease target sites in the donor polynucleotide can be for the same nuclease used to cleave the endogenous target into which the cleaved donor polynucleotide is integrated via homology-independent methods. The one or more nuclease target sites in the donor polynucleotide can be for different nuclease used to cleave the endogenous target into which the cleaved donor polynucleotide is integrated via homology-independent methods.

The donor polynucleotide can be cleaved and integrated into a cleaved target nucleic acid in a forward or in a reverse orientation. Targeted integration via donor polynucleotide cleavage that results in a perfectly ligated AB-orientation insertion can recreate the paired nuclease (e.g., ZFN, TALEN, Argonaute and/or Cas9) binding sites with the original spacing between the sites. Such recreated sites can be substrates for a second round of cleavage by the nucleases. Nuclease cleavage at the recreated sites can result in a DNA deletion at the transgene-chromosome junctions (as a result of inaccurate NHEJ-based repair) or even transgene excision. In contrast, reverse orientation insertions can result in formation of two different nuclease pair binding sites (e.g., homodimers of the left and right nucleases). Recreated BA sites may not be re-cleavable.

Changing the nucleotides in the transgene donor polynucleotide nuclease spacer that make up the single-strand 5' overhang as compared to the wild-type (genomic) sequence, to the reverse complement of the wild-type sequence favors reverse-orientation insertion of the cleaved donor (via Watson-Crick base-pairing with the overhangs on the cleaved chromosome) which would create an un-recleavable transgene integration.

Methods for Targeted Transgene Integration

The donor polynucleotides disclosed herein can be integrated into a genome of a cell via targeted, homology-independent methods. For such targeted integration, the genome can be cleaved at a desired location (or locations) using a nuclease, for example, an Argonaute.

Following the introduction of a double-stranded break in the target nucleic acid, the donor polynucleotide can be integrated into the cleaved target nucleic acid in a targeted manner via non-homology dependent methods (e.g., non-homologous end joining (NHEJ)) following linearization of a donor polynucleotide as described herein. The donor polynucleotide (e.g., double-stranded donor polynucleotide) can be with a nuclease, for example one or more of the same or different nucleases that are used to introduce the double-stranded break in the target nucleic acid. Synchronized cleavage of the target nucleic acid and the donor polynucleotide in the cell may limit donor polynucleotide degradation (as compared to linearization of the donor polynucleotide prior to introduction into the cell). The one or more nuclease target site(s) used for linearization of the donor polynucleotide may not disrupt the transgene(s) sequence(s).

The donor polynucleotide may be integrated into the genome in the direction expected by simple ligation of the nuclease overhangs (designated "forward" orientation) or in the alternate direction (designated "reverse" orientation). In some embodiments, the donor polynucleotide is integrated following accurate ligation of the donor polynucleotide and the target nucleic acid overhangs. In other embodiments, integration of the transgene in either the forward or reverse orientation results in deletion of several nucleotides.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Transformation efficiency of wildtype Argonaute and mutant Argonaute *T. thermophilus* strains To elucidate the physiological role of Argonaute in prokaryotes, Argonaute from *T. themophilus* was studied. Comparison of the ago genes of the type strain HB27 and a derivative with enhanced competence (HB27$^{EC}$; FIG. 27A and FIG. 31A), revealed that an insertion sequence (ISTth7)6 disrupts ago in HB27$^{EC}$. In line with a role of TtArgonaute in reducing competence, a generated Aago mutant (HB27Δago; FIG. 27A) has a natural transformation efficiency that is a factor often higher than the wild-type HB27 (P<0.02, FIG. 27B). Complementation of the knockout strain with ago (HB27Δago::$^s$ago (HR27Δago complemented with a strep(II)-tag-ago gene fusion insert); FIG. 27A-B) almost completely restored the wild-type phenotype. Moreover, isolation of plasmid and total DNA from the wild-type and the ago knockout strains revealed lower plasmid yields from the wild-type strain, indicating that TtΔgo reduces the intracellular plasmid concentration (P<0.02, FIG. 27C; P<0.02, FIG. 27D).

Strains

For in vivo experiments, *T. themophilus* HB27 (ATCC BAA-163, DSM 7039 and NBRC 101085) was used (e.g., HB27 or wild type). Furthermore, HB27$^{EC}$, and two genomic variants of the HB27 strain, HB27Δago (knockout strain) and HB27Δago::$^s$ago (knockout strain complemented with strep(II)-tag-ago fusion and kanamycin resistance marker insert), were used (FIG. 27A and FIG. 40A).

Genomic Mutants

HB27 genomic DNA including megaplasmid pTT27 was purified using the FastDNA SPIN Kit for Soil (MP Bio medicals). The genomic regions directly upstream (1 kb) and downstream (2.4 kb) of the ago gene (TT_P0026) were PCR amplified from *T. thermophilus* HB27 genomic DNA. These genomic regions contained pTT27 base-pair positions 26047-25061 (upstream sequence) and 22996-20583 (downstream sequence). The amplified DNA was cloned into the pUC18 vector (FIG. 41), and the insert was transferred to pK18 to generate pWUR701 (FIG. 41). Strain HB27 was grown to an $OD_{600\ nm}$ of 0.4 in TTH medium (0.8% (w/v) bacto-tryptone, 0.4% (w/v) yeast extract, 51.3 mM NaCl, pH to 7.5 with NaOH. dissolved in mineral water (Evian)). 0.5 ml of the culture was transferred to a new tube and naturally transformed by the addition of 1 μg plasmid pWUR701. The culture was incubated overnight in a shaker incubator at 65° C. and plated on TTH plates with 30 μg ml kauamycin. Cells were repetitively .streaked on non-selective TTH plates and grown in nonselective TTH medium until kanamycin$^R$ was lost. Genomic DNA of kanamvein5 cells was purified using the FASTDNA SPIN Kit for Soil (MP Biomedicals) and loss of the ago gene was confirmed by PCR amplification of genomic DNA and sequencing of the target region. This strain was named HB27Δago, or knockout strain.

The genes encoding Strep(II)-tagged TtArgonaute protein and kanamycin$^R$ marker with upstream pSLPa promoter were PCR amplified from pWUR627 and pMK184, respectively (FIG. 41). PCR products were cloned into pWUR676 Table 2. Hind III-linearized pWUR676 was used to transform strain HB27Δago as described earlier This strain is named HB27Δago::$^5$ago (FIG. 27A) Genomic DNA was purified using the FASTDNA SPIN Kit for Soil (MP Biomedicals) and insertion of the $^5$ago-kanamycin$^R$ cassette was confirmed by PCR amplification from genomic DNA and sequencing of the target region.

Transformations

T. thermophilus strains were cultivated in TTH medium in a 65° C. shaker incubator until an $OD_{600\ nm}$ of 0.4 was reached. The culture was diluted 1:1 in pre-warmed TTH medium and incubated for another hour at 65° C. 0.5 ml of the culture was transferred to a new tube, which was incubated at 65° C. for 30 min. One-hundred nanograms of plasmid pMK184 or pMHPnqosGFP was added and the mixture was incubated for 4 h at 65° C. without shaking, after which it was serial diluted and plated on TTH plates (TTH medium solidified with 1.5% agar) and on selective TTH plates (TTH plates supplied with 50 μg ml kana-mycin or 100 μg ml hygromycin). After 48 h of incubation at 65° C. colonies were counted. Competence was determined as the amount of kanarnycin$^R$ or hygromycin$^R$ colony-forming units (c.f.u.; counted on selective plates) per μg DNA, divided by total c.f.u. (counted on .non-selective plates). To show relative competence, HB27 wild-type transformation efficiency was set to 1, with the competences of other strains normalized against this number.

DNA purification

For piasmid purification, T. thermophilus HB27 and HB27Aago cultures were cultivated in triplicates in TTH medium supplied with 30 ng μl kanamycin and 100 ng μl hygromycin. Five $OD_{600\ nm}$ units of each overnight culture were harvested and piasmids were isolated with the Fermentas GeneJET plasmid Miniprep Kit (Thermo Scientific) according to the manual provided by the manufacturer and quantified using a NanoDrop ND1000 spectrophotometer. For complete DNA (containing both genomic and plasmid DNA) purification, T. thermophilus HB27 and HB27Δagp cultures were cultivated in triplicates to an $OD_{600\ nm}$ of 0.500. One $OD_{600\ nm}$ unit was harvested and complete DNA was isolated using the JGI 'bacterial genomic DNA isolation using CTAB' protocol. 2.5 mg DNA of each purification was resolved on 0.8% agarose gels and stained with SVBR Safe Nucleic Acid Stain (Invitrogen), visualized, using a G:BOX Chemi imager and analysed using GeneToois analysis software (Syngene).

Example 2

Transcriptome Analysis to Determine Influence of Prokaryotic Argonaute on Regulation of Gene Expression Transcriptome analysis of HB27 and HB27Δago was performed to determine whether TtArgonaute-mediated interference proceeds directly by targeting plasmid DNA, or indirectly by regulating gene expression. Although the comparison revealed pleiotropic changes in gene expression (FIG. 33A-C and 34A-D), no substantial differential expression of genes involved in plasmid uptake or host defense was observed (FIG. 37). Hence, RNA sequencing (RNA-seq) analysis suggests that TtArgonaute does not influence plasmid uptake and plasmid copy number at the level of transcriptional control.

RNA Sequencing

Triplicate T. thermophilus strains were cultivated in 20 ml TTH medium in a 65° C. shaker incubator overnight Cultures were diluted ¹⁄₁₀₀ and grown to an $OD_{600\ nm}$ of 0.500, after which cells were harvested by centrifugation. After harvesting, RNA was purified using the mirVana RNA isolation kit (Ambion) according to the instructions provided by the manufacturer. Biological triplicates of purified RNA were sequenced by BaseClear BV by Illumina sequencing. Reads were mapped on genomes and plasmid using Rockhopper, but rather than using the programs calculated expression rates and significance, the percentage of raw counts mapped on each gene were normalised against the total number of raw counts mapped on the genome. Variance in expression was calculated by dividing the average of the triplicate normalized counts mapped on single genes in strain HB27 by the average of the triplicate normalized counts mapped on the same gene in strain HB27Δago.

Example 3

Interaction of Prokaryotic Argonaute with Plasmid DNA

Affinity-purified TtArgonaute expressed from the chromosome of HB27Δago::$^s$ ago could be detected by protein mass spectrometry (FIG. 38). Molecular analysis of TtArgonaute expressed in T. thermophilus was hampered by the low TtArgonaute yield, and attempts to overexpress TtArgonaute in T. thermophilus from a plasmid were unsuccessful. By contrast, expression of Step(II)-tagged TtArgonaute (FIG. 28A) in Escherichia colt was successful when performed at 20° C. Under these conditions, TtArgonaute has no effect on plasrnid content (FIG. 31B). Analysis of co-purified nucleic acids revealed that TtArgonaute-associated RNA(10-150 nucleotides) is preferentially $^{32}$P-labelled in a polynucleotide kinase (PNK) forward reaction, indicating the presence of 5' hydroxyl groups (FIG. 32). By contrast, co-purified DNA had a more defined length (13-25 nucleotides), and was preferentially labelled in a PNK exchange reaction, indicating phosphorylated 3' ends (FIG. 28B). Δ 5' phosphate group is a general feature of Argonaute guides.

Example 4

Prokaryotic Argonaute Catalyzes DNA Cleavage with a ssDNA Guide

TtArgonaute catalyseD cleavage of ssDNA targets in vitro when supplied with complementary 5'-phosphorylated 21-nucleotide ssDNA guides, but not when supplied with analogous ssRNA guides (FIGS. 33A-C and 34A-D). During isolation of an active site double mutant, TtArgonauteDM (TtArgonaute (D478A, D546A); FIG. 28A), only RNAs co-purify (10-150 nucleotides; FIG. 32) This suggested that active site residues were involved in processing and/or binding of the ssDNA molecules.

Example 5

Prokaryotic Argonaute Preferentially Targets Plasmid DNA

Cloning and sequencing of TtArgonaute-hound DNA molecules resulted in 70.6 million sequences, of which 65% were mapped on the TtArgonaute expression plasmid pWUR702, 3% on the plasmid pRARE, and 32% on the chromosome of E. coli K12 (FIG. 39). Remarkably, when normalized for the DNA content in each cell. TtArgonaute predominantly co-purifieed with guides complementary to pWUR702 and pRARE (approximately 54 and 8.8 times more frequently, respectively), rather than with guides complementary to the E. coli K12 chromosome (FIG. 39).

Example 6

Prokaryotic Argonaute Preferentially Acquires DNA Guides from Plasmids

Analysis of unique guide sequences revealed two populations of DNA guides: one 15-nucleotides long, and the other ranging from 13 to 25 nucleotides in length (FIG. 28C). No obvious bias towards specific regions of the plasmids or the chromosome was detected: the guides target coding and non-coding regions on both strands independent of GC content (FIG. 28E). Some guides map on one of the piasmids as well as on the chromosome of E. coli (for example, on lacI and proL). The fact that these guides did not seem to be under-represented compared with other plasmid-targeting guides indicates that there was no selection against chromosome-targeting guides, but rather that the differential guide loading (FIG. 39) was a result of preferential acquisition of guides from plasmids.

Example 7

Prokaryotic Argonaute Preferentially Acquires DNA Guides with a 5'Deoxycytidine

89% of the DNA guides had a deoxycytidine (dC) at the first position at the 5' end and 72% had a deoxyadenosine (dA) at the second position (FIG. 28D). Despite this bias, identical TtArgonaute cleavage activities were observed with DNA guides containing a 5' dC, dT, dA or dG. The 5' dC preference may result from specific guide processing, or from preferential 5' nucleoside selection by TtArgoaaute. A bias for specific 5' nucleosides can occur in certain eukaryotic Argonaute proteins.

Example 8

In Vivo Acquired DNA Molecules Guide Prokaryotic Argouaute to Cleave dsDNA Targets Activity assays were performed to investigate whether the in vivo plasmid-derived ssDNAs can be functional guides that enable TtArgonaute to cleave double-stranded DNA (dsDNA) targets (expression plasmid pWUR702). Purified TtArgonaute linearized or nicked pWUR702, resulting in linear or open circular plasmid DNA, respectively (FIG. 29A, lane 4), whereas TtArgonauteDM did not show this activity (FIG. 29A, lane 3). The cleavage activity of TtArgonaute was strongly temperature dependent: whereas ssDNA was cleaved at temperatures ≥20° C., plasmid DNA was only cleaved at temperatures ≥65° C. (FIG. 35E-F). This agrees with the observation that during TtArgonaute expression in E. coli at 20° C., plasmid concentrations are not decreased (FIG. 31B).

Purified TtArgonaute was unable to cleave piasrnids that had no sequence similarity to pWUR702 or pRARE (for example, pWUR708). However, when supplied with two synthetic 5'-phosphorylated ssDNA guides that target both strands of the plasmid at the same locus (FIG. 30B), TtArgonaute was able to linearize or nick pWUR708 (FIG. 29B, lane 8). These findings, together with the guide sequence data, indicate that the in vivo acquired DNA molecules guide TtArgonaute to cleave dsDNA targets. These guides of TtArgonaute can he referred to as small interfering DNAs (siDNAs).

Example 9

Cleavage of dsDNA by Prokaryotic Argonatue Depends on Negatively Supercoiled Topology Of The Target DNA In vitro plasmid cleavage assays were performed using purified TtArgonaute loaded with synthetic siDNAs. Negatively super-coiled plasmids (isolated from E. coli) were used, because at least 95% of all plasmids isolated from T. thermophilus have a negatively super-coiled topology. Negative supercoiling facilitated melting of the DNA duplex, especially at elevated temperatures. Target plasmids pWUR704 and pWUR705 were identical except, for the flanking regions of the target site (AT-rich or GC-rich; FIG. 30A). Both pla.sra.ids shared no sequence similarity with TtArgonaute expression plasmid pWUR702, and they were not cleaved by TtArgonaute unless complementary siDNAs are added (FIG. 30C). When supplied with a single 21-nucleotide siDNA, TtArgonaute nicked the negatively supercoiled plasmid (FIG. 30C, lanes 3, 4), and when supplied with a mixture of two 21-nucleotide siDNAs that target both DNA strands at the same locus, TtArgonaute linearized the plasmid (FIG. 30B-C, lane 5). Both nicking and dsDNA cleavage were more efficient when the target sequence was flanked by AT-rich regions (FIG. 30A, C and FIG. 36A-B). Interestingly, the same TtArgonaute—siDNA complexes were not able to cleave linearized plasmids (FIG. 36C-D). This suggests that cleavage of dsDNA by TtArgonaute depends on the negatively supercoiled topology of the target DNA.

Example 10

Prokaryotic Argonaute—siDNA Complex is Able to Linearize a Relaxed, Nicked Plasmid The TtArgonaute—siDNA complex was able to linearize a relaxed, nicked plasmid if its target site was directly opposite the first nick (FIG. 36E). If the nicked site was located further away (33 bp) from the target site, linearization of the nicked plasmid occured only if the target region is AT-rich (FIG. 36E-F). Thus, although the negatively supercoiled topology of the plasmid was lost after the primary nick, the nick facilitated local melting of the dsDNA (especially in AT-rich DNA), which allowed TtArgonaute—siDNA complexes to nick the second strand, resulting in a dsDNA break. Like eukaryotic Argonaute proteins, the TtArgonaute—siDNA complex cleaveed a phosphate ester bond between the target nucleotides that base pair with guide nucleotides 10 and 11. Sequence analysis of a cleaved dsDNA target (FIG. 36H) demonstrated that dsDNA breaks also result from nicking both strands at the canonical Argonaute cleavage site.

Example 11

Prokaryotic Argonaute can Acquire mRNA-Derived RNA Guides

Despite similarities in the overall domain architecture of TtArgonaute and prokaryotic Argonaute protein from Rhodobacter sphaeroides (RsArgonaute), there are major functional differences between these proteins. RsArgonaute acquired mRNA-derived RNA guides with a 5' uridine (U), whereas TtArgonaute acquires DNA guides with a 5' dC. In both proteins, guides complementary to plasmids were overrepresented. However, RsArgonaute lacked a functional catalytic site and functions by target-binding alone. TtArgonaute, on the other hand, harboured a functional catalytic site allowing cleavage of both single- and double-stranded targets. The following is an exemplary model of TtArgonaute-mediated target nucleic acid cleaved. On the entry of plasmid DNA into the cell, TtArgonaute can acquire siDNA guides (13-25 nucleotides in length) from the invader. Guide acquisition by TtArgonaute can require the nuclease itself. TtArgonaute is loaded with siDNAs that are preferentially derived from plasmids; as such, single guides may allow for neutralization of multi-copy invaders. TtArgonaute uses siDNA guides to specifically cleave ssDNA targets, such as DNA taken up by the natural competence system or replication intermediated The siDNA-TtArgonaute complex targets negatively supercoiled dsDNA, which results in piasmid nicking. Especially in the case of plasmid DNA, single-strand breaks will result in loss of the supercoiled topology and, as such, in decreased transcription levels. Furthermo if the nick site is located in an AT-rich region, TtArgonaute loaded with an siDNA that targets the opposite strand may generate a dsDNA break, potentially leading to degradation of the plasmid by other nucleases. The observation that invading DNA elements generally have a lower GC content than their hosts may explain self/non-self discrimination by TtArgonaute.

Example 12

TtArgonaute Expression and Purification from E. coli KRX

The ago gene was PCR amplified from T. thermophilus (ATCC 27634) genomic DNA (gene TTHB0068, base positions on pTT27; 61573-59516), and directionally cloned into apET-52b(+) expression vector (pWUR627). By introduction of mutations according to the QuikChange Site-Directed Mutagenesis Kit instruction manual (Stratagene), pWUR642 was generated (FIG. 41). The inserts of pWUR627 and pWUR642 were PCR amplified and ligated into pCDF-1b (pWUR702 and pWUR703). These plasmids were transformed into E. coli KRX (Promega) simultaneously with pRARE (Novagen), purified from E. coli Rosetta DE3 (Novagen). Strains were cultivated in LB medium containing the corresponding antibiotics (50 ng ml streptomycin, 34 µg ml chloramphenicol) in a shaker incubator at 37° C. When the culture reached an $OD_{600\ nm}$ of 0.7-0.8, cells were cold-shocked by incubation in an ice bath for 15 min. Expression was induced by adding isopropyl-β-D-thiogalactoside (IPTG) and L-Rhamnose to a final concentration of 1 mM and 0.1% (w/v), respectively, and expression was continued for 16 h in a shaker incubator at 20° C. Cells were harvested by centrifugation. For plasmid quantification, piasrnids were isolated from 5 $OD_{600\ nm}$ units of harvested cells using the Ferrncntas GeneJET plasmid Mini prep Kit (Thermo Scientific) according to the manual provided by the manufacturer and quantified using a NanoDrop ND1000 spectrophotometer. For TtArgonaute purification, harvested celts were resuspended in Buffer I (20 mM Tris-HCl pH 8, 1 M NaCl, supplied with either 2 mM $MnCl_2$ or 2 mM $MgCl_2$), and disrupted using a French pressure cell. Expressed proteins have an N-terminal Strep(II)-tag and were isolated using Strep-Tactin affinity chromatography (IBA) with an adapted protocol. Before loading of the cell-free extract, columns were equilibrated in Buffer I. After loading, columns were washed with 9 column volumes of Buffer I and with 9 column volumes of Buffer II(20 mM Tris-HCl pH 8, 0.5 M NaCl, supplied with 2 mM $MnCl_2$). Proteins were eluted in Buffer III (Buffer II supplemented with 2.5 mM d-Desthiobiotin (Sigma-Aldrich)). For purification of TtArgonaute used in Mn/Mg gradient experiments, no Mn or Mg was added to purification buffers. For other activity assays, $MnCl_2$ or $MgCl_2$ was added to all buffers at a final concentration of 0.5 mM.

Example 13

TtArgonaute Purification from T. thermophilus

HB27Δago::$^s$ago was cultivated in TTH medium supplemented with 30 ng ml kanamycin at 65° C. After overnight growth, cells were harvested and TtArgonaute was purified as described earlier. After purification, ciution fractions were resolved on SDS-PAGE gels and purified proteins were stained using Coomassie brilliant blue stain. A band corresponding to the region with the molecular weight of Argonauts (75-80 kDa) was excised from the gel and subjected to in-gel digestion using a Perkin Elmer Janus Automated Workstation. Peptide mixtures were injected onto a nano-ACQUITY UPLC (Waters Corporation) coupled to a LTQ-Orbitap XL (Thermo Fisher Scientific) via an Advion Biosciences Nanomate. Peptides were eluted over a 30 mm gradient (5-40% ACN). MaxQuant (v.1.4.1.2) and its embedded Andromeda search engine were used to search the data against a database containing T. thermophilus sequences extracted from Uniprot. Methionine oxidation was used as a variable modification and a maximum of two missed trypsin cleavages were allowed. Peptide and protein posterior error probabilities (PEP) were calculated using a target-decoy search using the revert scheme. The light version of intensity-based absolute quantification (iBAQ) was used to rank the identified proteins by estimated relative abundance.

Example 14

Guide Co-Purification and Sequencing

Proteinase K (Ambion) and $CaCl_2$ (final concentration, 5 mM) were added to purified proteins and samples were incubated for 1 h at 37° C. Nucleic acids were separated from protein content using Roti phenol/chloroform/isoamyl alcohol pH 7.5-8.0 (Carl Roth GmbH) and further purified by ethanol precipitation. Precipitation was performed overnight at −20° C. in the presence of linear polymerized acryfamjde as carrier.

Purified nucleic acids were [γ-$^{32}$P]ATP labelled with T4 PNK. (Fermentas) in exchange- or forward-labelling reactions and thereafter separated from free [γ-$^{32}$P]ATP using a Sephadex G-25 column (GE). Labelled nucleic acids were incubated with nucleases (DNase-freeRNaseA (Fermentas), RQ1 RNase-freeDNaseI (Promega) or P1 nuclease (Sigma)) for 1 h at 37° C. After nuclease treatment, samples were mixed with Loading Buffer (95% (deionzed) formamide, 5 mM EDTA, 0.025% SDS, 0.025% bromophenol blue and 0.025% xylene cyanol), heated for 5 min at 95° C. and resolved on 15% or 20% denaturing polyacrylamide gels. Radioactivity was captured from gels using phosphor screens.

Nucleic acids were purified from TtA.rgonaute and treated with RNaseA, as described earlier. The small 5'-phosphorylated DNA molecules were poty-adenylated at their 3' end using recombinant terminal deoxynucleotidyl transferase (TdT, Invitrogen), according to the instructions of the manufacturer. After purification of the product using the QIAquick nucleotide removal kit (Qiagen), 5'-phosphorylated and 3'-polyadenylated products were ligated to the 3' end of oligonucleotide BG4409 using T4 RNA iigase (Ambion), according to the instructions of the manufacturer. After purification of the product using the QIAquick nucleotide removal kit (Qiagen), the product was PCR amplified using primers BG4409 and BG4436 (anchored poly-T primer (partially degenerate)). The PCR amplification product was gel purified using the GeneJET gel extraction kit (Fermentas) and sent for sequencing by Imagif, Plateforme de Sequencage a'Haul Debit by lllumina sequencing with an adapted RNA-seq protocol. Sequences were analyzed with FastQC software (Babraham Bioinformatics). After mapping on genome and plasmids, duplicate reads were removed using SAMtools software, to exclude a bias for preferentially PCR amplified reads in downstream analysis. Unique read data sets were reanalyzed with FastQC software and remapped on genome and plasmid DNA using Tablet software (James Hutton Institute).

Example 15:

Activity Assays

Purified TrArgonaute, ssDNA or ssRNA guides, and ssDNA targets (FIGS. 40B and 41) were mixed in 5:1:1 ratio (TtArgonaute:guide:target) in 2X Reaction Buffer (20 mM Tris-HCl pH 8, 250 mM NaCl supplied with varying awcentratioas of $MnCl_2$ or $MgCl_2$). Reaction mixtures were incubated for 1 h at 75° C. Reactions were stopped by the addition of Loading Buffer and heated for 5 min at 95° C. before the samples were resolved on 15% or 20% denaturing poly-aerylamide gels. Gels were stained using SYBR gold Nucleic Acid Gel Stain (invitrogen) and nucleic acids were visualized using a G:BOX Chemi imager (Syngene). Because DNA-guided cleavage of ssDNA is observed in the presence of 5-10 μM $Mn^{2+}$ (FIG. 36I), but comparable cleavage levels were observed in the presence of Mg21 only at tenfold higher concentrations (FIG. 36I), all activity assays were performed in the presence of 0.5 mM $MnCl_2$. Purified TtArgonaute, ssDNA guides and plasmid targets were mixed in a 25:5:1 ratio (TtArgonaute:guide:target) in 2X Reaction Buffer supplemented with 0.5 mM $MnCl_2$. Samples were incubated for 16 h at 75° C. Reactions were stopped by adding Proteinase K solution (Amhion) and $CaCl_2$ (final concentration, 5 mM) and samples were incubated for 1 h at 65° C. Samples were mixed with 63 loading dye (Fermentas) before they were resolved on 0.8% agarose gels. Agarose gels were stained with SYBR safe or SYBR gold Nucleic Acid Gel Stain (Invitrogen) and nucleic acids were visualized using a G:BOX Chemi imager (Syngene).

Plasmid pWUR704 was linearized with TtArgonaute-siDNA complexes as described earlier. The DNA was purified from the activity assay sample by PCI extraction followed by ethanol precipitation. Purified DNA was cut either byXbaI or by NheI. Restriction site overhangs were filled in with Klenow Fragment (Thermo Scientific) according to the manual provided by the manufacturer. Blunt-end linear ptesmid was closed by T4 ligase ligation according to the manual provided by the manufacturer (Thermo Scientific). Ligated plasmids were treated with HindIII (in the case of the XbaI-treated plasmids) or SalI (in the case of NheI-treated plasmids) to eliminate the possible background of the original plasmid. Plasmids were transformed to NEB 5-α E. coli competent cells (New England Biolabs) according to the manual provided by the manufacturer. Colonies were picked, grown overnight in LB medium at 37° C. and miniprepped with the Fermentas GeneJET Plasmid Miniprep Kit (Thermo Scientific). Purified plasmids were sent to GATC Biotech (Germany) for target site sequencing.

DNA Guides and Targets

The sequence of guide BG3466 is based on let-7miRNA, whereas the sequence of guide BG4017 is based on the reverse complementary sequence of let-7 miRNA. Both guides have a 5' phosphate, are 21-nucleotides long and have been PAGE purified after synthesis. Oligonucleotides BG4262--BG4265 (FIG. 40B) were used in activity assays as an ssDNA target or mixed together with 2X STE buffer (20 mM Tris-HCl pH 8, 100 mM NaCl, 2 mM EDTA) in a 1:1:2 ratio (BG4262:BG4263:2X STE or BG4264:BG4265:2X STE) and incubated at 95° C. for 5 min. Samples were cooled down to room temperature (20° C.). Annealed oligonucleotides were used as inserts for plasmid pWUR677 (generated from pFU98) to generate pWUR704 and pWUR705. For experiments with nicked and linearized targets, pWUR704 and pWUR705 were treated with Nb.B-smI or SpeI, respectively. Plasmid pWUR708 was generated as pWUR704 and pWUR705 but with annealed BG3467 and BG3468 oligonucleotides as insert.

Example 16

Recombinant Expression of an Argonaute

A recombinant DMA sequence can be assembled that encodes for an modified Argonaute protein of the disclosure, and enables the expression of the modified Argonaute in a host organism. The recombinant DNA sequence comprises a promoter sequence, and may additionally comprise an affinity tag for purification, or an epitope tag. In a non-limiting example, a plasmid comprises the recombinant DNA sequence tor expression of the modified Argonaute.

Production of Recombinant Protein

A plasmid encoding the modified Argonaute is introduced into bacterial cells (e.g., E coli). The polypeptide is expressed in bacterial cells, and then purified from cell lysate using chromatography methods. The activity of the modified Argonaute is measured using assay methods designed to determine the specificity of the modified Argonaute, the specificity profile of the Argonaute and the binding affinity to the target nucleic acid.

Software is designed to choose sites that can be cut using the Argonaute. Designed nucleic acid-targeting nucleic acid sequences are designed to direct the activity of the Argonaute. Once designed, the Argonaute is used to cleave nucleic acids.

Example 17

Sequence Enrichment of Site-Directed Polypeptide-Bound Target Nucleic Acid

The disclosure provides methods for sequence enrichment without amplification using modified Argonautes of the disclosure.

In some embodiments, the method will comprise a) contacting a target nucleic acid with a complex comprising a designed nucleic acid-targeting nucleic acid and a modified Argonaute, b) cleaving the target nucleic acid c) purifying the target nucleic acid, and d) sequencing the target nucleic acid, wherein said target nucleic acid is enriched.

In some embodiments, the Argonaute will be enzymatically inactive. Use of an enzymatically inactive Argonaute will facilitate binding of the target nucleic acid to the Argonaute complex. In some embodiments, the Argonaute will be enzymatically active.

In some embodiments, sequence enrichment will be performed outside of cells (e.g., cell-free sample). For example, a sample will comprise purified genomic DNA. In some embodiments, sequence enrichment will be performed on a cellular sample (e.g. cells, cell lysate).

In some instances, Argonaute—target nucleic acid complexes will be fixed or cross-linked to form complexes. If the method is being performed on cells, cells will be lysed. Lysis conditions will be chosen to maintain intact protein-DNA complexes.

The nucleic acid sample will be treated to fragment the target nucleic add before affinity purification. Fragmentation can be performed through physical, mechanical or enzymatic methods. Physical fragmentation will Include exposing a target polynucleotide to heat or to ultraviolet (UV) light. Mechanical disruption will be used to mechanically shear a target polynucleotide into fragments of the desired range. Mechanical shearing will be accomplished through a number of methods, including repetitive pipetting of the target polynucleotide, sonieation and nebulization. Target nucleic acids will also be fragmented using enzymatic methods. In some cases, enzymatic digestion will be performed using enzymes such as using restriction enzymes. Restriction enzymes will be used to perform specific or non-specific fragmentation of target polynucleotides. The methods will use one or more types of restriction enzymes, generally described as Type I enzymes. Type II enzymes, and/or Type III enzymes. Type II and Type III enzymes recognize specific sequences of nucleotides within a double stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single stranded nucleic acid, called a "sticky end." In other cases, cleavage will not result in a fragment with an overhang, creating a "blunt end." The methods may comprise use of restriction enzymes that generate either sticky ends or blunt ends.

Once fragmented, the complexes comprising the Argonaute will be purified by incubation with a solid support. For example, if the Argonaute comprises a biotin tag, the solid support will be coated with avidin or streptavidin to bind to the biotin tag.

In some embodiments, once fragmented, the complexes comprising the Argonaute, the target nucleic acid, and/or the designed nucleic acid-targeting nucleic acid, will be purified by incubation with a capture agent. The capture agent will bind to the affinity tag fused to the Argonaute. The capture agent will comprise an antibody. For example, if the affinity tag fused to the Argonaute is a FLAG tag, then the capture agent will be an anti-FLAG-tag antibody.

In some embodiments, the capture agent will be purified with a solid support. For example, if the capture agent comprises a biotin tag, the solid support will be coated with avidin or streptavidin to bind the biotinylated capture agent.

In some embodiments, the designed nucleic acid-targeting nucleic acid will comprise an affinity tag. The affinity tag will comprise a sequence that can bind to a DNA-binding protein. In some embodiments, the DNA-binding protein will comprise an affinity tag.

The DNA-binding protein will be purified with a solid support. The solid support will bind to the affinity tag of the DNA-binding protein. For example, if the DNA-binding protein comprises a biotin tag, the solid support will be coated with avidin or streptavidin to bind the biotinylated capture agent.

In some embodiments, the DNA-binding protein will be immobilized on any of a variety of insoluble support.

In some embodiments of the method, two rounds of purification will be performed. In some instances, a first round will comprise purification with a solid support that will bind to the affinity tag of the capture agent and a second round will comprise purification with a solid support that will bind to the affinity tag of the Argonaute and/or designed nucleic acid-targeting nucleic acid. In some instances, a first round will comprise purification with a solid support that will bind to the affinity tag of the Argonaute and/or the designed nucleic acid-targeting nucleic acid and a second round will comprise purification with a solid support that will bind to the affinity tag of the capture agent.

In some embodiments, the methods of the disclosure will be used for multiplex sequence enrichment. In this embodiment, a plurality of designed nucleic acid-targeting nucleic acids can be contacted with a nucleic acid sample, wherein each nucleic acid-targeting nucleic acid is engineered to target a different target nucleic acid (e.g., sequence in a genome) within the nucleic acid sample.

The captured complexes will comprise a target nucleic acid. The target nucleic acid will be eluted from the Argonaute complex by standard methods including high salt washing, ethanol precipitation, boiling, gel purification, and the like.

The eluted DNA will be prepared tor sequencing analysis by ligation of one or more adaptors. The sequencing libraries will be sequenced as described herein. Sequenced libraries will be analyzed to identify polymorphisms, diagnose a disease, determine a course of treatment for a disease, and/or generate antibody libraries.

Example 18

Sequence Enrichment of Target Nucleic Acid not Bound to a Complex Comprising a Site-Directed Polypeptide In some embodiments, sequence enrichment will be performed with an enxymatically active site-directed Argonaute polypeptide. In some instances, the Argonaute will be enzymatically active. In this instance, the target nucleic acid will not be bound to the Argonaute, but will be excised.

A target nucleic acid will be identified, and designed nucleic acid-targeting nucleic acids will be designed to direct the Argonaute to sequences that flank the target nucleic acid. The sample will he incubated with a complex comprising a designed nucleic acid-targeting nucleic acid and the Argonaute such that the Argonaute will cleave the DNA. at both ends of the target nucleic acid. Upon cleavage of the target nucleic acid, the target nucleic acid will be cleaved from the parent nucleic acid. The cleaved target nucleic acid will be purified (e.g., by gel electrophoresis, size-selective elution from beads, or other carboxyiate-derivatized beads, or by precipitation with appropriate concentrations of salt and PEG to preferentially precipitate larger or smaller DNA).

In some embodiments, sequence enrichment will be performed outside of cells (e.g., cell-free sample). For example, a sample will comprise purified genomic DNA. In some embodiments, sequence enrichment will be performed on a cellular sample (e.g. cells, cell lysate).

If the method is being performed on cells, cells will be lysed. Lysis conditions will be chosen to maintain intact protein-DNA complexes.

In some embodiments, the target nucleic acid to be sequenced will not be bound to a designed nucleic acid-targeting nucleic acid and/or a Argonaute. in this embodiment, the nucleic acid bound to the Argonaute and/or the designed nucleic acid-targeting nucleic acid will be purified away. The purification of the Argonaute will proceed as previously described herein. Briefly, the complexes comprising the Argonaute will be purified by incubation with a solid support. For example, if the Argonaute comprises a biotin tag. the solid support will be coated with avidin or strepiavidin to bind to the biotin tag.

In an alternative embodiment, once fragmented, the complexes comprising the Argonaute, the designed nucleic acid-targeting nucleic acid, and non-target nucleic acid, will be purified by incubation with a capture agent. The capture agent will bind to the affinity tag fused to the Argonaute. The capture agent will comprise an antibody. For example, if the affinity tag fused to the site-directed polypeptide is a FLAG tag, then the capture agent will be an anti-FLAG-tag antibody.

The capture agent will be purified with a solid support. For example, if the capture agent comprises a biotin tag, the solid support will be coated with avidin or streptavidin to bind the biotinylated capture agent.

In some embodiments, the methods of the disclosure will be used for multiplex sequence enrichment. In this embodiment, a plurality of designed nucleic acid-targeting nucleic acids can be introduced into a cell, wherein each designed nucleic acid-targeting nucleic acid is engineered to target a different target nucleic acid (e.g., sequence in a genome). The captured complex will not comprise a target nucleic acid.

The target nucleic acid will comprise, the nucleic acid that is not bound to the complexes comprising the Argonaute. The target nucleic acid can be collected by standard nucleic acid purification methods (e.g., a commercially available PCR purification kit, an agarose gel).

The collected target nucleic acid will be prepared for sequencing analysis (e.g., deep sequencing) by ligation of one or more adapters as described herein. Sequenced target nucleic acid will be analyzed to identify polymorphisms, diagnose a disease, determine a course of treatment for a disease, and/or generate antibody libraries.

Example 19

Sequencing Target Nucleic Acids

The eluted target, nucleic acids will be prepared for sequencing analysis. Preparation for sequencing analysis will include the generation of sequencing libraries of the eluted target nucleic acid. Sequencing analysis will determine the identity and frequency of off-target binding sites of site-directed polypeptides.

Sequence determination will be performed using methods that determine many (typically thousands to billions) nucleic acid sequences in an intrinsically parallel manner, where many sequences are read out preferably in parallel using a high throughput serial process. Such methods can include but are not limited to pyrosequencing (for example, as commercialized by 454 Life Sciences, Inc., Bradford, Conn.); sequencing by ligation (for example, as commercialized in the SOLID™ technology. Life Technology, Inc., Carlsbad, Calif.); sequencing by synthesis using modified nucleotides (such as commercialized in TRUSEQ™ and H1SEQ™ systems by Illumina, Inc., San Diego, Calif., HELISCOPE™ system by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanobails (Complete Genomics, Inc., Mountain View, Calif.); nanopore-based sequencing technologies (for example, as developed by Oxford Nanopore Technologies, LTD, Oxford, UK), capillary sequencing (e.g, such as commercialized in MegaBACE by Molecular Dynamics), electronic sequencing, single molecule sequencing (e.g., such as commercialized in SMRT™ technology by Pacific Biosciences, Menlo Park, Calif.), droplet microfluidic sequencing, sequencing by hybridization (such as commercialized by Affymetrix, Santa Clara, Calif.), bisulfate sequencing, and other known highly parallelized sequencing methods.

In some embodiments, sequencing will be performed by microairay analysis.

Example 20

Generation of Antibody Libraries

The methods disclosed herein will bo used to generate protein libraries (e.g., antibody libraries). Protein libraries will be useful for preparing expression libraries, which will be used for screening proteins (e.g. antibodies) for use in therapeutics, reagents, and/or diagnostics. Protein libraries will also be useful for synthesizing and/or cloning additional antibodies.

Protein libraries will be generated by engineering a nucleic acid-targeting nucleic acid to hybridize to target nucleic acid sequences encoding immunoglobulins. The complexes comprising a Argonaute and the designed nucleic acid-targeting nucleic acid will be purified using methods described herein. In some embodiments, the nucleic acid hybridizing to the designed nucleic acid-targeting nucleic acid will be the target nucleic acid and will, be eiuied and sequenced, using methods described herein. In some embodiments, the nucleic acid hybridizing to the designed nucleic-acid targeting nucleic acid will not be the target nucleic acid. The target nucleic acid will be the nucleic acid that is excised between the cleavage sites of a plurality of complexes (e.g., complexes comprising a site-directed polypeptide and nucleic acid-targeting nucleic acid). The excised target nucleic acid will be purified and sequenced, using methods described herein.

Example 21

Genotyping

The methods disclosed herein will be used to perform Human Leukocyte Antigen (HLA) typing, HLA genes are some of the most polymorphic genes in humans. Understanding the genotypes of these regions will be important for obtaining a good match for tissue and organ transplants.

To perform HLA typing, a designed nucleic acid-targeting nucleic acid will be engineered to hybridize to target nucleic acid sequences in HLA genes. The complexes comprising a Argonaute and the designed nucleic acid-targeting nucleic acid will be purified using methods described herein. In some embodiments, the nucleic acid hybridizing to the designed nucleic acid-targeting nucleic acid will be the target nucleic acid and will be eluted and sequenced, using methods described herein. In some embodiments, the nucleic acid hybridizing to the designed nucleic-acid targeting nucleic acid will not be the target nucleic acid. The target nucleic acid will be the nucleic acid that is excised between the cleavage sites of a plurality of complexes (e.g.. complexes comprising a site-directed polypeptide and nucleic acid-targeting nucleic acid). The excised target nucleic acid will be purified and sequenced, using methods described herein.

Example 22

Argonaute Immunoprecipitation

The disclosure provides methods for nuclease immunoprecipitation and sequencing (NIP-Seq). In some embodiments, the method will comprise a) contacting a nucleic acid sample with an enzymatically inactive Argonaute, wherein the enzymatically inactive Argonaute binds a target nucleic acid, thereby forming a complex, b) capturing the complex with a capture agent, and c) sequencing the target nucleic acid. In some embodiments, the method will further comprise d) determining the identity of the off-target binding site.

In some embodiments, the methods of the disclosure will be performed outside of cells. For example, a sample will comprise purified genomic DNA.

The Argonaute—target nucleic acid complexes will be fixed or cross-linked to form complexes.

The nucleic acid (e.g., genomic DNA) will be treated to fragment the DNA before affinity purification. Fragmentation can be performed through physical, mechanical or enzymatic methods. Physical fragmentation can include exposing a target polynucleotide to heat or to ultraviolet (UV) light. Mechanical disruption may be used lo mechanically shear a target polynucleotide into fragments of the desired range. Mechanical shearing may be accomplished through a number of methods known in the art, including repetitive pipetting of the target, polynucleotide, sonication and nebulization. Target polynucleotides may also be fragmented using enzymatic methods. In some cases, enzymatic digestion may be performed using enzymes such as using restriction enzymes. Restriction enzymes may be used to perform specific or non-specific fragmentation of target polynucleotides. The methods may use one or more types of restriction enzymes, generally described as Type I enzymes, Type II enzymes, and/or Type III enzymes. Type II and Type III enzymes are generally commercially available and well known in the art. Type II and Type III enzymes recognize specific sequences of nucleotide nucleotides within a double stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single stranded DNA, called a "sticky end." In other cases, cleavage will not result in a fragment with an overhang, creating a "blunt end." The methods may comprise use of restriction enzymes that generate either sticky ends or blunt ends.

Once fragmented, the complexes comprising the Argonaute will be purified by incubation with a solid support For example, if the Argonaute comprises a biotin tag, the solid support will be coated with avidin or streptavidin to bind to the biotin tag.

In an alternative embodiment, once fragmented, the complexes comprising the Argonaute, the target nucleic acid, and/or the designed nucleic acid-targeting nucleic acid, will be purified by incubation with a capture agent. The capture agent will bind to the affinity tag fused to the Argonaute. The capture agent will comprise an antibody. For example, if the affinity tag fused to the site-directed polypeptide is a FLAG tag, then the capture agent will be an anti-FLAG-tag antibody.

The capture agent will be purified with a solid support. For example, if the capture agent comprises a biotin tag, the bead will be coated with avidin or streptavidin to bind the biotinylated capture agent.

In some embodiments of the method, two or more rounds of purification will be performed. A first round will comprise purification with a solid support that can bind to the affinity tag of the capture agent and a second round will comprise purification with a solid support that can bind to the affinity tag of the Argonaute and/or designed nucleic acid-targeting nucleic acid. A first round will comprise purification with a solid support that will bind to the affinity tag of the Argonaute and/or designed nucleic acid-targeting nucleic acid and a second round will comprise purification with a solid support that will bind to the affinity tag of the capture agent.

In some embodiments, the method will be used to optimize the binding specificity of a Argonaute by performing the method more than once.

The captured complex will comprise Argonaute and a target nucleic acid. The target nucleic acid will be eluted from the Argonaute complex by standard methods including high salt washing, ethanol precipitation, boiling, gel purification, and the like, The eluted DNA will be prepared for sequencing analysis using standard, methods. The sequencing libraries will be sequenced and analyzed to identify the sequence, and frequency of nuclease-binding sites.

In some embodiments, the method will be performed a plurality of times. In some embodiments, the method further comprises collecting data and storing data. The data can be stored collected and stored on a computer server.

Example 23

Modification of a Target Nucleic Acid with an Effector Protein

A vector comprising an Argonaute, a designed nucleic acid-targeting nucleic acid, and/or an effector protein is introduced into a cell. Once inside the cell a complex is formed comprising the elements encoded in the vector. The designed nucleic acid-targeting nucleic acid is modified with a zinc finger binding sequence. The effector protein binds to the designed nucleic acid-targeting nucleic acid. The zinc finger comprises a non-native sequence (e.g., a fusion), that modifies a target nucleic acid. The non-native sequence is a sequence that modifies the transcription of the target nucleic acid. The non-native sequence is a transcription factor. The transcription factor increases the level of transcription of the target nucleic acid. In some cases, the non-native sequence is a meihylase. The methylase results in increases in methylation of the target nucleic acid. In some cases the non-native sequence is a demethylase. The demethylase results in decreases in methylation of the target nucleic acid. In some cases, the non-native sequence is a Rad51-recruiting peptide. The Rad51-recruiting peptide increases the level of homologous recombination at the target site. In some cases, the non-native sequence is a BCRA-2 recruiting peptide. The BRCA-2-recruiring peptide increases the level of homologous recombination at the target site.

Example 24

Use of an Argonaute as a Biosensor for a Genetic Mobility Event

A vector(s) comprising an Argonaute, a designed nucleic acid-targeting nucleic acid, and/or an effector protein is introduced into a cell The Argonaute and effector proteins are fused to cellular localization sequences (e.g. a nuclear localization signal). Once inside the cell a complex is formed comprising the elements encoded in the vectors). In some instances, two vectors are introduced into the cell. The vector(s) encodes for a first effector protein (zinc finger) that comprises a first inactive portion of a split green fluorescent protein (GFP) and binds to a first nucleic acid-targeting nucleic acid and a second effector protein (a second zinc finger) that comprises a second inactive portion of the split GFP and binds to a second nucleic acid-targeting nucleic acid. The first nucleic acid-targeting nucleic acid is modified with a first zinc finger protein, binding sequence that can be bound by a first zinc finger protein. The second nucleic acid-targeting nucleic acid is modified with a second zinc finger protein binding sequence that can be bound by a second zinc linger protein. In some embodiments, the first zinc finger protein interacts with the first zinc finger protein binding sequence, and the second zinc finger protein interacts with the second zinc finger protein binding sequence. When the first and second designed nucleic acid-targeting nueieic acids direct the Argonaute to bind to two sequences that are in close proximity, the first effector protein and the second effector protein will bring the first inactive portion of the split GFP into contact with the second inactive portion of the split GFP, to generate an active GFP. The designed nucleic acid-targeting nucleic acids of the complex are designed such that one designed nucleic acid-targeting nucleic acid guides the complex to for example, a region at or near the Bcr gene, and another designed nucleic acid-targeting nucleic acid guides the complex to. for example, a region at or near the Abl gene. If a translocation event has not occurred the Bcr gene is on chromsome 22 and the Abl gene is on chromosome 9, and the target nucleic acid sequences are sufficiently far enough apart such that the two inactive portions of the split GFP system are unable to interact, thereby not generating a signal. If a translocation event has occurred, the Bcr gene and the Abl gene are translocated such that the genes are close together. In this instance, the target nucleic acid sequences are sufficiently close enough together such that the two inactive portions of the split GFP system come together to form an active GFP. A GFP signal can be detected by a fluorometer. The signal is indicative of a particular genotype resulting from the genetic mobility event.

Example 25

Use of an Argonaute as a Biosensor for a Genetic Mutation

The system described in Example 24 can also be used to detect the presence of specific mutation within a cell. In this example, a first designed nucleic-acid targeting nucleic acid is chosen to direct the Argonaute to a native sequence located near a mutation, site. The second designed nucleic-acid targeting nucleic acid is chosen to recognize a mutant sequence (e.g., the mutant sequence having been identified by DNA sequencing). The target nucleic acid sequences are sufficiently close enough together such that the two inactive portions of the split GFP system come together to form an active GFP. A GFP signal can be detected by a flourometer. The signal is indicative of a particular genotype Example 26

Use of an Argonaute as as a Therapeutic for Diseases that Comprise a Genetic Mobility Event A vector(s) comprising an Argonaute, a designed nucleic acid-targeting nucleic acid, and/or an effector protein, a nucleic acid comprising a cell-lysis inducing peptide (e.g. Adenovirus death protein) operably linked to a first promoter will also be introduced into the cell. Once inside the cell a complex is formed comprising the elements encoded in the vector(s). In some instances, two vectors are introduced into the cell. The vector (s) encodes for a first effector protein (zinc finger protein sequence) that binds to a first designed nucleic acid-targeting nucleic acid and comprises an activator domain for a first transcription factor that binds to the first promoter and a second effector protein (comprising a second zinc finger protein sequence) that binds to a second designed nucleic acid-targeting nucleic acid and comprises the DNA binding domain for the first transcription factor. The first designed nucleic acid-targeting nucleic acid is modified with a first zinc finger protein binding sequence that can be bound by a first zinc finger protein sequence. The second designed nucleic acid-targeting nucleic acid is modified with a second zinc finger protein binding sequence that can be bound by a second zinc finger protein. In some embodiments, the first zinc finger protein interacts preferentially with the first zinc finger protein binding sequence, and the second zinc finger protein interacts preferentially with the second zinc finger protein binding sequence. If a diseased cell comprises a genome containing a genetic mobility event, when the first and second designed nucleic acid-targeting nucleic acids direct Argonaute to bind to two sequences that are in close proximity, the first effector protein and the second effector protein will bring the activator domain and the DNA-binding domain of the first transcription factor into close proximity. The DNA-binding domain of the first transcription factor can bind to the first promoter operably linked to the cell-lysis inducing peptide, and the proximal activator domain will induce transcription of RNA encoding the cell-lysis inducing peptide. In a non-diseased cell, that does not comprise the genetic mobility event, the DNA-binding domain and the activator domains of the first transcription factor will not be brought into close proximity, and there will be no transcription of the cell-lysis inducing peptide. In this way, the diseased cell is lysed and killed.

The designed nucleic acid-targeting nucleic acids of the complex are designed such that one designed nucleic acid-targeting nucleic acid guides the complex to, for example, a region at or near the Bcr gene, and another nucleic acid-targeting nucleic acid guides the complex to, for example, a region at or near the Abl gene. In a non-diseased cell, a translocation event has not occurred, the Bcr gene is on chromsome 22 and the Abl gene is on chromsome 9, and the target nucleic acid sequences are sufficiently far enough apart such that the two inactive portions of the transcription factor system are unable to interact, and cannot induce transcription of the cell-lysis inducing peptide. In a diseased cell, in which a translocation event has occurred, the Bcr gene and the Abl gene are translocated such that the genes are close together. In this instance, the target nucleic acid sequences are sufficiently close enough together such that the two inactive portions of the transcription factor system come together to induce transcription of the cell-death inducing peptide. Cell-lysis will be dependent upon a particular genotype resulting from the genetic mobility event.

Example 27

Recruiting the Immune System to Attack Diseased Tissue Containing a Genetic Mobility Event or a Genetic Mutation The system described in Example 25 and/or 26 can also be used to direct transcription by the split transcription factor system that will result in the display of an antigen on the cell surface. In some instances, the antigen is a peptide displayed by an MHC class II molecules. In some instances, the antigen is a cell-surface protein that recruits immune effector cells to the site.

Example 28

Detecting Three-Dimensional Position of Nucleic Acids

A vector (s) comprising an Argonaute, a designed nucleic acid-targeting nucleic acid, and/or an effector protein is introduced into a cell. Once inside the cell a complex is formed comprising the elements encoded in the vector(s). Two vectors are introduced into the cell. One vector encodes for an effector protein (e.g., zinc finger) that comprises a first inactive portion of a split affinity tag system. A second vector encodes for an effector protein (e.g., a second zinc finger) that comprises a second inactive portion of the split affinity tag. The designed nucleic acid-targeting nucleic acid of the complexes is modified with a zinc finger protein binding sequence. The effector proteins bind to the modified nucleic acid-targeting nucleic acid. The nucleic acid-targeting nucleic acids are designed to guide the complexes to regions of interest in a three-dimensional nucleic acid structure (e.g., chromatin). If the target sequences are not close together in space, the two inactive portions of the split affinity tag are unable to interact. If the target sequences are close together in space, then the two inactive portions of the split affinity tag can come together to form the whole affinity tag.

The cells are lysed and the cell lysis is incubated with an antibody that binds to the affinity tag. The antibody is purified, thereby purifying the affinity tag and tfie nucleic acid to which the complexes arc bound. The purified nucleic acid is dissociated from the complexes using high salt wash. The dissociated purified nucleic acid is prepared for sequencing analysis, and sequenced. The sequencing results correspond to regions of chromatin that are close together in three-dimensional space. The sequencing results can be used to further understand gene expression and treat disease.

Example 29

Multiplex Genome Engineering

A vector comprising a multiplexed genetic targeting agent comprising nucleic acid modules which comprise a designed nucleic acid-targeting nucleic acid and an nuclease binding sequence is introduced into a cell. In some embodiments, the cell already comprises an Argonaute and an nuclease. In some instances, the cell is contacted with a vector comprising a polynucleotide sequence encoding an Argonaute and a vector comprising a polynucleotide sequence encoding an nuclease. In some instances, the cell is contacted with a vector comprising a polynucleotide sequence encoding both the Argonaute and the nuclease. In some embodiments, the vector comprises a polynucleotide sequence encoding one or more nucleases. In some embodiments, the vector comprises a polynucleotide sequence encoding a multiplexed genetic targeting agent, an Argonaute, and one or more nucleases. The one or more nucleases binds to the one or more nuclease binding sequences in the multiplexed genetic targeting agent. The one or more nucleases cleaves the one or more nuclease binding sequences in the multiplexed genetic targeting agent, thus liberating the individual nucleic acid modules. In some embodiments, the nucleic acid modules comprise all, some, or none, of the nuclease binding sequence.

The liberated nucleic acid modules bind to Argonautes, thereby forming complexes. The complexes are targeted to one or more target nucleic acids. The one or more nucleic acid modules hybridizes to the one or more target nucleic acids. The one or more Argonautes cleaves the one or more target nucleic acids at a cleavage site defined by the nucleic acid module, thus resulting in one or more modified target nucleic acids.

In some embodiments, one or more donor polynucleotides and/or a vectors encoding the same are introduced into the cell. One or more donor polynucleotides are incorporated into the one or more cleaved target nucleic acids, thereby resulting in one or more modified target nucleic acids (e.g., addition). In some instances, the same donor polynucleotide is incorporated into multiple cleavage sites. In some instances, one or more donor polynucleotides are incorporated into multiple cleavage sites. In some instances, no donor polynucleotide and/or vector encoding the same are introduced into the cells. In these instances, the modified target nucleic acid can comprise a deletion.

Example 30

Method of Stoichiometric Delivery of RNA to a Cell

In some embodiments, the disclosure provides for a method for stoichiometric delivery of nucleic acids to the nucleus of a cell. In some embodiments, three stoichiometrically deliverable nucleic acid are used: one encoding for Argonaute, one encoding for a designed nucleic-acid targeting nucleic acid, and one encoding a nuclease. Each of the three nucleic acids comprises a DNA-binding protem-binding site. A vector encoding the three stoichiometrically deliverable nucleic acids is introduced into the cell. Three different vectors encoding one of each of the three stoichiometrically deliverable nucleic acids is introduced the cell. Two vectors are introduced into the cell, wherein one of the two vectors encodes for two stoichiometrically deliverable nucleic acids and one of the two vectors encodes for one stoichiometrically deliverable nucleic acid. Any of the vectors can encode the tandem fusion polypeptide.

In some embodiments, the method provides for a tandem fusion polypeptide. The fusion polypeptide comprises three DNA-binding proteins. The three DNA-binding proteins are separated by a linker. The three DNA-binding proteins bind to the DNA-binding protein binding sites on each of the three nucleic acid molecules, thereby forming a complex.

In some embodiments, the complex is formed outside of a cell and introduced into the cell. The complex is formed by mixing the three stoichiometrically deliverable nucleic acids and the fusion protein and letting the reaction occur to allow binding between the tandem fusion polypeptide and three DNA-binding protein-binding sites. The complex is introduced by injection, etectroporation, transection, transformation, viral transduction, and the like. Inside the cell, some of the nucleic acids of the complex are translated. In some embodiments, the resulting translation, products are the nuclease and NLS—Argonaute (e.g., Argonaute comprising an NLS. The NLS may not have to be at the N-terminus), The nuclease cleaves the DNA-binding protein-binding she on the nucleic acid encoding the nucleic acid-targeting nucleic acid, thereby liberating the nucleic acid-targeting nucleic acid from the tandem fusion polypeptide. NLS—Argonaute binds the liberated nucleic acid-targeting nucleic acid, thereby forming a unit. This unit translocates to the nucleus. Inside the nucleus, the unit is guided to a target nucleic acid that hybridizes with the the designed nucleic acid-targeting nucleic acid. The Argonaute of the unit cleaves the target nucleic acid. The cleavage of the target nucleic acid by Argonaute is referred to as genome engineering.

Example 31

Seamless Selection of Genetically Modified Cells

A plurality of cells is contacted with a vector comprising sequences encoding a polypeptide homologous to Argonaute, a designed nucleic acid-targeting nucleic acid and a donor polynucleotide. In some cases, one or more of the sequences encoding the Argonaute, the designed nucleic acid-targeting nucleic acid and the donor polynucleotide are located on different vectors. The cells are transfected with the vector. In some instances, the cells are infected with a virus carrying the vector. In some instances, the cell already comprises an Argonaute and the vector does not encode this polypeptide. In some instances, the vector only encodes the donor polynucleotide. The donor polynucleotide comprises sequences encoding a genetic element of interest and a reporter element. The reporter element comprises designed nucleic acid-targeting nucleic acid sequences, an Argonaute and a fluorescent protein. The designed nucleic acid-targeting nucleic acids guide Argonaute to a target nucleic acid (e.g. a site in the host cell genome), resulting in a double stranded DNA break of the target nucleic acid and insertion of the donor polynucleotide. Insertion of the donor polynucleotide is screened for by screening for the reporter. In some cases, screening comprises fluorescence-activated cell sorting. Screening comprises multiple selection methods. Argonaute and/or the designed nucleic acid-targeting nucleic acids are controlled by an inducible promoter After selecting a population of cells that comprise the reporter signal, the reporter element is removed by activating the inducible promoter, which transcribes the designed nucleic acid-targeting nucleic acids and the Argonauts. The transcribed designed nucleic acid-targeting nucleic acids and the transcribed Argonautc can form complexes. One complex can be targeted to the 3' end of the reporter element of the donor polynucleotide. One complex can be targeted to the 5' end of the reporter element of the donor polynucleotide. The 3' and 5' ends of the reporter element can be cleaved- The cleaved target nucleic acid can be rejoined by cellular mechanisms, thereby resulting in an in-frame nucleic acid sequence encoding the same nucleic acid sequence as prior to insertion of the donor polynucleotide. In this way, the reporter element is seamlessly inserted and removed from cells.

Example 32

Sequencing Analysis Systems

Figure 17:
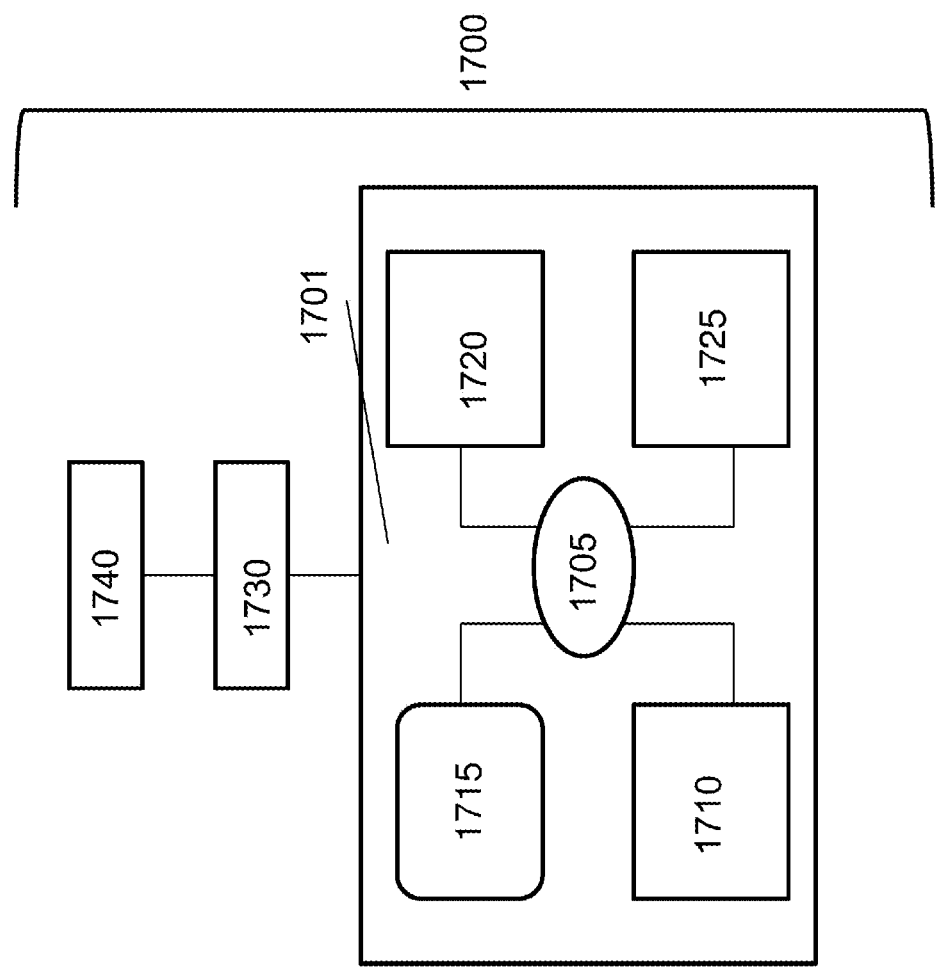
FIG. 17 depicts a system for storing and sharing electronic information.

FIG. 17 depicts a system that is configured to implement the methods of the disclosure The system can include a computer server ("server") that is programmed to implement the methods described herein. FIG. 17 depicts a system 1700 adapted to enable a user to detect, analyze, and communicate sequencing results of for example, mjclease-iargetcd enriched nucleic acids, sequenced target nucleic acids, data concerning the methods of the disclosure, diagnose a disease, genotype a patient, make a patient-specific treatment decision, or any combination thereof The system 1700 includes a central computer server 1701 that is programmed to implement exemplary methods described herein. The server 1701 includes a central processing unit (CPU, also "processor") 1705 which can be a single core processor, a multi core processor, or plurality of processors for parallel processing. The server 1701 also includes memory 1710 (e.g. random access memory, read-only memory, flash memory); electronic storage unit 1715 (e.g. hard disk); communications interface 1720 (e.g. network adaptor) for communicating with one or more other systems; and peripheral devices 1725 which may include cache, other memory, data storage, and/or electronic display adaptors. The memory 1710, storage unit 1715, interface 1720, and peripheral devices 1725 are in communication with the processor 1705 through a communications bus (solid lines), such as a motherboard. The storage unit 1715 can be a data storage unit for storing data. The server 1701 is operatively coupled to a computer network ("network") 1730 with the aid of the communications interface 1720. The network 1730 can be the Internet, an intranet and/or an extranet, an intranet and/or extranet that is in communication with the Internet, a telecommunication or data network. The network 1730 in some cases, with the aid of the server 1701, can implement a peer-to-peer network, which may enable devices coupled to the server 1701 to behave as a client or a server. The microscope and micromanipulator can be peripheral devices 1725 or remote computer systems 1740.

The storage unit 1715 can store files, such as sequencing results, target binding sites, personalized genetic data, genotypes, images, data anlysis of images and/or sequencing results, or any aspect of data associated with the disclosure.

The server can communicate with one or more remote computer systems through the network 1730. The one or more remote computer systems may be, for example, personal computers, laptops, tablets, telephones. Smart phones, or personal digital assistants.

In some situations the system 1700 includes a single server 1701. In other situations, the system includes multiple servers in communication with one another through an intranet, extranet and/or the Internet.

The server 1701 can be adapted to store sequencing results, target binding sites, personalized genetic data, and/or other information of potential relevance. Such information can be stored on the storage unit 1715 or the server 1701 and such data can be transmitted through a network.

Methods as described herein can be implemented by way of machine (or computer processor) executable code (or software) stored on an electronic storage location of the server 1701, such as, for example, on the memory 1716, or electronic storage unit 1715. During use, the code can be executed by the processor 1705. In some cases, the code can be retrieved from the storage unit 1715 and stored on the memory 1710 tor ready access by the processor 1705. In some situations, the electronic storage unit 1715 can be precluded, and machine-executable instructions are stored on memory 1710. Alternatively, the code can be executed on a second computer system 1740.

Aspects of the systems and methods provided herein, such as the server 1701, can be embodied in programming. Various aspects of the technology maybe thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landlinc networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such, as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications, Common forms of computer-readable media therefore include, for example: a floppy disk, a flexible disk, hard disk, magnetic tape, any other magnetic medium, a CD-ROM DVD, DVD-ROM, any other optical medium, punch cards, paper tame, any other physical storage medium with patterns of holes, a RAM, a ROM, a PROM and BPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

Example 33

Array-Based Sequencing Using an Argonaute

A nucleic acid sample is ligated with a nucleic acid lag comprising a designed nucleic acid-targeting uc13eic acid and a detectable label Together, the nucleic acid sample ligated to the nuclei acid tag preferred to as a tagged lest sample. The tagged test sample is contacted to a mieroarray comprising immobilized oligonucleotides. The immobilized oligonucleotides are a double stranded nucleic acid library. The oligonucleotides comprise a detectable label (e.g., fluorescent, label). The individual members of the tagged test sample hybridize to the oligonucleotides to which they share enough complementarity to facilitate hybridization. The amount of hybridization can be quantified by comparing the intensities of the two detectable labels from the sample library and the immobilized oligonucleotides. For example, hybridized oligonucleotides can display two detectable labels (that from the sample library and the oligonucleotide). Unhybridized oligonucleotides can display one detectable label (that from the oligonucleotide). The hybridized probes are contacted with Argonauts. Argonauts cleaves the oligonucleotides in the microarray that have hybridized with members of the tagged test sample. Cleavage by the Argonaute allows the hybridized members of the tagged test sample to be removed. After cleavage by the Argonaute, only unhybridized oligonucleotide detectable labels remain on the microarray. The remaining detectable label is quantified. The quantification of the remaining detectable labels is correlated to which .sequences were represented in the nucleic acid sample and which were not (e.g., by position mapping). Oligonucleotides that do not display a remaining detectable label correspond to sequences that were represented in the nucleic acid sample. Oligonucleotides that display a remaining detectable label correspond to .sequences that were not represented in the nucleic acid sample.

Example 34

Determining a Cell Fate with a Tagged Cell

This example describes how to track a cell developing from a cell lineage. A hematopoietic stem cell (e.g., a hemocytoblast) is contacted with an Argonaute. a designed nucleic acid-targeting nucleic acid, and a donor polynucleotide. The Argonaute of the disclosure and designed nucleic acid-targeting nucleic acid form a complex and target a region of the hematopoietic genome for cleavage. Once cleaved, the donor polynucleotide is inserted into the cleaved site in the hepatopoietic cell's genome. The hematopoietic stem cell is induced to differentiate through normal differentiation processes. At different stages of differentiation the sample comprising the differenfitated hematopoietic cells can be assayed for the presence of the donor polynucleotide. In this way, the differentiation process of a cell can be tracked.

Example 35

Clone Double-Stranded Oligonucleotide Encoding a Designed Nucleic Acid-Targeting Nucleic Acid into a Linearized Vector This example describes how to generate a double-stranded oligonucleotide encoding a portion of designed nucleic acid-targeting nucleic acid (e.g., a spacer) and insert it into a linearized vector The linearized vector or a closed supercoiled vector comprises a sequence encoding a site-directed polypeptide (e.g., Cas9), a promoter driving expression of the sequence encoding the site-directed polypeptide (eg., CMV promoter), a sequence encoding a linker (e.g., 2A), a sequence encoding a marker (e.g., CD4 or OFP), a sequence encoding portion of a nucleic acid-targeting nucleic acid, a promoter driving expression of the sequence encoding a portion of the nucleic acid-targeting nucleic acid, and a sequence encoding a selectable marker (e.g., ampicillin), or any combination thereof.

Equal amounts of two single-stranded oligonucleotides are annealed together (e.g., 50 micromolar). The two single-stranded oligonucleotides can hybridize together. At least one of the two single-stranded oligonucleotides is complementary to a target nucleic acid. At least one of the two single-stranded nucleotides comprises a 3' overhang sequence comprising the sequence 5'-GTTT-3'. At least one of the two single-stranded oligonucleotides comprises a 3' overhang comprising the sequence 5'-CGGTG-3'. In some instances, one of the two single-stranded oligonucleotides comprises a 5'-GTTT-3' overhang and the other of the two single-stranded oligonucleotides comprises a 5'-CGGTG-3'. Annealing is performed in an annealing buffer comprising at least 10 mM tris HCl pH 8.0, 1 mM EDTA, pH 8.0, and 100 mM NaCl. Annealing is performed by heating the oligonucleotide mixture at 95° C. for 3-5 minutes, removing the oligonucleotide mixture from the heating source, and allowing the mixture to cool to roomtemperature for 5-10 minutes. The double-stranded oligonucleotide mixture is centrifuged gently. After annealing the mixture may be stored at 4° C. or −20° C. The mixture, now of double-stranded oligonucleotides, is diluted to prepare two stock solutions of 500 nanomolar and 5 nanomolar. The stock solutions are prepared by diluting the oligonucleotide mixture in water.

The double-stranded oligonucleotide (dsOligonucleotide) is ligated into a linearized vector. The linearized vector comprises a sequence encoding an Argonaute of the disclosure, a marker protein (e.g., orange fluorescent protein), and/or a sequence encoding a nucleic acid-targeting nucleic acid, wherein the linearized vector is linearized at a region of the sequence encoding the nucleic acid-targeting nucleic acid, such that the sticky ends generated match the overhang ends of the dsOligonucleotide. The ligation reaction can comprise 1× ligation buffer (e.g., 50 mM Tris-HCl pH 7.6, 5 mM MgCl$_2$, 1 mM ATP, 1 mM DTT, and/or 5% PEG 8000), 30 nanogram linearized vector, 5 nM dsOligonucleotide, and DNA ligase (e.g., 4 microliters 5× ligation buffer, 2 microliters linearized vector at 15 nanogram/microliter, 2 microliters 5 nanomolar dsOligonucleotide. 11 microliters water, 1 microliter T4 DNA ligase). The reaction is mixed. The reaction is incubated at room temperature for 10 minutes-2 hours. The reaction is placed on ice and transformed into competent cells.

Transformation into competent cells comprises transforming into chemically competent TOP10 *E. coli* cells. Competent cells are thawed on ice. 3 microliters of the reaction mixture is added to the competent cells and mixed gently. The cells are incubated on ice for 10-30 minutes. The ceils are heat-shocked for 30 seconds at 42° C. The cells are transferred to ice for 2 minutes. 250 microliters of medium (SOC or LB) is added to the cells. The cells are shaked at 200 rpm for 1 hour at 37° C. The cells are then spread on an agar plate comprising 100 micrograms/milliliter ampicillin and stored overnight at 37° C.

The transformants are analyzed. For example, the transformants are analyzed to determine the identity of the dsOligonucleotide ligated into the vector, and/or confirm the ligation is not a false positive. To analyze transformants, colonies are picked and cultured overnight in LB medium comprising 100 micrograms/milliliter amplicillin at 37° C.The plasmid comprising the site-directed polypeptide and dsOligonucleotide is isolatd (e.g., by miniprep kit). A sequencing reaction is performed on the isolated plasmid. The sequencing rection utilizes a sequencing primer that is designed to sequence the dsOligonucleotide (e.g., the sequencing primer is a U6 sequencing primer that binds to the U6 promoter which is located just upstream of the sequence encoding the dsOligonucleotide.

Once a desired dsOligonucleotide insertion is identified, the piasmid can be stored at −20° C. or in a glycerol stock at −80° C. To make a glycerol stock, the original colony comprising the desired piasmid is streaked on an agar plate comprising 100 micrograms/milliliter ampicillin and incubated overnight at 37° C. A single colony is isolated grown in LB comprising 100 micrograms/milliliter ampicillin until the culture reaches stationary phase. The culture is mixed with glycerol and flash frozen in liquid nitrogen (e.g., 0.85 mL culture is mixed with 0.15 mL glycerol).

The purified piasmid comprising the desired dsOligo-nucleotide is inserted into a cell line (e.g., mammalian cell line, HeLa) by transaction. To transfect the plasmid, the plasmid is purified at high concentrations using for example, a maxi prep kit. The plasmid is transfected with lipid-based buffer (e.g., Lipofectamine 2000) into cells which are plated at 70% conflueney. 3 micrograms of the vector is transfectcd into the cells.

Example 36

Nanoparticle Delivery of an Designed Nucleic Acid-Targeting Nucleic Acid

A nanoparticle encapsulating a nucleic acid encoding a designed nucleic acid-targeting nucleic acid and an Argonaute of the disclosure will be prepared, Nanoparticles will be prepared by mixing DOPE, Chol, DSPE-PEG and C$_{16}$mPEG-Ceramide at a molar ratio of 18:60:20:1:1 in 10 mL of 90% elhanol (total lipid 30 μmole). The nucleic acid will be dissolved in 10 ml, of 20 mM Tris buffer (pH 7.4-7.6). After being heated to 37° C., the two solutions will be mixed together through a duel syringe pump and the mixed .solution will be subsequently diluted with 20 ml, of 20 mM Tris buffer (300 mM NaCl, pH 7.4-7.6). The mixture will be incubated at 37° C. for 30 minutes and dialysed in 10 mM PBS buffer (138 mM NaCl, 2.7 mM KCL pH 7.4). Stable particles will be obtained after the removal of elhanol from the mixture by dialysis. The nanoparticle solution will be concentrated by centrifugation at 3,000 rpm and a temperature of 4° C. The concentrated suspension wiii be collected after a given time and will be sterilized by filtration through a 0.22 μm syringe filter (Millex-GV, Millipore, USA). A homogeneous suspension of the nanopariicles comprising the nucleic acid encoding the designed nucleic acid-targeting nucleic acid and the Argonaute will be obtained.

The nanoparticles will be contacted to a cell. The nanoparticle will enter the cell. Inside the cell, the nanoparticle will release the nucleic acid encoding the designed nucleic acid-targeting nucleic acid and the Argonaute of the disclosure. The nucleic acid will be transcribed and/or translated to produce a designed nucleic acid-targeting nucleic acid that binds to an Argonaute protein of the disclosure, thereby forming a complex. The complex will target a target nucleic acid that hybridizes with the designed nucleic acid-targeting nucleic acid. The complex will cleave the target nucleic acid.

In some instances, the nanoparticle will further comprise a nucleic acid encoding a donor polynucleotide. When the target nucleic acid is cleaved by the site-directed polypeptide, the donor polynucleotide will be inserted into the site of the cleaved target nucleic acid.

Example 37

Strains, Plasmids, and Oligonucleotides Used to Determine That Argonaute can Cleave Double-Stranded Target Nucleic Acid

TABLE 1

*T. thermophilus* and *E. coli* strains used.

| Strain | Abbreviation | Description |
| --- | --- | --- |
| *T. thermophilus* HB27 | HB27, wild-type | ATCC BAA-163/DSM 7039/NBRC 101085 |
| *T. thermophilus* HB27$^{EC}$ | HB27Spain or HB27$^{EC}$ | TtAgo::TtAgoISTth7 and multiple SNPs, selected for enhanced competence |
| *T. thermophilus* HB27 ΔAgo | HB27ΔAgo, knock out | ΔAgo |
| *T. thermophiles* HB27 ΔAgo::strep(II)-Ago | HB27ΔAgo::strep (II)-Ago | HB27ΔAgo complemented with strep(II)-tagged TtAgo gene and kanamycin marker insert |
| *E coli* Rosetta DE3 | *E. coli* Rosetta | F ompT hsdS$_B$(r$^-_B$ m$^-_B$) gal dcm |
| *E. coli* KRX | *E. coli* KRX | [F, traD36, ΔompP, proA$^+$B$^+$, lacI$^q$, Δ(lacZ)M15] Δompl-, endA1, recA1, gyrA96 (Nalr), thi-1, hsdR17 (r$_K$− · m$_K$+), e14-(McrA−), relA1, supE44, Δ(lac-proAB), Δ(rhaBAD)::T7 RNA polymerase |

TABLE 2

Plasmids and dsDNA fragments used

| Plasmid | Description | Restriction sites | Primers |
| --- | --- | --- | --- |
| pRARE | *E. coli* Rosetta (DE3) plasmid, encodes rare tRNAs, Cam$^R$ | | |
| pET-52b$^{(+)}$ | T7 RNA polymerase based expression vector, Amp$^R$ | | |
| pWUR627 | *T thermophilus* HB8 TtAgo with N-term. Strep(II)- tag in pET-52b(+) Expression vector for Strep(II)-FtAgo | Kpnl Notl | Ago(fw) Ago(rv) |
| pWUR641 | pWUR627, TtAgo active site residue codon mutated (D546A) | — | BG3456 BG3457 |
| pWUR642 | pWUR641, TtAgo active site residue codon mutated (D478A) Expression vector for Strep(II)-tAgoD478AD546A | — | BG3454 BG3455 |
| pCDF-1b | T7 RNA polymerase based expression vector, Sm$^R$ | | |
| pWUR702 | Strep(II)-TtAgo insert from pWUR627inserted in pCDF-1 b Expression vector for Strep(II)-TtAgo | Avrll Ncol | BG4207 BG4208 |
| pWUR703 | Strep(II)-TtAgoD478AD546A insert from pWUR642 inserted in pCDF-1 b Expression vector for Strep(II)-TtAgoD478AD546A | Awll Ncol | BG4207 BG4208 |
| pUC18 | Amp$^R$ | | |
| pWUR673 | 2.4 kb downstream sequence of TtAgo inserted in pUC18 | Xbal EcoRl | BG3528 BG3529 |

TABLE 2-continued

Plasmids and dsDNA fragments used

| Plasmid | Description | Restriction sites | Primers |
|---|---|---|---|
| pWUR674 | 1 kb upstream sequence of TtAgo inserted in pWUR673 | Hindlll Sall | BG3524 BG3525 |
| pWUR675 | TtAgo with N-terminal Strep(II)-tag inserted in pWUR674 | Sall Xbal | BG3526 BG3527 |
| pWUR676 | Kan ® marker with pSLPa promoter inserted in pWUR675 | Xbal Xbal | BG3563 BG3564 |
| pK18 | Recombination vector | | |
| pWUR701 | Insert from pWUR674 transferred to pK18 | Hindlll EcoRI | |
| pMHPnqosGFP | E. coli/T. thermophilus shuttle vector, Hyg$^R$, sGFP under control of Pnqo promoter | | |
| pMK184 | E. coli/T. thermophilus shuttle vector, Kan$^R$ | | |
| pFU98 | pSC101 oh, rbs-IuxCDABE, Cam$^R$ | | |
| pWUR677 | pFU98, Care marker replaced by Hye marker | Sacl Nhel | BG3870 BG3871 |
| dsDNA target A | Double stranded DNA oligonucleotide, 15% GC- content target region 92 bp with Notl and Sall sticky ends | | BG4262 BG4263 |
| dsDNA target B | Double stranded DNA oligonucleotide, 58% GC- content target region 92 bp with Notl and Sall sticky ends | | BG4264 BG4265 |
| pWUR704 | pWUR677, rbs-IuxCDABE replaced by dsDNA target A | Notl Sall | BG4262 BG4263 |
| pWUR705 | pWUR677, rbs-IuxCDABE replaced by dsDNA target B | Notl Sall | BG4264 BG4265 |

TABLE 3

Oligonucleotides used.

| Experiment | Primers | Sequence (5'-3') | Description, restriction sites |
|---|---|---|---|
| Genomic mutants | BG3524 | AAAAAAAAGCTTCCTCAACGGGGAGGT TC CGGA (SEQ. ID NO: 1) | upstream region TtAgo (fw) Hindlll |
| | BG3525 | AAAAAAGTCGACGCTCAGATTTGCATA GG AGCTGC (SEQ. ID NO: 2) | upstream region TtAgo (rv) Sall |
| | BG3526 | AAAAAAGTCGACATGGCAAGCTGGAGC C ACCCG (SEQ. ID. NO: 3) | Strep(II)-tag TtAgo(fw) Sall |
| | BG3527 | AAAAAATCTAGACTAAACGAAGAAGA GCT TTTCCCG (SEQ. ID. NO: 4) | Strep(II)-tag TtAgo(rv) Xbal |
| | BG3528 | AAAAAATCTAGATGCCCAAGCGGGGCG G AACC (SEQ. ID. NO: 5) | downstream region TtAgo (fw) Xbal |
| | BG3529 | AAAAAAGAATTCGGTCAATCCGCCCCG CT TCCA (SEQ. ID. NO: 6) | downstream region TtAgo (rv) EcoRI |
| | BG3563 | GGCCGTCTAGACCCGGGAGTATAACAG A AACCTT (SEQ. ID. NO: 7) | PspIA-Kan$^R$-stop (fw) Xbal |
| | BG3564 | GCGCGTCTAGATCAAAATGGTATGCGT TT TGACAC (SEQ. ID. NO: 8) | PsIpA-Kan$^R$-stop (rv) Xbal |
| Expression vectors TtAgo | Agofw | GCGCGCGGTACCAGATGAACCACCTTG G AAAAACGG (SEQ. ID. NO: 9) | T. thermophilus HB8 TtAgo (fw) Kpnl |
| | Agorv | GCGCGCGCGGCCGCGAATTCCTAAACG A AGAAGCTTTTCCC (SEQ. ID. NO: 10) | T. thermophilus HB8 TtAgo (rv) Notl |
| | BG4207 | GCGCGCACATGTCAAGCTGGAGCCACC C GCAG (SEQ. ID. NO: 11) | Strep(II)TtAgo (FW) Pcil |
| | BG4208 | GCGCGCCCTAGGTTAATTAGTGGTGGT G ATGG (SEQ. ID. NO: 12) | Strep(II)TtAgo (rv) Awll |
| Site directed mutagenesis of TtAgo gene | BG3454 | GGCGGAGCTCGCCGTGGGCTIGCCGC CGGCGGAAGGGAGTCCTTTCG (SEQ.ID. NO. 13) | HB8 Ago D478A (fw) |
| | BG3455 | CGAAAGGACTCCCTTCCGCCGGCGGCA A AGCCCACGGCGAGCTCCGCC (SEQ. NO. ID. 14) | HB8 Ago D478A (rv) |
| | BG3456 | CCCGGGTCCTCCTCCTTCGGGCCGGCCG CGTGCCCCAGGACGAG (SEQ. ID. NO: 15) | HB8 Ago D546A (fw) |

TABLE 3-continued

Oligonucleotides used.

| Experiment | Primers | Sequence (5'-3') | Description, restriction sites |
|---|---|---|---|
| | BG34 57 | CTCGTCCTGGGGCACGCGGCCGGCCCG AAGGAGGAGGACCCGGG (SEQ. ID NO: 16) | HB8 Ago D546A (rv) |
| Target sequences | BG42 62 | GGCCAtttaattaaattaaAAGCTTGAATGCaatat ttatttaaaaatttataCGAGGTAGTAGGTTGTAT A GTatattaaattatttaaatataaaG (SEQ. ID. NO. 17) | Low GC-content target oligonucleotide 'FW-target' |
| | BG42 63 | TCGACtttatatttaaataatttaatatACTATACA ACCTACTACCTCGtataaattttaaataaatattG CATTCAAGCTTttaatttaattaaat (SEQ. ID. NO. 18) | Low GC-content target oligonucleotide 'RV-target' |
| | BG42 64 | GGCCaggtccaccatgcgtAAGCTTGAATGCcgg ccagcccaagggctctgcaCGAGGTAGTAGGTTG TATAGTtgctggcaggcgtaggtctaagcG (SEQ. ID. No: 19) | High GC-content target oligonucleotide FW-target' |
| | BG42 65 | TCGACgcttagacctacgcctgccagcaACTATACA ACCTACTACCTCGtgcagagcccttgggctggccg GCATTCAAGCTTacgcatggtggaccT (SEQ. ID. NO: 20) | High GC-content target oligonucleotide RV-target' |
| Guide sequences | BG34 66 | P-TGAGGTAGTAGGTTGTATAGT(SEQ. ID. NO: 21) | FW-guide, based on let-7 miRNA |
| | BG40 17 | P-TTATACAACCTACTACCTCGT (SEQ. ID NO: 22) | RV-guide, based on reverse complement of let-7 miRNA |

Example 38

Figure 19:
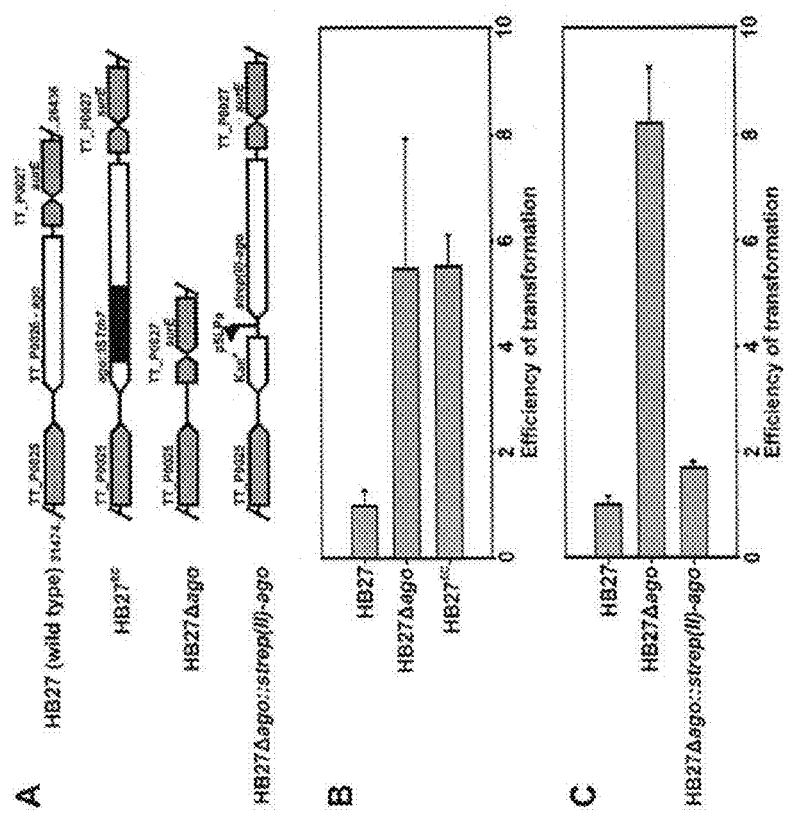
FIG. 19A shows diagrammatic representations of pAgo-encoding genome fragments of *T. thermophilus* HB27 (wild type strain) and derivatives thereof referred to in the exemplification.
FIG. 19B shows pMK184 plasmid transformation efficiency of strain HB27 (wild-type) and derivatives thereof (ago gene knock out and insertion mutant with insertion sequence in the ago gene) normalized to the transformation efficiency of strain HB27.
FIG. 19C shows pMHPnqosGFP plasmid transformation efficiency of strain HB27 and derivatives thereof (ago gene knock out and knock out with TtAgo gene restored), normalized to the transformation efficiency of strain HB27.

T. thermophilus Argonaute (TtAgo) Descreases Plasmid Transformation Efficiency TtAgo was shown to decrease ptasmid transformation frequency of T. themophilus indicating a role in defence against invading DNA. T. themophilus is naturally competent, i.e. it encodes membrane-embedded machinery thai imports extracellular DNA into the cytoplasm. A derivative of the T. themophilus HB27 wild type strain with an insertion sequence in the ago gene which affects its functional expression caw have enhanced efficiency for take up of plasmid DNA. The HB27-Spain strain (also referred to as HB27$^{EC}$) has multiple point mutations. Comparison of the transformation efficiencies of the T. themophilus HB27 wild type strain (ATCC BAA-163/DSM 7039/NBRC 101085; referred to further herein as HB27) and the same strain in which the ago gene was knocked out (strain H827ΔAgo) was performed using two E.coli-T. themophilus shuttle vectors with different selection markers, one with KanR and one with Hyg$^R$. The genomes of the various T. themophilus strains which were employed are shown in FIG. 19A. The transformation efficiency of the knock out strain was several fold higher compared to the wild type strain with both plasmids as shown in FIG. 19B-C. When a strep-tagged TtAgo gene was inserted into the knock out strain with a kanamycin marker (HB27ΔAgol:strep(11)-Ago), the phenotype of the wild type was partially restored (see FIG. 19C).

Preparation of the Wild Type Derivative Strains

HB27 genomic DNA including mcgaplasmid pTT27 was purified using the FASTDNA® SPIN Kit for Soil (MP Biomedicals). The genomic regions directly upstream (1 kb) and downstream (2.4 kb) of the TtAgo gene (TT_P0026) were PCR amplified from T. themophilus HB27 genomic DNA. These genomic regions contained pTT27 base positions 26047-25061 (upstream sequence) and 22996-20583 (downstream sequence). The amplified DNA was cloned into the pUC18 vector (Thermoscientiflc). The insert was transferred to pK18 forming pWUR701, HB27 was grown to an OD$_{600}$ of 0.4 in TTH-medinm (0.8% (w/v) Bactotryptone. 0.4% (w/v) yeast extract, 51.3 mM NaCI. pH to 7.5 with NaOH, dissolved in mineral water (Evian)). 0.5 mL of the culture was transferred to a new tube and naturally transformed by addition of 1 µg plasmid pWUR701. The culture was incubated o/n in a shaker incubator at 65° C. and then plated on TTH-plates with 30 µg/mL kanamycin. Cells were repetitively streaked on non-selective TTH-plates and grown in non-selective TTH-medium until Kan$^R$ was lost. Genomic DNA of Kan$^s$ cells was purified using the FASTDNA® SPIN Kit for Soil (MP Biomedicals) and loss of the TtAgo gene was confirmed by PCR-arnplification from genomic DNA and sequencing of the target region. This strain is named HB27ΔAgo, or knock-out strain.

The gene encoding Strep(II)-tagged TtAgo protein and Kan$^R$ marker with upstream pSLPa promoter were PCR amplified from pWUR627 and pMK, respectively. PCR products were cloned into a pWUR676 vector as indicated in Table 2. Hindlll-linearized pWUR676 was used to transform HB27AAgo as described above. This strain is named HB27 ΔAgo::Strep(II)-Ago (HB27ΔAgo with re-insertion of a TtAgo gene with N-terminal Strep(II)-tag and insertion of a Kan$^R$ marker). Genomic DNA was purified using the FASTDNA® SPIN Kit for Soil (MP Biomedicals) and insertion of the Strep(II)-TtAgo-Kan$^R$ cassette was confirmed by PCR-amplification from genomic DNA and sequencing of the target region.

Plasmid Transformations

The transformation efficiencies of the following two plasmids were looked at in different strains: pMK184 (an E.coli/T. thermophilus shuttle vector with KanR; and µMHPnqosGFP (an E.coli/T. thermophilus shuttle vector with HygR. sGFP under control of the Pnqo promoter.

*T. thermophilus* strains were cultivated in TTH-medium (0.8% (w/v) Bacto-tryptone, 0.4% (w/v) yeast extract, 51.3 mM NaCl, pH to 7.5 with NaOH. dissolved in mineral water (Evian)) in a 65° C. shaker incubator until an $OD_{600}$ of 0.4 was reached. The culture was diluted 1:1 in pre-warmed TTH-medium and incubated for another hour at 65° C. 0.5 mL of the culture was transferred to a new tube which was incubated at 65° C. without shaking for 30 min. 10Ong of plasmid was added and the mixture was incubated 4 h at 65° C. without shaking after which it was serial diluted and plated on TTH-plates (TTH-medium solidified with 1.5% agar), TTH-hygromycin plates or TTH-kanamycin plates (TTH-plates supplied with 100 pg/mL hygromycin or 50 pg/mL kanamycin. After 48 h of incubation at 65° C., colonics were counted. Competence was determined as the amount of $Kanamycin^R$ or $Hygromycin^R$ CFU (colony forming units counted on selective plates) per µg DNA, per total CFU (counted on non-selective plates). To show relative competence, HB27 wild-type transformation was set to 1 while other strain competencies were normalized to this.

Example 39

Strep(II) tagged-TtAgo Co-Purified with Nucleic Acid-Targeting Nucleic Acids of 13-25 nt when Expressed in *E. Coli*

Figure 21:
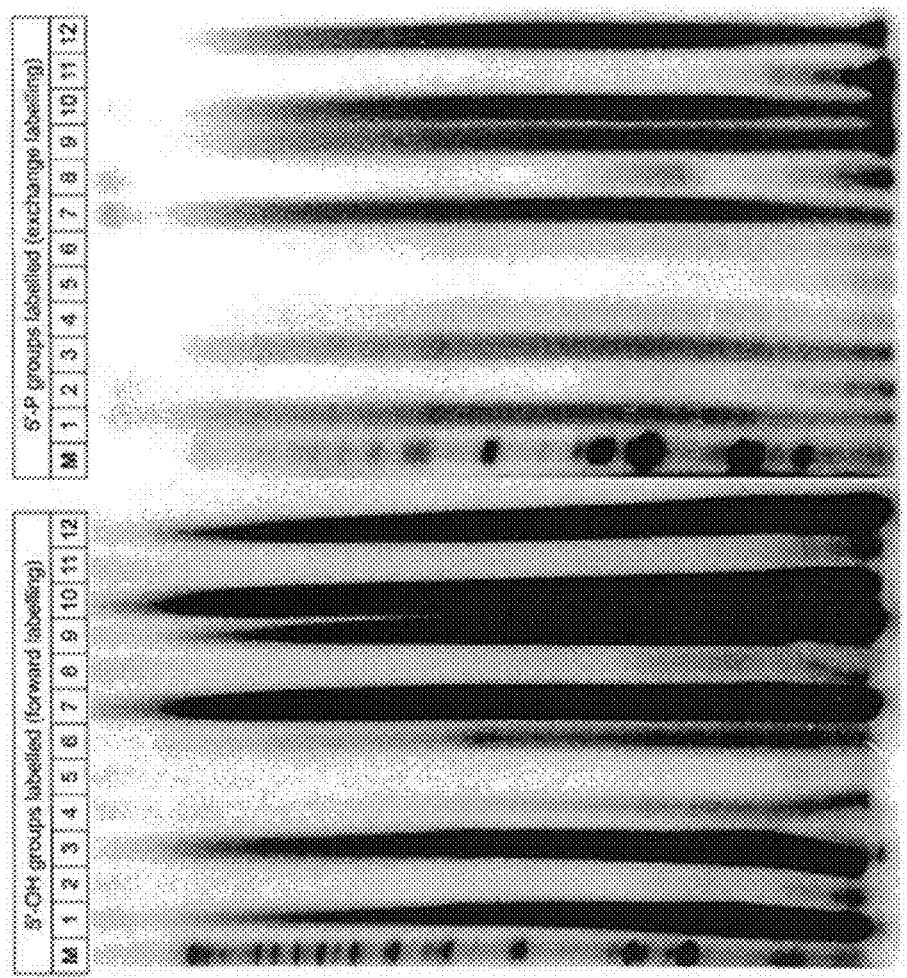
FIG. 21 depicts nucleic acids that co-purified with TtAgo resolved on 15% polyacrylamide gels. Left-hand gel: nucleic acids forward labelled with T4 PNK. Right-hand gel: nucleic acids exchange labelled with T4 PNK. Both gels contain nucleic acids co-purified with TtAgo (lanes 1-3) and TtAgoDM (lanes 4-6) purified in buffer containing 2 mM $Mg^{2+}$ and nucleic acids co-purified with TtAgo (lanes 7-9) and TtAgoDM (lanes 10-12) purified in buffer containing 2 mM $Mg^{2+}$ Nucleic acids were untreated (lanes 1, 4, 7, 10). RNase A treated (lanes 2, 5, 8. 11) or DNase 1 treated (lanes 3, 6, 9. 12).

TtAgo could not be expressed in *T. thermophilus* due to apparent toxicity. However, it was found that Strep(II)-tagged TtAgo could be heterologously expressed in *E. coli* and purified to apparent homogeneity when the lagged TtAgo was under the control of an inducible promoter at an expression temperature of 20° C. (see method below). Induction of expression of TtAgo in the late-log growth phase (0D603 0.7-0.8) yielded enough TtAgo to analyze co-purifying nucleic acids. Both RNA and DNA were co-purified with TtAgo (see FIGS. 20A and B). Quantities of associated nucleic acids were higher in a buffer with $Mn^{2+}$ than with $Mg^{2+}$ (FIG. 21).

Co-purified RNA varied in length from 10-150 nt and was 32P labelled with a polynucleotide kinase (PNK) forward reaction, which indicateed a 5'-OH group (see FIGS. 20A and B). The phosphate binding pocket in the MID domain of TtAgo can be useful for cleavage suggesting TtAgo selects for a guide with a 5'-phosphate. The fact that these RNA molecules were highly variable in size and did not possess a 5'-phosphate strongly suggested that they are not guide molecules, but rather non-specificaliy bound RNA. The co-purified DNA molecules, on the other hand, were single-stranded, have a 5'-phosphate and a more defined length of approximately 13-25 nucleotides (FIGS. 20A and B). Besides a 5'-phosphate group, the size of DNA molecules can be at least 9 nucleotides to allow TtAgo cleavage of complementary RNA targets in vitro. This suggested that the co-purified DNA molecules are genuine TtAgo DNA guides. As TtAgo was expressed in *E. coil* in these experiments, it can be concluded that TtAgo was able to acquire DNA guides by itself, or guide acquisition requires a common host factor.

Sequence analysis of co-purified ssDNAs has been carried and suggested preference for a 51 cytokine. In preliminary sequencing of 42 such DNAs, interestingly all were found to have a cytokine at the 5' end.

During purification of an active site double mutant TtAgoDM (TtAgo478A-D546A), only RNA molecules co-purified (FIGS. 20A/B and 21). The co-purified RNAs were a result of non-specific binding to TtAgo. It is possible that the RNAs bind TtAgo and TtAgoDM due to the high predicted pI of the proteins (pI 9.7, charge at pH 8=15.2). TtAgo contains a basic nucleic acid-binding channel, which could accommodate non-specific binding to nucleic acids.

DNA Guide Co-Purification Method

The ago gene was PCR amplified from *Thermus thermophilus* HB8 (ATCC 27634) genomic DNA (gene TT_P0026, base positions on pTT27; 25054-22997), and directionally cloned into a pET-52b(+) expression vector as indicated in Table 2 (pWUR627). By introduction of mutations. according to the QuikChange Site-Directed Mutagenesis Kit instruction manual (Stratagene) pWUR642 was generated (Table 2). Plasmids pWUR627 and pWUR642 were transformed into *E. coli* Rosetia (DE3) (Novagen) containing the pRARE plasmid (Novagen) which encodes rare tRNAs required for TtAgo expression. Strains were cultivated in LB medium containing the corresponding antibiotics (100 µg/ml Ampicillin, 34 µg/mL Chloramphenicol) in a shaker incubator at 37° C. When an $OD_{600}$ of 0.7-0.8 was reached, a cold shock was applied to the culture by incubation in an ice bath for 15 min. Immediately after, protein expression was induced by adding IPTG (isopropyl-β-D-thiogalactopyranoside, Invitrogen) to a final concentration of 0.1 mM. Protein expression was continued for 16 h at 20° C. in a shaker incubator.

Cells were harvested, re-suspended in Buffer I (20 mM Tris/HCl (pH8), 1 M NaCl, and 2 mM $MnCl_2$ or 2 mM $MgCl_2$), and disrupted using a French Pressure Cell. Expressed proteins had an N-terminal Strep(II)-tag and were isolated using Strep-Tactin affinity chromatography (IBA, Germany) with an adapted protocol Before loading of the cell free extract, columns were equilibrated in Buffer I, After loading, columns were washed with 9CV (column volumes) Buffer I and with 9CV Buffer II (20 mM Tris/HCl (pH8), 0.5M NaCl, 2 mM $MnCl_2$ or 2 mM $MgCl_2$). Proteins were eluted in Buffer III (Buffer II supplied with 2.5 mM d-destiobiotin (Sigma-Aldnch)). Proteinase K (Ambion) and $CaCl_2$ were added to purified proteins and samples were incubated for 1 h at 37° C. Nucleic acids were separated from protein content using Phenol/Chloroform/Isoamyl alcohol pH7.5-8.0 (Carl Roth GmbH) and further purified by ethanoi precipitation. Precipitation was performed o/n at −2° C. in the presence of linear polymerized acrylamide as carrier.

To determine the identity of purified nucleic acids, they were $^{32}P$-labeled with T4 PNK (Fermentas) in exchange or toward labeling reactions and thereafter separated from free $^{32}P$ using a Sephadex G25 column. Labelled nucleic acids were incubated with nucleases (DNase free RNase A (Fermentas), RQ1 RNasc-free DNase I (Promega) or P1 nuclease (Sigma) for 1 h at 37° C. After nuclease treatment, samples were mixed with RNA Loading Buffer (95% (de-ionized) formamide, 5 mM EDTA, 0.025% SDS, 0.025% Bromophenol blue, and 0.025% xylene cyanol), heated for 5 min at 95° C. and resolved on 15% or 20% denaturing polyacrylamide gels. Radioactivity was captured from gels using phosphor screens.

Example 40

Co-purified Nucleic Acid-Targeting Nucleic Acids Allow Cleavage of dsDNA Plasmids Purified TtAgo with co-purified DNA guides was used in an activity assay with various plasrnid targets. TtAgo may have acquired guides from its expression vector. Induction of TtAgo expression was performed as detailed below in the presence or absence of antibiotics. Absence of antibiotics allowed acquisition of anti-plasmid guides and subsequent plasmid removal without inducing cell death due to loss of antibiotic resistance.

Protein Expression for Ttago Activity Assays

The inserts of pWUR627 and pWUR642 were PCR amplified and ligated into pCDF-1b as indicated in Table 2 to give pWUR702 and pWUR703, expression vectors for Strep(II)-TtAgo and Strep(II)-TtAgo with an active site residue mutation (D478A,D546A) respectively. These plasmids were transformed into E. coli KRX (Promega) simultaneously with pRARE (Novagen), purified from E. coli Rosetta DE3 (Novagen). Expression of TtAgo was identical as described for guide co-purification, with minor changes to the protocol. Expression was induced by adding IPTG and L-arabinose to a final concentration of 1 mM and 0.1% (w/v), respectively. Before induction of expression of TtAgo used in plasmid cleavage assays, the cells were harvested by centrifugation when the culture reached an $OD_{600}$ of 0.7-0.8. The supernatant was removed and cell pellets were resuspended in LB medium with or without antibiotics, after which expression was induced and continued as described above. Purification of TtAgo was identical as described for guide co-purification, with modification to Buffers I, II and III. For purification of TtAgo used in $Mn^{2+}/Mg^{2+}$ gradient experiments, no $Mn^{2+}$ or $Mg^{2+}$ was added to the purification buffers. For other experiments $MnCl_2$ or $MgCl_2$ was added to all buffers to a final concentration of 500 µM.

Activity Assay

Purified TtAgo and DNA plasmid targets were mixed in 125:1 ratio in 2× reaction buffer (20 mM Tris-HCl pH8. 250 mM NaCl and 500 µM $MnCl_2$ or $MgCl_2$). Reaction mixtures were incubated for 16 h at 75° C. Reactions were stopped by adding proteinase K solution (Ambion) and $CaCl_2$ (final concentration 5 mM) and samples were incubated for 1 hr at 65° C. Samples were mixed with 6× loading dye (Fermentas) before they were resolved on 0.8% agarose gels. Agarose gels were stained with SYBR or SYBR gold Nucleic Acid gel Stain (Invitrogen).

Results

Figure 22:
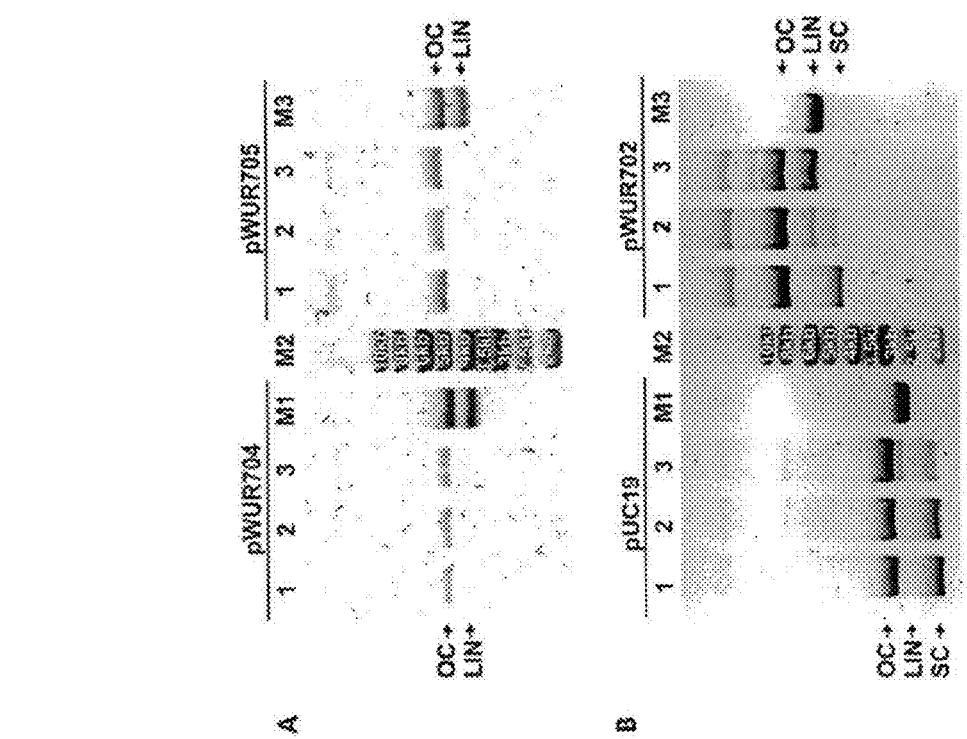
FIG. 22A/B depicts plasmid cleavage by TtAgo with co-purified guides. OC: open circular, LIN: linear, SC: supercoiled (A) M1: linearized and open circular pWUR704. M2: Fermentas 1 kb generuler marker. M3: linearized and open circular pVVUR705. Plasmids have an open circular conformation in the absence of TtAgo (lane 1), in the presence of TtAgo (lane 2) and TtAgo expressed in absence of antibiotics (lane 3); no activity is observed. (B) M1: linearized pUC19. M2: Fermentas 1 kb generuler marker. M3: linearized pWUR702. Plasmid pUC19 is partially complementary to pWUR702, from which TtAgo is expressed. No cleavage is observed when TtAgo is absent (lane 1), while TtAgo is able to (partially) linearize pUC19 and pWUR702 plasmids (lane 2-3). Linearization is more effective when TtAgo is expressed in absence of antibiotics (lane 3).

TtAgo purified from medium with or without antibiotics was unable to linearize pWUR704 or pWUR705, plasmids that shared no sequence homology with the expression vector (pWUR702) used to produce the purified TtAgo (FIG. 22A). In contrast, TtAgo expressed in medium without antibiotics was able to linearize both that expression vector and plasmid pUC19, the sequence of which is partially homologous to pWUR702 (FIG. 22B, lane 3). Cleavage by TtAgo produced in the presence of antibiotics was substantially less effective (FIG. 22B, lane 2).

Figure 23:
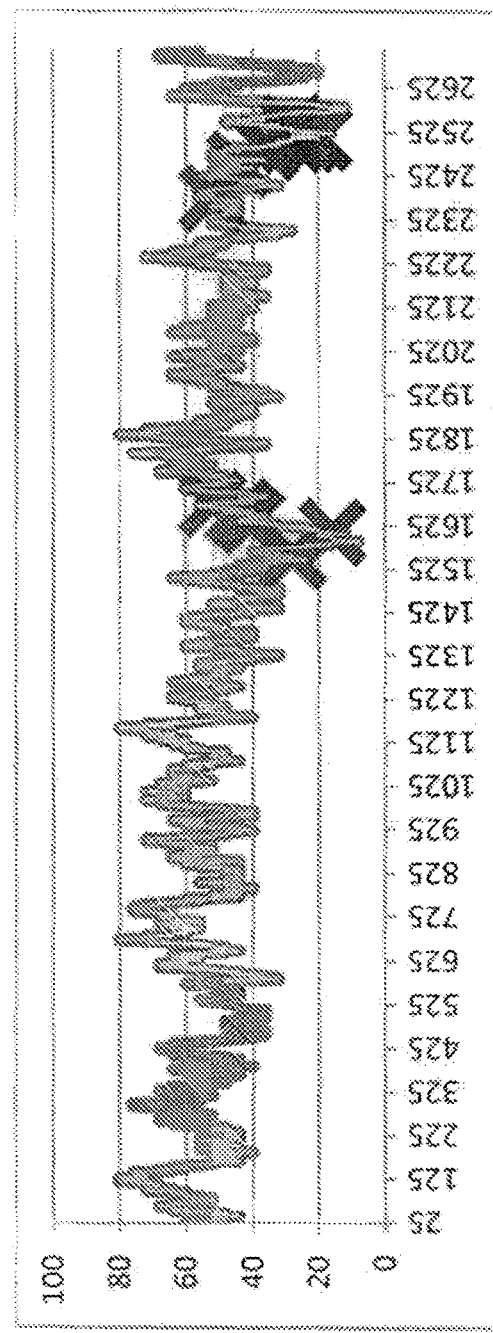
FIG. 23 shows GC-content of pUC19, sequence homology to pWUR627 and cleavage positions. The GC-content (Y-axis) of 25bp patches of pUC19 is displayed. Sequences homologous to pWUR627 are shown in the light grey.

Sequencing of the cleaved pUC-T fragments of pUC19 showed that cleavage indeed took place in the sequences homologous to pWUR627 (FIG. 23). Interestingly, cleavage only took place in the AT-rich regions.

These findings suggested that the DNA guides of TtAgo were acquired from, plasmicb in vivo and that they are utilized by TtAgo to cleave complementary dsDNA targets.

Example 41

TtAgo is Able to Use an In Vitro Loaded DNA Nucleic Acid-Targeting Nucleic Acid to Cleave both ssDNA and dsDNA Plasmids DNA-guided cleavage of ssDNA is possible in the presence of 50-100 pM $Mg^{2+}$, but $Mn^{2+}$ allowed comparable levels of ssDNA cleavage at lower concentration (see FIG. 24), TtAgo, when supplemented with a 21nt DNA guide in viera in the presence of $Mn^{2+}$ or $Mg^{2+}$ ions, can cleave dsDNA plasmids. Double stranded breaks were found to be generated when using TtAgo supplemented with two partially overlapping complementary 21-nt DNA guides. Negatively supercoiled plasmids were employed since this is the biologically relevant plasrnid topology; at least 95% of plasmids isolated from T. thermophilus are in the negative supercoiled state DNA Guides and Targets The sequence of the guide BG3466 (SEQ. ID NO: 21) is based on Let-7 miRNA. The sequence of guide BG4017 (SEQ. ID NO: 22) is based on the reverse complementary sequence of Let-7 miRNA (Table 3). Both guides have a 5-phosphate, are 21 nt long and were PAGE-purified after synthesis to guarantee guide length.

Oligonucleotides BG4264 and BG4265 (SEQ. ID NOs: 19 and 20; see Table 3) were mixed with 2× STE buffer (20 mM TrisHCl pH8, 100 mM NaCl, 2 mM EDTA) in a 1:1:2 ratio (BG4264:BG4265:2× STE) and incubated at 95° C. for 5 min, Samples were then cooled down to room temperature, forming dsDN A target sequence B (high 58% GC-eontent target region 92 bp with Notl and Sall sticky ends as noted in Table 2).

The dsDNA target sequence A as noted in Table 2 above was generated with the same protocol using BG4262 (SEQ. ID NO: 17) and BG4263 (SEQ. ID. NO: 18) (see Table 3). Target sequence A had the same double-stranded length as target sequence B with again Notl and Sall sticky ends, but a far lower GC content in the target region (15%).

Plasmids pWUR704 and pWUR705 were constructed by insertion of dsDNA target A and dsDNA target B respectively into pWUR677 using ihe Notl and Sall sticky-ends present on these fragments and T4 ligase ligation.

Activity Assays

Purified TtAgo, (ssRNA or ssDNA) guides and (ssDNA or dsDNA) targets were mixed in 5:1:1 ratio (ssDNA targets) or 25:25; 1/250:250; 1 ratio (dsDNA targets) in 2× reaction buffer (20 mM Tris-HCl pH8, 250 mM NaCl supplied with varying concentrations of $MnCl_2$ or $MgCl_2$). Reaction mixtures were incubated for 1 h at 75° C. Reaction mixtures were incubated ih at 75° C. Reaction were stopped by the addition of Loadiug Buffer (95% (deionized) formamide, 5 mM EDTA, 0.025% SDS. 0.025% Bromophcnol blue, and 0.025% xylene cyanol) and heated for 5 min at 95° C. before the samples were resolved on 15% or 20% denaturing polyacrylamide gels. Gels were stained using SYBR gold Nucleic Acid Gel Stain (Invitrogen).

Results

When TtAgo was provided with a 21-nt RNA guide, if was unable to cleave ssDNA target complementary to the guide, while under the same conditions a 21-nt DNA guide supported Cleavage of ssDNA target (see FIG. 24). Under the conditions tested, TtAgo is a DNA-guided Argonaute protein. Furthermore, it was found to exhibit preference for $Mn^{2+}$ ions compared to $Mg^{2+}$ ions for carrying out ssDNA cleavage. While DNA-guided cleavage of ssDNA is observed in the presence of 5-10 pM $Mn^{2+}$, comparable cleavage levels are absent in the presence of $Mg^{2+}$ only at 10-fold higher concentration. 25 µM $Mn^{2+}$ was sufficient to facilitate full target cleavage (see FIG. 25). Lower concentrations suffice with longer incubation time.

Significantly, TtAgo was also shown to exhibit cleavage activity on plasmid dsDNA, Plasmid cleavage assays showed that TtAgo was able to induce nicks in negatively supereoiled plasmid DNA when a 21nt plasmid-targeting DNA guide was provided. When provided with two 21nt guides targeting either strand of the supereoiled plasmid, the plasmid was linearised. Both nicking and double-stranded cleavage are more efficient within AT-rich regions (pWUR704; insert of 98 bps with 15% GC content) as compared to within GC-rich regions (pWUR705, insert, of 98 bps with 58% GC content) (see FIG. 26). Under the tested conditions, linearized plasraids were not cleaved by TtAgo supplied with guides.

Example 42

Purification of SeAgo

FIG. 43 shows that SeAgo can be affinity purified using strep(ii)-tag affinity purification, SeAgo was purified with with Mn2+ buffer. Three elution fractions are shown in lanes 2-4. Lane 1 is the molecular weight marker. FIG. 43 shows that SeAgo purifies to near 100% purity. Multiple bands may reflect partial denaturation, or heterogeneity due to different co-purified nucleic acids; this has also been observed with similar purification of TtAgo.

Example 43

Activity Analysis of SeAgo on dsDNA Target pCDF-SeAgo plasmid and E. coli-purified SeAgo (with in vivo aquired DNA guides that target expression plasmid) was incubated with either $Mn^{2+}$ or $Mg^{2+}$. 15 uL of SeAgo (0.4 μM) was purified in buffer containing 0.5 mM $MnCl_2$ or 0.5 mM $MgCl_2$ and was added to 5 uL 30 ng/uL pCDF-SeAgo. Samples were incubated overnight at 40° C. When incubated with SeAgo purified in $Mn^{2+}$ buffer, a band is generated that matches the linearized form of pCDF-SeAgo. FIG. 44 shows that in the presence of $Mn^{2+}$ SeAgo is active and can cleave a plasmid (lane 2). M, marker.

Example 44

Activity Analysis of SeAgo on ssDNA Target

FIG. 45 shows degradation of 45 nt ssDNA target by SeAgo with supplied complementary DNA nucleic acid-targeting nucleic acid varies in presence of $Mn^{2+}$ or $Mg^{2+}$. The nucleic acid-targeting nucleic acid sequence is: 5'-P-AGAGGTAGTAGGTTGTATAGT (SEQ ID NO: 31). The ssDNA target was incubated for 16 hr at 40° C.

What is claimed is:

1. A method of cutting a double-stranded DNA target sequence in a host cell in vitro, wherein the double-stranded DNA target sequence comprises a first DNA strand and a second DNA strand, the method comprising: introducing into the host cell:
   a first complex comprising a first TtArgonaute protein and a first guide nucleic acid, wherein the first guide nucleic acid hybridizes with the first strand of the double-stranded DNA target sequence in the host cell and the first complex cuts the first strand of the double-stranded DNA target sequence, and
   a second complex comprising a second TtArgonaute protein and a second guide nucleic acid, wherein the second guide nucleic acid hybridizes with the second strand of the double-stranded DNA target sequence in the host cell and the second complex cuts the second strand of the double-stranded DNA target sequence.

2. The method of claim 1, wherein the first strand cut and the second strand cut of the double-stranded DNA target sequence are such that the cutting of the double-stranded DNA target sequence is a blunt-end cut.

3. The method of claim 1, wherein the first strand cut and the second strand cut of the double-stranded DNA taret sequence are such that the cutting of the double-stranded DNA target sequence is a staggared-end cut.

4. The method of claim 1, wherein the first guide nucleic acid and the second guide nucleic acid comprise DNA.

5. The method of claim 1, wherein the first guide nucleic acid and the second guide nucleic acid comprise RNA.

6. The method of claim 5, wherein the first guide nucleic acid and the second guide nucleic acid further comprise DNA.

7. The method of claim 1, wherein the double-stranded DNA target sequence is within a genomic DNA of a cukaryotic host cell.

8. The method of claim 1, wherein the host cell is a eukaryotic cell.

9. The method of claim 1, wherein the host cell is a plant cell, an algal cell, a fungal cell, a cell from a vertebrate animal, or a cell from a mammal.

10. The method of claim 1, wherein the introducing is carried out ex vivo.

11. The method of claim 1, wherein the double-stranded DNA target sequence comprises DNA, the first guide nucleic acid comprises DNA, and the second guid nucleic acid comprises DNA.

12. The method of claim 11, wherein the host cell is a eukaryotic cell.

* * * * *

UNITED STATES PATENT AND TRADEMARK OFFICE
CERTIFICATE OF CORRECTION

PATENT NO. : 9,902,973 B2
APPLICATION NO. : 14/250224
DATED : February 27, 2018
INVENTOR(S) : John Van Der Oost et al.

Page 1 of 3

It is certified that error appears in the above-identified patent and that said Letters Patent is hereby corrected as shown below:

On the Title Page

On page 2, Column 1, Line 20, delete "in argonature silencing", and insert -- in argonaute silencing --, therefor.

In the Specification

In Column 54, Lines 45-46, delete
"domain. An
        Argonaute can", and insert -- domain. An Argonaute can --, therefor.

In Column 56, Line 24, delete "Argonauts", and insert -- Argonaute --, therefor.

In Column 56, Line 43, delete "Argonauts", and insert -- Argonaute --, therefor.

In Column 74, Line 46, delete "thereof", and insert -- thereof. --, therefor.

In Column 80, Line 51, delete "thereof", and insert -- thereof. --, therefor.

In Column 81, Line 26-27, delete
"regions of the
        Argonaute protein.", and insert -- regions of the Argonaute protein --, therefor.

In Column 86, Line 19, delete "emthods", and insert -- methods --, therefor.

In Column 87, Line 2, delete "Argonauie", and insert -- Argonaute --, therefor.

In Column 102, Line 9, delete "Argonauts", and insert -- Argonaute --, therefor.

Signed and Sealed this
Fifteenth Day of May, 2018

Andrei Iancu
*Director of the United States Patent and Trademark Office*

CERTIFICATE OF CORRECTION (continued)

In Column 109, Line 26, delete "thereof", and insert -- thereof. --, therefor.

In Column 137, Line 39, delete "piasmid", and insert -- plasmid --, therefor.

In Column 137, Line 43, delete "piasmids", and insert -- plasmids --, therefor.

In Column 139, Line 29, delete "piasmids", and insert -- plasmids --, therefor.

In Column 140, Line 4, delete "piasrnids", and insert -- plasmids --, therefor.

In Column 140, Line 18, delete "Argonatue", and insert -- Argonaute --, therefor.

In Column 141, Lines 32-33, delete "pias-mid", and insert -- plas-mid --, therefor.

In Column 142, Lines 35-36, delete "Argo-nauts", and insert -- Argo-naute --, therefor.

In Column 142, Line 65, delete "acryfamjde", and insert -- acrylamide --, therefor.

In Column 143, Line 43, delete "TrArgonaute,", and insert -- TtArgonaute, --, therefor.

In Column 144, Line 48, delete "DMA", and insert -- DNA --, therefor.

In Column 148, Line 41, delete "microairay", and insert -- microarray --, therefor.

In Column 150, Line 51, delete "like,", and insert -- like. --, therefor.

In Column 156, Line 10, delete "Argonauts.", and insert -- Argonaute. --, therefor.

In Column 156, Line 17, delete "cleaved-", and insert -- cleaved. --, therefor.

In Column 158, Line 43, delete "Argonauts. Argonauts", and insert -- Argonaute. Argonaute --, therefor.

In Column 160, Line 35, delete "piasmid", and insert -- plasmid --, therefor.

In Column 160, Line 37, delete "piasmid", and insert -- plasmid --, therefor.

In Column 160, Line 44, delete "piasmid", and insert -- plasmid --, therefor.

In Column 163, Table 2, row 3 (i.e., pWUR676), Column 2, delete "Kan ® marker", and insert -- Kan$^R$ marker --, therefor.

In Column 163, Table 3, Experiment 3, Column 1, delete "Site directed mutagene sis of TtAgo gene", and insert -- Site directed mutagenesis of TtAgo gene --, therefor.

CERTIFICATE OF CORRECTION (continued)

In Column 163, Table 3, Experiment 3, row 2, Column 2, beneath "BG34", insert -- 55 --, therefor.

In Column 165, Line 33, delete "Descreases", and insert -- Decreases --, therefor.

In the Claims

Column 239, Lines 51-67 (Claim 1), delete
"1. A method of cutting a double-stranded DNA target sequence in a host cell in vitro, wherein the double-stranded DNA target sequence comprises a first DNA strand and a second DNA strand, the method comprising: introducing into the host cell:
 a first complex comprising a first TtArgonaute protein and a first guide nucleic acid, wherein the first guide nucleic acid hybridizes with the first strand of the double-stranded DNA target sequence in the host cell and the first complex cuts the first strand of the double-stranded DNA target sequence, and
 a second complex comprising a second TtArgonaute protein and a second guide nucleic acid, wherein the second guide nucleic acid hybridizes with the second strand of the double-stranded DNA target sequence in the host cell and the second complex cuts the second strand of the double-stranded DNA target sequence.", and insert
-- 1. A method of cutting a double-stranded DNA target sequence in a host cell in vitro, wherein the double-stranded DNA target sequence comprises a first DNA strand and a second DNA strand, the method comprising:
 introducing into the host cell:
  a first complex comprising a first TtArgonaute protein and a first guide nucleic acid, wherein the first guide nucleic acid hybridizes with the first strand of the double-stranded DNA target sequence in the host cell and the first complex cuts the first strand of the double-stranded DNA target sequence, and
  a second complex comprising a second TtArgonaute protein and a second guide nucleic acid, wherein the second guide nucleic acid hybridizes with the second strand of the double-stranded DNA target sequence in the host cell and the second complex cuts the second strand of the double-stranded DNA target sequence. --, therefor.

Column 240, Line 55 (Claim 3, Line 2), delete "taret", and insert -- target --, therefor.

Column 240, Line 55 (Claim 3, Line 4), delete "staggared-end", and insert -- staggered-end --, therefor.

Column 240, Lines 66-67 (Claim 7, Lines 2-3), delete "cukary-otic", and insert -- eukaryotic --, therefor.

Column 241, Line 10 (Claim 11, Line 3), delete "guid", and insert -- guide --, therefor.

```
SEQUENCE LISTING

<160> NUMBER OF SEQ ID NOS: 125

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaaaaaagc ttcctcaacg gggaggttcc gga                                      33

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaaaagtcg acgctcagat ttgcatagga gctgc                                    35

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 aaaaagtcg acatggcaag ctggagccac ccg                                       33

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 4
aaaaaatcta gactaaacga agaagagctt ttcccg                              36

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaaaatcta gatgcccaag cggggcggaa cc                                  32

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaaaaagaat tcggtcaatc cgccccgctt cca                                 33

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggccgtctag acccgggagt ataacagaaa cctt                                34

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcgcgtctag atcaaaatgg tatgcgtttt gacac                               35

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcgcgcggta ccagatgaac caccttggaa aaacgg                              36

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 10
gcgcgcgcgg ccgcgaattc ctaaacgaag aagagctttt ccc                    43

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgcgcacat gtcaagctgg agccacccgc ag                                32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgcgcccta ggttaattag tggtggtgat gg                                32

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: Inosine

<400> SEQUENCE: 13
ggcggagctc gccgtgggct ntgccgccgg cggaagggag tcctttcg               48

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgaaaggact cccttccgcc ggcggcaaag cccacggcga gctccgcc               48

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccgggtcct cctccttcgg gccggccgcg tgcccagga cgag                    44

<210> SEQ ID NO 16
<211> LENGTH: 44
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 16
ctcgtcctgg ggcacgcggc cggcccgaag gaggaggacc cggg                           44

<210> SEQ ID NO 17
<211> LENGTH: 98
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggccatttaa ttaaattaaa agcttgaatg caatatttat ttaaaaattt atacgaggta         60
gtaggttgta tagtatatta aattatttaa atataaag                                 98

<210> SEQ ID NO 18
<211> LENGTH: 98
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcgactttat atttaaataa tttaatatac tatacaacct actacctcgt ataaattttt         60
aaataaatat tgcattcaag cttttaattt aattaaat                                 98

<210> SEQ ID NO 19
<211> LENGTH: 98
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggccaggtcc accatgcgta agcttgaatg ccggccagcc caagggctct gcacgaggta         60
gtaggttgta tagttgctgg caggcgtagg tctaagcg                                 98

<210> SEQ ID NO 20
<211> LENGTH: 98
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcgacgctta gacctacgcc tgccagcaac tatacaacct actacctcgt gcagagccct         60
tgggctggcc ggcattcaag cttacgcatg gtggacct                                 98

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-phosphate

<400> SEQUENCE: 21

```
tgaggtagta ggttgtatag t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-phosphate

<400> SEQUENCE: 22
ttatacaacc tactacctcg t                                              21

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      9xHis tag

<400> SEQUENCE: 24

His His His His His His His His His
1               5

<210> SEQ ID NO 25
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 3-50 "Arg"
      residues, wherein some positions may be absent

<400> SEQUENCE: 25

Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg Arg
            20                  25                  30

Arg Arg Arg Arg Arg Arg Arg Arg Arg Arg Arg Arg Arg Arg Arg
        35                  40                  45

Arg Arg
    50

<210> SEQ ID NO 26
<211> LENGTH: 9
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 26

Arg Arg Arg Arg Arg Arg Arg Arg
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Glu Glu Glu Glu Glu Glu Glu Glu
1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Glu Asp Asp
1

<210> SEQ ID NO 29
<211> LENGTH: 34
<212> TYPE: PRT
<213> ORGANISM: Xanthomonas sp.

<400> SEQUENCE: 29

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 30
<211> LENGTH: 7
<212> TYPE: PRT
<213> ORGANISM: Unknown
<220> FEATURE:
<223> OTHER INFORMATION: Description of Unknown: Nuclear
      localization signal peptide

<400> SEQUENCE: 30

Pro Lys Lys Lys Arg Lys Val
1               5

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-phosphate

<400> SEQUENCE: 31
agaggtagta ggttgtatag t                                      21

<210> SEQ ID NO 32
<211> LENGTH: 11
<212> TYPE: PRT
<213> ORGANISM: Aquifex aeolicus

<400> SEQUENCE: 32

Ala Phe Val Gly Ile Asp Ile Ser Arg Ile Thr
1               5                   10

<210> SEQ ID NO 33
<211> LENGTH: 9
<212> TYPE: PRT
<213> ORGANISM: Aquifex aeolicus

<400> SEQUENCE: 33

Ser Lys Ile Val Val His Arg Asp Gly
1               5

<210> SEQ ID NO 34
<211> LENGTH: 9
<212> TYPE: PRT
<213> ORGANISM: Aquifex aeolicus

<400> SEQUENCE: 34

Asp Glu Val Ala Ala Phe Lys Lys Tyr
1               5

<210> SEQ ID NO 35
<211> LENGTH: 11
<212> TYPE: PRT
<213> ORGANISM: Lyngbya sp.

<400> SEQUENCE: 35

Tyr Phe Ile Gly Leu Asp Ile Ser Arg Thr Pro
1               5                   10

<210> SEQ ID NO 36
<211> LENGTH: 9
<212> TYPE: PRT
<213> ORGANISM: Lyngbya sp.

<400> SEQUENCE: 36

Lys Thr Val Leu Ile Tyr Arg Asp Gly
1               5

<210> SEQ ID NO 37
<211> LENGTH: 9
<212> TYPE: PRT
<213> ORGANISM: Lyngbya sp.

<400> SEQUENCE: 37

Asp Glu Ile Lys His Leu Arg Glu Arg
1               5

<210> SEQ ID NO 38
<211> LENGTH: 11
<212> TYPE: PRT
<213> ORGANISM: Microcycstis aeruginosa

<400> SEQUENCE: 38

Tyr Phe Ile Gly Leu Asp Val Gly Arg Met Pro
1               5                   10

```
<210> SEQ ID NO 39
<211> LENGTH: 8
<212> TYPE: PRT
<213> ORGANISM: Microcycstis aeruginosa

<400> SEQUENCE: 39

Thr

```
<210> SEQ ID NO 46
<211> LENGTH: 9
<212> TYPE: PRT
<213> ORGANISM: Clostridium bartlettii

<400> SEQUENCE: 46

Glu Asp Ile Asp Leu Leu Lys Glu Ile
1 5

<210> SEQ ID NO 47
<211> LENGTH: 11
<212> TYPE: PRT
<213> ORGANISM: Exiguobacterium sp.

<400> SEQUENCE: 47

Cys Phe Val Gly Leu Asp Val Ser His Glu Asn
1 5 10

<210> SEQ ID NO 48
<211> LENGTH: 9
<212> TYPE: PRT
<213> ORGANISM: Exiguobacterium sp.

<400> SEQUENCE: 48

Lys His Ile Thr Phe His Arg Asp Gly
1 5

<210> SEQ ID NO 49
<211> LENGTH: 9
<212> TYPE: PRT
<213> ORGANISM: Exiguobacterium sp.

<400> SEQUENCE: 49

Glu Asp Leu Thr Leu Ile Asp Ser Ile
1 5

<210> SEQ ID NO 50
<211> LENGTH: 11
<212> TYPE: PRT
<213> ORGANISM: Anoxybacillus flavithermus

<400> SEQUENCE: 50

Cys Phe Ile Gly Leu Asp Val Ser His Glu Gln
1 5 10

<210> SEQ ID NO 51
<211> LENGTH: 9
<212> TYPE: PRT
<213> ORGANISM: Anoxybacillus flavithermus

<400> SEQUENCE: 51

Ser His Ile Thr Phe His Arg Asp Gly
1 5

<210> SEQ ID NO 52
<211> LENGTH: 9
<212> TYPE: PRT
<213> ORGANISM: Anoxybacillus flavithermus

<400> SEQUENCE: 52

Glu Asp Leu Ala His Leu Thr Gln Tyr
1 5

<210> SEQ ID NO 53
<211> LENGTH: 11

```
<212> TYPE: PRT
<213> ORGANISM: Halogeometricum borinquense

<400> SEQUENCE: 53

Ala Phe Val Gly Leu Asp Val Thr Tyr Asp His
1               5                   10

<210> SEQ ID NO 54
<211> LENGTH: 9
<212> TYPE: PRT
<213> ORGANISM: Halogeometricum borinquense

<400> SEQUENCE: 54

Arg His Val Val Ile His Arg Asp Gly
1               5

<210> SEQ ID NO 55
<211> LENGTH: 9
<212> TYPE: PRT
<213> ORGANISM: Halogeometricum borinquense

<400> SEQUENCE: 55

Leu Asp Ile Glu Ser Leu Ile Lys Arg
1               5

<210> SEQ ID NO 56
<211> LENGTH: 11
<212> TYPE: PRT
<213> ORGANISM: Halorubrum lacusprofundi

<400> SEQUENCE: 56

Leu Phe Ile Gly Ile Asp Val Ser His Arg Tyr
1               5                   10

<210> SEQ ID NO 57
<211> LENGTH: 9
<212> TYPE: PRT
<213> ORGANISM: Halorubrum lacusprofundi

<400> SEQUENCE: 57

Asp Arg Ile Val Ile His Arg Asp Gly
1               5

<210> SEQ ID NO 58
<211> LENGTH: 9
<212> TYPE: PRT
<213> ORGANISM: Halorubrum lacusprofundi

<400> SEQUENCE: 58

Glu Asp Leu Asp Gln Val Glu Glu Met
1               5

<210> SEQ ID NO 59
<211> LENGTH: 11
<212> TYPE: PRT
<213> ORGANISM: Aromatoleum aromaticum

<400> SEQUENCE: 59

Leu Phe Ile Gly Leu Asp Leu Gly Gly Val Ser
1               5                   10

<210> SEQ ID NO 60
<211> LENGTH: 9
<212> TYPE: PRT
<213> ORGANISM: Aromatoleum aromaticum
```

-continued

```
<400> SEQUENCE: 60

Arg Arg Ile Ala Leu His Arg Asp Gly
1               5

<210> SEQ ID NO 61
<211> LENGTH: 9
<212> TYPE: PRT
<213> ORGANISM: Aromatoleum aromaticum

<400> SEQUENCE: 61

Glu Ser Leu Asp Val Ile Arg Asn Phe
1               5

<210> SEQ ID NO 62
<211> LENGTH: 11
<212> TYPE: PRT
<213> ORGANISM: Thermus thermophilus

<400> SEQUENCE: 62

Leu Ala Val Gly Phe Asp Ala Gly Gly Arg Glu
1               5                   10

<210> SEQ ID NO 63
<211> LENGTH: 9
<212> TYPE: PRT
<213> ORGANISM: Thermus thermophilus

<400> SEQUENCE: 63

Ser Arg Val Leu Leu Arg Asp Gly
1               5

<210> SEQ ID NO 64
<211> LENGTH: 9
<212> TYPE: PRT
<213> ORGANISM: Thermus thermophilus

<400> SEQUENCE: 64

Asp Glu Phe Ala Leu Ala Leu Glu Ala
1               5

<210> SEQ ID NO 65
<211> LENGTH: 11
<212> TYPE: PRT
<213> ORGANISM: Thermus thermophilus

<400> SEQUENCE: 65

Leu Ala Val Gly Phe Asp Ala Gly Gly Arg Glu
1               5                   10

<210> SEQ ID NO 66
<211> LENGTH: 9
<212> TYPE: PRT
<213> ORGANISM: Thermus thermophilus

<400> SEQUENCE: 66

Ser Arg Val Leu Leu Arg Asp Gly
1               5

<210> SEQ ID NO 67
<211> LENGTH: 9
<212> TYPE: PRT
<213> ORGANISM: Thermus thermophilus

<400> SEQUENCE: 67
```

Asp Glu Phe Ala Leu Ala Leu Glu Ala
1               5

<210> SEQ ID NO 68
<211> LENGTH: 11
<212> TYPE: PRT
<213> ORGANISM: Synechococcus sp.

<400> SEQUENCE: 68

Leu Val Ile Gly Phe Asp Ala Gly Arg Asn Glu
1               5                   10

<210> SEQ ID NO 69
<211> LENGTH: 9
<212> TYPE: PRT
<213> ORGANISM: Synechococcus sp.

<400> SEQUENCE: 69

Lys Arg Ile Leu Leu Met Arg Asp Gly
1               5

<210> SEQ ID NO 70
<211> LENGTH: 9
<212> TYPE: PRT
<213> ORGANISM: Synechococcus sp.

<400> SEQUENCE: 70

Gln Glu Phe Ser Leu Ile Thr Glu Ala
1               5

<210> SEQ ID NO 71
<211> LENGTH: 11
<212> TYPE: PRT
<213> ORGANISM: Thermosynechococcus elongatus

<400> SEQUENCE: 71

Leu Ile Ile Gly Phe Asp Thr Ser Thr Asn Arg
1               5                   10

<210> SEQ ID NO 72
<211> LENGTH: 9
<212> TYPE: PRT
<213> ORGANISM: Thermosynechococcus elongatus

<400> SEQUENCE: 72

Lys Lys Ile Leu Leu Met Arg Asp Gly
1               5

<210> SEQ ID NO 73
<211> LENGTH: 10
<212> TYPE: PRT
<213> ORGANISM: Thermosynechococcus elongatus

<400> SEQUENCE: 73

Gly Glu Phe Glu Gln Thr Ile Arg Glu Leu
1               5                   10

<210> SEQ ID NO 74
<211> LENGTH: 11
<212> TYPE: PRT
<213> ORGANISM: Synechococcus elongatus

<400> SEQUENCE: 74

Leu Ile Ile Gly Phe Asp Thr Gly Thr Asn Arg

<210> SEQ ID NO 75
<211> LENGTH: 9
<212> TYPE: PRT
<213> ORGANISM: Synechococcus elongatus

<400> SEQUENCE: 75

Gln Lys Leu Leu Leu Met Arg Asp Gly
1               5

<210> SEQ ID NO 76
<211> LENGTH: 9
<212> TYPE: PRT
<213> ORGANISM: Synechococcus elongatus

<400> SEQUENCE: 76

Gly Glu Phe Gln Gln Thr Ile Glu Leu
1               5

<210> SEQ ID NO 77
<211> LENGTH: 11
<212> TYPE: PRT
<213> ORGANISM: Synechococcus sp.

<400> SEQUENCE: 77

Leu Thr Ile Gly Phe Asp Val Gly Thr Asn Arg
1               5                   10

<210> SEQ ID NO 78
<211> LENGTH: 9
<212> TYPE: PRT
<213> ORGANISM: Synechococcus sp.

<400> SEQUENCE: 78

Arg Lys Val Leu Leu Met Arg Asp Gly
1               5

<210> SEQ ID NO 79
<211> LENGTH: 10
<212> TYPE: PRT
<213> ORGANISM: Synechococcus sp.

<400> SEQUENCE: 79

Gly Glu Phe Asp Lys Thr Ile Glu Glu Leu
1               5                   10

<210> SEQ ID NO 80
<211> LENGTH: 11
<212> TYPE: PRT
<213> ORGANISM: Synechococcus sp.

<400> SEQUENCE: 80

Leu Ile Ile Gly Phe Asp Val Gly Thr Asn Arg
1               5                   10

<210> SEQ ID NO 81
<211> LENGTH: 9
<212> TYPE: PRT
<213> ORGANISM: Synechococcus sp.

<400> SEQUENCE: 81

Ser Lys Val Leu Leu Met Arg Asp Gly
1               5

<210> SEQ ID NO 82
<211> LENGTH: 10
<212> TYPE: PRT
<213> ORGANISM: Synechococcus sp.

<400> SEQUENCE: 82

Gly Glu Phe Ser Arg Thr Ile Glu Glu Leu
1               5                   10

<210> SEQ ID NO 83
<211> LENGTH: 11
<212> TYPE: PRT
<213> ORGANISM: Synechococcus elongatus

<400> SEQUENCE: 83

Leu Ile Ile Gly Phe Asp Thr Gly Thr Asn Arg
1               5                   10

<210> SEQ ID NO 84
<211> LENGTH: 9
<212> TYPE: PRT
<213> ORGANISM: Synechococcus elongatus

<400> SEQUENCE: 84

Gln Lys Leu Leu Leu Met Arg Asp Gly
1               5

<210> SEQ ID NO 85
<211> LENGTH: 9
<212> TYPE: PRT
<213> ORGANISM: Synechococcus elongatus

<400> SEQUENCE: 85

Gly Glu Phe Gln Gln Thr Ile Glu Leu
1               5

<210> SEQ ID NO 86
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aaacgacggc cagtgccaag cttactatac aacctactac ctcat            45

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-phosphate

<400> SEQUENCE: 87
ugagguagua gguuguauag u                                       21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
actatacaac ctactacctc g                                              21

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
actatacaac ctactacctc gt                                             22

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
acgaggtagt aggttgtata gt                                             22

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
acgaggtagt aggttgtata g                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-phosphate

<400> SEQUENCE: 92
ggaggtagta ggttgtatag t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-phosphate

<400> SEQUENCE: 93
cgaggtagta ggttgtatag t                                              21

<210> SEQ ID NO 94
<211> LENGTH: 103
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 94
gtcgacttta tatttaaata atttaatata ctatacaacc tactacctcg tataaatttt      60
taaataaata ttgcattcaa gcttttaatt taattaaatg gcc                      103

<210> SEQ ID NO 95
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
ggccatttaa ttaattaaa agcttgaatg caatatttat ttaaaaattt atacgaggta      60
gtaggttgta tagtatatta aattatttaa atataaagtc gac                      103

<210> SEQ ID NO 96
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gtcgacgctt agacctacgc ctgccagcaa ctatacaacc tactacctcg tgcagagccc      60
ttgggctggc cggcattcaa gcttacgcat ggtggacctg gcc                      103

<210> SEQ ID NO 97
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
ggccaggtcc accatgcgta agcttgaatg ccggccagcc caagggctct gcacgaggta      60
gtaggttgta tagttgctgg caggcgtagg tctaagcgtc gac                      103

<210> SEQ ID NO 98
<211> LENGTH: 10
<212> TYPE: PRT
<213> ORGANISM: Thermus thermophilus

<400> SEQUENCE: 98

Ala Phe Gly Ala Ser Gly Ala Ser Leu Arg
1               5                   10

<210> SEQ ID NO 99
<211> LENGTH: 10
<212> TYPE: PRT
<213> ORGANISM: Thermus thermophilus

<400> SEQUENCE: 99

Ala Gln Glu Thr Ala Leu Ala Leu Leu Arg
1               5                   10
```

```
<210> SEQ ID NO 100
<211> LENGTH: 10
<212> TYPE: PRT
<213> ORGANISM: Thermus thermophilus

<400> SEQUENCE: 100

Ala Val Ser Lys Pro Ala Asp Ala Leu Arg
1               5                   10

<210> SEQ ID NO 101
<211> LENGTH: 11
<212> TYPE: PRT
<213> ORGANISM: Thermus thermophilus

<400> SEQUENCE: 101

Glu Gly Ile Ala Tyr Asp Leu Val Ser Val Arg
1               5                   10

<210> SEQ ID NO 102
<211> LENGTH: 8
<212> TYPE: PRT
<213> ORGANISM: Thermus thermophilus

<400> SEQUENCE: 102

Glu Ile Ala Ser Trp Ile Gly Arg
1               5

<210> SEQ ID NO 103
<211> LENGTH: 12
<212> TYPE: PRT
<213> ORGANISM: Thermus thermophilus

<400> SEQUENCE: 103

Leu Ala Asp Gly Leu Tyr Val Pro Leu Glu Asp Lys
1               5                   10

<210> SEQ ID NO 104
<211> LENGTH: 7
<212> TYPE: PRT
<213> ORGANISM: Thermus thermophilus

<400> SEQUENCE: 104

Leu Gly Glu Glu Asp Pro Lys
1               5

<210> SEQ ID NO 105
<211> LENGTH: 10
<212> TYPE: PRT
<213> ORGANISM: Thermus thermophilus

<400> SEQUENCE: 105

Leu Gly Leu Gly Thr Pro Glu Ala Val Arg
1               5                   10

<210> SEQ ID NO 106
<211> LENGTH: 11
<212> TYPE: PRT
<213> ORGANISM: Thermus thermophilus

<400> SEQUENCE: 106

Leu Tyr Pro Ala Ser Gly Phe Ala Phe Pro Arg
1               5                   10

<210> SEQ ID NO 107
<211> LENGTH: 8
```

```
<212> TYPE: PRT
<213> ORGANISM: Thermus thermophilus

<400> SEQUENCE: 107

Met Gly Gln Asn Tyr Ala Tyr Arg
1               5

<210> SEQ ID NO 108
<211> LENGTH: 8
<212> TYPE: PRT
<213> ORGANISM: Thermus thermophilus

<400> SEQUENCE: 108

Ser Val Leu Ser Ala Leu Ala Arg
1               5

<210> SEQ ID NO 109
<211> LENGTH: 7
<212> TYPE: PRT
<213> ORGANISM: Thermus thermophilus

<400> SEQUENCE: 109

Thr Glu Val Phe Leu Asn Arg
1               5

<210> SEQ ID NO 110
<211> LENGTH: 11
<212> TYPE: PRT
<213> ORGANISM: Thermus thermophilus

<400> SEQUENCE: 110

Val Ala Trp Val Ala Asp Pro Lys Asp Pro Arg
1               5                   10

<210> SEQ ID NO 111
<211> LENGTH: 7
<212> TYPE: PRT
<213> ORGANISM: Thermus thermophilus

<400> SEQUENCE: 111

Val Tyr Pro Val Gln Gly Arg
1               5

<210> SEQ ID NO 112
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ggcggagctc gccgtgggct ttgccgccgg cggaagggag tcctttcg          48

<210> SEQ ID NO 113
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gagagaggat cccgaattgt gcagctgtca atcaacc                      37
```

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (40)..(40)
<223> OTHER INFORMATION: a, c, t, g, unknown or other

<400> SEQUENCE: 114
gagagaggat ccttttttttt tttttttttt tttttttttvn          40

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
ctagacgagg tagtaggttg tatagta          27

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
agcttactat acaacctact acctcgt          27

<210> SEQ ID NO 117
<211> LENGTH: 685
<212> TYPE: PRT
<213> ORGANISM: Thermus thermophilus

<400> SEQUENCE: 117

Met Asn His Leu Gly Lys Thr Glu Val Phe Leu Asn Arg Phe Ala Leu
1               5                   10                  15

Arg Pro Leu Asn Pro Glu Glu Leu Arg Pro Trp Arg Leu Glu Val Val
            20                  25                  30

Leu Asp Pro Pro Pro Gly Arg Glu Glu Val Tyr Pro Leu Leu Ala Gln
        35                  40                  45

Val Ala Arg Arg Ala Gly Gly Val Thr Val Arg Met Gly Asp Gly Leu
    50                  55                  60

Ala Ser Trp Ser Pro Pro Glu Val Leu Val Leu Glu Gly Thr Leu Ala
65                  70                  75                  80

Arg Met Gly Gln Thr Tyr Ala Tyr Arg Leu Tyr Pro Lys Gly Arg Arg
                85                  90                  95

Pro Leu Asp Pro Lys Asp Pro Gly Glu Arg Ser Val Leu Ser Ala Leu
            100                 105                 110

Ala Arg Arg Leu Leu Gln Glu Arg Leu Arg Leu Glu Gly Val Trp
        115                 120                 125

Val Glu Gly Leu Ala Val Tyr Arg Arg Glu His Ala Arg Gly Pro Gly
    130                 135                 140

Trp Arg Val Leu Gly Gly Ala Val Leu Asp Leu Trp Val Ser Asp Ser
145                 150                 155                 160

-continued

```
Gly Ala Phe Leu Leu Glu Val Asp Pro Ala Tyr Arg Ile Leu Cys Glu
            165                 170                 175

Met Ser Leu Glu Ala Trp Leu Ala Gln Gly His Pro Leu Pro Lys Arg
        180                 185                 190

Val Arg Asn Ala Tyr Asp Arg Arg Thr Trp Glu Leu Leu Arg Leu Gly
            195                 200                 205

Glu Glu Asp Pro Lys Glu Leu Pro Leu Pro Gly Gly Leu Ser Leu Leu
        210                 215                 220

Asp Tyr His Ala Ser Lys Gly Arg Leu Gln Gly Arg Glu Gly Gly Arg
225                 230                 235                 240

Val Ala Trp Val Ala Asp Pro Lys Asp Pro Arg Lys Pro Ile Pro His
            245                 250                 255

Leu Thr Gly Leu Leu Val Pro Val Leu Thr Leu Glu Asp Leu His Glu
            260                 265                 270

Glu Glu Gly Ser Leu Ala Leu Ser Leu Pro Trp Glu Glu Arg Arg Arg
        275                 280                 285

Arg Thr Arg Glu Ile Ala Ser Trp Ile Gly Arg Arg Leu Gly Leu Gly
        290                 295                 300

Thr Pro Glu Ala Val Arg Ala Gln Ala Tyr Arg Leu Ser Ile Pro Lys
305                 310                 315                 320

Leu Met Gly Arg Arg Ala Val Ser Lys Pro Ala Asp Ala Leu Arg Val
            325                 330                 335

Gly Phe Tyr Arg Ala Gln Glu Thr Ala Leu Ala Leu Leu Arg Leu Asp
            340                 345                 350

Gly Ala Gln Gly Trp Pro Glu Phe Leu Arg Arg Ala Leu Leu Arg Ala
        355                 360                 365

Phe Gly Ala Ser Gly Ala Ser Leu Arg Leu His Thr Leu His Ala His
    370                 375                 380

Pro Ser Gln Gly Leu Ala Phe Arg Glu Ala Leu Arg Lys Ala Lys Glu
385                 390                 395                 400

Glu Gly Val Gln Ala Val Leu Val Leu Thr Pro Pro Met Ala Trp Glu
            405                 410                 415

Asp Arg Asn Arg Leu Lys Ala Leu Leu Leu Arg Glu Gly Leu Pro Ser
            420                 425                 430

Gln Ile Leu Asn Val Pro Leu Arg Glu Glu Arg His Arg Trp Glu
        435                 440                 445

Asn Ala Leu Leu Gly Leu Leu Ala Lys Ala Gly Leu Gln Val Val Ala
    450                 455                 460

Leu Ser Gly Ala Tyr Pro Ala Glu Leu Ala Val Gly Phe Asp Ala Gly
465                 470                 475                 480

Gly Arg Glu Ser Phe Arg Phe Gly Gly Ala Ala Cys Ala Val Gly Gly
            485                 490                 495

Asp Gly Gly His Leu Leu Trp Thr Leu Pro Glu Ala Gln Ala Gly Glu
            500                 505                 510

Arg Ile Pro Gln Glu Val Val Trp Asp Leu Leu Glu Thr Leu Trp
        515                 520                 525

Ala Phe Arg Arg Lys Ala Gly Arg Leu Pro Ser Arg Val Leu Leu Leu
    530                 535                 540

Arg Asp Gly Arg Val Pro Gln Asp Glu Phe Ala Leu Ala Leu Glu Ala
545                 550                 555                 560

Leu Ala Arg Glu Gly Ile Ala Tyr Asp Leu Val Ser Val Arg Lys Ser
            565                 570                 575
```

-continued

```
Gly Gly Gly Arg Val Tyr Pro Val Gln Gly Arg Leu Ala Asp Gly Leu
            580                 585                 590

Tyr Val Pro Leu Glu Asp Lys Thr Phe Leu Leu Leu Val His Arg
        595                 600                 605

Asp Phe Arg Gly Thr Pro Arg Pro Leu Lys Leu Val His Glu Ala Gly
            610                 615                 620

Asp Thr Pro Leu Glu Ala Leu Ala His Gln Ile Phe His Leu Thr Arg
625                 630                 635                 640

Leu Tyr Pro Ala Ser Gly Phe Ala Phe Pro Arg Leu Pro Ala Pro Leu
                645                 650                 655

His Leu Ala Asp Arg Leu Val Lys Glu Val Gly Arg Leu Gly Ile Arg
            660                 665                 670

His Leu Lys Glu Val Asp Arg Glu Lys Leu Phe Phe Val
        675                 680                 685

<210> SEQ ID NO 118
<211> LENGTH: 660
<212> TYPE: PRT
<213> ORGANISM: Thermus thermophilus

<400> SEQUENCE: 118

Met Asn His Leu Gly Lys Thr Glu Val Phe Leu Asn Arg Phe Ala Leu
1               5                   10                  15

Arg Pro Leu Asn Pro Glu Glu Leu Arg Pro Trp Arg Leu Glu Val Val
            20                  25                  30

Leu Asp Pro Pro Gly Arg Glu Val Tyr Pro Leu Leu Ala Gln
        35                  40                  45

Val Ala Arg Arg Ala Gly Gly Val Thr Val Arg Met Gly Asp Gly Leu
    50                  55                  60

Ala Ser Trp Ser Pro Pro Glu Val Leu Val Leu Glu Gly Thr Leu Ala
65                  70                  75                  80

Arg Met Gly Gln Thr Tyr Ala Tyr Arg Leu Tyr Pro Lys Gly Arg Arg
                85                  90                  95

Pro Leu Asp Pro Lys Asp Pro Gly Glu Arg Ser Ala Leu Ser Ser Leu
            100                 105                 110

Ala Arg Arg Leu Leu Gln Glu Arg Leu Arg Arg Leu Glu Gly Val Trp
        115                 120                 125

Val Glu Gly Leu Ala Val Tyr Arg Arg Glu His Ala Arg Gly Pro Gly
    130                 135                 140

Trp Arg Val Leu Gly Gly Ala Val Leu Asp Leu Trp Val Ser Asp Ser
145                 150                 155                 160

Gly Ala Phe Leu Leu Glu Val Asp Pro Ala Tyr Arg Ile Leu Cys Glu
                165                 170                 175

Met Ser Leu Glu Ala Trp Leu Ala Gln Gly His Pro Leu Pro Lys Arg
            180                 185                 190

Val Arg Asn Ala Tyr Asp Arg Arg Thr Trp Glu Leu Leu Arg Leu Gly
        195                 200                 205

Glu Glu Asp Pro Lys Glu Leu Pro Leu Pro Gly Gly Leu Ser Leu Leu
    210                 215                 220

Asp Tyr His Ala Ser Lys Gly Arg Leu Gln Gly Arg Glu Gly Gly Arg
225                 230                 235                 240

Val Ala Trp Val Ala Asp Pro Lys Asp Pro Arg Lys Pro Ile Pro His
                245                 250                 255

Leu Thr Gly Leu Leu Val Pro Val Leu Thr Leu Glu Asp Leu His Glu
            260                 265                 270
```

Glu Glu Gly Gly Leu Ala Leu Ser Leu Pro Trp Glu Arg Arg
                275                 280                 285

Arg Thr Arg Glu Ile Ala Ser Trp Ile Gly Arg Arg Leu Gly Leu Gly
290                 295                 300

Thr Pro Glu Ala Val Arg Ala Gln Ala Tyr Arg Leu Ser Ile Pro Lys
305                 310                 315                 320

Leu Met Gly Arg Arg Ala Val Ser Lys Pro Ala Asp Ala Leu Arg Val
                325                 330                 335

Gly Leu Tyr Arg Ala Gln Glu Thr Ala Leu Ala Leu Leu Arg Leu Asp
                340                 345                 350

Gly Ala Gln Gly Trp Pro Glu Phe Leu Arg Arg Ala Leu Leu Gln Ala
                355                 360                 365

Phe Gly Ala Gly Gly Ala Ser Leu Arg Leu His Thr Leu His Ala His
370                 375                 380

Pro Ser Gln Gly Leu Ala Phe Arg Glu Ala Leu Arg Lys Ala Lys Glu
385                 390                 395                 400

Lys Gly Val Gln Ala Val Leu Val Leu Thr Pro Pro Met Ala Trp Glu
                405                 410                 415

Asp Arg Asn Arg Leu Lys Ala Leu Leu Leu Arg Glu Gly Leu Pro Ser
                420                 425                 430

Gln Ile Leu Asn Val Pro Leu Arg Glu Glu Arg His Arg Trp Glu
                435                 440                 445

Asn Ala Leu Leu Gly Leu Leu Ala Lys Ala Gly Leu Gln Val Val Ala
450                 455                 460

Leu Ser Gly Ala Tyr Pro Ala Glu Leu Ala Val Gly Phe Asp Ala Gly
465                 470                 475                 480

Gly Arg Glu Ser Phe Arg Phe Gly Ala Ala Cys Ala Val Gly Gly
                485                 490                 495

Asp Gly Gly His Leu Leu Trp Thr Leu Pro Glu Ala Gln Ala Gly Glu
                500                 505                 510

Arg Ile Pro Gln Glu Val Val Trp Asp Leu Leu Glu Glu Thr Leu Trp
                515                 520                 525

Ala Phe Arg Arg Lys Ala Gly Arg Leu Pro Ser Arg Val Leu Leu Leu
                530                 535                 540

Arg Asp Gly Arg Val Pro Gln Asp Glu Phe Ala Leu Ala Leu Glu Ala
545                 550                 555                 560

Leu Ala Arg Glu Gly Ile Ala Tyr Asp Leu Val Ser Val Arg Lys Ser
                565                 570                 575

Gly Gly Gly Arg Val Tyr Pro Val Gln Gly Arg Leu Ala Asp Gly Leu
                580                 585                 590

Tyr Val Pro Leu Glu Asp Arg Thr Phe Leu Leu Leu Thr Val His Arg
                595                 600                 605

Asp Phe Arg Gly Thr Pro Arg Pro Leu Lys Leu Val His Glu Ala Gly
610                 615                 620

Asp Thr Pro Leu Glu Ala Leu Ala His Gln Ile Phe His Leu Thr Arg
625                 630                 635                 640

Leu Tyr Pro Ala Ser Gly Phe Ala Phe Pro Arg Leu Pro Ala Pro Leu
                645                 650                 655

His Leu Ala Asp
                660

<210> SEQ ID NO 119
<211> LENGTH: 706

<212> TYPE: PRT
<213> ORGANISM: Aquifex aeolicus

<400> SEQUENCE: 119

```
Met Gly Lys Glu Ala Leu Leu Asn Leu Tyr Arg Ile Glu Tyr Arg Pro
1               5                   10                  15
Lys Asp Thr Thr Phe Thr Val Phe Lys Pro Thr His Glu Ile Gln Lys
            20                  25                  30
Glu Lys Leu Asn Lys Val Arg Trp Arg Val Phe Leu Gln Thr Gly Leu
        35                  40                  45
Pro Thr Phe Arg Arg Glu Asp Glu Phe Trp Cys Ala Gly Lys Val Glu
    50                  55                  60
Lys Asp Thr Leu Tyr Leu Thr Leu Ser Asn Gly Glu Ile Val Glu Leu
65                  70                  75                  80
Lys Arg Val Gly Glu Glu Glu Phe Arg Gly Phe Gln Asn Glu Arg Glu
                85                  90                  95
Cys Gln Glu Leu Phe Arg Asp Phe Leu Thr Lys Thr Lys Val Lys Asp
            100                 105                 110
Lys Phe Ile Ser Asp Phe Tyr Lys Lys Phe Arg Asp Lys Ile Thr Val
        115                 120                 125
Gln Gly Lys Asn Arg Lys Ile Ala Leu Ile Pro Glu Val Asn Glu Lys
    130                 135                 140
Val Leu Lys Ser Glu Glu Gly Tyr Phe Leu His Leu Asp Leu Lys
145                 150                 155                 160
Phe Arg Ile Gln Pro Phe Glu Thr Leu Gln Thr Leu Leu Glu Arg Asn
                165                 170                 175
Asp Phe Asn Pro Lys Arg Ile Arg Val Lys Pro Ile Gly Ile Asp Phe
            180                 185                 190
Val Gly Arg Val Gln Asp Val Phe Lys Ala Lys Glu Lys Gly Glu Glu
        195                 200                 205
Phe Phe Arg Leu Cys Met Glu Arg Ser Thr His Lys Ser Ser Lys Lys
    210                 215                 220
Ala Trp Glu Glu Leu Leu Lys Asn Arg Glu Leu Arg Glu Lys Ala Phe
225                 230                 235                 240
Leu Val Val Leu Glu Lys Gly Tyr Thr Tyr Pro Ala Thr Ile Leu Lys
                245                 250                 255
Pro Val Leu Thr Tyr Glu Asn Leu Glu Asp Glu Glu Arg Asn Glu Val
            260                 265                 270
Ala Asp Ile Val Arg Met Glu Pro Gly Lys Arg Leu Asn Leu Ile Arg
        275                 280                 285
Tyr Ile Leu Arg Arg Tyr Val Lys Ala Leu Arg Asp Tyr Gly Trp Tyr
    290                 295                 300
Ile Ser Pro Glu Glu Glu Arg Ala Lys Gly Leu Asn Phe Lys Asp
305                 310                 315                 320
Thr Val Leu Asp Ala Lys Gly Lys Asn Thr Lys Val Ile Thr Asn Leu
                325                 330                 335
Arg Lys Phe Leu Glu Leu Cys Arg Pro Phe Val Lys Asp Val Leu
            340                 345                 350
Ser Val Glu Ile Ile Ser Val Ser Val Tyr Lys Leu Glu Trp Arg
        355                 360                 365
Lys Glu Glu Phe Leu Lys Glu Leu Ile Asn Phe Leu Lys Asn Lys Gly
    370                 375                 380
Ile Lys Leu Lys Ile Lys Gly Lys Ser Leu Ile Leu Ala Gln Thr Arg
385                 390                 395                 400
```

```
Glu Glu Ala Lys Glu Lys Leu Ile Pro Val Ile Asn Lys Ile Lys Asp
            405                 410                 415
Val Asp Leu Val Ile Val Phe Leu Glu Glu Tyr Pro Lys Val Asp Pro
        420                 425                 430
Tyr Lys Ser Phe Leu Leu Tyr Asp Phe Val Lys Arg Glu Leu Leu Lys
    435                 440                 445
Lys Met Ile Pro Ser Gln Val Ile Leu Asn Arg Thr Leu Lys Asn Glu
450                 455                 460
Asn Leu Lys Phe Val Leu Leu Asn Val Ala Glu Gln Val Leu Ala Lys
465                 470                 475                 480
Thr Gly Asn Ile Pro Tyr Lys Leu Lys Glu Ile Glu Gly Lys Val Asp
                485                 490                 495
Ala Phe Val Gly Ile Asp Ile Ser Arg Ile Thr Arg Asp Gly Lys Thr
            500                 505                 510
Val Asn Ala Val Ala Phe Thr Lys Ile Phe Asn Ser Lys Gly Glu Leu
        515                 520                 525
Val Arg Tyr Tyr Leu Thr Ser Tyr Pro Ala Phe Gly Glu Lys Leu Thr
    530                 535                 540
Glu Lys Ala Ile Gly Asp Val Phe Ser Leu Leu Glu Lys Leu Gly Phe
545                 550                 555                 560
Lys Lys Gly Ser Lys Ile Val Val His Arg Asp Gly Arg Leu Tyr Arg
                565                 570                 575
Asp Glu Val Ala Ala Phe Lys Lys Tyr Gly Glu Leu Tyr Gly Tyr Ser
            580                 585                 590
Leu Glu Leu Leu Glu Ile Ile Lys Arg Asn Asn Pro Arg Phe Phe Ser
        595                 600                 605
Asn Glu Lys Phe Ile Lys Gly Tyr Phe Tyr Lys Leu Ser Glu Asp Ser
    610                 615                 620
Val Ile Leu Ala Thr Tyr Asn Gln Val Tyr Glu Gly Thr His Gln Pro
625                 630                 635                 640
Ile Lys Val Arg Lys Val Tyr Gly Glu Leu Pro Val Glu Val Leu Cys
                645                 650                 655
Ser Gln Ile Leu Ser Leu Thr Leu Met Asn Tyr Ser Ser Phe Gln Pro
            660                 665                 670
Ile Lys Leu Pro Ala Thr Val His Tyr Ser Asp Lys Ile Thr Lys Leu
        675                 680                 685
Met Leu Arg Gly Ile Glu Pro Ile Lys Lys Glu Gly Asp Ile Met Tyr
    690                 695                 700
Trp Leu
705

<210> SEQ ID NO 120
<211> LENGTH: 770
<212> TYPE: PRT
<213> ORGANISM: Pyrococcus furiosus

<400> SEQUENCE: 120

Met Lys Ala Lys Val Val Ile Asn Leu Val Lys Ile Asn Lys Lys Ile
1               5                   10                  15
Ile Pro Asp Lys Ile Tyr Val Tyr Arg Leu Phe Asn Asp Pro Glu Glu
            20                  25                  30
Glu Leu Gln Lys Glu Gly Tyr Ser Ile Tyr Arg Leu Ala Tyr Glu Asn
        35                  40                  45
Val Gly Ile Val Ile Asp Pro Glu Asn Leu Ile Ile Ala Thr Thr Lys
```

```
                50                  55                  60
Glu Leu Glu Tyr Glu Gly Phe Ile Pro Glu Gly Glu Ile Ser Phe
 65                  70                  75                  80

Ser Glu Leu Arg Asn Asp Tyr Gln Ser Lys Leu Val Leu Arg Leu Leu
                 85                  90                  95

Lys Glu Asn Gly Ile Gly Glu Tyr Glu Leu Ser Lys Leu Leu Arg Lys
                100                 105                 110

Phe Arg Lys Pro Lys Thr Phe Gly Asp Tyr Lys Val Ile Pro Ser Val
                115                 120                 125

Glu Met Ser Val Ile Lys His Asp Glu Asp Phe Tyr Leu Val Ile His
                130                 135                 140

Ile Ile His Gln Ile Gln Ser Met Lys Thr Leu Trp Glu Leu Val Asn
145                 150                 155                 160

Lys Asp Pro Lys Glu Leu Glu Glu Phe Leu Met Thr His Lys Glu Asn
                165                 170                 175

Leu Met Leu Lys Asp Ile Ala Ser Pro Leu Lys Thr Val Tyr Lys Pro
                180                 185                 190

Cys Phe Glu Glu Tyr Thr Lys Lys Pro Lys Leu Asp His Asn Gln Glu
                195                 200                 205

Ile Val Lys Tyr Trp Tyr Asn Tyr His Ile Glu Arg Tyr Trp Asn Thr
210                 215                 220

Pro Glu Ala Lys Leu Glu Phe Tyr Arg Lys Phe Gly Gln Val Asp Leu
225                 230                 235                 240

Lys Gln Pro Ala Ile Leu Ala Lys Phe Ala Ser Lys Ile Lys Lys Asn
                245                 250                 255

Lys Asn Tyr Lys Ile Tyr Leu Leu Pro Gln Leu Val Val Pro Thr Tyr
                260                 265                 270

Asn Ala Glu Gln Leu Glu Ser Asp Val Ala Lys Glu Ile Leu Glu Tyr
                275                 280                 285

Thr Lys Leu Met Pro Glu Glu Arg Lys Glu Leu Leu Glu Asn Ile Leu
                290                 295                 300

Ala Glu Val Asp Ser Asp Ile Ile Asp Lys Ser Leu Ser Glu Ile Glu
305                 310                 315                 320

Val Glu Lys Ile Ala Gln Glu Leu Glu Asn Lys Ile Arg Val Arg Asp
                325                 330                 335

Asp Lys Gly Asn Ser Val Pro Ile Ser Gln Leu Asn Val Gln Lys Ser
                340                 345                 350

Gln Leu Leu Leu Trp Thr Asn Tyr Ser Arg Lys Tyr Pro Val Ile Leu
                355                 360                 365

Pro Tyr Glu Val Pro Glu Lys Phe Arg Lys Ile Arg Glu Ile Pro Met
370                 375                 380

Phe Ile Ile Leu Asp Ser Gly Leu Leu Ala Asp Ile Gln Asn Phe Ala
385                 390                 395                 400

Thr Asn Glu Phe Arg Glu Leu Val Lys Ser Met Tyr Tyr Ser Leu Ala
                405                 410                 415

Lys Lys Tyr Asn Ser Leu Ala Lys Lys Ala Arg Ser Thr Asn Glu Ile
                420                 425                 430

Gly Leu Pro Phe Leu Asp Phe Arg Gly Lys Glu Lys Val Ile Thr Glu
                435                 440                 445

Asp Leu Asn Ser Asp Lys Gly Ile Ile Glu Val Val Glu Gln Val Ser
                450                 455                 460

Ser Phe Met Lys Gly Lys Glu Leu Gly Leu Ala Phe Ile Ala Ala Arg
465                 470                 475                 480
```

```
Asn Lys Leu Ser Ser Glu Lys Phe Glu Glu Ile Lys Arg Arg Leu Phe
            485                 490                 495

Asn Leu Asn Val Ile Ser Gln Val Val Asn Glu Asp Thr Leu Lys Asn
            500                 505                 510

Lys Arg Asp Lys Tyr Asp Arg Asn Arg Leu Asp Leu Phe Val Arg His
            515                 520                 525

Asn Leu Leu Phe Gln Val Leu Ser Lys Leu Gly Val Lys Tyr Tyr Val
            530                 535                 540

Leu Asp Tyr Arg Phe Asn Tyr Asp Tyr Ile Ile Gly Ile Asp Val Ala
545                 550                 555                 560

Pro Met Lys Arg Ser Glu Gly Tyr Ile Gly Gly Ser Ala Val Met Phe
            565                 570                 575

Asp Ser Gln Gly Tyr Ile Arg Lys Ile Val Pro Ile Lys Ile Gly Glu
            580                 585                 590

Gln Arg Gly Glu Ser Val Asp Met Asn Glu Phe Phe Lys Glu Met Val
            595                 600                 605

Asp Lys Phe Lys Glu Phe Asn Ile Lys Leu Asp Asn Lys Lys Ile Leu
            610                 615                 620

Leu Leu Arg Asp Gly Arg Ile Thr Asn Asn Glu Glu Glu Gly Leu Lys
625                 630                 635                 640

Tyr Ile Ser Glu Met Phe Asp Ile Glu Val Val Thr Met Asp Val Ile
            645                 650                 655

Lys Asn His Pro Val Arg Ala Phe Ala Asn Met Lys Met Tyr Phe Asn
            660                 665                 670

Leu Gly Gly Ala Ile Tyr Leu Ile Pro His Lys Leu Lys Gln Ala Lys
            675                 680                 685

Gly Thr Pro Ile Pro Ile Lys Leu Ala Lys Lys Arg Ile Ile Lys Asn
            690                 695                 700

Gly Lys Val Glu Lys Gln Ser Ile Thr Arg Gln Asp Val Leu Asp Ile
705                 710                 715                 720

Phe Ile Leu Thr Arg Leu Asn Tyr Gly Ser Ile Ser Ala Asp Met Arg
            725                 730                 735

Leu Pro Ala Pro Val His Tyr Ala His Lys Phe Ala Asn Ala Ile Arg
            740                 745                 750

Asn Glu Trp Lys Ile Lys Glu Glu Phe Leu Ala Glu Gly Phe Leu Tyr
            755                 760                 765

Phe Val
    770

<210> SEQ ID NO 121
<211> LENGTH: 770
<212> TYPE: PRT
<213> ORGANISM: Pyrococcus furiosus

<400> SEQUENCE: 121

Met Lys Ala Lys Val Val Ile Asn Leu Val Lys Ile Asn Lys Lys Ile
1               5                   10                  15

Ile Pro Asp Lys Ile Tyr Val Tyr Arg Leu Phe Asn Asp Pro Glu Glu
            20                  25                  30

Glu Leu Gln Lys Glu Gly Tyr Ser Ile Tyr Arg Leu Ala Tyr Glu Asn
            35                  40                  45

Val Gly Ile Val Ile Asp Pro Glu Asn Leu Ile Ile Ala Thr Thr Lys
            50                  55                  60

Glu Leu Glu Tyr Glu Gly Glu Phe Ile Pro Glu Gly Glu Ile Ser Phe
```

```
                65                  70                  75                  80
Ser Glu Leu Arg Asn Asp Tyr Gln Ser Lys Leu Val Leu Arg Leu Leu
                    85                  90                  95

Lys Glu Asn Gly Ile Gly Tyr Glu Leu Ser Lys Leu Leu Arg Lys
            100                 105                 110

Phe Arg Lys Pro Lys Thr Phe Gly Asp Tyr Lys Val Ile Pro Ser Val
            115                 120                 125

Glu Met Ser Val Ile Lys His Asp Glu Asp Phe Tyr Leu Val Ile His
            130                 135                 140

Ile Ile His Gln Ile Gln Ser Met Lys Thr Leu Trp Glu Leu Val Asn
145                 150                 155                 160

Lys Asp Pro Lys Glu Leu Glu Phe Leu Met Thr His Lys Glu Asn
                165                 170                 175

Leu Met Leu Lys Asp Ile Ala Ser Pro Leu Lys Thr Val Tyr Lys Pro
            180                 185                 190

Cys Phe Glu Glu Tyr Thr Lys Lys Pro Lys Leu Asp His Asn Gln Glu
                195                 200                 205

Ile Val Lys Tyr Trp Tyr Asn Tyr His Ile Glu Arg Tyr Trp Asn Thr
            210                 215                 220

Pro Glu Ala Lys Leu Glu Phe Tyr Arg Lys Phe Gly Gln Val Asp Leu
225                 230                 235                 240

Lys Gln Pro Ala Ile Leu Ala Lys Phe Ala Ser Lys Ile Lys Lys Asn
                245                 250                 255

Lys Asn Tyr Lys Ile Tyr Leu Leu Pro Gln Leu Val Val Pro Thr Tyr
                260                 265                 270

Asn Ala Glu Gln Leu Glu Ser Asp Val Ala Lys Glu Ile Leu Glu Tyr
            275                 280                 285

Thr Lys Leu Met Pro Glu Glu Arg Lys Glu Leu Leu Glu Asn Ile Leu
            290                 295                 300

Ala Glu Val Asp Ser Asp Ile Ile Asp Lys Ser Leu Ser Glu Ile Glu
305                 310                 315                 320

Val Glu Lys Ile Ala Gln Glu Leu Glu Asn Lys Ile Arg Val Arg Asp
                325                 330                 335

Asp Lys Gly Asn Ser Val Pro Ile Ser Gln Leu Asn Val Gln Lys Ser
            340                 345                 350

Gln Leu Leu Leu Trp Thr Asn Tyr Ser Arg Lys Tyr Pro Val Ile Leu
            355                 360                 365

Pro Tyr Glu Val Pro Glu Lys Phe Arg Lys Ile Arg Glu Ile Pro Met
            370                 375                 380

Phe Ile Ile Leu Asp Ser Gly Leu Leu Ala Asp Ile Gln Asn Phe Ala
385                 390                 395                 400

Thr Asn Glu Phe Arg Glu Leu Val Lys Ser Met Tyr Tyr Ser Leu Ala
                405                 410                 415

Lys Lys Tyr Asn Ser Leu Ala Lys Lys Ala Arg Ser Thr Asn Glu Ile
            420                 425                 430

Gly Leu Pro Phe Leu Asp Phe Arg Gly Lys Glu Lys Val Ile Thr Glu
            435                 440                 445

Asp Leu Asn Ser Asp Lys Gly Ile Ile Glu Val Val Glu Gln Val Ser
            450                 455                 460

Ser Phe Met Lys Gly Lys Glu Leu Gly Leu Ala Phe Ile Ala Ala Arg
465                 470                 475                 480

Asn Lys Leu Ser Ser Glu Lys Phe Glu Glu Ile Lys Arg Arg Leu Phe
                485                 490                 495
```

```
Asn Leu Asn Val Ile Ser Gln Val Val Asn Glu Asp Thr Leu Lys Asn
            500                 505                 510

Lys Arg Asp Lys Tyr Asp Arg Asn Arg Leu Asp Leu Phe Val Arg His
        515                 520                 525

Asn Leu Leu Phe Gln Val Leu Ser Lys Leu Gly Val Lys Tyr Tyr Val
    530                 535                 540

Leu Asp Tyr Arg Phe Asn Tyr Asp Tyr Ile Ile Gly Ile Asp Val Ala
545                 550                 555                 560

Pro Met Lys Arg Ser Glu Gly Tyr Ile Gly Gly Ser Ala Val Met Phe
                565                 570                 575

Asp Ser Gln Gly Tyr Ile Arg Lys Ile Val Pro Ile Lys Ile Gly Glu
            580                 585                 590

Gln Arg Gly Glu Ser Val Asp Met Asn Glu Phe Phe Lys Glu Met Val
        595                 600                 605

Asp Lys Phe Lys Glu Phe Asn Ile Lys Leu Asp Asn Lys Lys Ile Leu
    610                 615                 620

Leu Leu Arg Asp Gly Arg Ile Thr Asn Asn Glu Glu Glu Gly Leu Lys
625                 630                 635                 640

Tyr Ile Ser Glu Met Phe Asp Ile Glu Val Val Thr Met Asp Val Ile
                645                 650                 655

Lys Asn His Pro Val Arg Ala Phe Ala Asn Met Lys Met Tyr Phe Asn
            660                 665                 670

Leu Gly Gly Ala Ile Tyr Leu Ile Pro His Lys Leu Lys Gln Ala Lys
        675                 680                 685

Gly Thr Pro Ile Pro Ile Lys Leu Ala Lys Lys Arg Ile Ile Lys Asn
    690                 695                 700

Gly Lys Val Glu Lys Gln Ser Ile Thr Arg Gln Asp Val Leu Asp Ile
705                 710                 715                 720

Phe Ile Leu Thr Arg Leu Asn Tyr Gly Ser Ile Ser Ala Asp Met Arg
                725                 730                 735

Leu Pro Ala Pro Val His Tyr Ala His Lys Phe Ala Asn Ala Ile Arg
            740                 745                 750

Asn Glu Trp Lys Ile Lys Glu Glu Phe Leu Ala Glu Gly Phe Leu Tyr
        755                 760                 765

Phe Val
    770

<210> SEQ ID NO 122
<211> LENGTH: 427
<212> TYPE: PRT
<213> ORGANISM: Archaeoglobus fulgidus

<400> SEQUENCE: 122

Met Met Glu Tyr Lys Ile Val Glu Asn Gly Leu Thr Tyr Arg Ile Gly
1               5                   10                  15

Asn Gly Ala Ser Val Pro Ile Ser Asn Thr Gly Glu Leu Ile Lys Gly
            20                  25                  30

Leu Arg Asn Tyr Gly Pro Tyr Glu Val Pro Ser Leu Lys Tyr Asn Gln
        35                  40                  45

Ile Ala Leu Ile His Asn Asn Gln Phe Ser Ser Leu Ile Asn Gln Leu
    50                  55                  60

Lys Ser Gln Ile Ser Ser Lys Ile Asp Glu Val Trp His Ile His Asn
65                  70                  75                  80

Ile Asn Ile Ser Glu Phe Ile Tyr Asp Ser Pro His Phe Asp Ser Ile
```

85                  90                  95
Lys Ser Gln Val Asp Asn Ala Ile Asp Thr Gly Val Asp Gly Ile Met
            100                 105                 110

Leu Val Leu Pro Glu Tyr Asn Thr Pro Leu Tyr Tyr Lys Leu Lys Ser
            115                 120                 125

Tyr Leu Ile Asn Ser Ile Pro Ser Gln Phe Met Arg Tyr Asp Ile Leu
        130                 135                 140

Ser Asn Arg Asn Leu Thr Phe Tyr Val Asp Asn Leu Val Gln Phe
145                 150                 155                 160

Val Ser Lys Leu Gly Gly Lys Pro Trp Ile Leu Asn Val Asp Pro Glu
                165                 170                 175

Lys Gly Ser Asp Ile Ile Ile Gly Thr Gly Ala Thr Arg Ile Asp Asn
                180                 185                 190

Val Asn Leu Phe Cys Phe Ala Met Val Phe Lys Lys Asp Gly Thr Met
            195                 200                 205

Leu Trp Asn Glu Ile Ser Pro Ile Val Thr Ser Ser Glu Tyr Leu Thr
        210                 215                 220

Tyr Leu Lys Ser Thr Ile Lys Lys Val Val Tyr Gly Phe Lys Lys Ser
225                 230                 235                 240

Asn Pro Asp Trp Asp Val Glu Lys Leu Thr Leu His Val Ser Gly Lys
                245                 250                 255

Arg Pro Lys Met Lys Asp Gly Glu Thr Lys Ile Leu Lys Glu Thr Val
            260                 265                 270

Glu Glu Leu Lys Lys Gln Glu Met Val Ser Arg Asp Val Lys Tyr Ala
        275                 280                 285

Ile Leu His Leu Asn Glu Thr His Pro Phe Trp Val Met Gly Asp Pro
290                 295                 300

Asn Asn Arg Phe His Pro Tyr Glu Gly Thr Lys Val Lys Leu Ser Ser
305                 310                 315                 320

Lys Arg Tyr Leu Leu Thr Leu Leu Gln Pro Tyr Leu Lys Arg Asn Gly
                325                 330                 335

Leu Glu Met Val Thr Pro Ile Lys Pro Leu Ser Val Glu Ile Val Ser
            340                 345                 350

Asp Asn Trp Thr Ser Glu Glu Tyr Tyr His Asn Val His Glu Ile Leu
        355                 360                 365

Asp Glu Ile Tyr Tyr Leu Ser Lys Met Asn Trp Arg Gly Phe Arg Ser
        370                 375                 380

Arg Asn Leu Pro Val Thr Val Asn Tyr Pro Lys Leu Val Ala Gly Ile
385                 390                 395                 400

Ile Ala Asn Val Asn Arg Tyr Gly Gly Tyr Pro Ile Asn Pro Glu Gly
                405                 410                 415

Asn Arg Ser Leu Gln Thr Asn Pro Trp Phe Leu
            420                 425

<210> SEQ ID NO 123
<211> LENGTH: 707
<212> TYPE: PRT
<213> ORGANISM: Anoxybacillus flavithermus

<400> SEQUENCE: 123

Met Asn Gln Tyr Tyr Ile Thr Glu Cys Met Ala Asn Glu Asn Ala Asn
1               5                   10                  15

Asn Ile Pro Leu His Ile Tyr Thr Val Ser Leu Leu Asn Pro Asn Gln
            20                  25                  30

-continued

```
Lys Tyr Ser Phe Ala His His Ile Val Tyr Glu Leu Arg Lys Arg Asn
             35                  40                  45

Pro Asn Val Thr Ile Ala Val His Gly Gln Tyr Ile Ala Ser Phe Gln
 50                  55                  60

Glu Ile Ala His Trp Gly Asp His Glu Tyr Ile Lys His Glu Tyr Arg
 65                  70                  75                  80

Ala Ile Glu Cys Phe Asn Ala Thr Glu Arg Thr Val Leu Glu Arg Leu
                 85                  90                  95

Leu Lys Gln Glu Leu Ile Glu Arg Cys Lys Ser Asp Tyr Lys Ile Tyr
            100                 105                 110

Lys Asp Leu Phe Cys Leu Lys Thr Glu Gln Ser Ile Glu Met Asn Glu
            115                 120                 125

Ile Ile Val Tyr Pro Ala Ile Tyr Leu Ser Phe Thr Val Glu Glu Asn
130                 135                 140

Gly Asn Ile Leu Ile Gly Phe Glu Tyr Gln His Arg Phe Glu Tyr Lys
145                 150                 155                 160

Lys Thr Leu Glu Asp Leu Leu Arg Asp Arg Ser Pro Leu Ile Lys Glu
                165                 170                 175

Gly Val Glu Val Val Asp Ser Tyr Asn Lys Lys Ser Tyr Tyr Tyr Thr
            180                 185                 190

Phe Val Glu Val Ala Pro Tyr Thr Ala Gly Glu Lys Ser Pro Tyr Leu
            195                 200                 205

Gln Gln Ser Val Ile Asp Tyr Tyr Ile Thr Lys Asn Glu Lys Trp Lys
            210                 215                 220

Leu Lys Gly Val His Asn Lys Thr Pro Ile Val His Val Arg Ser Gln
225                 230                 235                 240

Thr Gly Asp Ile Phe Pro Tyr Leu Pro His Leu Leu Arg Leu Thr Cys
                245                 250                 255

Ser Tyr Glu Gln Leu Met Pro Ser Thr Ala Lys Gln Val Asn Arg Ile
            260                 265                 270

Ile Lys Leu Pro Pro Asn Lys Lys Met Pro Lys Leu Tyr Gln Glu Ile
            275                 280                 285

Phe Arg Leu Leu Gln Tyr Gln Asp Met Leu Thr Phe Arg Lys Glu Asn
290                 295                 300

Val Arg Ala Ala Asn Leu Asn Tyr Asn Ile Phe Lys Leu Ser Pro Pro
305                 310                 315                 320

Leu Met Lys Phe Gly Arg Asn Tyr Thr Thr Thr Lys Val Ser Asp Gly
                325                 330                 335

Leu Gly Gln Ala Gly Val Tyr Glu Pro Lys Ser Val Thr Val Ser Tyr
            340                 345                 350

Phe Val Asp Pro Glu Leu Asn Tyr Asp Gln Arg Lys Lys Asp Glu Ile
            355                 360                 365

Leu Asp Phe Thr Lys Lys Leu Gln Asp Leu Ser Gly Lys Leu Gly Val
370                 375                 380

Lys Leu Asn Val Ser Lys Lys Pro Arg Gln Leu Phe Gly Val Leu Pro
385                 390                 395                 400

Val Asp Phe Phe Lys Ser Glu Arg Leu Ser Phe Glu Leu Lys Ser Ile
                405                 410                 415

Thr Asn Ala Phe Glu Gly Thr Ile Val Ile Gly Thr Glu Glu Asn
            420                 425                 430

Ile Glu Arg Ala Tyr Met Ala Ile Lys Lys Glu Phe Gly Ala Lys Ala
            435                 440                 445

Asp Ile Met Thr Gln Phe Val Ile Phe Asp Ser Ser Ile Val Asn Asn
```

```
                  450                 455                 460

Ser Phe Tyr Tyr Tyr Asn Val Leu Leu Gly Ile Tyr Ala Lys Ser Gly
465                 470                 475                 480

Val Gln Pro Trp Ile Leu Leu Asp His Met Asn Ser Asp Cys Phe Ile
                485                 490                 495

Gly Leu Asp Val Ser His Glu Gln Gly Lys His Ala Ser Gly Ile Ile
                500                 505                 510

Gln Val Ile Gly Lys Asp Gly Arg Ile Ile Lys Gln Lys Ser Val Met
                515                 520                 525

Ala Thr Glu Ala Gly Glu Thr Ile Ala Arg Cys Thr Met Glu Glu Ile
                530                 535                 540

Ile Asn Glu Ser Ile Phe Ser Tyr Glu Lys Met Tyr Gly Met Lys Pro
545                 550                 555                 560

Ser His Ile Thr Phe His Arg Asp Gly Val Cys Arg Glu Asp Leu Ala
                565                 570                 575

His Leu Thr Gln Tyr Met Gln Ser Phe Gln Ile Pro Phe Asp Phe Val
                580                 585                 590

Glu Ile Ile Lys Lys Pro Arg Arg Met Ala Val Tyr Lys Asn Lys
                595                 600                 605

Ser Trp Phe Thr Glu Gln Gly Leu Cys Tyr Ala Lys Glu Arg Met Ala
610                 615                 620

Tyr Leu Cys Ala Thr Asp Pro Arg Glu Ser Val Gly Met Ala Gln Val
625                 630                 635                 640

Val Lys Ile Val Gln Lys Thr Asn Cys Leu Ser Ile Arg Asp Ile Val
                645                 650                 655

Ser Asp Ala Tyr Lys Leu Ser Phe Met His Ile His Ser Met Leu Lys
                660                 665                 670

Thr Arg Leu Pro Ile Thr Ile His Tyr Ala Asp Leu Ser Ser Thr Phe
                675                 680                 685

His Asn Arg Gly Leu Ile His Pro Arg Ser Val His Glu Arg Ala Leu
                690                 695                 700

Pro Phe Val
705

<210> SEQ ID NO 124
<211> LENGTH: 895
<212> TYPE: PRT
<213> ORGANISM: Halogeometricum borinquense

<400> SEQUENCE: 124

Met Ala Val Lys Ala Asp Ile Glu Asp Gly Glu Glu Ile Asp Ile Ala
1               5                   10                  15

Leu His Val Thr Gly Ile Asp Glu Trp Glu His Asp Ala Ile Ala Arg
                20                  25                  30

Lys Ile Gln Leu Glu Asp Val Asp Gly Ala Ala Ile Asp Leu Thr Val
                35                  40                  45

Phe His Asn Asn Asp Val Ser Asp Phe Glu Trp Ile Gly Glu Trp
                50                  55                  60

Tyr Leu Leu Glu Asn Val Val Gly Asn Glu Phe Arg Gly Glu Met Gln
65                  70                  75                  80

Leu Asn Pro Gly Tyr Asp Leu Thr Val Thr Leu Leu Asn Asp Pro Pro
                85                  90                  95

Ala Ala Ala Gly Asn Asp Lys Ser Pro Gly Ser Val Pro Pro Glu Glu
                100                 105                 110
```

```
Pro Val Asp Gln Ser Gly Glu Ser Gly Ser Gly Ala Ala Ala Ser
            115                 120                 125

Thr Ser Gly Glu Pro Gly Asp Ala Glu Phe Val Arg Gly Ser Glu Val
    130                 135                 140

Asp Asp Gly Ser Arg Pro Thr Ala Asp Gly Gly Gly Lys Leu Leu His
145                 150                 155                 160

Gln Gln Pro Leu Ser Asp Gly Asn Tyr Leu Leu Gln Phe Glu Leu Gly
                165                 170                 175

Ser Leu Pro Glu Leu Pro Val His Glu Tyr Glu Leu Arg Ala Thr Gly
            180                 185                 190

Ser Gly Gly Ile Asp Pro Asp Asp Phe Thr Asn Gly Ile Glu Gly Phe
            195                 200                 205

Thr Ala Lys Ala Ala Asn Tyr Tyr Gln Ser Arg Ile Gly Ser Pro Val
    210                 215                 220

Thr Thr Ala Asp Ala Ser Arg Arg Ile Tyr Ala Thr Glu Lys Leu
225                 230                 235                 240

His Gly Thr Ile Ser Met His Gly Tyr Thr Val Lys Pro Val His Gln
                245                 250                 255

Gly Glu Thr Thr Leu Glu Ala Arg Ser Tyr Thr Asn Asp Gly Pro Leu
            260                 265                 270

Gln Glu Phe Val Lys Gln Asp Val Lys Arg Ala Val Ala Gly Arg Phe
    275                 280                 285

Glu Val Ser Gly Ile Asp Ser Ile Ile Glu Pro Thr Pro Gln Arg Thr
290                 295                 300

Ala Asn Ser Gly Leu Phe Glu Ala Tyr Arg Lys Tyr Lys Cys Arg Ile
305                 310                 315                 320

Arg Val Asp Ala Asp Gly Thr Val Ile Cys Gly Val Asn Val Ala Tyr
                325                 330                 335

His Leu Glu Ser Thr Phe Ser Ala Ala Glu Trp Val Gln Arg Gly His
            340                 345                 350

Asp Ile Ala Asp Val Thr Val Glu His Asp Thr Asp Leu Tyr Asp Ser
            355                 360                 365

Ala Arg Thr Ala Thr Val Lys Glu Ile Ile Asp Met Asp Tyr Asp Asp
    370                 375                 380

Met Leu Asp Gly Pro Gly Val Pro Met Ser Glu Tyr His Glu Lys His
385                 390                 395                 400

Val Glu Gln Asp Val Ile Asp Ser Met Arg Ala Gly Asn Pro Val Ile
                405                 410                 415

Ala Asp Leu Gln Tyr Gly Ser Gly Glu Asp Ser Ile Phe Pro Gln Leu
            420                 425                 430

Leu Glu Tyr Cys Lys Val Ile Pro Thr Phe Asp Gln Leu Gly Arg Val
    435                 440                 445

Asp Glu Thr Phe Leu Asn Val Ile His Asn Glu Ser Arg Met Lys Pro
450                 455                 460

Glu Glu Arg Phe Asn Val Val Thr Ser Phe Val Asp Leu Leu Gly Pro
465                 470                 475                 480

Thr Pro Tyr Phe Asp Phe Gly Pro Val Pro Gln Pro Thr Asn Ala Gly
                485                 490                 495

Tyr Arg Glu Gln Lys Thr Pro Asn Ile Pro Asn Leu Arg Phe Gly Asp
            500                 505                 510

Gly Arg Thr Gly Tyr Tyr Gly Ala Gly Gly Leu Glu Arg Lys Gly Tyr
    515                 520                 525

Gly Val Tyr Lys Ala Pro Glu Ser Phe Asp Ile Ile Ala Leu Tyr Pro
```

```
                530                 535                 540
Asp Ser Glu Gln Ala Ala Arg Pro Tyr Val Leu Ser Val Leu Gly
545                 550                 555                 560

Lys Leu Ala Glu Tyr Asp Gly Lys Pro Thr Lys Phe Asp Gln Glu Thr
                565                 570                 575

Tyr Glu Leu Gly Ser Glu Phe His Tyr Ser Gln His Ala Gln Lys Thr
                580                 585                 590

Ser Asp Tyr Asp Ala Ala Leu Ile Val Val Pro Asp Lys Asp Lys Ala
                595                 600                 605

Ala Ala Ala Asp Tyr Asp Asp Pro Tyr Pro Glu Phe Lys Arg Arg Leu
            610                 615                 620

Gly Gln Leu Gly Val Pro Ser Gln Met Ile Thr Ile Asp Asn Leu Gly
625                 630                 635                 640

Asn Asp Ser Tyr Leu Gly Asn Ile Ser Ser Leu Ile Gly Lys Ala
                645                 650                 655

Gly Gly Val Pro Trp Arg Ile Asp Asp Val Pro Gly Asp Val Asp Ala
                660                 665                 670

Phe Val Gly Leu Asp Val Thr Tyr Asp His Ala Thr Lys Gln His Leu
                675                 680                 685

Gly Ala Ala Ala Asn Val Ile Met Ala Asp Gly Thr Ile Leu Ala Ser
            690                 695                 700

Glu Ala Val Thr Lys Gln Ala Gly Glu Thr Phe Asp Glu Asp Val
705                 710                 715                 720

Ala Asn Val Ile Lys His Val Leu Glu Ile Phe Ala Glu Glu Gly
                725                 730                 735

Arg Pro Pro Arg His Val Ile His Arg Asp Gly Lys Phe Tyr Leu
                740                 745                 750

Asp Ile Glu Ser Leu Ile Lys Arg Leu Asp Lys Ala Arg Asp Leu Ile
                755                 760                 765

Gln Arg Phe Asp Leu Val Glu Ile Arg Lys Ser Gly Asn Pro Arg Ile
                770                 775                 780

Ala Glu Tyr Asp Glu Ser Lys Ser Arg Phe Asp Ile Ala Asp Lys Gly
785                 790                 795                 800

Val Ala Phe His Val His Asn Gly Asp His Ser Tyr Leu Thr Thr Thr
                805                 810                 815

Gly Gly Lys Glu Gly Ser Pro Gly Thr Pro Arg Pro Leu Gln Ile Val
                820                 825                 830

Lys Arg His Gly Ser Thr Asp Leu Asp Thr Leu Ala Glu Gln Thr Tyr
                835                 840                 845

Trp Leu Ser Glu Ala His Val Gly Ser Leu Ser Arg Ser Thr Arg Leu
850                 855                 860

Pro Ile Thr Thr Tyr Tyr Ala Asp Lys Cys Ala Asp Phe Ala Met Lys
865                 870                 875                 880

Gly Tyr Leu Thr Lys Gly Ser Val Ile Arg Gly Val Pro Tyr Ile
                885                 890                 895

<210> SEQ ID NO 125
<211> LENGTH: 735
<212> TYPE: PRT
<213> ORGANISM: Synococchus elongatus

<400> SEQUENCE: 125

Met Asp Leu Leu Ser Asn Leu Arg Arg Ser Ser Ile Val Leu Asn Arg
1               5                   10                  15
```

```
Phe Tyr Val Lys Ser Leu Ser Gln Ser Asp Leu Thr Ala Tyr Glu Tyr
             20                  25                  30

Arg Cys Ile Phe Lys Lys Thr Pro Glu Leu Gly Asp Glu Lys Arg Leu
         35                  40                  45

Leu Ala Ser Ile Cys Tyr Lys Leu Gly Ala Ile Ala Val Arg Ile Gly
     50                  55                  60

Ser Asn Ile Ile Thr Lys Glu Ala Val Arg Pro Glu Lys Leu Gln Gly
 65                  70                  75                  80

His Asp Trp Gln Leu Val Gln Met Gly Thr Lys Gln Leu Asp Cys Arg
                 85                  90                  95

Asn Asp Ala His Arg Cys Ala Leu Glu Thr Phe Glu Arg Lys Phe Leu
             100                 105                 110

Glu Arg Asp Leu Ser Ala Ser Ser Gln Thr Glu Val Arg Lys Ala Ala
         115                 120                 125

Glu Gly Gly Leu Ile Trp Trp Val Gly Ala Lys Gly Ile Glu Lys
     130                 135                 140

Ser Gly Asn Gly Trp Glu Val His Arg Gly Arg Arg Ile Asp Val Ser
145                 150                 155                 160

Leu Asp Ala Glu Gly Asn Leu Tyr Leu Glu Ile Asp Ile His His Arg
                 165                 170                 175

Phe Tyr Thr Pro Trp Thr Val His Gln Trp Leu Glu Gln Tyr Pro Glu
             180                 185                 190

Ile Pro Leu Ser Tyr Val Arg Asn Asn Tyr Leu Asp Glu Arg His Gly
         195                 200                 205

Phe Ile Asn Trp Gln Tyr Gly Arg Phe Thr Gln Glu Arg Pro Gln Asp
     210                 215                 220

Ile Leu Leu Asp Cys Leu Gly Met Ser Leu Ala Glu Tyr His Leu Asn
225                 230                 235                 240

Lys Gly Ala Thr Glu Glu Val Gln Gln Ser Tyr Val Val Tyr Val
                 245                 250                 255

Lys Pro Ile Ser Trp Arg Lys Gly Lys Leu Thr Ala His Leu Ser Arg
             260                 265                 270

Arg Leu Ser Pro Ser Leu Thr Met Glu Met Leu Ala Lys Val Ala Glu
         275                 280                 285

Asp Ser Thr Val Cys Asp Arg Glu Lys Arg Glu Ile Arg Ala Val Phe
     290                 295                 300

Lys Ser Ile Lys Gln Ser Ile Asn Gln Arg Leu Gln Glu Ala Gln Lys
305                 310                 315                 320

Thr Ala Ser Trp Ile Leu Thr Lys Thr Tyr Gly Ile Ser Ser Pro Ala
                 325                 330                 335

Ile Ala Leu Ser Cys Asp Gly Tyr Leu Leu Pro Ala Ala Lys Leu Leu
             340                 345                 350

Ala Ala Asn Lys Gln Pro Val Ser Lys Thr Ala Asp Ile Arg Asn Lys
         355                 360                 365

Gly Cys Ala Lys Ile Gly Glu Thr Ser Phe Gly Tyr Leu Asn Leu Tyr
     370                 375                 380

Asn Asn Gln Leu Gln Tyr Pro Leu Glu Val His Lys Cys Leu Leu Glu
385                 390                 395                 400

Ile Ala Asn Lys Asn Asn Leu Gln Leu Ser Leu Asp Gln Arg Arg Val
                 405                 410                 415

Leu Ser Asp Tyr Pro Gln Asp Asp Leu Asp Gln Gln Met Phe Trp Gln
             420                 425                 430
```

-continued

```
Thr Trp Ser Ser Gln Gly Ile Lys Thr Val Leu Val Val Met Pro Trp
        435                 440                 445

Asp Ser His His Asp Lys Gln Lys Ile Arg Ile Gln Ala Ile Gln Ala
    450                 455                 460

Gly Ile Ala Thr Gln Phe Met Val Pro Leu Pro Lys Ala Asp Lys Tyr
465                 470                 475                 480

Lys Ala Leu Asn Val Thr Leu Gly Leu Leu Cys Lys Ala Gly Trp Gln
                485                 490                 495

Pro Ile Gln Leu Glu Ser Val Asp His Pro Glu Val Ala Asp Leu Ile
            500                 505                 510

Ile Gly Phe Asp Thr Gly Thr Asn Arg Glu Leu Tyr Tyr Gly Thr Ser
        515                 520                 525

Ala Phe Ala Val Leu Ala Asp Gly Gln Ser Leu Gly Trp Glu Leu Pro
    530                 535                 540

Ala Val Gln Arg Gly Glu Thr Phe Ser Gly Gln Ala Ile Trp Gln Thr
545                 550                 555                 560

Val Ser Lys Leu Ile Ile Lys Phe Tyr Gln Ile Cys Gln Arg Tyr Pro
                565                 570                 575

Gln Lys Leu Leu Leu Met Arg Asp Gly Leu Val Gln Glu Gly Glu Phe
            580                 585                 590

Gln Gln Thr Ile Glu Leu Leu Lys Glu Arg Lys Ile Ala Val Asp Val
        595                 600                 605

Ile Ser Val Arg Lys Ser Gly Ala Gly Arg Met Gly Gln Glu Ile Tyr
    610                 615                 620

Glu Asn Gly Gln Leu Val Tyr Arg Asp Ala Ala Ile Gly Ser Val Ile
625                 630                 635                 640

Leu Gln Pro Ala Glu Arg Ser Phe Ile Met Val Thr Ser Gln Pro Val
                645                 650                 655

Ser Lys Thr Ile Gly Ser Ile Arg Pro Leu Arg Ile Val His Glu Tyr
            660                 665                 670

Gly Ser Thr Asp Leu Glu Leu Leu Ala Leu Gln Thr Tyr His Leu Thr
        675                 680                 685

Gln Leu His Pro Ala Ser Gly Phe Arg Ser Cys Arg Leu Pro Trp Val
    690                 695                 700

Leu His Leu Ala Asp Arg Ser Ser Lys Glu Phe Gln Arg Ile Gly Gln
705                 710                 715                 720

Ile Ser Val Leu Gln Asn Ile Ser Arg Asp Lys Leu Ile Ala Val
                725                 730                 735
```